(12) United States Patent
Slobitker et al.

(10) Patent No.: US 12,102,337 B2
(45) Date of Patent: Oct. 1, 2024

(54) BONE MATERIAL REMOVAL DEVICE AND A METHOD FOR USE THEREOF

(71) Applicant: T.A.G. Medical Products Corporation Ltd., Kibbutz Gaaton (IL)

(72) Inventors: Leon Slobitker, Carmiel (IL); Alexander Kotov, Kiryat-Ata (IL); Aviram Alfia, Karmiel (IL); Dima Gurevich, Carmiel (IL); Roy Zilberman, Qadarim (IL); Hagay Sitry, Haifa (IL); Hagay Botansky, Haifa (IL); Dror Biton, Karmiel (IL)

(73) Assignee: T.A.G. Medical Products Corporation Ltd., Kibbutz Gaaton (IL)

( * ) Notice: Subject to any disclaimer, the term of this patent is extended or adjusted under 35 U.S.C. 154(b) by 209 days.

(21) Appl. No.: 17/938,981

(22) Filed: Sep. 7, 2022

(65) Prior Publication Data

US 2022/0409216 A1    Dec. 29, 2022

Related U.S. Application Data

(63) Continuation of application No. 16/877,551, filed on May 19, 2020, now Pat. No. 11,446,042, which is a continuation of application No. 16/059,098, filed on Aug. 9, 2018, now Pat. No. 10,660,657, which is a continuation of application No. PCT/IL2017/050170, filed on Feb. 10, 2017.

(60) Provisional application No. 62/436,243, filed on Dec. 19, 2016, provisional application No. 62/360,434, filed on Jul. 10, 2016, provisional application No.
(Continued)

(51) Int. Cl.
*A61B 17/16* (2006.01)

(52) U.S. Cl.
CPC ...... *A61B 17/1617* (2013.01); *A61B 17/1631* (2013.01)

(58) Field of Classification Search
CPC .................................................. A61B 17/1617
See application file for complete search history.

(56) References Cited

U.S. PATENT DOCUMENTS

| 854,956 A | 5/1907 | Martin |
| 1,006,468 A | 10/1911 | Isles |

(Continued)

FOREIGN PATENT DOCUMENTS

| CN | 1203518 | 12/1998 |
| CN | 2469895 | 1/2002 |

(Continued)

OTHER PUBLICATIONS

Notice of Allowance Dated May 22, 2023 from the US Patent and Trademark Office Re. U.S. Appl. No. 16/561,089. (7 pages).

(Continued)

*Primary Examiner* — Christian A Sevilla

(57) ABSTRACT

A bone material removal device, including a tubular element comprising a proximal end and a distal end, a shaft received within the tubular element and comprising a proximal end and a distal end, a cutting tooth movably coupled to the distal end of the shaft and a shaft displacement actuator at the proximal end of the tubular element rotatably coupled to the shaft, wherein at least partial rotation of the actuator in a first direction brings the cutting tooth to travel from a closed retracted position to an open extended position.

22 Claims, 92 Drawing Sheets

Related U.S. Application Data

62/352,184, filed on Jun. 20, 2016, provisional application No. 62/336,715, filed on May 15, 2016, provisional application No. 62/294,108, filed on Feb. 11, 2016.

(56) References Cited

U.S. PATENT DOCUMENTS

| | | |
|---|---|---|
| 1,106,767 A | 8/1914 | Young |
| 1,173,882 A | 2/1916 | Smith |
| 1,204,330 A | 11/1916 | Adair |
| 1,237,142 A | 8/1917 | Aase |
| 1,958,399 A | 5/1934 | Stephens |
| 3,195,378 A | 7/1965 | Cogsdill |
| 3,540,324 A | 11/1970 | Johansson |
| 3,690,357 A | 9/1972 | Lugo |
| 3,702,611 A | 11/1972 | Fishbein |
| 3,945,076 A | 3/1976 | Sung |
| 4,411,324 A | 10/1983 | Liebig |
| 4,475,852 A | 10/1984 | Koppelmann |
| 4,541,423 A | 9/1985 | Barber |
| 4,635,737 A | 1/1987 | Miyanaga |
| 4,708,139 A | 11/1987 | Dunbar, IV |
| 4,710,070 A | 12/1987 | Alsen et al. |
| 4,738,255 A | 4/1988 | Goble et al. |
| 4,739,751 A | 4/1988 | Sapega et al. |
| 4,883,048 A | 11/1989 | Purnell et al. |
| 4,920,958 A | 5/1990 | Walt et al. |
| 4,992,010 A | 2/1991 | Fischer |
| 4,998,981 A | 3/1991 | Miyanaga |
| 5,112,337 A | 5/1992 | Paulos et al. |
| 5,330,468 A | 6/1994 | Burkhart |
| 5,445,639 A | 8/1995 | Kuslich et al. |
| 5,507,606 A | 4/1996 | Steiner |
| 5,514,136 A | 5/1996 | Richelsoph |
| 5,591,170 A | 1/1997 | Spievack et al. |
| 5,643,273 A | 7/1997 | Clark |
| 5,645,589 A | 7/1997 | Li |
| 5,681,320 A | 10/1997 | McGuire |
| 5,797,709 A | 8/1998 | Payne |
| 5,817,095 A | 10/1998 | Smith |
| 5,839,860 A | 11/1998 | Steiner |
| 6,015,411 A | 1/2000 | Ohkoshi et al. |
| 6,120,511 A | 9/2000 | Chan |
| 6,162,227 A | 12/2000 | Eckhardt et al. |
| 6,210,415 B1 | 4/2001 | Bester |
| 6,336,931 B1 | 1/2002 | Hsu et al. |
| 6,358,251 B1 | 3/2002 | Mirza |
| 6,383,188 B2 | 5/2002 | Kuslich et al. |
| 6,679,886 B2 | 1/2004 | Weikel et al. |
| 6,746,451 B2 | 6/2004 | Middleton et al. |
| 6,780,175 B1 | 8/2004 | Sachdeva et al. |
| 6,884,246 B1 | 4/2005 | Sonnabend et al. |
| 6,923,813 B2 | 8/2005 | Phillips et al. |
| 7,097,648 B1 | 8/2006 | Globerman et al. |
| 7,172,374 B2 | 2/2007 | Burr et al. |
| 7,179,024 B2 | 2/2007 | Greenhalgh |
| 7,485,119 B2 | 2/2009 | Thelen et al. |
| 7,637,910 B2 | 12/2009 | Schmieding et al. |
| 7,682,378 B2 | 3/2010 | Truckai et al. |
| 7,914,545 B2 | 3/2011 | Ek |
| 7,927,332 B2 | 4/2011 | Huebner et al. |
| 7,938,835 B2 | 5/2011 | Boucher et al. |
| RE42,757 E | 9/2011 | Kuslich et al. |
| 8,038,678 B2 * | 10/2011 | Schmieding ....... A61B 17/1675 606/80 |
| 8,038,679 B2 | 10/2011 | Wieland |
| 8,048,079 B2 | 11/2011 | Iannarone |
| 8,388,621 B2 | 3/2013 | Bourque et al. |
| 9,198,676 B2 | 12/2015 | Pilgeram et al. |
| 9,295,479 B2 | 3/2016 | Hibri et al. |
| 9,381,021 B2 | 7/2016 | Wagner et al. |
| 9,795,395 B2 | 10/2017 | Lizardi et al. |
| 9,848,890 B2 | 12/2017 | Yoon et al. |
| 9,918,722 B2 | 3/2018 | Tally et al. |
| 9,950,445 B2 | 4/2018 | Miyanaga |
| 10,405,872 B2 | 9/2019 | Victor et al. |
| 11,033,283 B2 | 6/2021 | Mirochinik et al. |
| 11,517,329 B2 | 12/2022 | Koogle, Jr. |
| 2002/0165550 A1 * | 11/2002 | Frey ................ A61B 17/1671 606/85 |
| 2002/0183758 A1 | 12/2002 | Middleton et al. |
| 2002/0193799 A1 | 12/2002 | Chappuis et al. |
| 2004/0106928 A1 | 6/2004 | Ek |
| 2004/0126196 A1 | 7/2004 | Burr et al. |
| 2004/0208717 A1 | 10/2004 | Greenhalgh |
| 2004/0254585 A1 | 12/2004 | Whittaker et al. |
| 2005/0113836 A1 | 5/2005 | Lozier et al. |
| 2005/0131345 A1 | 6/2005 | Miller |
| 2005/0240193 A1 | 10/2005 | Layne et al. |
| 2006/0025774 A1 | 2/2006 | Fishbein et al. |
| 2006/0106393 A1 | 5/2006 | Huebner et al. |
| 2006/0149268 A1 | 7/2006 | Truckai et al. |
| 2006/0195112 A1 | 8/2006 | Ek |
| 2006/0241629 A1 | 10/2006 | Krebs et al. |
| 2006/0264957 A1 | 11/2006 | Cragg et al. |
| 2007/0123889 A1 | 5/2007 | Malandain et al. |
| 2007/0276392 A1 | 11/2007 | Beyar et al. |
| 2007/0282345 A1 | 12/2007 | Yedlicka et al. |
| 2008/0103506 A1 | 5/2008 | Volpi et al. |
| 2008/0114364 A1 * | 5/2008 | Goldin ............... A61B 17/1617 606/170 |
| 2008/0140078 A1 | 6/2008 | Nelson et al. |
| 2008/0154271 A1 | 6/2008 | Berberich et al. |
| 2008/0183174 A1 | 7/2008 | Sikora et al. |
| 2009/0018468 A1 | 1/2009 | Janssens |
| 2009/0171359 A1 | 7/2009 | Sterrett |
| 2009/0254092 A1 * | 10/2009 | Albiol Llorach .. A61B 17/1617 606/87 |
| 2010/0168747 A1 | 7/2010 | Lynch et al. |
| 2010/0241124 A1 | 9/2010 | Housman et al. |
| 2010/0249785 A1 | 9/2010 | Betts |
| 2010/0268234 A1 | 10/2010 | Aho et al. |
| 2011/0034910 A1 | 2/2011 | Ross et al. |
| 2011/0087257 A1 | 4/2011 | To et al. |
| 2011/0098709 A1 | 4/2011 | Malandain et al. |
| 2011/0130760 A1 | 6/2011 | Anderson et al. |
| 2011/0164937 A1 | 7/2011 | Byrne et al. |
| 2011/0166575 A1 | 7/2011 | Assell et al. |
| 2011/0166581 A1 | 7/2011 | Van Der Merwe et al. |
| 2011/0190832 A1 | 8/2011 | Taylor et al. |
| 2011/0251616 A1 | 10/2011 | Osman et al. |
| 2012/0022568 A1 | 1/2012 | Koblish et al. |
| 2012/0059382 A1 | 3/2012 | Paulos |
| 2012/0209274 A1 | 8/2012 | Belaney et al. |
| 2012/0239072 A1 * | 9/2012 | Rodriguez ......... A61B 17/1617 606/185 |
| 2012/0245585 A1 | 9/2012 | Kaiser et al. |
| 2013/0030442 A1 | 1/2013 | Pilgeram et al. |
| 2013/0150859 A1 | 6/2013 | Kehres et al. |
| 2013/0165935 A1 | 6/2013 | Griffiths et al. |
| 2014/0039552 A1 | 2/2014 | Pilgeram |
| 2014/0194880 A1 | 7/2014 | Schmieding et al. |
| 2014/0257297 A1 | 9/2014 | Koogle, Jr. et al. |
| 2014/0276844 A1 | 9/2014 | Bourque et al. |
| 2014/0316413 A1 | 10/2014 | Burger et al. |
| 2014/0324052 A1 | 10/2014 | Carrison et al. |
| 2015/0073417 A1 | 3/2015 | Norton et al. |
| 2015/0150570 A1 | 6/2015 | Okuno et al. |
| 2015/0265287 A1 | 9/2015 | Berberich |
| 2016/0038157 A1 | 2/2016 | Mirochinik et al. |
| 2016/0199145 A1 | 7/2016 | Haidukewych et al. |
| 2017/0007272 A1 | 1/2017 | Weitzman et al. |
| 2017/0128086 A1 | 5/2017 | Slobitker et al. |
| 2017/0224359 A1 | 8/2017 | Mirochinik et al. |
| 2017/0245869 A1 | 8/2017 | Mirochinik et al. |
| 2018/0360467 A1 | 12/2018 | Slobitker et al. |
| 2019/0059910 A1 | 2/2019 | Adams et al. |
| 2019/0167281 A1 | 6/2019 | Zilberman et al. |
| 2019/0388102 A1 | 12/2019 | Slobitker et al. |
| 2020/0163684 A1 | 5/2020 | Mirochinik et al. |
| 2020/0246023 A1 | 8/2020 | Forsell |
| 2020/0275939 A1 | 9/2020 | Slobitker et al. |
| 2020/0405327 A1 | 12/2020 | Zilberman et al. |

(56) References Cited

U.S. PATENT DOCUMENTS

| | | | |
|---|---|---|---|
| 2021/0259710 | A1 | 8/2021 | Mirochinik et al. |
| 2021/0259714 | A1 | 8/2021 | Zilberman et al. |
| 2021/0298768 | A1 | 9/2021 | Biton et al. |
| 2022/0104834 | A1 | 4/2022 | Biton et al. |
| 2023/0255643 | A1 | 8/2023 | Biton |

FOREIGN PATENT DOCUMENTS

| | | |
|---|---|---|
| CN | 1925798 | 3/2007 |
| CN | 201394046 | 2/2010 |
| CN | 101677823 | 3/2010 |
| CN | 101795629 | 8/2010 |
| CN | 201617897 | 11/2010 |
| CN | 105592805 | 5/2016 |
| CN | 107106186 | 8/2017 |
| CN | 108113731 | 6/2018 |
| DE | 19501027 | 7/1996 |
| EP | 1535579 | 6/2005 |
| EP | 1785103 | 5/2007 |
| ES | 2351563 | 2/2011 |
| JP | H02-184409 | 7/1990 |
| JP | 11-514905 | 12/1999 |
| JP | 2003-531676 | 10/2003 |
| JP | 2006-523542 | 10/2006 |
| JP | 2008-521511 | 6/2008 |
| JP | 2009-533159 | 9/2009 |
| JP | 2011-529365 | 12/2011 |
| JP | S48-62067 | 1/2012 |
| JP | 2012-522604 | 9/2012 |
| JP | 2012-187384 | 10/2012 |
| JP | 2013-516275 | 5/2013 |
| JP | 2014-171864 | 9/2014 |
| JP | 2015-136589 | 7/2015 |
| JP | 2016-516524 | 6/2016 |
| JP | 2016-523542 | 8/2016 |
| JP | 2017-531518 | 10/2017 |
| JP | 2018-513735 | 5/2018 |
| JP | 7189317 | 12/2022 |
| WO | WO 97/16118 | 5/1997 |
| WO | WO 01/58629 | 8/2001 |
| WO | WO 01/82838 | 11/2001 |
| WO | WO 2006/060420 | 6/2006 |
| WO | WO 2007/120903 | 10/2007 |
| WO | WO 2010/013027 | 2/2010 |
| WO | WO 2010/065047 | 6/2010 |
| WO | WO 2010/111246 | 9/2010 |
| WO | WO 2010/115134 | 10/2010 |
| WO | WO 2013/192080 | 12/2013 |
| WO | WO 2014/089198 | 6/2014 |
| WO | WO 2014/174521 | 10/2014 |
| WO | WO 2016/063279 | 4/2016 |
| WO | WO 2016/162869 | 10/2016 |
| WO | WO 2017/137998 | 8/2017 |
| WO | WO 2017/187436 | 11/2017 |
| WO | WO 2018/051356 | 3/2018 |
| WO | WO 2020/026252 | 2/2020 |

OTHER PUBLICATIONS

Notice of Allowance Dated Aug. 4, 2023 from the US Patent and Trademark Office Re. U.S. Appl. No. 17/319,116. (3 pages).
Supplementary European Search Report Dated Jun. 21, 2023 From the European Patent Office Re. Application No. 23156825.4. (5 Pages).
Restriction Official Action Dated Sep. 20, 2022 from US Patent and Trademark Office Re. U.S. Appl. No. 17/016,458. (7 pages).
Advisory Action Dated Mar. 21, 2024 From the US Patent and Trademark Office Re. U.S. Appl. No. 17/016,458. (6 Pages).
Pre-Appeal Examination Dated Mar. 5, 2024 From the Japan Patent Office Re. Application No. 2022-001060 and Its Translation Into English. (6 Pages).
Notice of Allowance Dated Sep. 13, 2023 together with Interview Summary Dated Aug. 17, 2023 from the US Patent and Trademark Office Re. U.S. Appl. No. 17/316,866. (19 pages).
Notice of Reason(s) for Rejection Dated Sep. 12, 2023 From the Japan Patent Office Re. Application No. 2022-001060 and Its Translation Into English. (30 Pages).
Relatório de Busca e Parecer [Search Report and Opinion] Dated Jun. 6, 2023 From the Serviço Público Federal, Ministério da Economia, Instituto Nacional da Propriedade Industrial do Brasil Re. Application No. BR 12 2022 014776 3 and Its Translation Into English. (12 Pages).
English Summary Dated Feb. 22 of Notification of Office Action Dated Feb. 4, 2024 From the National Intellectual Property Administration of the People's Republic of China Re. Application No. 201980058843.8. (2 Pages).
Notice of Allowance Dated Feb. 3, 2023 from the US Patent and Trademark Office Re. U.S. Appl. No. 17/319,116. (81 pages).
Official Action Dated May 3, 2023 from the US Patent and Trademark Office Re. U.S. Appl. No. 17/316,866. (85 pages).
Office Action Dated Dec. 10, 2023 From the Israel Patent Office Re. Application No. 280574. (7 Pages).
Official Action Dated Aug. 2, 2023 from the US Patent and Trademark Office Re. U.S. Appl. No. 17/016,458. (84 pages).
Advisory Action Before the Filing of An Appeal Brief Dated Apr. 1, 2019 From the US Patent and Trademark Office Re. U.S. Appl. No. 15/318,677. (8 pages).
Advisory Action Before the Filing of An Appeal Brief Dated Feb. 28, 2018 From the US Patent and Trademark Office Re. U.S. Appl. No. 15/498,731. (3 pages).
Applicant-Initiated Interview Summary Dated Jul. 18, 2018 From the US Patent and Trademark Office Re. U.S. Appl. No. 15/498,731. (4 pages).
Applicant-Initiated Interview Summary Dated Feb. 26, 2019 From the US Patent and Trademark Office Re. U.S. Appl. No. 15/318,677. (3 pages).
Communication Pursuant to Article 94(3) EPC Dated Mar. 1, 2018 From the European Patent Office Re. Application No. 15804626.8. (3 Pages).
Communication Pursuant to Article 94(3) EPC Dated Jun. 8, 2018 From the European Patent Office Re. Application No. 17205443.9. (5 Pages).
Communication Pursuant to Article 94(3) EPC Dated Nov. 11, 2021 From the European Patent Office Re. Application No. 17205443.9. (5 Pages).
Communication Pursuant to Article 94(3) EPC Dated Mar. 16, 2021 From the European Patent Office Re. Application No. 17205443.9. (6 Pages).
Communication Pursuant to Article 94(3) EPC Dated Mar. 16, 2022 From the European Patent Office Re. Application No. 15804626.8. (5 Pages).
Communication Pursuant to Article 94(3) EPC Dated May 17, 2021 From the European Patent Office Re. Application No. 17788940.9. (6 Pages).
Communication Pursuant to Article 94(3) EPC Dated Jul. 27, 2021 From the European Patent Office Re. Application No. 15804626.8. (7 Pages).
Communication Relating to the Results of the Partial International Search Dated May 19, 2016 From the International Searching Authority Re. Application No. PCT/IL2015/051033.
English Translation Dated May 16, 2022 of Examination Report Dated Apr. 20, 2022 From the Servico Publico Federal, Ministerio da Economia, Instituto Nacional da Propriedade Industrial do Brasil Re Application No. BR11 2017 008135 0 . (3 Pages).
European Search Report and the European Search Opinion Dated Mar. 2, 2021 From the European Patent Office Re. Application No. 20209453.8. (5 Pages).
European Search Report Dated Apr. 30, 2018 From the European Patent Office Re. Application No. 17205443.9. (5 Pages).
Examination Report Dated Sep. 1, 2021 From the Servico Publico Federal, Ministerio da Economia, Instituto Nacional da Propriedade Industrial do Brasil RE Application No. BR12 2020 008361 1 and Its Summary Into English. (8 Pages).

(56) References Cited

OTHER PUBLICATIONS

Examination Report Dated Jan. 15, 2020 From the Servico Publico Federal, Ministerio da Economia, Instituto Nacional da Propriedade Industrial do Brasil Re. Application No. BR112015026975-3 and Its Summary in English. (4 Pages).
Examination Report Dated Apr. 20, 2022 From the Servico Publico Federal, Ministerio da Economia, Instituto Nacional da Propriedade Industrial do Brasil Re Application No. BR11 2017 008135 0 and Its Summary Into English. (8 Pages).
Examination Report Under Sections 12 & 13 of the Patents Act, 1970 and the Patents Rules, 2003 Dated Mar. 5, 2021 From the Government of India, Intellectual Property India, Patents, Designs, Trade Marks, Geographical Indications, The Patent Office Re. Application No. 201727016824. (7 Pages).
Examination Report Under Sections 12 & 13 of the Patents Act, 1970 and the Patents Rules, 2003 Dated Sep. 28, 2020 From the Government of India, Intellectual Property Indis, Patents, Designs, Trade Marks, Geographical Indications, The Patent Office Re. Application No. 2954/MUMNP/2015. (7 Pages).
Final Office Action Dated May 11, 2021 From the Japan Patent Office Re. Application No. 2018-241087 and Its Translation Into English. (4 Pages).
Final Official Action Dated Mar. 11, 2022 together with Interview Summay Dated Feb. 23, 2022 from US Patent and Trademark Office Re. U.S. Appl. No. 17/552,393. (8 pages).
International Preliminary Report on Patentability Dated May 4, 2017 From the International Bureau of WIPO Re. Application No. PCT/IL2015/051033. (11 Pages).
International Preliminary Report on Patentability Dated Nov. 5, 2015 From the International Bureau of WIPO Re. Application No. PCT/IL2014/050381.
International Preliminary Report on Patentability Dated Feb. 11, 2021 From the International Bureau of WIPO Re. Application No. PCT/IL2019/050876. (11 Pages).
International Preliminary Report on Patentability Dated Oct. 19, 2017 From the International Bureau of WIPO Re. Application No. PCT/IL2016/050370. (12 Pages).
International Preliminary Report on Patentability Dated Aug. 23, 2018 From the International Bureau of WIPO Re. Application No. PCT/IL2017/050170. (16 Pages).
International Search Report and the Written Opinion Dated Aug. 4, 2016 From the International Searching Authority Re. Application No. PCT/IL2015/051033.
International Search Report and the Written Opinion Dated Oct. 7, 2016 From the International Searching Authority Re. Application No. PCT/IL2016/050370.
International Search Report and the Written Opinion Dated Sep. 10, 2014 From the International Searching Authority Re. Application No. PCT/IL2014/050381.
International Search Report and the Written Opinion Dated Aug. 11, 2017 From the International Searching Authority Re. Application No. PCT/IL2017/050170. (24 Pages).
International Search Report and the Written Opinion Dated Jan. 22, 2020 From the International Searching Authority Re. Application No. PCT/IL2019/050876. (19 Pages).
International Search Report and the Written Opinion Dated Aug. 29, 2017 From the International Searching Authority Re. Application No. PCT/IL2017/050469. (17 Pages).
Interview Summary Dated Dec. 11, 2020 from the US Patent and Trademark Office Re. U.S. Appl. No. 16/090,820. (2 pages).
Invitation to Pay Additional Fees Dated Aug. 1, 2016 From the International Searching Authority Re. Application No. PCT/IL2016/050370.
Invitation to Pay Additional Fees Dated Nov. 13, 2019 From the International Searching Authority Re. Application No. PCT/IL2019/050876. (3 Pages).
Invitation to Pay Additional Fees Dated May 17, 2017 From the International Searching Authority Re. Application No. PCT/IL2017/050170. (2 Pages).
Notice of Allowance Dated Feb. 3, 2021 From the US Patent and Trademark Office Re. U.S. Appl. No. 16/090,820. (22 Pages).
Notice Of Allowance Dated Feb. 8, 2017 From the US Patent and Trademark Office Re. U.S. Appl. No. 14/919,921. (7 pages).
Notice of Allowance Dated Jun. 11, 2019 From the US Patent and Trademark Office Re. U.S. Appl. No. 15/318,677. (3 Pages).
Notice Of Allowance Dated Sep. 13, 2019 From the US Patent and Trademark Office Re. U.S. Appl. No. 15/519,844. (6 pages).
Notice of Allowance Dated Aug. 16, 2021 from the US Patent and Trademark Office Re. U.S. Appl. No. 17/264,895. (35 pages).
Notice Of Allowance Dated Jan. 16, 2020 From the US Patent and Trademark Office Re. U.S. Appl. No. 16/059,098. (23 pages).
Notice of Allowance Dated Feb. 18, 2021 From the US Patent and Trademark Office Re. U.S. Appl. No. 16/740,597. (44 Pages).
Notice of Allowance Dated Oct. 22, 2020 From the US Patent and Trademark Office Re. U.S. Appl. No. 16/090,820. (12 Pages).
Notice Of Allowance Dated Oct. 26, 2018 From the US Patent and Trademark Office Re. U.S. Appl. No. 15/498,731. (9 pages).
Notice of Allowance with Interview Summary Dated May 4, 2022 From the US Patent and Trademark Office Re. U.S. Appl. No. 16/877,551. (80 Pages).
Notice of Decision of Rejection Dated Sep. 4, 2018 From the Japan Patent Office Re. Application No. 2016-509605. (4 Pages).
Notice of Reason for Rejection Dated Feb. 27, 2018 From the Japan Patent Office Re. Application No. 2016-509605. (2 Pages).
Notice of Reason(s) for Rejection Dated Aug. 3, 2021 From the Japan Patent Office Re. Application No. 2017-552067 and Its Translation Into English. (9 Pages).
Notice of Reasons for Rejection Dated Dec. 1, 2020 From the Japan Patent Office Re. Application No. 2017-552067 and Its Translation Into English. (9 Pages).
Notice of Reasons for Rejection Dated Jul. 7, 2020 From the Japan Patent Office Re. Application No. 2017-521086. (3 Pages).
Notice of Reasons for Rejection Dated Dec. 8, 2020 From the Japan Patent Office Re. Application No. 2018-241087. (4 Pages).
Notice of Reasons for Rejection Dated Dec. 10, 2019 From the Japan Patent Office Re. Application No. 2017-521086. (7 Pages).
Notice of Reasons for Rejection Dated Mar. 10, 2020 From the Japan Patent Office Re. Application No. 2018-241087 and Its Translation Into English. (13 Pages.
Notice of Reasons for Rejection Dated Apr. 12, 2022 From the Japan Patent Office Re. Application No. 2021-503166 and Its Translation Into English. (9 Pages).
Notice of Reasons for Rejection Dated Feb. 18, 2020 From the Japan Patent Office Re. Application No. 2017-552067 and Its Translation Into English. (18 Pages).
Notice of Reasons for Rejection Dated Aug. 20, 2019 From the Japan Patent Office Re. Application No. 2017-521086. (7 Pages).
Notice of Reasons for Rejection Dated Jan. 21, 2020 From the Japan Patent Office Re. Application No. 2016-509605. (3 Pages).
Notification of Office Action and Search Report Dated Aug. 1, 2019 From the State Intellectual Property Office of the People's Republic of China Re. Application No. 201680027825.X. (7 Pages).
Notification of Office Action and Search Report Dated Jun. 1, 2020 From the State Intellectual Property Office of the People's Republic of China Re. Application No. 201810460549.7. (8 Pages).
Notification of Office Action and Search Report Dated May 6, 2020 From the State Intellectual Property Office of the People's Republic of China Re. Application No. 201680027825.X. (6 Pages).
Notification of Office Action and Search Report Dated Jul. 9, 2019 From the State Intellectual Property Office of the People's Republic of China Re. Application No. 201580069380.7. (5 Pages).
Notification of Office Action and Search Report Dated Nov. 10, 2020 From the State Intellectual Property Office of the People's Republic of China Re. Application No. 201680027825.X. (4 Pages).
Notification of Office Action and Search Report Dated Aug. 15, 2017 From the State Intellectual Property Office of the People's Republic of China Re. Application No. 201480035299.2. (6 Pages).
Notification of Office Action Dated Dec. 4, 2018 From the State Intellectual Property Office of the People's Republic of China Re. Application No. 201580069380.7 and Its Translation Into English. (4 Pages).

(56) References Cited

OTHER PUBLICATIONS

Notification of Office Action Dated Nov. 30, 2020 From the State Intellectual Property Office of the People's Republic of China Re. Application No. 201810460549.7. (5 Pages).
Official Action Dated Nov. 2, 2016 From the US Patent and Trademark Office Re. U.S. Appl. No. 14/919,921.
Official Action Dated Nov. 8, 2017 From the US Patent and Trademark Office Re. U.S. Appl. No. 15/318,677. (17 pages).
Official Action Dated Dec. 13, 2017 From the US Patent and Trademark Office Re. U.S. Appl. No. 15/498,731. (12 pages).
Official Action Dated Jul. 17, 2017 From the US Patent and Trademark Office Re. U.S. Appl. No. 15/498,731. (13 Pages).
Official Action Dated Apr. 18, 2017 From the US Patent and Trademark Office Re. U.S. Appl. No. 15/318,677. (21 pages).
Official Action Dated Jul. 19, 2022 from US Patent and Trademark Office Re. U.S. Appl. No. 16/561,089. (95 pages).
Official Action Dated Jan. 23, 2019 From the US Patent and Trademark Office Re. U.S. Appl. No. 15/318,677. (16 pages).
Official Action Dated Jun. 24, 2022 from US Patent and Trademark Office Re. U.S. Appl. No. 17/552,393. (138 pages).
Official Action Dated May 24, 2019 From the US Patent and Trademark Office Re. U.S. Appl. No. 15/519,844. (28 pages).
Official Action Dated Mar. 27, 2018 From the US Patent and Trademark Office Re. U.S. Appl. No. 15/318,677. (15 pages).
Official Action Dated Aug. 29, 2018 From the US Patent and Trademark Office Re. U.S. Appl. No. 15/318,677. (17 pages).
Official Action Dated Mar. 29, 2018From the US Patent and Trademark Office Re. U.S. Appl. No. 15/498,731. (15 pages).
Relatorio de Busca e Parecer [Search Report and Opinion] Dated Mar. 24, 2021 From the Servico Publico Federal, Ministerio da Economia, Instituto Nacional da Propriedade Industrial do Brasil, INPI Re. Application No. BR122020008361-1 and Its Translation Into English. (8 Pages).
Restriction Official Action Dated Jul. 8, 2016 From the US Patent and Trademark Office Re. U.S. Appl. No. 14/919,921.
Restriction Official Action Dated Feb. 11, 2016 From the US Patent and Trademark Office Re. U.S. Appl. No. 14/919,921.
Restriction Official Action Dated Jul. 2, 2020 From the US Patent and Trademark Office Re. U.S. Appl. No. 16/090,820. (7 pages).
Search Report and Explanation Dated Apr. 16, 2020 From the Servico Publico Federal, Ministerio da Economia, Instituto Nacional da Propriedade Industrial do Brasil Re. Application No. BR112017008135-0 and Its Summary in English. (5 Pages).
Supplementary European Search Report and the European Search Opinion Dated Mar. 2, 2022 From the European Patent Office Re. Application No. 19845184.1.(10 Pages).
Supplementary European Search Report and the European Search Opinion Dated Apr. 6, 2020 From the European Patent Office Re. Application No. 17788940.9. (5 Pages).
Supplementary European Search Report and the European Search Opinion Dated Dec. 13, 2018 From the European Patent Office Re. Application No. 16776225.1. (8 Pages).
Supplementary European Search Report and the European Search Opinion Dated Jan. 30, 2019 From the European Patent Office Re. Application No. 17749987.8. (6 Pages).
Translation Dated Jun. 4, 2020 of Notification of Office Action Dated May 6, 2020 From the State Intellectual Property Office of the People's Republic of China Re. Application No. 201680027825.X. (4 Pages).
Translation Dated Sep. 4, 2019 of Notice of Reasons for Rejection Dated Aug. 20, 2019 From the Japan Patent Office Re. Application No. 2017-521086. (7 Pages).
Translation Dated Oct. 5, 2018 of Notice of Decision of Rejection Dated Sep. 4, 2018 From the Japan Patent Office Re. Application No. 2016-509605. (4 Pages).
Translation Dated Feb. 7, 2020 of Notice of Reasons for Rejection Dated Jan. 21, 2020 From the Japan Patent Office Re. Application No. 2016-509605. (3 Pages).
Translation Dated Dec. 9, 2020 of Notification of Office Action Dated Nov. 30, 2020 From the State Intellectual Property Office of the People's Republic of China Re. Application No. 201810460549.7. (6 Pages).
Translation Dated Jan. 9, 2020 of Notice of Reasons for Rejection Dated Dec. 10, 2019 From the Japan Patent Office Re. Application No. 2017-521086. (8 Pages).
Translation Dated Jul. 14, 2019 of Notification of Office Action Dated Jul. 9, 2019 From the State Intellectual Property Office of the People's Republic of China Re. Application No. 201580069380.7. (1 Page).
Translation Dated Jun. 22, 2020 of Notification of Office Action Dated Jun. 1, 2020 From the State Intellectual Property Office of the People's Republic of China Re. Application No. 201810460549.7. (4 Pages).
Translation Dated Mar. 22, 2018 of Notice of Reason for Rejection Dated Feb. 27, 2018 From the Japan Patent Office Re. Application No. 2016-509605. (2 Pages).
Translation Dated Aug. 23, 2019 of Notification of Office Action Dated Aug. 1, 2019 From the State Intellectual Property Office of the People's Republic of China Re. Application No. 201680027825.X. (4 Pages).
Translation Dated Nov. 26, 2020 of Notification of Office Action Dated Nov. 10, 2020 From the State Intellectual Property Office of the People's Republic of China Re. Application No. 201680027825.X. (3 Pages).
Translation Dated Dec. 30, 2020 of Notice of Reasons for Rejection Dated Dec. 8, 2020 From the Japan Patent Office Re. Application No. 2018-241087. (4 Pages).
Translation of Notification of Office Action Dated Aug. 15, 2017 From the State Intellectual Property Office of the People's Republic of China Re. Application No. 201480035299.2. (3 Pages).
Notice of Reason(s) for Rejection Dated Sep. 5, 2023 From the Japan Patent Office Re. Application No. 2022-192926 and Its Translation Into English. (4 Pages).
Supplementary European Search Report and the European Search Opinion Dated Sep. 7, 2023 From the European Patent Office Re. Application No. 23166977.1. (10 Pages).
Notice of Allowance Dated Apr. 26, 2023 from the US Patent and Trademark Office Re. U.S. Appl. No. 17/319,116. (5 pages).
Examination Report Under Sections 12 & 13 of the Patents Act, 1970 and the Patents Rules, 2003 Dated Aug. 31, 2022 From the Government of India, Intellectual Property India, Patents, Designs, Trade Marks, Geographical Indications, The Patent Office Re. Application No. 202128040474. (6 Pages).
Communication Pursuant to Article 94(3) EPC Dated Jan. 27, 2023 From the European Patent Office Re. Application No. 16776225.1 (7 Pages).
Final Official Action Dated Jan. 27, 2023 together with Interview Summary Dated Jan. 6, 2023 from the US Patent and Trademark Office Re. U.S. Appl. No. 16/561,089, (43 pages).
Notice of Reason(s) for Rejection Dated Jan. 17, 2023 From the Japan Patent Office Re. Application No. 2022-001060 and Its Translation Into English. (20 Pages).
Notification of Office Action and Search Report Dated Feb. 4, 2024 From the National Intellectual Property Administration of the People's Republic of China Re. Application No. 201980058843.8 and Its Machine Translation Into English. (21 Pages).
Final Official Action together with Interview Summary Dated Oct. 13, 2022 from the US Patent and Trademark Office Re. U.S. Appl. No. 17/552,393. (18 pages).
Official Action Dated Nov. 13, 2023 from the US Patent and Trademark Office Re. U.S. Appl. No. 17/016,458. (19 pages).
Hearing Notice Dated Jul. 3, 2023 From the Government of India, Intellectual Property India, The Patent Office Re. Application No. 201727016824. (4 Pages).
Hearing Notice Dated Oct. 4, 2023 From the Government of India, Intellectual Property India, The Patent Office Re. Application No. 2954/MUMNP/2015. (3 Pages).
Communication Pursuant to Article 94(3) EPC Dated Apr. 24, 2024 From the European Patent Office Re. Application No. 20209453.8 (4 Pages).

(56) References Cited

OTHER PUBLICATIONS

Official Action Dated Apr. 24, 2024 From the US Patent and Trademark Office Re. U.S. Appl. No. 17/016,458. (12 Pages).
Notice of Allowance Dated Mar. 1, 2023 from the US Patent and Trademark Office Re. U.S. Appl. No. 17/552,393. (8 pages).
Second Restriction Official Action Dated Feb. 28, 2023 from the US Patent and Trademark Office Re. U.S. Appl. No. 17/016,458. (7 pages).

* cited by examiner

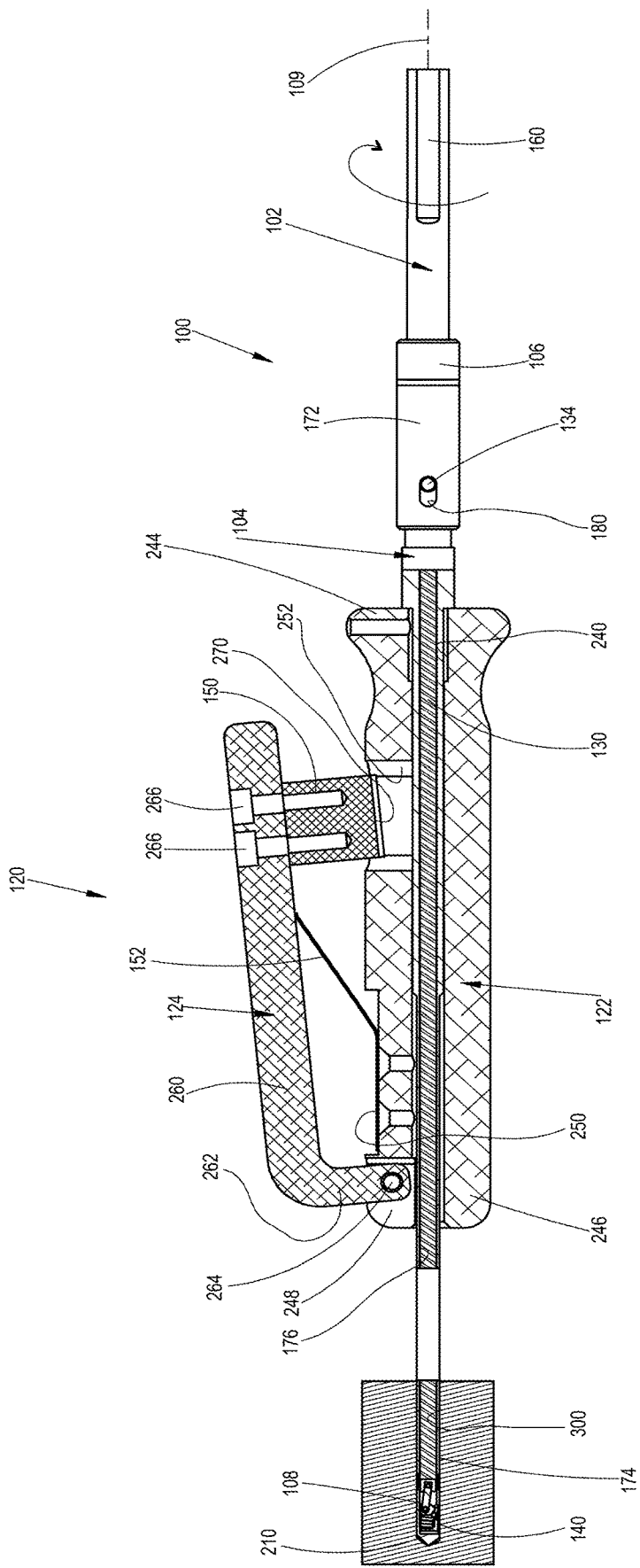

1. Operative state – Prior to surgical procedure:
   1.1. Shaft element 130 is threaded into rotating element 102 and connected to the reamer element 104 by indicating pin 134
   1.2. Rotating element 102 freely rotates with respect to the reamer element 104
   1.3. Shaft element 130 pulls the hinge element 136 and keeps the cutting tooth 140 at its CLOSED operative orientation
   1.4. Indicating pin 134 is positioned at its proximal position in the guiding slot 180 of the reamer element 104
2. Operative state - Initial Drilling – CLOSED operative orientation:
   2.1. Initiate rotation of rotating element 102 at clockwise direction while bone material removal device 100 is inserted into cannula assembly 120
   2.2. Cannula lever 124 is released
   2.3. Indicating pin 134 is positioned at its proximal position in the guiding slot 180 of the reamer element 104, thus urging the reamer element 104 to rotate in a clockwise direction and perform initial bore 300 in the bone of a patient
3. Operative state - Transition to an OPEN operative orientation:
   3.1. Initiate rotation of the rotating element 102 in a counterclockwise direction
   3.2. Press the cannula lever 124 to create friction force between the reamer element 104 and the cannula lever 124 in order to stop the rotation of the reamer element 104 momentarily
   3.3. As a result, threaded portion 132 of shaft element 130 is threaded out from rotating element 102
   3.4. Rotation of the shaft element 130 is restricted by indication pin 134 being guided within guiding slot 180, thus shaft element 130 is displaced axially in a distal direction
   3.5. Shaft element 130 pushes the hinge element 136 and urges the cutting tooth 140 to pivot up to 90° over axis 214 to its OPENED operative orientation
   3.6. Indicating pin 134 is displaced to its distal position in the guiding slot 180 of the reamer element 104
   3.7. Release the cannula lever 124
   3.8. Drilling forward and backwards to create the desired undercut bore 302 length
4. Operative state - Transition to CLOSED operative orientation:
   4.1. Initiate rotation of rotating element 102 in a clockwise direction
   4.2. Press the cannula lever 124 to create friction force between the cannula lever 124 and the reamer element 104, thus stopping the rotation of the reamer element 104 momentarily
   4.3. As a result, threaded portion 132 of shaft element 130 is threaded into the rotating element 102
   4.4. Rotation of shaft element 130 is restricted by indication pin 134 being guided within guiding slot 180, thus shaft element 130 is displaced axially in a proximal direction
   4.5. Shaft element 130 pulls the hinge element 136 and urges the cutting tooth 140 to pivot up to 90° over axis 214 to its CLOSED operative orientation
   4.6. Indicating pin 134 is displaced to its proximal position in the guiding slot 180 of the reamer element 104
   4.7. Release the cannula lever 124
   4.8. Drilling backwards to pull the reamer element 104 out of the bone of the patient.

FIG. 21

```
┌─────────────────────────────────────────────────────────────────┐
│ Ensure that the bone material removal device 100 is in a closed │
│ operative orientation and the indicating pin 134 in its proximal│
│ position                                                        │
└─────────────────────────────────────────────────────────────────┘
                                 ↓
┌─────────────────────────────────────────────────────────────────┐
│ Insert the bone material removal device 100 into cannula        │
│ assembly 120                                                    │
└─────────────────────────────────────────────────────────────────┘
                                 ↓
┌─────────────────────────────────────────────────────────────────┐
│ Engage the bone of the patient by the drilling tip 210 of the   │
│ bone material removal device 100                                │
└─────────────────────────────────────────────────────────────────┘
                                 ↓
┌─────────────────────────────────────────────────────────────────┐
│ Drill an initial hole 300 by pushing the bone material removal  │
│ device 100 in a distal direction toward the bone of the patient │
│ and rotating the reamer element 104 in a clockwise direction    │
└─────────────────────────────────────────────────────────────────┘
                                 ↓
┌─────────────────────────────────────────────────────────────────┐
│ Once the desired depth of penetration is achieved, press the    │
│ cannula lever 124                                               │
└─────────────────────────────────────────────────────────────────┘
                                 ↓
┌─────────────────────────────────────────────────────────────────┐
│ Rotate the reamer element 104 in a counter-clockwise direction  │
│ in order to open the cutting tooth 140 and create undercut bore │
│ 302, having an enlarged diameter as compared to the initial     │
│ bore 300.                                                       │
│ The cannula lever 124 remains pressed until the indicating pin  │
│ 134 reaches its distal position                                 │
└─────────────────────────────────────────────────────────────────┘
                                 ↓
┌─────────────────────────────────────────────────────────────────┐
│ Release the cannula lever 124 and proceed drilling proximally   │
│ and distally having the cutting tooth 140 open in order to      │
│ achieve a desired length of the undercut bore 302               │
└─────────────────────────────────────────────────────────────────┘
                                 ↓
┌─────────────────────────────────────────────────────────────────┐
│ Once the desired undercut bore 302 is achieved, press the       │
│ cannula lever 124                                               │
└─────────────────────────────────────────────────────────────────┘
                                 ↓
┌─────────────────────────────────────────────────────────────────┐
│ Cutting tooth 140 is closing and the indicating pin 134 is      │
│ axially displaced to its proximal position                      │
└─────────────────────────────────────────────────────────────────┘
                                 ↓
┌─────────────────────────────────────────────────────────────────┐
│ Pull out the reamer element 104 from the bone of the patient    │
└─────────────────────────────────────────────────────────────────┘
                                 ↓
┌─────────────────────────────────────────────────────────────────┐
│ Removing bone material removal device 100 from the cannula      │
│ assembly 120                                                    │
└─────────────────────────────────────────────────────────────────┘
```

FIG. 22

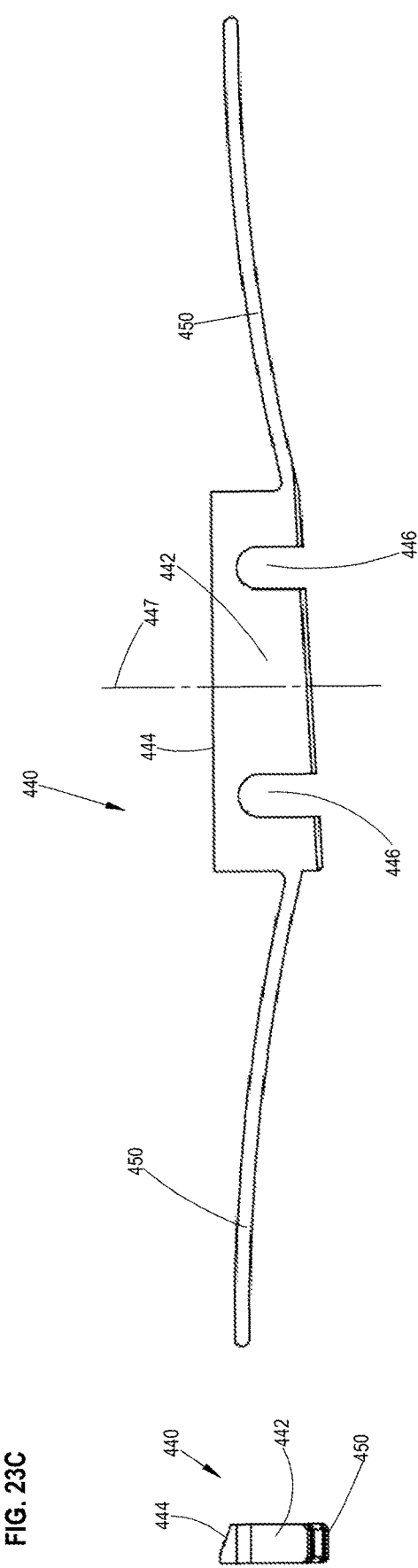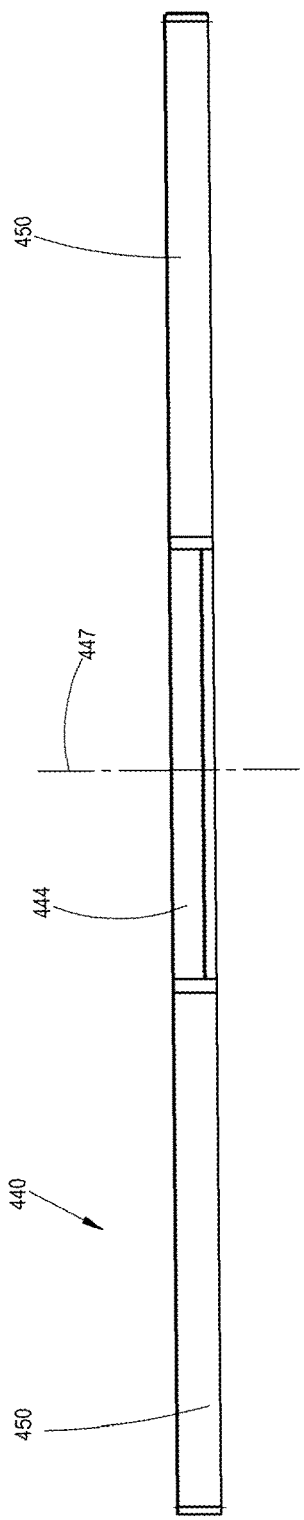

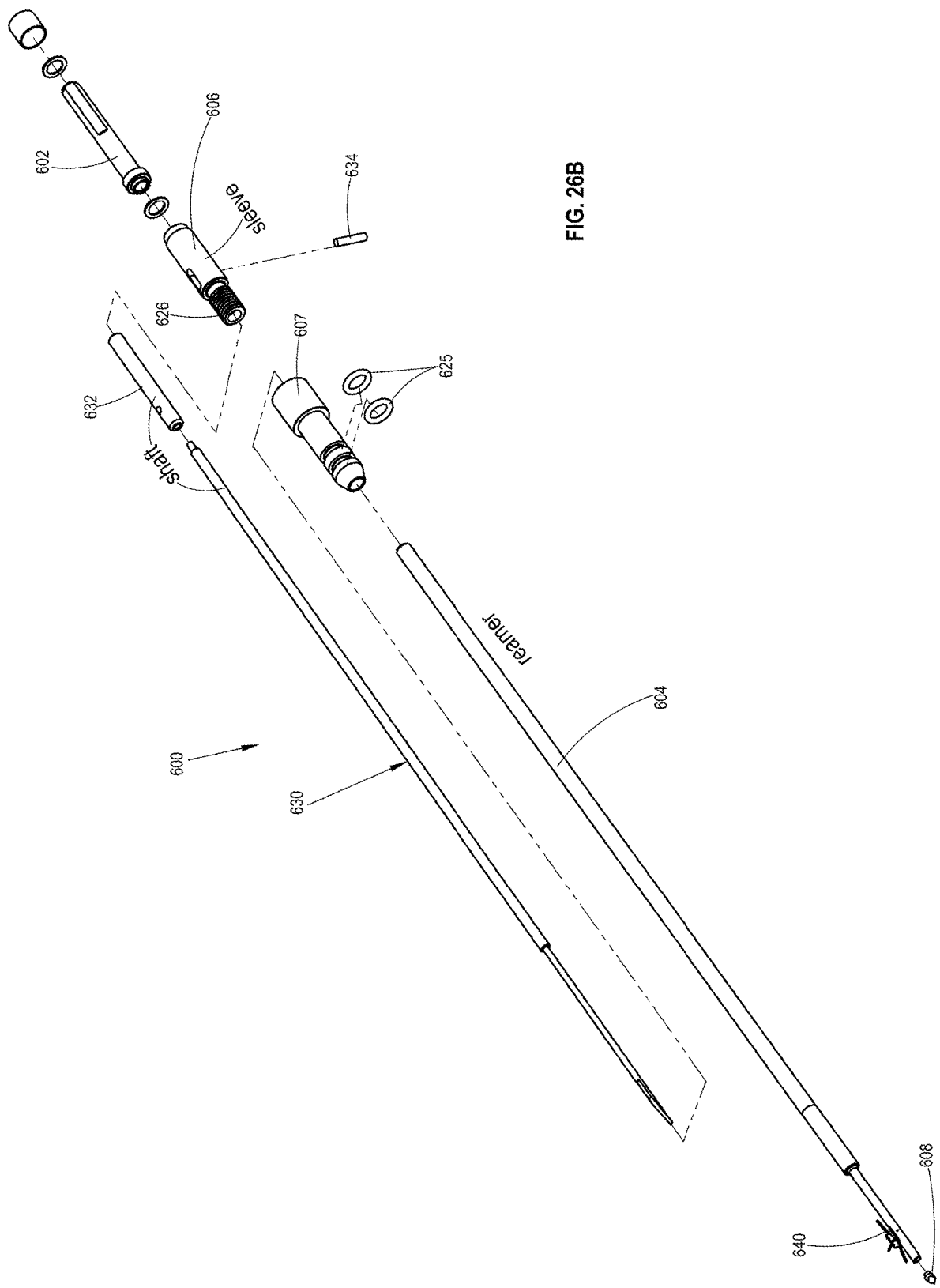

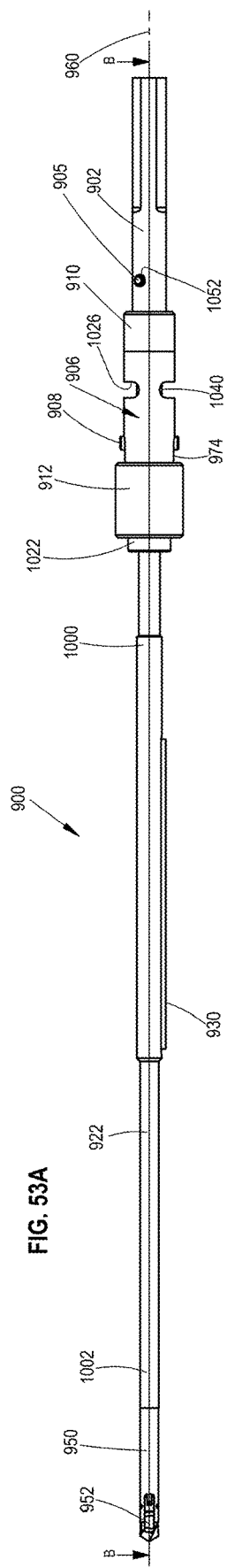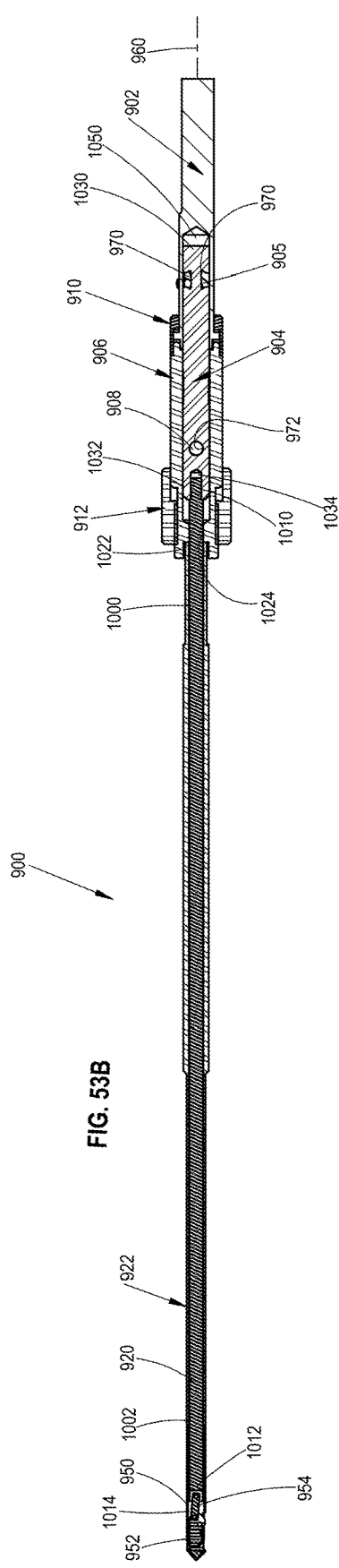

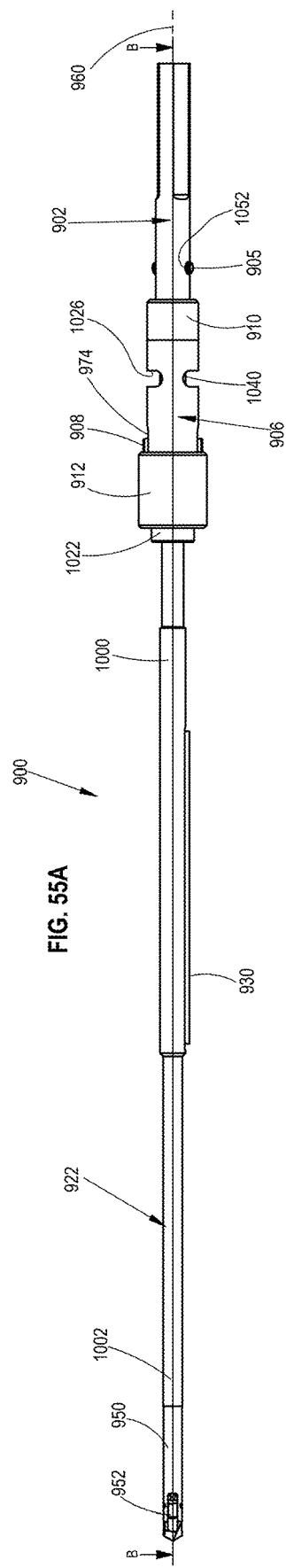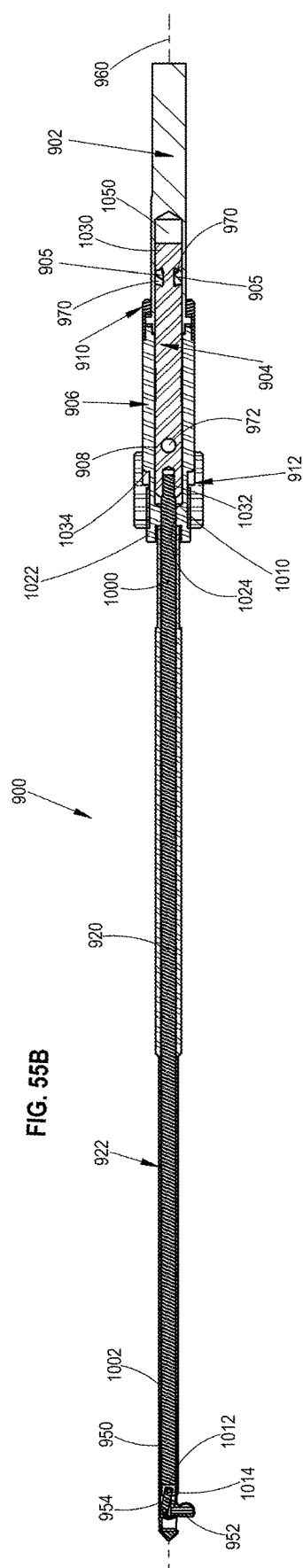

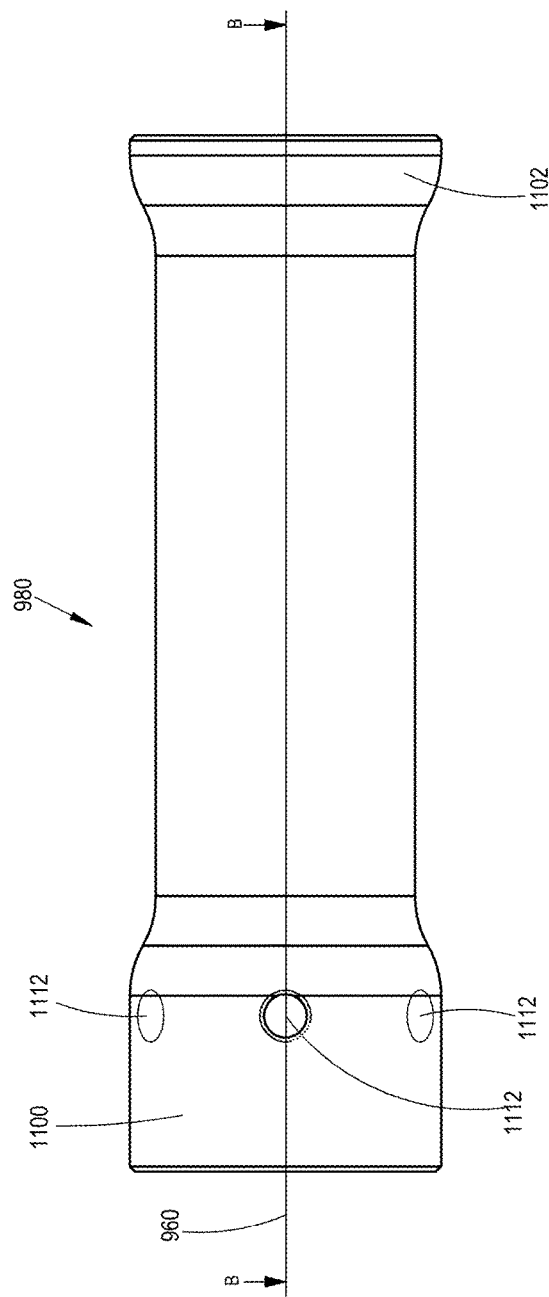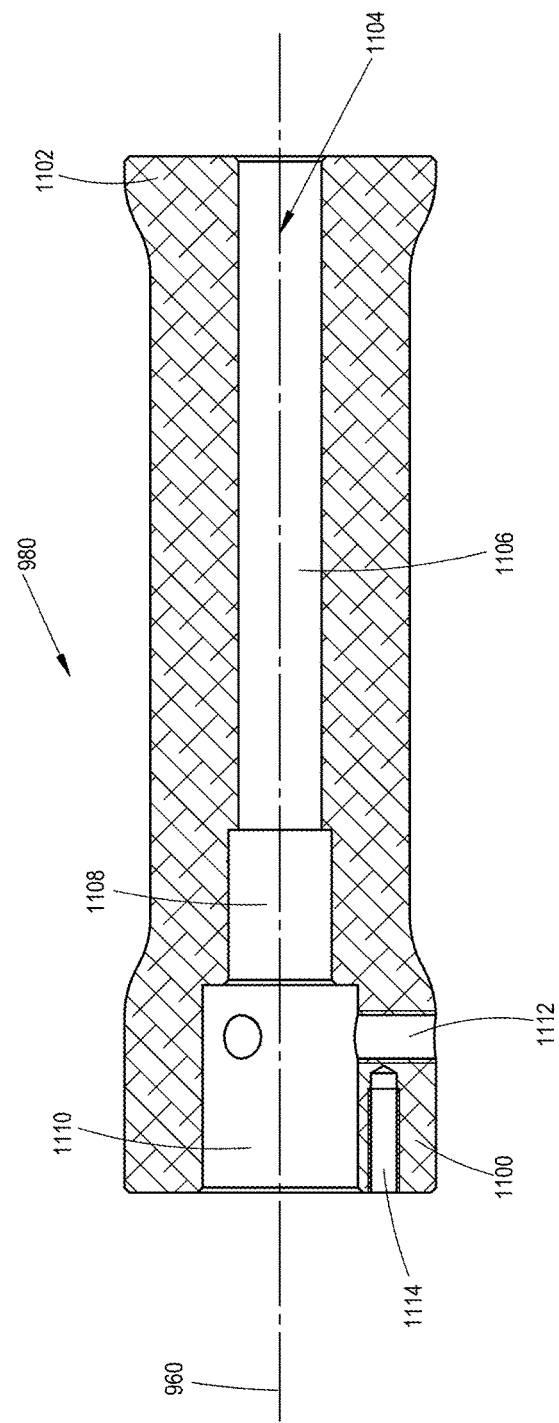

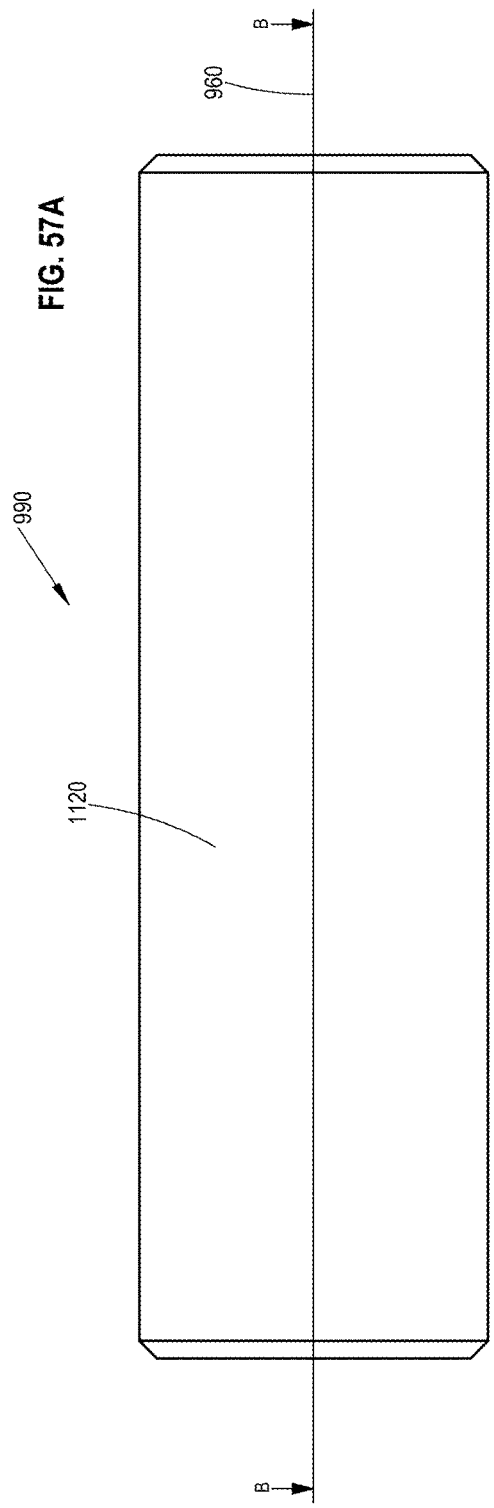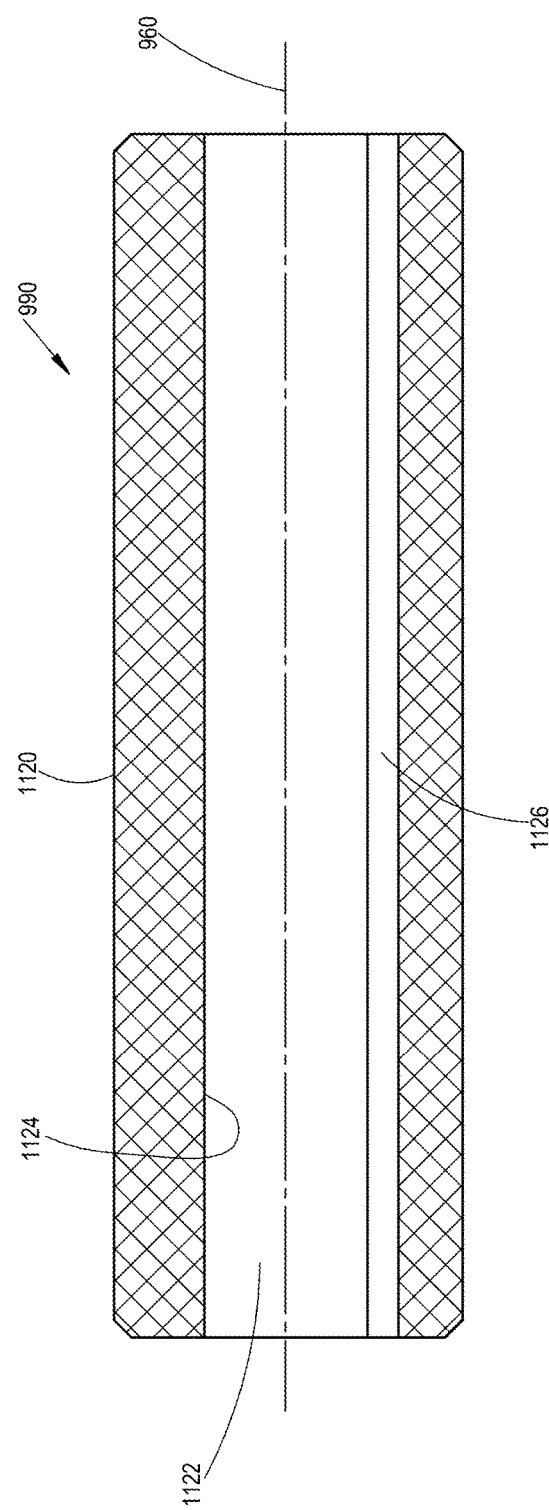

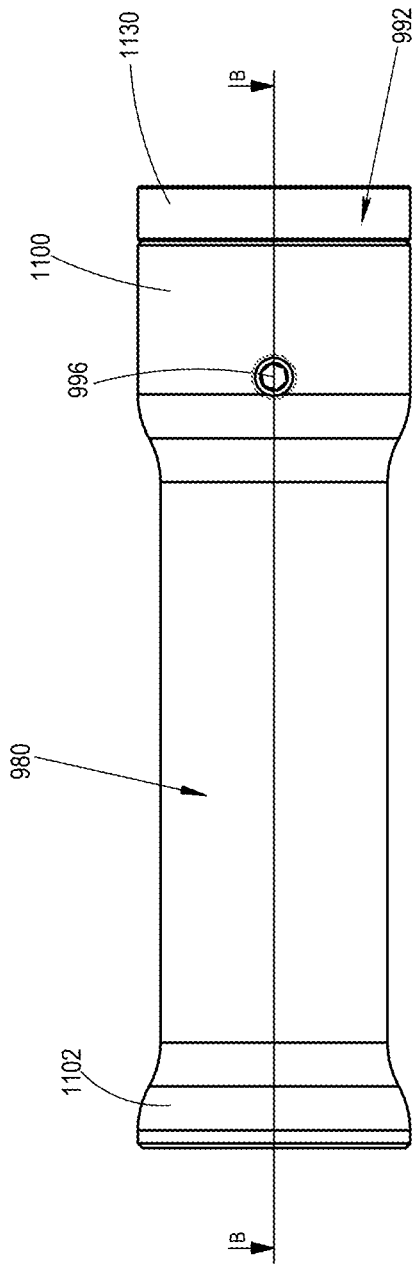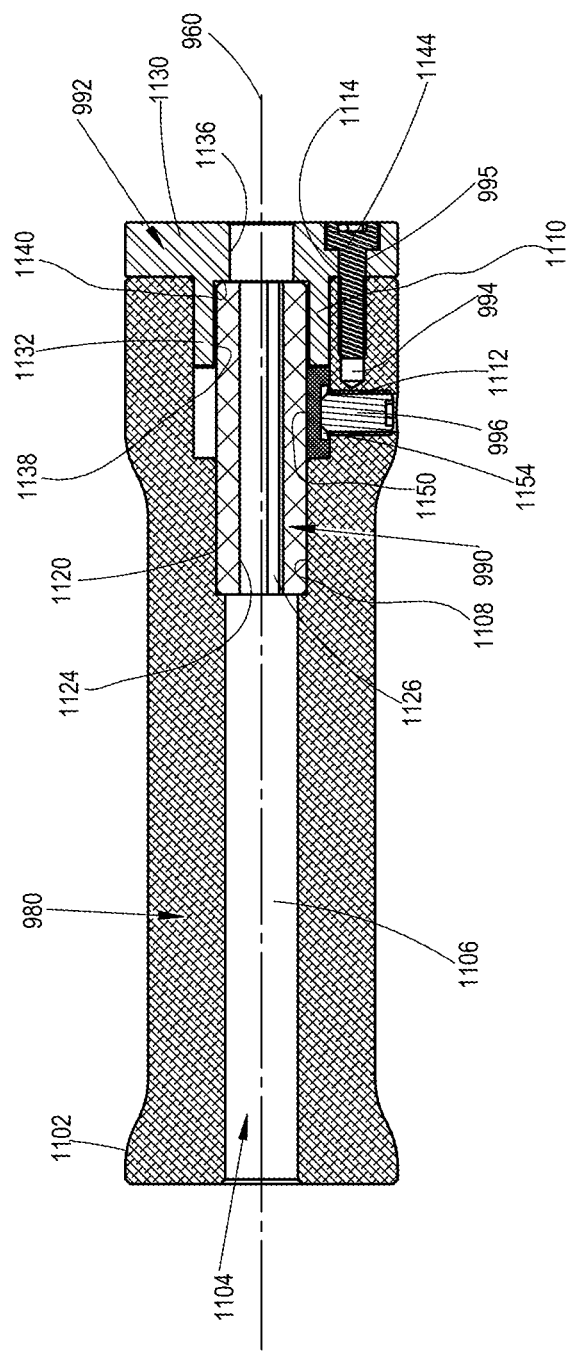

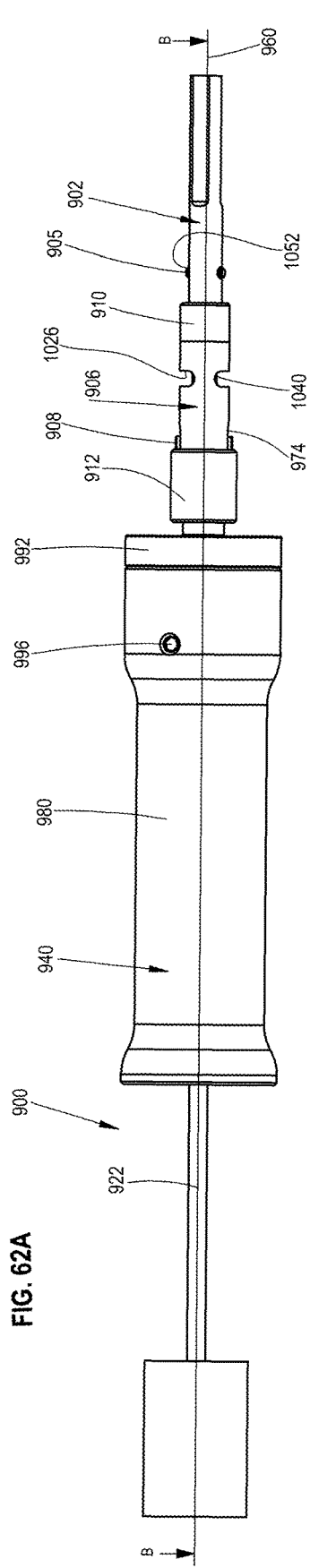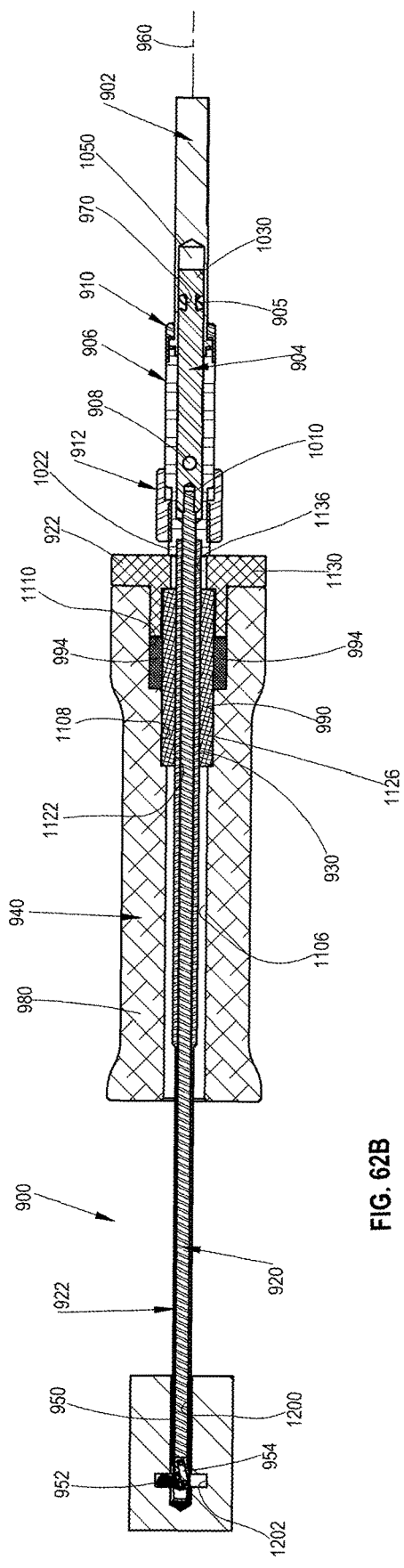
FIG. 62A
FIG. 62B

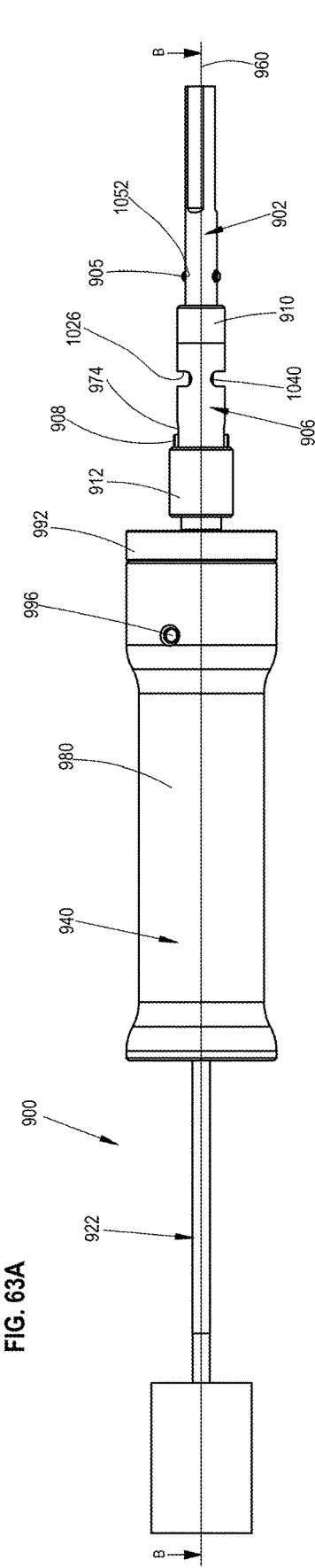

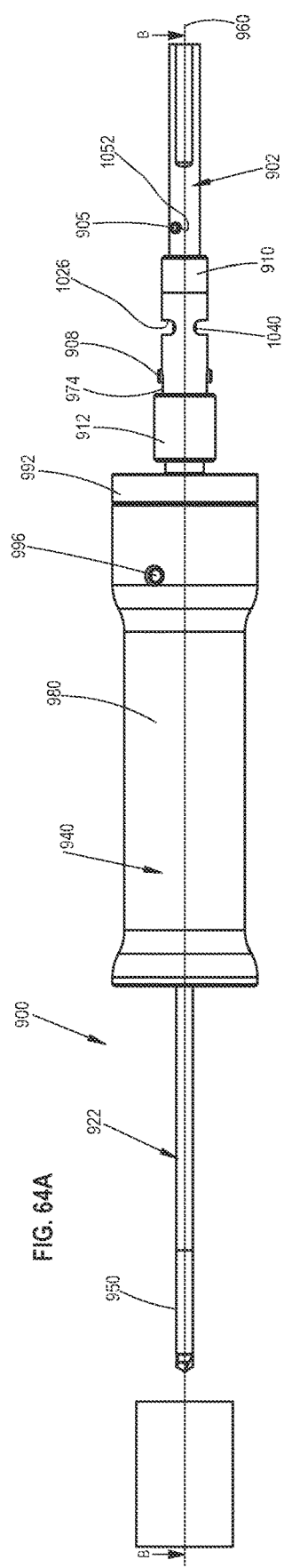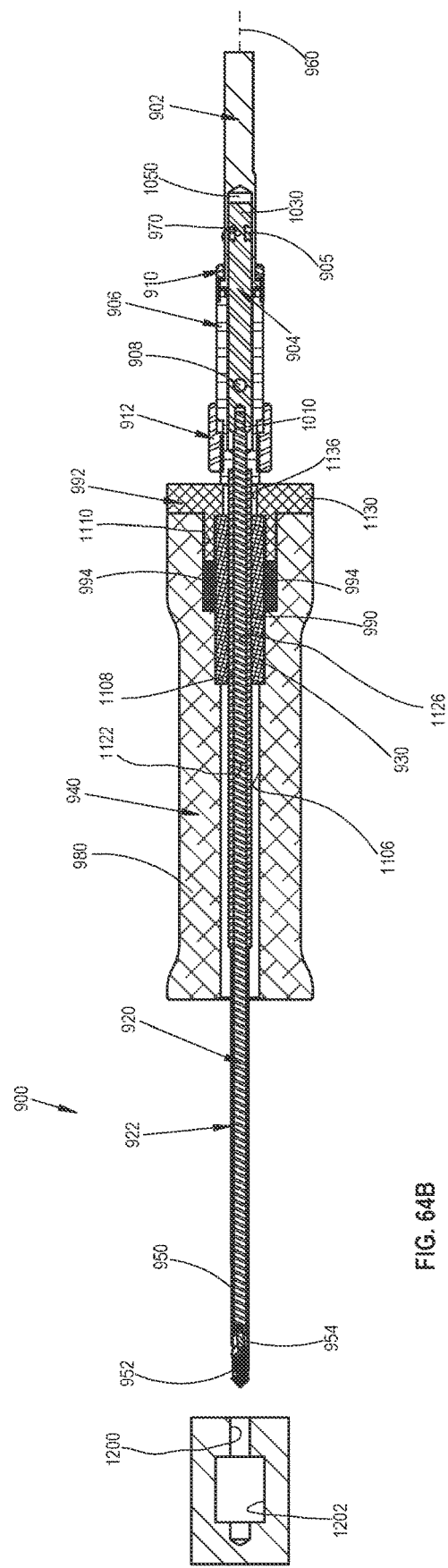
FIG. 64A
FIG. 64B

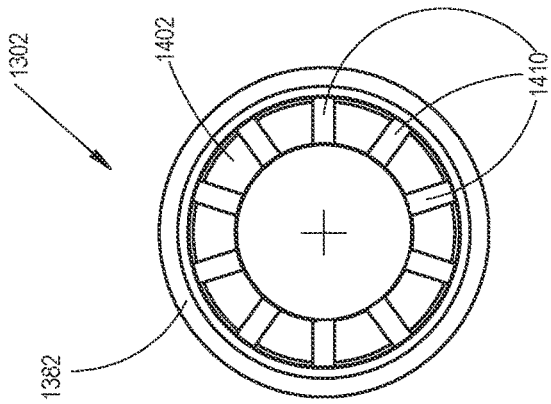
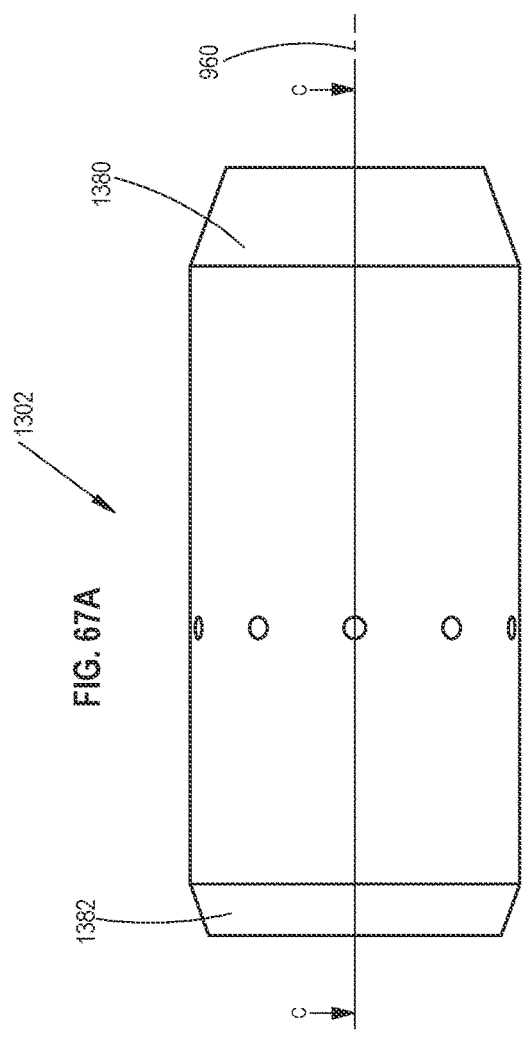
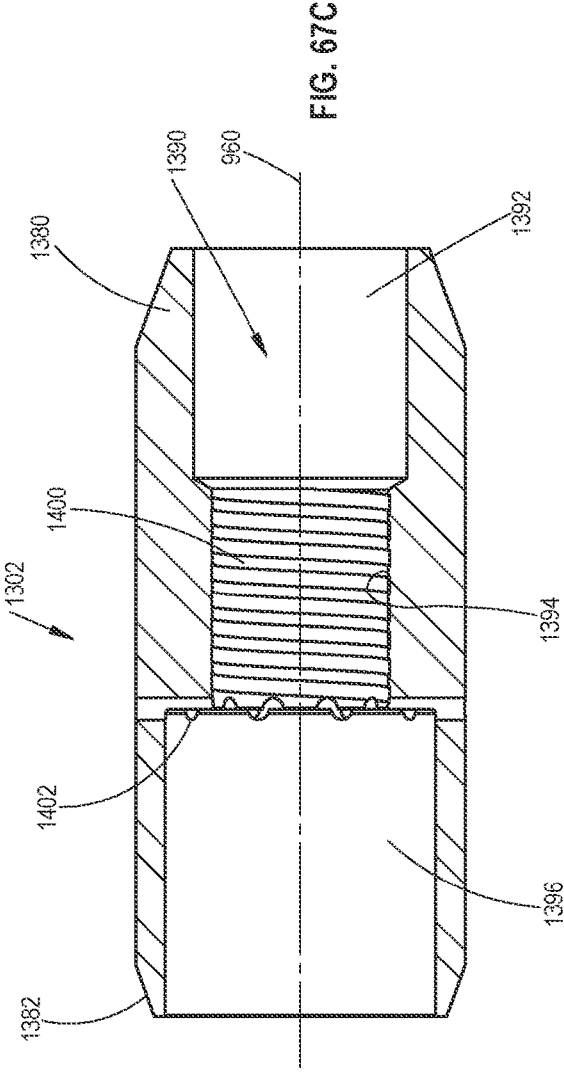

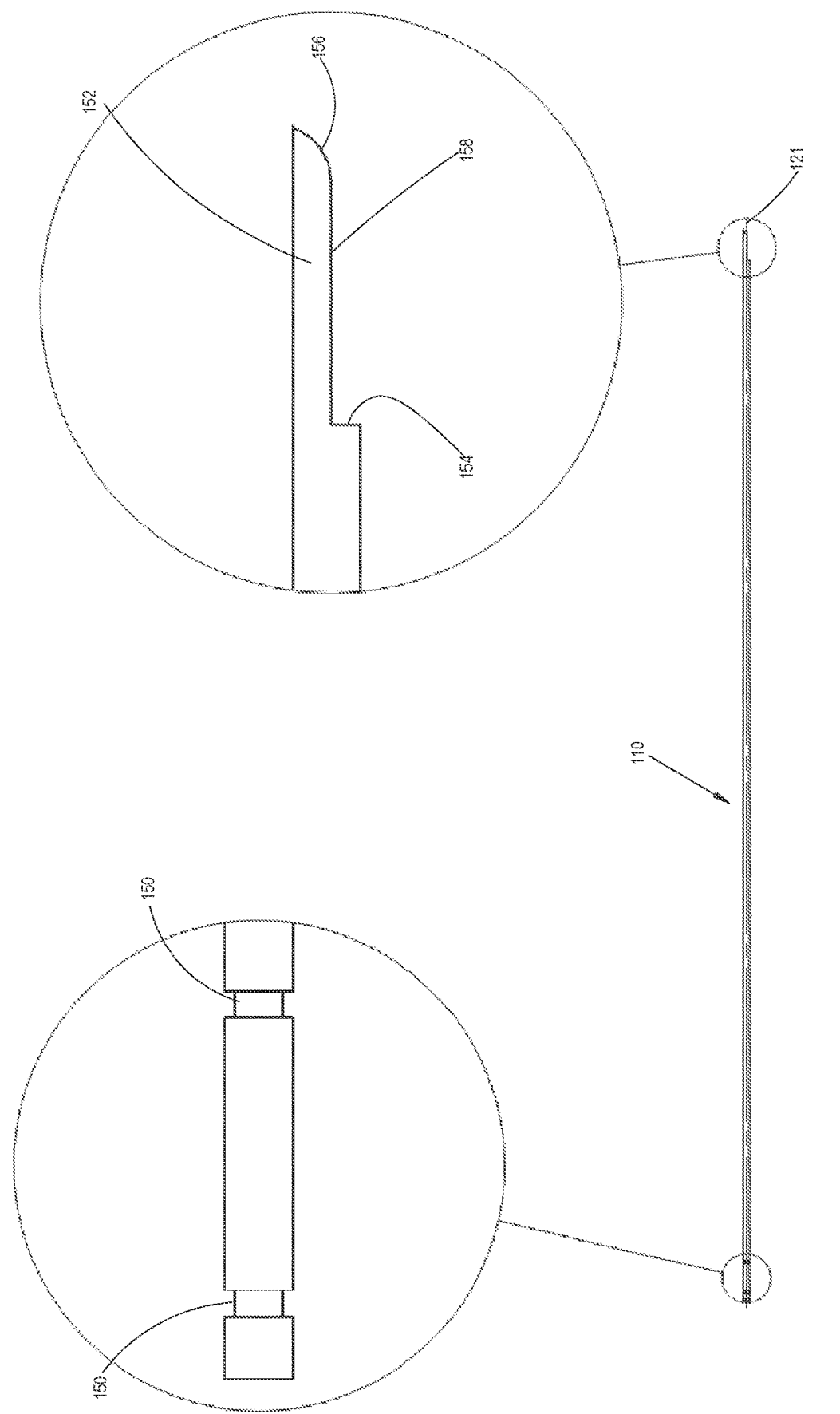

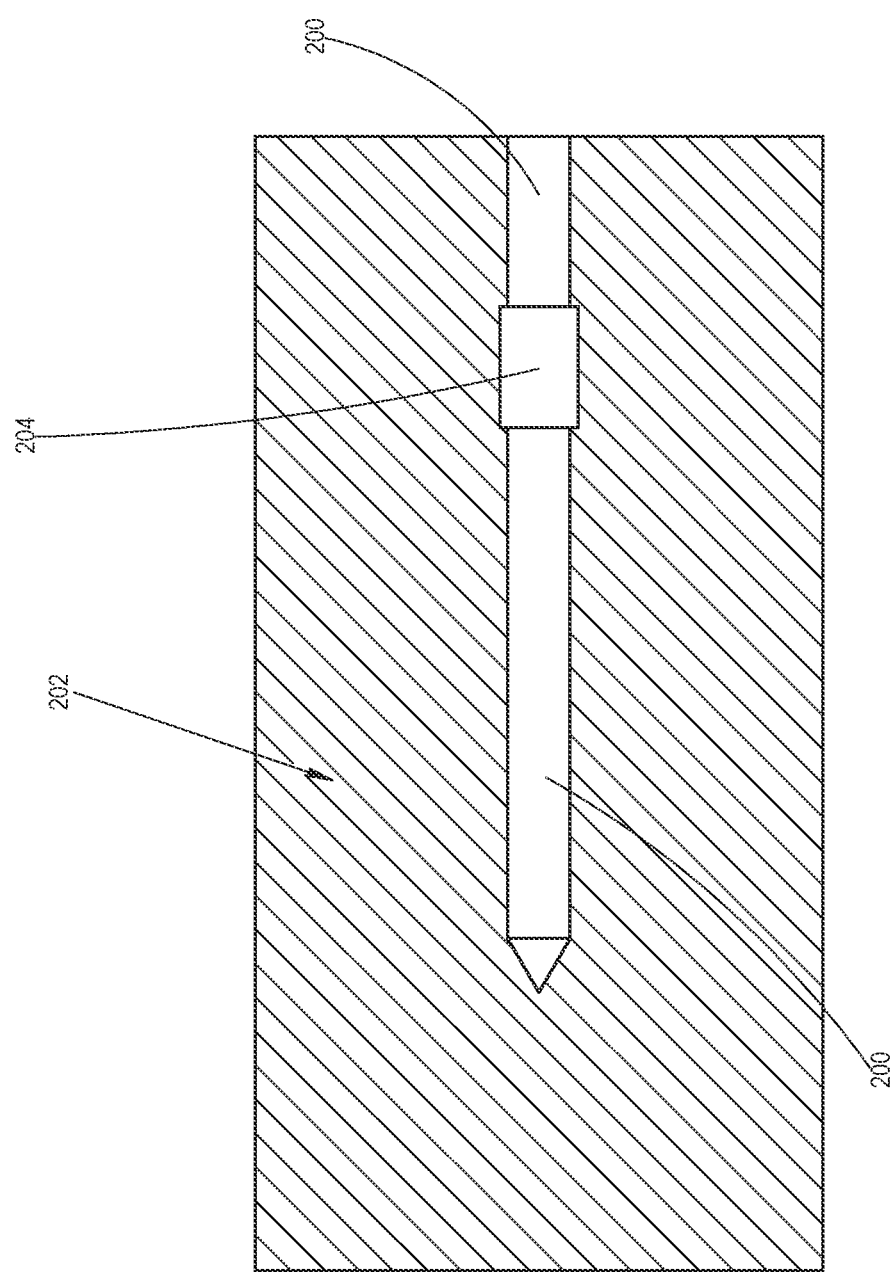

BONE MATERIAL REMOVAL DEVICE AND A METHOD FOR USE THEREOF

RELATED APPLICATIONS

This application is a continuation of U.S. patent application Ser. No. 16/877,55 1 filed on May 19, 2020, now U.S. Pat. No. 11,446,042, which is a continuation of U.S. patent application Ser. No. 16/059,098 filed on Aug. 9, 2018, now U.S. Pat. No. 10,660,657, which is a continuation of PCT Patent Application No. PCT/IL2017/050170, having International Filing Date of Feb. 10, 2017, which claims the benefit of priority under 35 USC § 119(e) of U.S. Provisional Patent Application Nos. 62/294,108 filed on Feb. 11, 2016; 62/336,715 filed on May 15, 2016; 62/352,184 filed on Jun. 20, 2016; 62/360,434 filed on Jul. 10, 2016 and 62/436,243 filed on Dec. 19, 2016.

PCT Patent Application No. PCT/IL2017/050170 is also related to U.S. Provisional Patent Application No. 62/144, 991 filed on Apr. 9, 2015.

The contents of the above applications are all incorporated by reference as if fully set forth herein in their entirety.

FIELD AND BACKGROUND OF THE INVENTION

The present invention, in some embodiments thereof, relates to bone removal tools and more particularly, but not exclusively, to tools that change an effective diameter of a bore in bone.

It is known that during various arthroscopic procedures drilling of a bore is required within a bone of a patient. In many occasions the bore may need to have portions having various diameters. Enlarged diameters may be needed for one or more surgical procedures such as, for example, insertion of an anchor, administration of a drug or biologicals, insertion of a graft and insertion of an implant in AVN treatment procedures.

In other examples, in various arthroscopic procedures e.g., rotator cuff repair and hip labrum replacement, an anchor is inserted into the bone in order to reattach injured tissue. Different drilling tools are employed in order to drill a bore having predetermined dimensions.

Drilling tools are also used for insertion of biological material or providing for bone bleeding to induce cartilage healing.

SUMMARY OF THE INVENTION

The present invention in some embodiments seeks to provide an improved bone material removal device.

There is thus provided in accordance with some embodiment of the present invention a bone material removal device, including a tubular element arranged along a longitudinal axis and comprising a proximal end and a distal end; a rotating body operatively attached to the proximal end of the tubular element and comprising an inner threading; a shaft element disposed within the tubular element and comprising a threaded portion engageable with the inner threading; a cutting tooth operatively pivotably connected to the shaft element; the shaft element is positionable in a proximal operative orientation causing the cutting tooth to assume a closed operative orientation; and the shaft element is positionable in a distal operative orientation, upon axial displacement of the threaded portion over the inner threading, causing the cutting tooth to assume an open operative orientation.

Preferably, the shaft element is operatively connected to the tubular element by an indicating pin. Further preferably, the tubular element has a guiding slot configured to receive the indicating pin therein and allow axial movement of the indicating pin therealong. Additionally, the indicating pin is positioned in a proximal position when the shaft element is positioned in the proximal operative orientation and the indicating pin is positioned in a distal position when the shaft element is positioned in the distal operative orientation.

In accordance with some embodiments of the present invention, a method of drilling a varying diameter bore, including the steps of: providing a cannula comprising a cannula lever; providing a bone material removal device comprising a drilling tip and a selectably openable cutting tooth; insert the bone material removal device into the cannula; forms an initial bore in a bone of a patient while pushing said drilling tip into a bone of a patient in a distal direction and rotating the bone material removal device in a first direction; pressing the cannula lever in order to enable engagement between the cannula lever and at least part of the bone material removal device; reversing the drilling rotational direction to a second direction, which is opposite to the first direction, thus opening the cutting tooth; forms an undercut bore in the bone of the patient by the cutting tooth, while pulling the bone material removal device in a proximal direction and rotating the bone material removal device in the second direction.

In accordance with some embodiments of the present invention, a bone material removal device, including a tubular element arranged along a longitudinal axis and comprising a proximal end and a distal end, a rotating body operatively attached to the proximal end of the tubular element and comprising an inner threading, a shaft element disposed within the tubular element and comprising a threaded portion engageable with the inner threading, a cutting tooth operatively engageable with the shaft element, the shaft element is positionable in a proximal operative orientation causing the cutting tooth to assume a closed operative orientation and the shaft element is positionable in a distal operative orientation, upon axial displacement of the threaded portion over the inner threading, causing the cutting tooth to assume an open operative orientation.

Preferably, the cutting tooth includes at least one leaf spring portion configured for biasing the cutting tooth to the closed operative orientation. Further preferably, the shaft element is configured to exert force on the at least one leaf spring portion for urging the cutting tooth to the open operative orientation.

According to an aspect of some embodiments of the present invention there is provided a bone material removal device, including a tubular element including a proximal end and a distal end, a shaft received within the tubular element and including a proximal end and a distal end, a cutting tooth movably coupled to the distal end of the shaft and a shaft displacement actuator at the proximal end of the tubular element rotatably coupled to the shaft at least partial rotation of the actuator in a first direction brings the cutting tooth to travel from a closed retracted position to an open extended position. According to some embodiments, the actuator is activated manually and/or with a tool and includes a first portion fixedly attached to the shaft and a second portion rotatably coupled to the first portion. According to some embodiments of the invention, the actuator is rotatable about a long axis of the shaft.

According to some embodiments of the invention the actuator is configured to rotate in a second opposite direction and bring the cutting tooth to travel from the open extended position to the closed retracted position and each increment of rotation of the actuator corresponds to an increment of travel of the cutting tooth between the open extended position and the closed retracted position. 1 the actuator is According to some embodiments of the invention the device also includes an indicator indicating a degree of cutting tooth extension at any point of rotation of the actuator. According to some embodiments, the actuator blocks back pressure generated during operation.

According to some embodiments of the invention the actuator is configured to be partially rotated to set the cutting tooth at a predetermined position between the open extended position and the closed retracted position. According to some embodiments, the actuator includes a rotatable coupling including at least one slot in a wall of the tubular element proximal end, the slot having a longitudinal axis, the axis being at an angle between 10 and 40 degrees in respect to the shaft.

According to some embodiments of the invention the tubular element proximal end is attached to the shaft via a pin-in-slot coupling. According to some embodiments, the angle determines the ratio of axial displacement of the shaft in respect to amount of rotation of the actuator. According to some embodiments, the slot includes an at least partially spiral geometry and extends the full thickness of the tubular element wall. According to some embodiments the coupling includes a threaded portion at the proximal end of the shaft interthreaded with a threaded portion of the actuator.

According to some embodiments of the invention the actuator includes at least one eccentric rotatable mass. According to some embodiments, the rotatable eccentric mass includes a flywheel.

According to an aspect of some embodiments of the present invention there is provided a bone material removal device, including: a tubular element including a proximal end and a distal end, a shaft received within the tubular element and including a proximal end and a distal end; a cutting tooth movably coupled to at least one of the tubular element and the distal end of the shaft and wherein displacement of the shaft axially distally relative to the tubular element brings the cutting tooth to travel from a closed retracted position to an open extended position in which at least a portion of the cutting tooth extends in a radial direction beyond an outside surface of the tubular element.

According to some embodiments of the invention displacement of the shaft axially proximally relative to the tubular element brings the cutting tooth to travel from the open extended position to a closed retracted position at least partially within the tubular element. According to some embodiments of the invention the shaft is configured to be axially incrementally displaced relative to the tubular element and bring the cutting tooth to pivot about a hinge and travel incrementally from the open extended position to the closed retracted position and vice versa. According to some embodiments of the invention the cutting tooth is configured to be set at any point between the open extended position and the closed retracted position and vice versa the point determines a degree of extension of the cutting tooth and a diameter of an undercut created thereby.

According to some embodiments of the invention the distal end of the tubular element includes a slot and wherein the cutting tooth travels radially outwards and inwards via the slot and the cutting tooth pivots about a hinge to travel from the closed retracted position to the open extended position beyond an outer surface of the tubular element.

According to some embodiments of the invention the cutting tooth includes at least one resilient portion and engages the tubular element via the resilient portion. According to some embodiments the cutting tooth engages the distal end of the tubular element via the resilient portion of the cutting tooth the resilient portion exerts constant bias in a radially inward direction that resists outward radial extension of the cutting tooth.

According to some embodiments of the invention the cutting tooth includes at least one leaf spring portion configured for biasing the cutting tooth to the closed operative orientation. According to some embodiments the cutting tooth includes a base and a resiliently cantilevered arm supporting a cutting edge. According to some embodiments, the cantilevered arm is arced radially inwards to interfere with a path of axial distally displacement of the shaft.

According to an aspect of some embodiments of the present invention there is provided a bone material removal device, including a tubular element including a proximal end and a distal end, a shaft received within the tubular element and including a distal tapered end, a shaft displacement actuator rotatably coupled to the tubular element proximal end and movably coupled to the shaft at least partial rotation of the actuator displaces the shaft axially, a cutting tooth including a base and a resiliently cantilevered arm supporting a cutting edge, the cantilevered arm is arced radially inwards to interfere with a path of axial distally directed displacement of the shaft and wherein axial distally directed displacement of the shaft urges the tapered distal end under the radially inwards arced cantilevered arm forcing the arm radially outwardly and bringing the cutting tooth cutting edge to extend radially outwards beyond a surface of the reaming tubular element. According to some embodiments of the invention the arced radially inwards position includes a resting state of the cantilevered arm, forcing the arm radially outwardly places the arm in a loaded-stressed position. According to some embodiments of the invention axial proximally displacement of the shaft withdraws the tapered distal end proximally from under the cantilevered loaded-stressed arm bringing the arm to return to its rest unstressed position withdrawing the cutting tooth cutting edge into the tubular element. According to some embodiments the cutting tooth travels radially against bias exerted by a resilient attachment of the cutting tooth to the tubular element.

According to an aspect of some embodiments of the present invention there is provided a bone material removal device, including a tubular element including a proximal end and a distal end, a shaft received within the tubular element and including a proximal end and a distal end, a shaft displacement actuator at the proximal end of the tubular element rotatably coupled to the shaft at least partial rotation of the actuator second portion displaces the shaft axially, a cutting tooth movably coupled to at least one of the tubular element and the shaft and positioned in the tubular element distal end to interfere with a path of axial displacement of the shaft and wherein at least partial rotation of the actuator in a first direction displaces the shaft axially distally relative to the tubular element, the axially displaced shaft, being engaged with at least a portion of the cutting tooth, brings the cutting tooth to travel from a closed retracted position to an open extended position in which at least a portion of the cutting tooth extends in a radial direction beyond an outside surface of the tubular element.

According to some embodiments of the present invention axial proximal displacement of the shaft brings the cutting tooth to rotate and move radially inwards. According to some embodiments the cutting tooth includes at least one resilient portion and is resiliently attached to the distal end of the tubular element via the resilient portion of the cutting tooth, the resilient portion exerts constant bias in a radially inward direction that resists outward radial extension of the cutting tooth. According to some embodiments the shaft is configured to disengage the cutting tooth and bring the cutting tooth to move inwardly to the closed retracted position tubular element.

According to some embodiments, the device also includes a cannula body having a bore extending throughout the length of the cannula configured to rotatingly receive at least a portion of the tubular element. According to some embodiments the cannula body includes a lever including the break at one end and movably coupled at a second end to the cannula body, the break configured to generate friction and stop rotation of the tubular element when the lever is pressed down and urges the break against the tubular element that stops rotation of the tubular element inside the bore when actuated.

According to an aspect of some embodiments of the present invention there is provided a bone material removal device, including a tubular element including a proximal end and a distal end, a shaft received within the tubular element and including a proximal end and a distal end, a shaft displacement actuator rotatably coupled to the tubular element proximal end and including an eccentric rotatable mass that movably couples the tubular element to the shaft via pins configured to travel along a slot in a wall of the tubular element, the slot being angled between 10 and 40 degrees in respect to the shaft at least partial rotation of the eccentric rotatable mass in a first direction effects a force that moves the pins within the slot from a first position to a second position and brings the cutting tooth to travel from a closed retracted position to an open extended position.

According to some embodiments, the actuator and eccentric rotatable mass are configured to rotate in a second direction opposite to the first direction and to effect a force in an opposite direction that moves the pins within the slot from the second position to the first position and displaces the shaft axially proximally relative to the tubular element and brings the cutting tooth to travel from the open extended position to the closed retracted position in which the cutting tooth is received within the tubular element. According to some embodiments, axial proximal displacement of the shaft brings the cutting tooth to move radially inwards to the closed retracted position in which the cutting tooth is received in its entirety inside the tubular element.

According to some embodiments, the distal end of the tubular element includes a slot and wherein the cutting tooth travels radially outwards and inwards via the slot, the cutting tooth includes at least one resilient portion and the eccentric rotatable mass includes a flywheel.

According to an aspect of some embodiments of the present invention there is provided a bone material removal device, including a tubular element arranged along a longitudinal axis and including a proximal end and a distal end, a rotating body operatively attached to the proximal end of the tubular element and including an inner threading, a shaft element disposed within the tubular element and including a threaded portion engageable with the inner threading, a cutting tooth operatively pivotably connected to the tubular element, the shaft is positionable in a proximal operative orientation causing the cutting tooth to assume a closed operative orientation; and the shaft causing the cutting tooth to assume an open operative orientation by assuming a distal operative orientation.

According to some embodiments of the present invention, the shaft element is operatively connected to the reamer element by an indicating pin that indicates the degree of shaft displacement and extension of the cutting tooth. According to some embodiments the tubular element has a guiding slot configured to receive an indicating pin therein and allow movement of the indicating pin within the slot and the indicating pin is positioned in a proximal position when the shaft is positioned in the proximal operative orientation and the indicating pin is positioned in a distal position when the shaft is positioned in the distal operative orientation.

According to an aspect of some embodiments of the present invention there is provided a method of drilling a varying diameter bore, including providing a cannula including a cannula lever, providing a bone material removal device including a drilling tip and a selectably openable cutting tooth, inserting the bone material removal device into the cannula, forming an initial bore in a bone of a patient while pushing the drilling tip into a bone of a patient in a distal direction and rotating the bone material removal device in a first direction, pressing the cannula lever in order to enable engagement between the cannula lever and at least part of the bone material removal device, reversing the drilling rotational direction to a second direction, thus opening the cutting tooth and forming an undercut bore in the bone by the cutting tooth, while pulling the bone material removal device in a proximal direction and continuing rotating the bone material removal device in the second direction. According to some embodiments of the present invention the device further includes a shaft displacement indicator According to an aspect of some embodiments of the present invention there is provided a bone material removal device, including a cylindrical tubular element arranged along a longitudinal axis and having a proximal end and a distal end an eccentric rotatable mass is operatively engaged to the distal end, the cylindrical tubular element having a cutting tooth wherein the cutting tooth is positioned in a normally inwardly deflected orientation and wherein the cutting tooth is radially outwardly deflected due to force exerted by the eccentric rotatable mass.

According to an aspect of some embodiments of the present invention there is provided a method of drilling a varying diameter bore, including providing a bone material removal device including a shaft including a drilling tip and a selectably openable cutting tooth at one end received inside a tubular element and coupled to a rotatable actuator at a second end, rotating the actuator in a first direction and displacing the shaft axially proximally and withdrawing the cutting tooth into the tubular element, forming a bore in a bone by rotating the drilling tip in a first direction and urging the tip into the bone in a distal direction, stopping the drilling rotation;

reversing the drilling rotational direction to a second direction, opposite to the first direction, rotating the actuator in a second direction and bringing the cutting tooth from a closed retracted position to an open extended position in which at least a portion of the cutting tooth extends in a radial direction beyond an outside surface of the device and continuing rotating and pulling the device proximally and forming an undercut bore in the bone.

According to an aspect of some embodiments of the present invention there is provided a bone material removal device, including a tubular element including a proximal end and a distal end, a shaft received within the tubular element and including a distal tapered end, a shaft displacement actuator rotatably coupled to the tubular element proximal end and movably coupled to the shaft at least partial rotation of the actuator displaces the shaft axially, a cutting tooth including a base and a resiliently cantilevered arm supporting a cutting edge, the cantilevered arm is arced radially inwards to interfere with a path of axial distally displacement of the shaft and wherein axial distally displacement of the shaft urges the tapered distal end under the radially inwards arced cantilevered arm forcing the arm radially outwardly and bringing the cutting tooth cutting edge to extend radially outwards beyond a surface of the reaming tubular element.

According to some embodiments of the present invention the arced radially inwards position includes a resting state of the cantilevered arm and forcing the arm radially outwardly places the arm in a loaded-stressed position. According to some embodiments axial proximally displacement of the shaft withdraws the tapered distal end proximally from under the cantilevered loaded-stressed arm bringing the arm to return to its rest unstressed position withdrawing the cutting tooth cutting edge into the tubular element. According to some embodiments of the present invention the cutting tooth travels radially against bias exerted by a resilient attachment of the cutting tooth to the tubular element and axial proximal displacement of the shaft moves the sloped portion from with-under the angled surface of the cutting tooth.

According to some embodiments a distal end of the cantilevered arm is attached to the base portion and the arm is arced proximally radially inwards and the shaft rests on an inside surface of the tubular element and supports the cantilevered arm and the cutting tooth. According to some embodiments radially inwardly directed bias exerted on the cutting tooth drives the cutting tooth radially inward into the lumen of the tubular element once the shaft has been withdrawn axially proximally.

According to an aspect of some embodiments of the present invention there is provided a bone material removal device, including a tubular element including a proximal end and a distal end, a shaft received within the tubular element and including a distal sloping end, a cutting tooth including a cutting edge, an angled surface on an opposite side to the cutting edge corresponding to the angled surface of the distal end of the shaft and at least one slot oriented radially to the shaft and configured to slide along at least one pin fixedly attached to the tubular element and restricts movement of the cutting tooth to a radial direction and wherein axial displacement of the shaft urges the sloped distal end under the angled surface of the cutting tooth bringing the cutting tooth to travel radially and extend beyond the surface of the tubular element.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

The present invention will be understood and appreciated more fully from the following detailed description, taken in conjunction with the drawings in which:

FIGS. 16A and 16B is a simplified partial sectional view illustration of the bone material removal device and the cannula assembly of FIG. 1 shown in the closed operative orientation partially inserted into a bone of as patient and an enlargement thereof;

FIG. 21 is a simplified flow chart illustrating the use of the bone material removal device with the cannula assembly of FIG. 1;

FIG. 22 is a simplified block diagram illustrating the method of using the bone material removal device and cannula assembly of FIG. 1;

FIGS. 23A-23C are three simplified plan view illustrations of a cutting tooth element, forming part of the bone material removal device of FIG. 2, constructed and operative in accordance with some embodiments of the present invention;

FIG. 26B is a simplified exploded view illustration of the bone material removal device of FIG. 26A;

FIGS. 53A and 53B are respective plan view and section view illustration of the bone material removal device of FIG. 44 shown in the closed operative orientation;

FIGS. 55A and 55B are respective plan view and section view illustration of the bone material removal device of FIG. 44 shown in the open operative orientation;

FIGS. 56A and 56B are respective simplified pictorial and sectional illustrations of a cannula body, forming part of the cannula assembly of FIG. 45;

FIGS. 57A and 57B are respective simplified pictorial and sectional illustrations of a cannula inner sleeve, forming part of the cannula assembly of FIG. 45;

FIGS. 60A and 60B are a simplified planar and sectional view illustrations of the cannula assembly of FIG. 45;

FIGS. 62A and 62B are simplified planar and sectional view illustrations of the bone material removal device and the cannula assembly of FIGS. 44 and 45 shown in an open operative orientation partially inserted into a bone of the patient;

FIGS. 63A and 63B are simplified planar and sectional view illustrations of the bone material removal device and the cannula assembly of FIGS. 44 and 45 shown in the open operative orientation while an undercut is created within the bone of the patient;

FIGS. 64A and 64B are simplified planar and sectional view illustrations of the bone material removal device and the cannula assembly of FIGS. 44 and 45 shown in the closed operative orientation following removal from the bone of the patient;

FIGS. 67A, 67B and 67C are simplified pictorial illustration, end plan view and a section view of an adjusting element, forming part of the bone material removal device of FIG. 65, section being taken along lines C-C in FIG. 67A;

FIG. 79 is a simplified pictorial side view illustration of an embodiment of an activating rod of the bone material removal device of FIG. 75;

FIG. 86 is a simplified partial sectional view illustration of an embodiment of the patient bone following removal of the bone material removal device.

Figure 1:
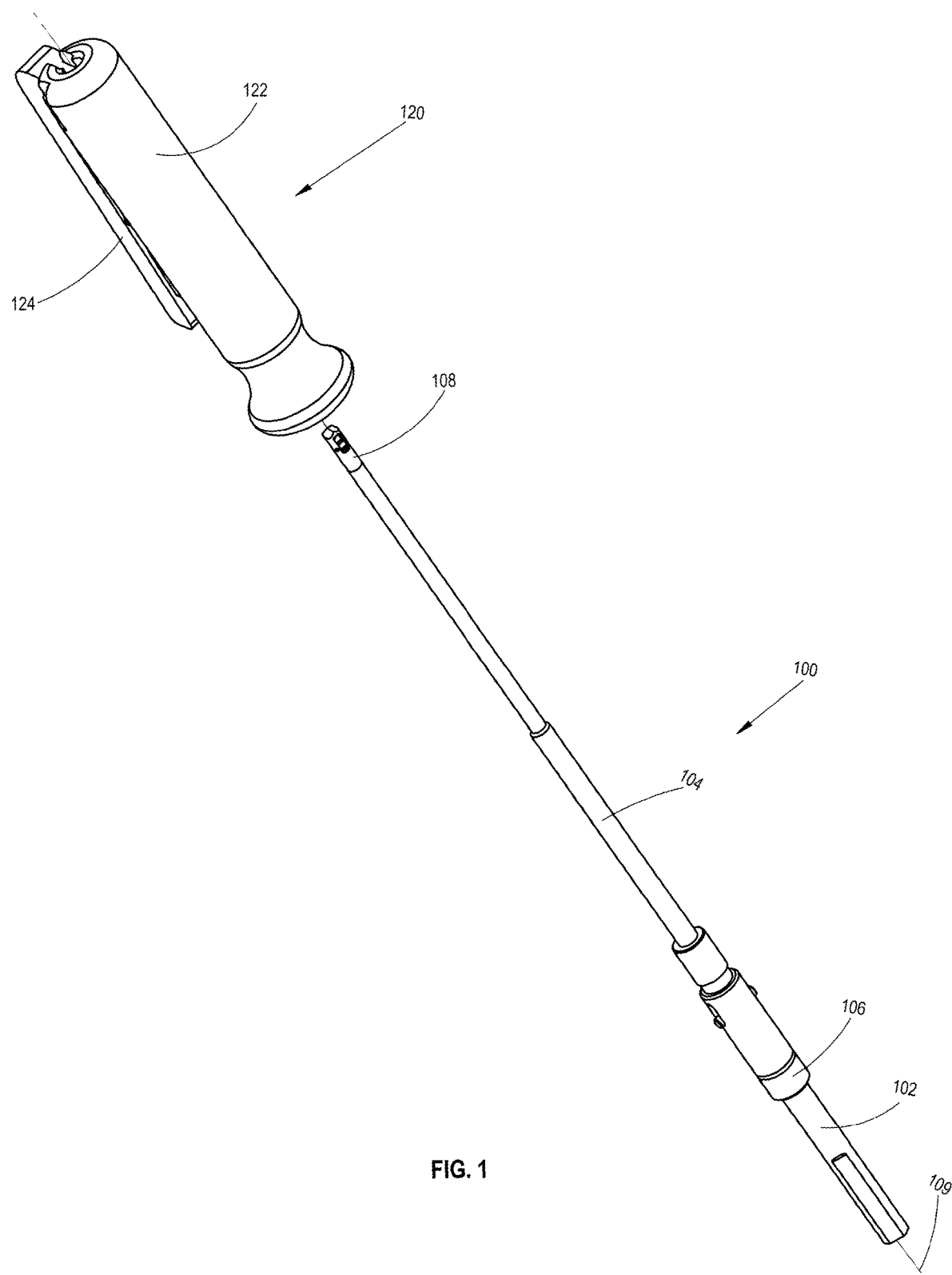
FIG. 1 is a simplified exploded view illustration of a bone material removal device and a cannula assembly, constructed and operative in accordance with some embodiments of the present invention.

DESCRIPTION OF SPECIFIC EMBODIMENTS
OF THE INVENTION

The present invention, in some embodiments thereof, relates to bone material removal tools and more particularly, but not exclusively, to tools that change an effective diameter of a bore in bone.

A bone material removal device is disclosed herein, which is particularly useful for drilling a bore with varying diameters within a bone of a patient.

It is a particular feature of some embodiments of the present invention that the bone material removal device is useful for forming a cavity in the bone for positioning a soft anchor and allow its expansion within the formed cavity volume, thus preventing removal of the anchor therefrom.

It is another particular feature of some embodiments of the present invention that the bone material removal device is also useful for forming a cavity inside the bone of a patient for retaining biological material, such as medicament, therein and prevent from the material to leak outside of the formed cavity. Particularly, the bone material removal device is useful for forming a cavity for subchondral biologics introduction.

An aspect of some embodiments of the invention relates to a bone material removal device configured to drill a bore in bone and selectively expand the diameter of the bore to form an undercut and a mechanism to control the diameter of the undercut. In some embodiments, the device comprises a shaft received within a tubular element. In some embodiments, the device comprises a cutting tooth movably coupled to a distal end of the shaft. In some embodiments, the device comprises a shaft displacement actuator at a proximal end of the tubular element rotatably coupled to the shaft. In some embodiments, at least partial rotation of the actuator in a first direction brings the cutting tooth to travel from a closed retracted position to an open extended position.

In some embodiments, the degree of rotation of the actuator corresponds to the degree of radial movement of the cutting tooth. In some embodiments, the actuator is configured to rotate incrementally and bring the cutting tooth to travel incrementally from a closed retracted position to a radially extended position and vice versa. In some embodiments, the actuator is configured to rotate less than a maximal range of rotation and set the cutting tooth at a degree of extension between a closed retracted position and an open extended position. In some embodiments, the degree of extension of the cutting tooth set by the actuator defines a diameter of an expanded portion of the bore (e.g., undercut) to be made in the bone.

In some embodiments, the actuator is rotatingly coupled to the shaft. In some embodiments, the actuator comprises a first portion fixedly attached to the shaft and a second portion rotatably coupled to the first portion. In some embodiments, the actuator is rotatable about a longitudinal axis of the shaft.

In some embodiments, the actuator comprises a rotatable coupling comprising at least one slot in a wall of a proximal end of the tubular element. In some embodiments, the slot comprises a longitudinal axis, the axis being at an angle between 10 and 40 degrees in respect to the shaft. In some embodiments, the slot comprises a portion of a pin-in-slot coupling that couples the tubular element proximal end to the shaft. In some embodiments, the slot comprises at least a partial helix. In some embodiments, the angle of the slot and/or the helix determines the ratio of axial displacement of the shaft in respect to a degree of rotation of the actuator.

In some embodiments, rotatable coupling comprises a threaded portion at said proximal end of the shaft interthreaded with a threaded portion of the actuator. In some embodiments, the actuator comprises at least one eccentric rotatable mass. In some embodiments, the rotatable mass comprises an eccentric flywheel.

In some embodiments, the rotatable actuator blocks back pressure generated during operation.

An aspect of some embodiments of the invention relates to types of cutting teeth of a bone material removal device configured to drill a bore in bone and selectively expand the diameter of the bore to form an undercut in bone. In some embodiments, the device comprises a cutting tooth positioned at a distal end of the tubular element. In some embodiments, the cutting tooth is positioned inside the tubular element lumen so that to interfere with a path of axial displacement of the shaft. In some embodiments, the cutting tooth extends outward and is drawn inward out of and into a lumen of the tubular element lumen via a slot in a wall of the element.

In some embodiments, the cutting tooth is movably coupled to the tubular element.

In some embodiments, the coupling comprises a pin hinge and the cutting tooth moves rotatively about the pin. In some embodiments, the coupling comprises at least one pin-in-slot hinge in which at least one slot in the cutting tooth blade is configured to slide along at least one pin. In some embodiments, the pin is fixedly attached to the tubular element and restricts direction of movement (extension and retraction) of the cutting tooth.

In some embodiments, the pin restricts the movement of the cutting tooth to radial movement in and out of the slot.

In some embodiments, the hinged coupling comprises a resilient attachment. In some embodiments, the resilient attachment is a leaf spring. In some embodiments, the resilient attachment exerts constant bias in a radially inward direction. In some embodiments, the resilient attachment resists outward radial extension of the cutting tooth. In some embodiments, the cutting tooth comprises a base and a cantilevered arm supporting a cutting edge. In some embodiments, the cantilevered arm is arced distally to proximally radially inwards to interfere with a path of axial distally displacement of the shaft. In some embodiments, the distal end of the shaft is tapered. In some embodiments, axial distally displacement of the shaft urges the tapered distal end of the shaft under the radially inwards arced cantilevered arm forcing the arm radially and bringing the cutting tooth cutting edge to extend radially outwards beyond the surface of the tubular element.

In some embodiments, a portion of the distal end of the shaft is sloped. In some embodiments, the cutting tooth comprises an angled surface on an opposite side to the cutting edge of the blade, and corresponding to the sloped surface of the distal end of the shaft. In some embodiments, the cutting tooth travels radially against bias exerted by a resilient attachment of the cutting tooth to the tubular element. In some embodiments, radially inwardly directed bias exerted on the cutting tooth drives the cutting tooth radially inward, into the lumen of the tubular element once the shaft has been withdrawn axially proximally.

An aspect of some embodiments of the invention relates to a bone material removal device comprising a shaft displacement actuator configured to control and select the diameter of the undercut. In some embodiments, the actuator comprises a rotatable eccentric mass. In some embodiments, the rotatable eccentric mass comprises a flywheel. In some embodiments, the device comprises a tubular element that houses a shaft axially movable within a lumen of the element. In some embodiments, the rotatable eccentric mass movably couples the tubular element to the shaft via pins configured to travel along a slot in a wall of the tubular element. In some embodiments, the slot is angled in respect to a long aspect of the shaft. In some embodiments, at least partial rotation of the rotatable eccentric mass in a first direction effects a force that moves the pins within the slot from a first position to a second position and displaces the shaft axially distally. In some embodiments, the shaft is displaced axially and distally against a bias of a spring.

An aspect of some embodiments of the invention relates to mechanisms that enable an operator of a bone material removal device to selectively expand a diameter of a bore to form an undercut in bone. In some embodiments, the device comprises a shaft received within a tubular element. In some embodiments, the device comprises a cutting tooth movably coupled to a distal end of the shaft. In some embodiments, the device comprises a shaft displacement actuator at a proximal end of the tubular element rotatably coupled to the shaft.

In some embodiments, the device comprises at least one rotating component (e.g., the cutting tooth and/or the actuator) and at least linearly displaceable component (e.g., the cutting tooth and/or the shaft). In some embodiments, the actuator is configured to rotate and axially displace the shaft that in turn rotates the cutting tooth. In some embodiments, an actuator-shaft coupling is configured to convert rotational movement of the actuator into linear axial movement of the shaft. In some embodiments, a shaft-cutting tooth coupling is configured to convert linear-axial movement of the shaft into rotational movement of the cutting tooth. In some embodiments, a shaft-cutting tooth coupling is configured to convert linear axial movement of the shaft into radially directed displacement of the cutting tooth.

In some embodiments, the actuator is configured to rotate about the longitudinal axis of the shaft. In some embodiments, a plane of rotation of the cutting tooth is angled in respect to the plane of rotation of the actuator. In some embodiments, the angle is 90 degrees. In some embodiments, the angle is between 0 and 180 degrees.

In some embodiments, the device comprises a shaft received within a tubular element. In some embodiments, the shaft is axially displaceable within a lumen of the element. In some embodiments, the actuator is rotatably coupled to the tubular element proximal end and movably coupled to the shaft so that at least partial rotation of the actuator displaces the shaft axially. In some embodiments, axial displacement of the shaft relative to the tubular element brings a cutting tooth at a distal end of the tubular element to travel from a closed retracted position to an open extended position in which at least a portion of the cutting tooth extends in a radial direction beyond an outside surface of the tubular element to carve bone from a wall of the bore expanding the diameter of the bore.

In some embodiments, rotation of the actuator in the second direction displaces the shaft axially and proximally and brings the cutting tooth to travel from an open extended position to a at least partially closed retracted position inside the lumen of the tubular element.

In some embodiments, the cutting tooth is movably coupled to at least one of the tubular element and the shaft and positioned at a distal end of the tubular element such that to interfere with a path of axial displacement of said shaft. In some embodiments, the cutting tooth comprises a cutting edge and an angled surface on an opposite side to the cutting edge. In some embodiments, the shaft comprises a sloped distal end. In some embodiments, the angled edge of the cutting tooth corresponds to the sloped distal end of the shaft. In some embodiments, axial displacement of the shaft urges the sloped distal end under the angled surface of the cutting tooth bringing the cutting tooth to travel radially and extend beyond the surface of the tubular element. In some embodiments, axial proximal displacement of the shaft moves the angled portion from with under the angled surface of the cutting tooth.

Reference is now made to FIG. 1, which is a simplified perspective view simplified illustration of a bone material removal device and a cannula assembly, constructed and operative in accordance with some embodiments of the present invention.

As seen in the exemplary embodiment of FIG. 1, a bone material removal device 10000 comprises a shaft displacement actuator that comprises a rotating element 102 configured to be rotatably attached to a tubular element 104 (e.g., a reamer element or a drilling element) by a sleeve 106. A tip element 108 is attached or integrally made with the tubular element 104. A potential advantage of a rotating shaft displacement actuator is in that the actuator-shaft coupling prevents back pressure applied axially in a proximal direction along shaft 130 do directly affect and displace the shaft displacement actuator proximally and changing the setting to the cutting tooth during operation. A shaft-rotating actuator coupling converts the displacement back forces from axial forces applied proximally along the shaft to rotational forces applied perpendicularly to the axial forces. Thus the rotating actuator at least partially blocks the back pressure generated during operation as a reaction to pressure exerted during drilling. It is seen that rotating element 102, tubular element 104, sleeve 106 and tip element 108 are all arranged along a single mutual longitudinal axis 109.

It is additionally seen in FIG. 1 that a cannula assembly 120 is configured to be mounted over the tubular element 104 and arranged along longitudinal axis 109. Cannula assembly 120 includes a cannula body 122 and a cannula lever 124.

Figure 2:
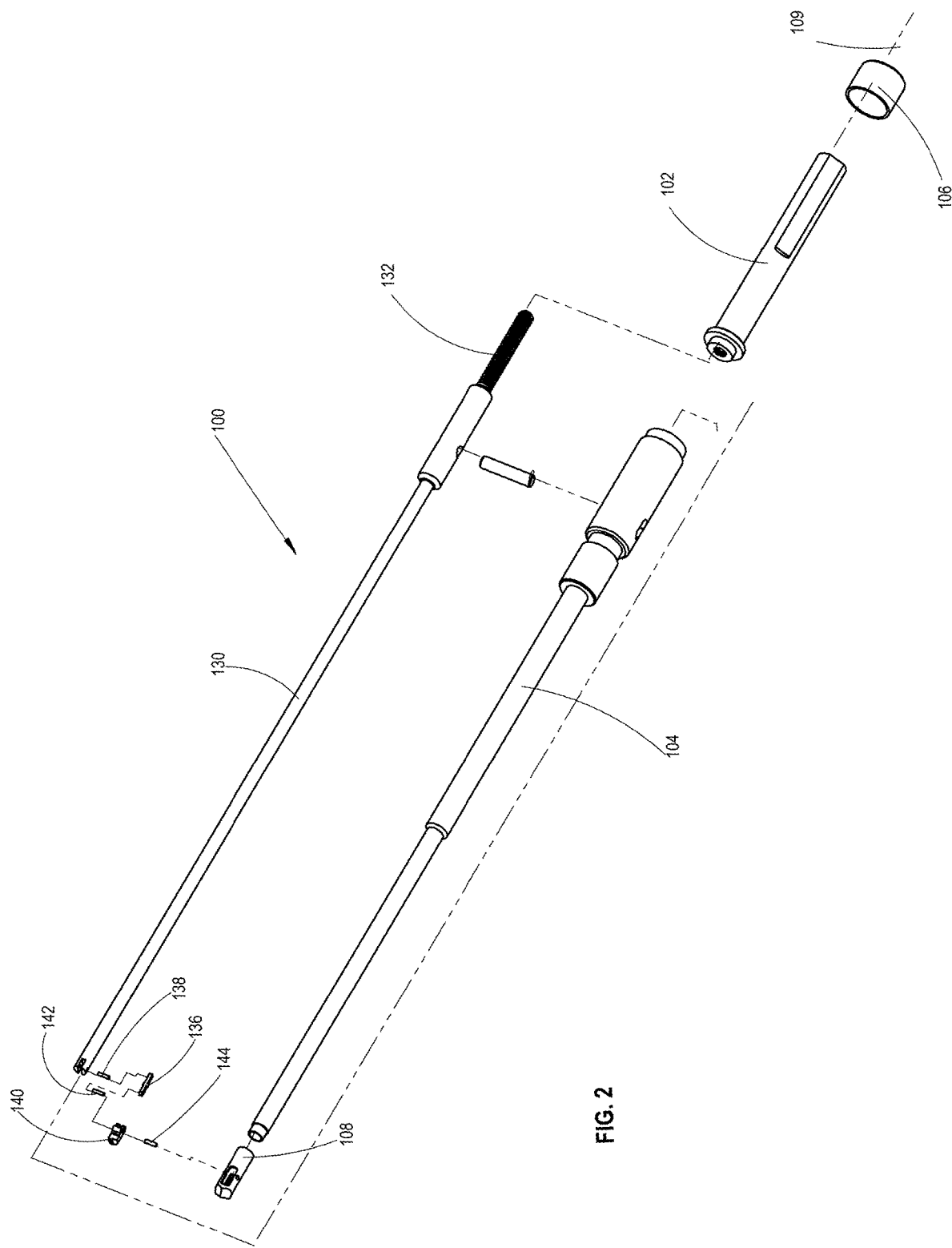
FIG. 2 is a simplified exploded view illustration of the bone material removal device, constructed and operative in accordance with some embodiments of the present invention.

It is appreciated that the tubular element is preferably made of a biocompatible material, e.g., biocompatible metal. Reference is now made to FIG. 2, which is a simplified exploded view illustration of the bone material removal device 100, constructed and operative in accordance with some embodiments of the present invention.

It is seen in the embodiment depicted in FIG. 2 that the rotating element 102 is configured to be attached to the tubular element 104 and retained by fixed attachment of sleeve 106 to the tubular element 104, such as, for example, by heat welding. The sleeve 106 enables free rotational movement of the rotating element 102 relative to the tubular element 104.

It is noted, as will be described in detail hereinbelow, that the rotating element 102 includes internal threading as explained in greater detail elsewhere herein. A longitudinal shaft 130 comprising a threaded portion 132 is configured to be at least partially inserted into the tubular element 104 and at least partially into rotating element 102, such that the threaded portion 132 of shaft 130 engages the internal threading of the rotating element 102. The shaft 130 is configured to be connected to the tubular element 104 by an indicating pin 134.

It is seen in embodiment in FIG. 2 that a hinge element 136 is configured to be rotatably attached at a first end by a pin 138 to an end of the shaft element 130 and at a second end to a cutting tooth 140 via pin 142. The cutting tooth 140 is configured to be rotatably attached to a tip element 108 via a pin 144.

Figure 3:
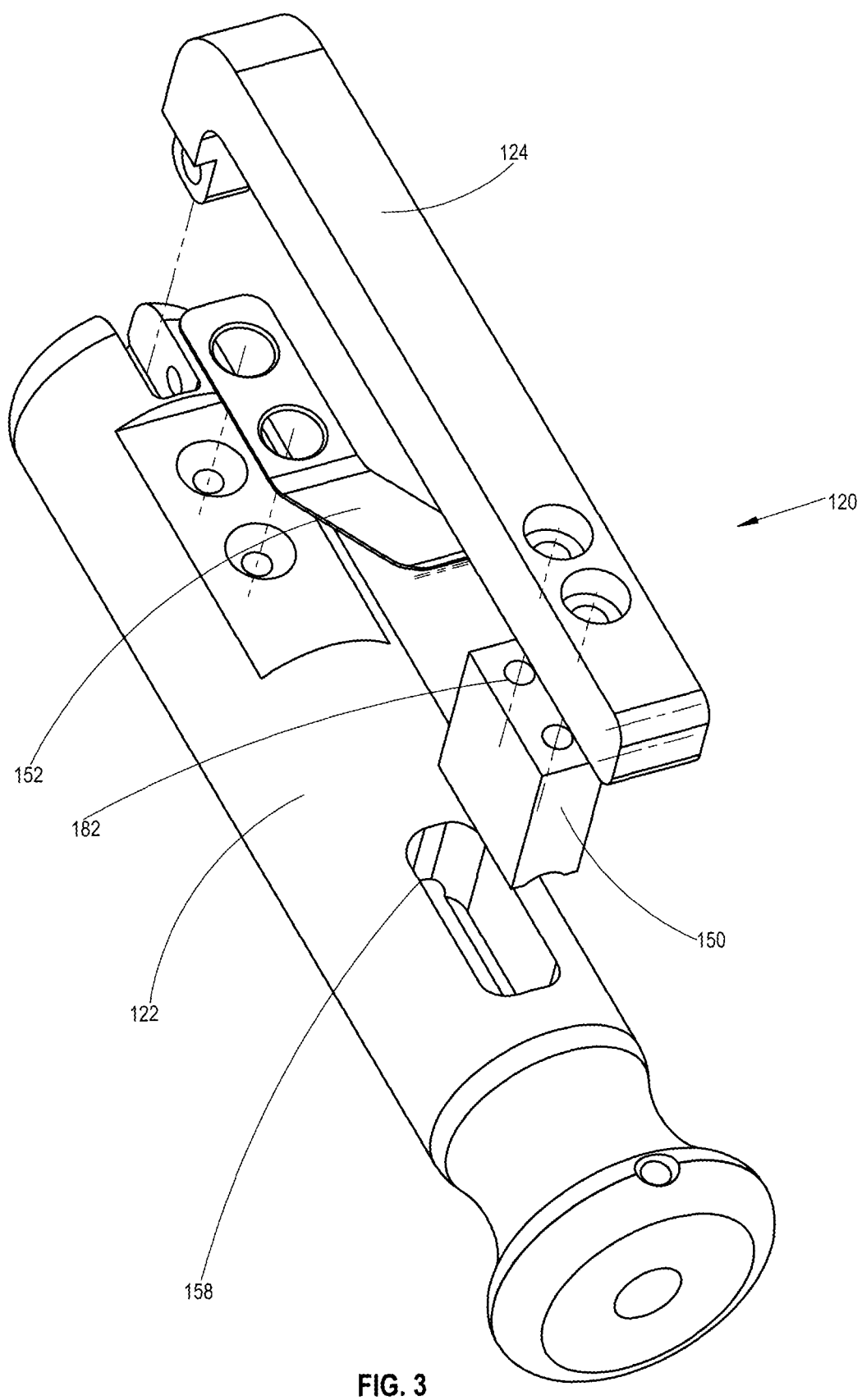
FIG. 3 is a simplified exploded view illustration of the cannula assembly, constructed and operative in accordance with some embodiments of the present invention.

Reference is now made to FIG. 3, which is a simplified exploded view illustration of the cannula assembly 120, constructed and operative in accordance with some embodiments of the present invention.

It is seen in the embodiment in FIG. 3 that the cannula assembly 120 includes hollow cannula body 122, which is configured to be mounted over the bone material removal device 100 and arranged along longitudinal axis 109. Cannula assembly 120 further includes cannula lever 124, which is configured to be pivotably attached to the cannula body 122.

It is seen in FIG. 3 that a cannula break 150 is fixedly attached to cannula lever 124. The cannula break 150 is configured to be partially inserted through an opening 158 in cannula body 122.

A cannula lever biasing element 152 is configured to be fixedly attached to the cannula body 122 and configured to urge and return the cannula lever 124 to its initial, e.g., elevated position after it is pressed down. It is appreciated that cannula lever biasing element 152 can be made of a resilient material and in some embodiments formed as a leaf spring.

Figure 4:
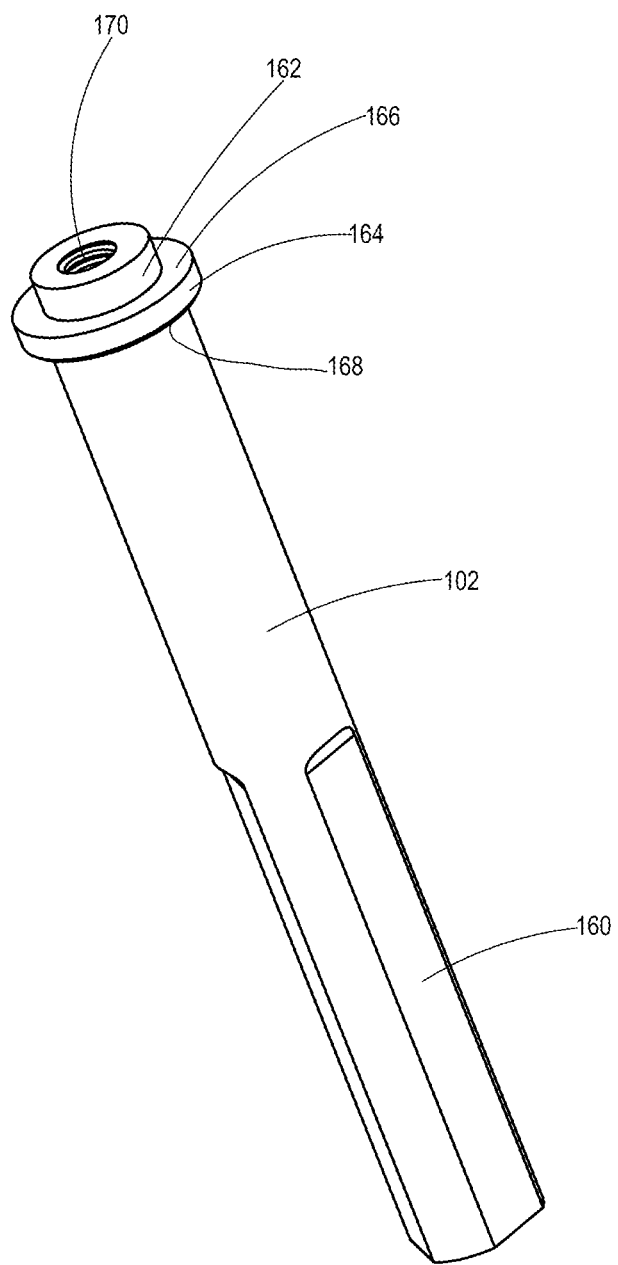
FIG. 4 is a simplified pictorial illustration of a rotating element, forming part of the bone material removal device of FIG. 2.

Reference is now made to FIG. 4, which is a simplified pictorial illustration of an exemplary embodiment of a rotating element 102, forms part of the bone material removal device 100 depicted in FIG. 2.

Rotating element 102 is a generally longitudinal hollow cylindrical integrally made element comprising a proximal end 160 configured to be optionally inserted into a power tool (not shown) and a distal end 162 configured to be optionally inserted into the tubular element 104. The term "Proximal" as used herein when relates to position refers to a position closest to an operator (e.g., surgeon). The term "Proximal" as used herein when relates to direction refers to a direction towards an operator (e.g., surgeon). The term "Distal" as used herein when relates to position refers to a position farthest from an operator (e.g., surgeon). The term "Distal" as used herein when relates to direction refers to a direction away from an operator (e.g., surgeon). A flange 164 is disposed adjacent distal end 162, defining a distally facing shoulder 166 and a proximally facing shoulder 168. It is further seen that an internal threading 170 is formed along at least part of the length of rotating element 102.

Figure 5:
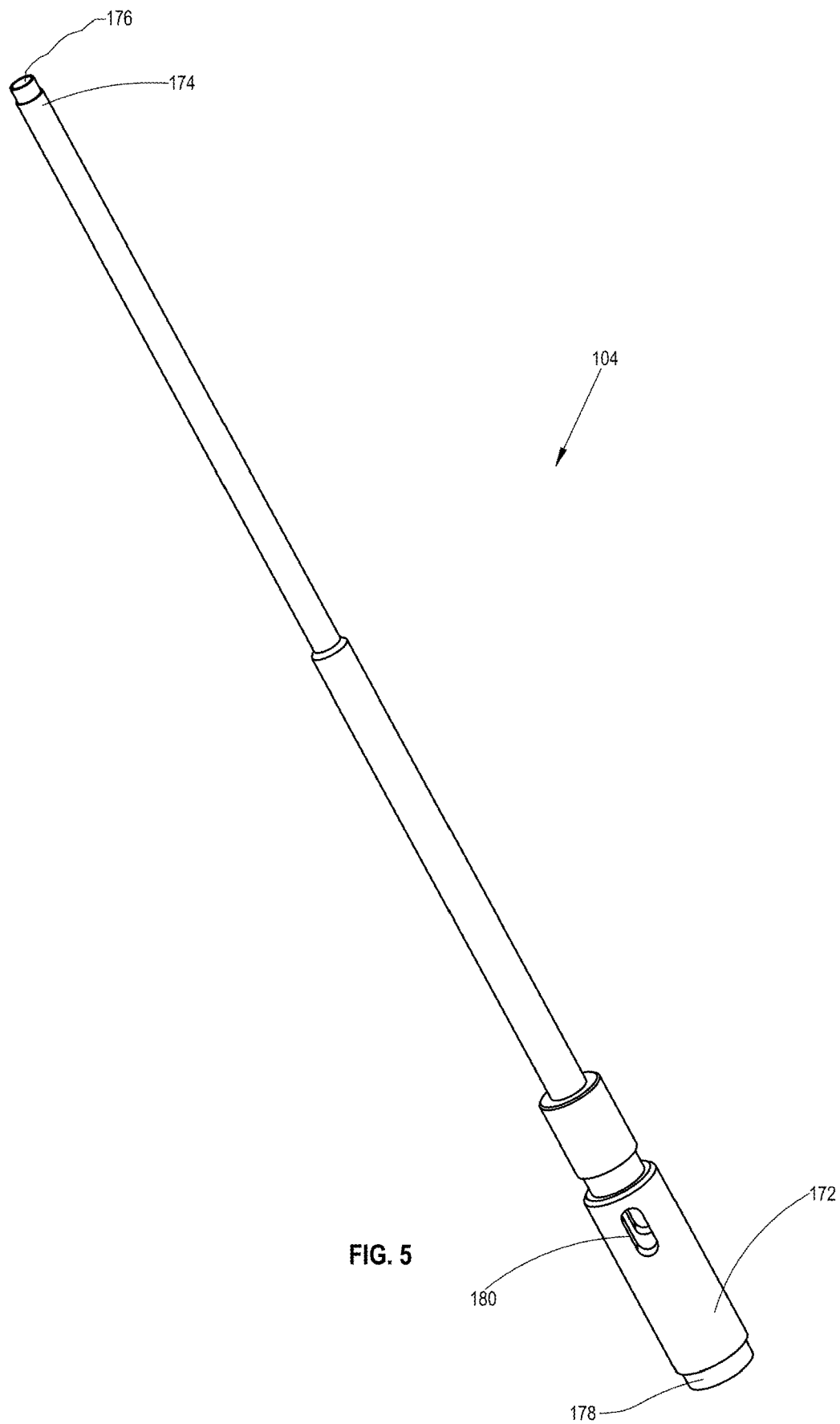
FIG. 5 is a simplified pictorial illustration of a tubular element, forming part of the bone material removal device of FIG. 2.

Reference is now made to FIG. 5, which is a simplified pictorial illustration of an exemplary embodiment of a tubular element 104, forming part of the bone material removal device 100 depicted in FIG. 2.

Tubular element 104 is a generally longitudinal hollow cylindrical integrally made element comprising a proximal end 172 configured to be attached to rotating element 102 and a distal end 174 configured to be attached to tip element 108 or integrally made therewith. Tubular element 104 comprises a bore 176 throughout at least a portion of its length, which is configured to receive and enclose shaft element 130. In some embodiments, bore 176 extends throughout the entire length of tubular element 104.
An engagement surface 178 is located at the proximal end 172 for engagement with sleeve 106.

It is further seen in FIG. 5 that preferably two longitudinally oriented guiding slots 180 are formed on tubular element 104 adjacent proximal end 172. Guiding slots 180 extend along an axis, which is transversely disposed with respect to longitudinal axis 109 and are preferably aligned with each other. In some embodiments, tubular element 104 guiding slots 180 are positioned diametrically opposed.

Figure 6:
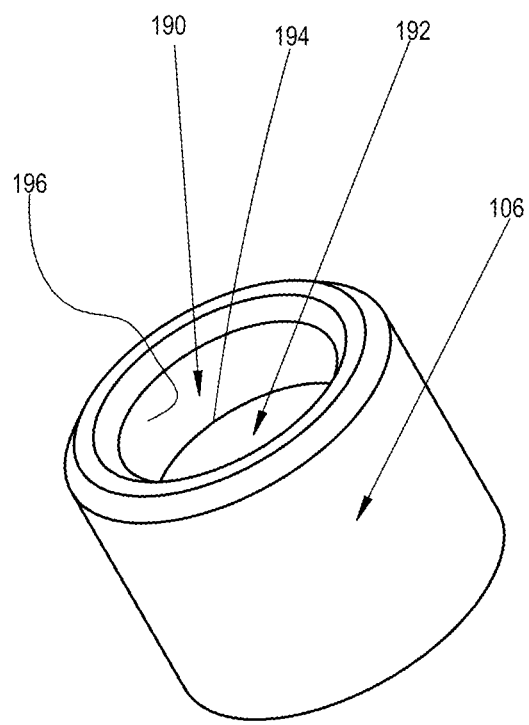
FIG. 6 is a simplified pictorial illustration of a sleeve element, forming part of the bone material removal device of FIG. 2.

Reference is now made to FIG. 6, which is a simplified pictorial illustration of an exemplary embodiment sleeve element 106, forming part of the bone material removal device 100 shown, for example, in FIG. 2.

It is seen in FIG. 6 that the sleeve element 106 is a cylindrical hollow integrally made element comprising a proximal bore 190 of a first diameter and a distal bore 192 of a second diameter, generally greater than the first diameter and a distally facing shoulder 194 defined therebetween. In FIG. 6, inner circumference 196 defines proximal bore 190.

Figure 7:
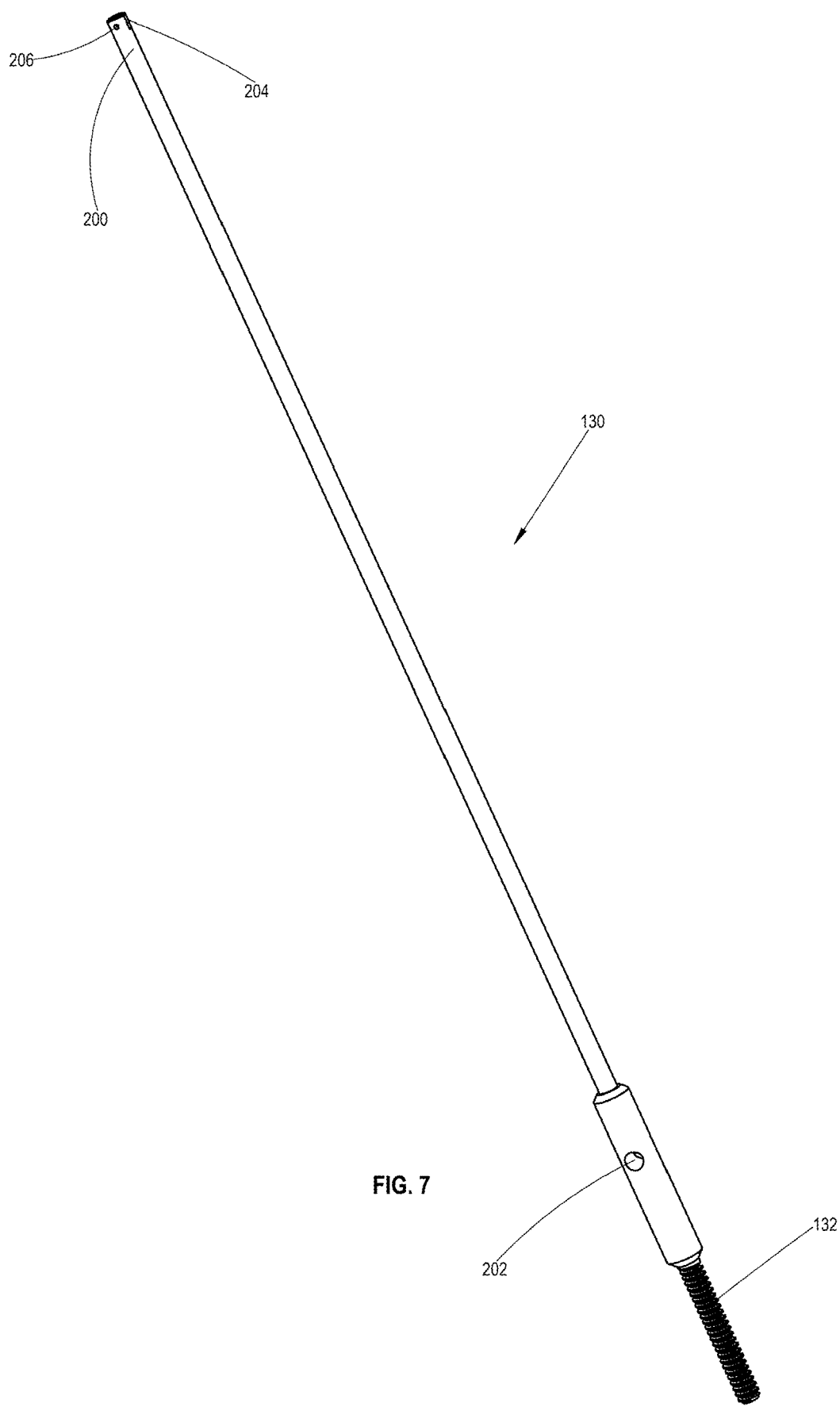
FIG. 7 is a simplified pictorial illustration of a shaft element, forming part of the bone material removal device of FIG. 2.

Reference is now made to FIG. 7, which is a simplified pictorial illustration of an exemplary embodiment of a shaft element 130, that forms part of the bone material removal device 100 as shown for example in FIG. 2.

In FIG. 7 shaft element 130 is preferably longitudinal integrally made element comprising a proximal end with threaded portion 132 and a distal end 200 for partial insertion into the tip element 108. A through bore 202 extending transversely with respect to longitudinal axis 109 is located adjacent and slightly distally from threaded portion 132. Through bore 202 is configured for insertion of positioning pin 134 therethrough.
It is further shown in FIG. 7 that a recess 204 is formed at the distal end 200 of shaft element 130 and extends slightly longitudinally therefrom. A bore 206 is also formed at the distal end 200 of shaft element 130 and extends transversely with respect to recess 204. The recess 204 and bore 206 are configured for attachment of the hinge element 136 to shaft element 130.

Figure 8:
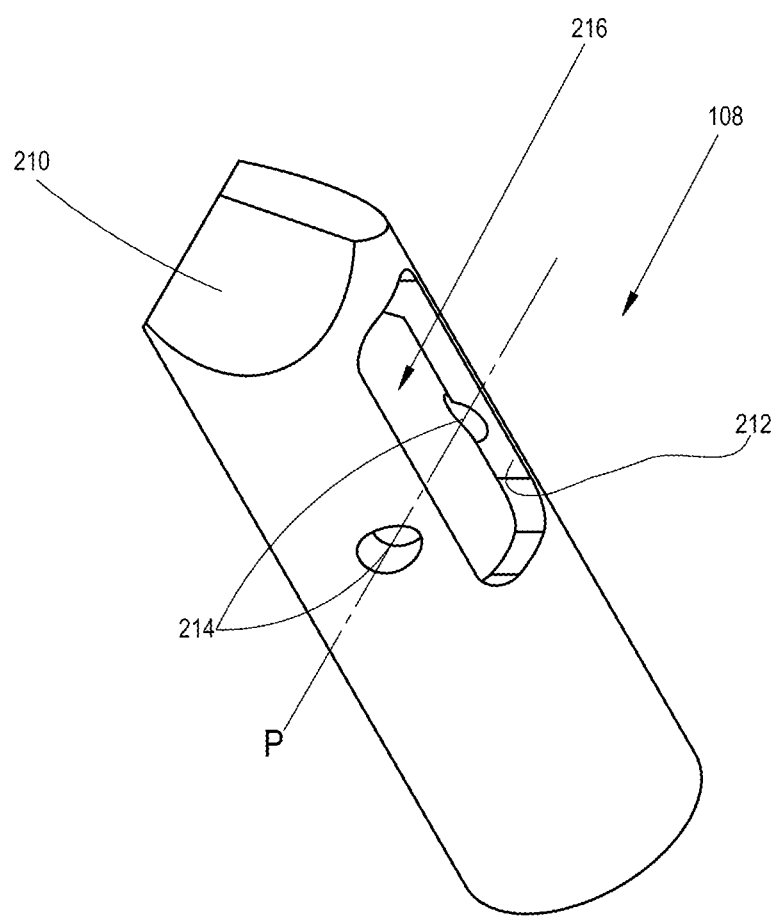
FIG. 8 is a simplified pictorial illustration of a tip element, forming part of the bone material removal device of FIG. 2.

Reference is now made to FIG. 8, which is a simplified pictorial illustration of an exemplary embodiment of a tip element 108, forming part of the bone material removal device 100, as shown for example in FIG. 2.

As shown in FIG. 8 the tip element 108 is a preferably longitudinally hollow element having a distal sharp drilling edge 210. The tip element 108 can alternatively be integrally made with tubular element 104.

Preferably two or more longitudinal guiding slots 212 are formed on tip element 108 adjacent drilling edge 210. Guiding slots 212 extend along an axis, which is transversely disposed with respect to longitudinal axis 109 and are preferably aligned with each other. In some embodiments, guiding slots 212 are positioned diametrically opposed. Guiding slots 212 lead to a hollow 216 configured to at least partially accommodate cutting tooth 140. A through bore 214 is formed through tip element 108 and extends transversely with respect to guiding slot 212, bore 214 additionally extends transversely with respect to longitudinal axis 109. The through bore 214 is utilized for insertion of an axle, acting as a pivotal axis P of cutting tooth 140.

Figure 9:
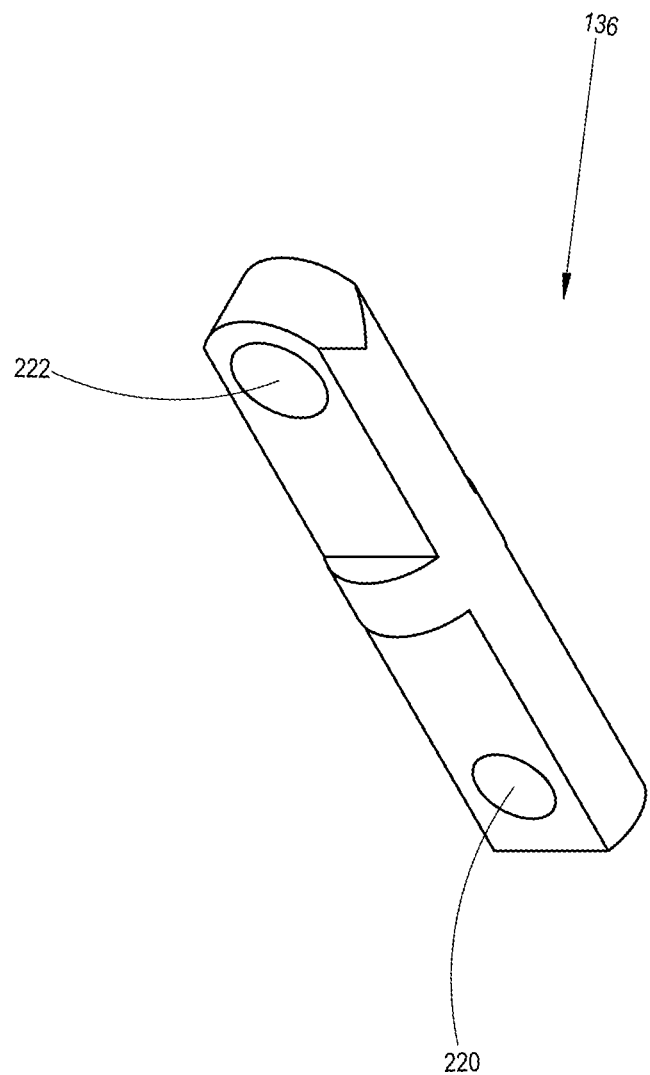
FIG. 9 is a simplified pictorial illustration of a hinge element, forming part of the bone material removal device of FIG. 2.

Reference is now made to FIG. 9, which is a simplified pictorial illustration of an exemplary embodiment of a hinge element 136, forming part of the bone material removal device 100 of FIG. 2.

Hinge element 136 comprises an integrally formed longitudinal element having a proximal bore 220 for attachment of an axle enabling pivotal connection between the hinge element 136 and the shaft element 130, and a distal bore 222 for attachment of an axle enable pivotal connection between the hinge element 136 and cutting tooth 140.

Figure 10:
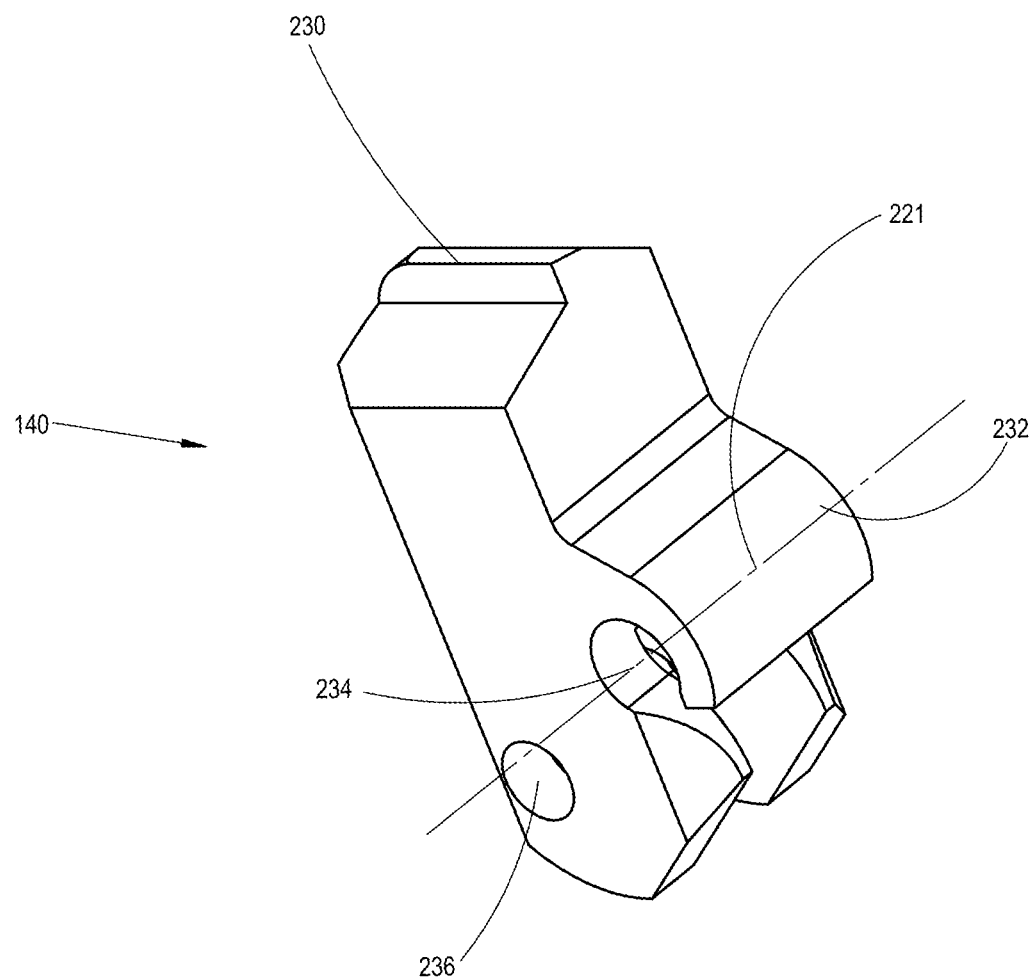
FIG. 10 is a simplified pictorial illustration of a cutting tooth element, forming part of the bone material removal device of FIG. 2.

Reference is now made to FIG. 10, which is a simplified pictorial illustration of cutting tooth element 140, forming part of the bone material removal device 100 of FIG. 2.
Cutting tooth element 140 comprises an integrally made element having a sharp cutting edge 230.

A hook-like element 232 is formed on cutting tooth element 140 defining an aperture 234 for insertion of an axle therethrough enabling pivotal attachment of the cutting tooth element 140 with tip element 108.

Cutting tooth 140 further comprises a through bore 236 for insertion of an axle e.g., pin 142 therethrough enabling pivotal attachment of the cutting tooth 140 to hinge element 136. In some embodiments, bore 236 is positioned off-center, close to one edge of tooth 140. In some embodiments, pin 142, pivotly attaching tooth 140 to tip element 108 acts as a selective stopper, stopping tooth 140 from axial displacement but allowing movement in other directions, e.g., allowing cutting tooth 140 to rotate about pin 142 when urged axially distally or pulled axially proximally.

Figure 11:
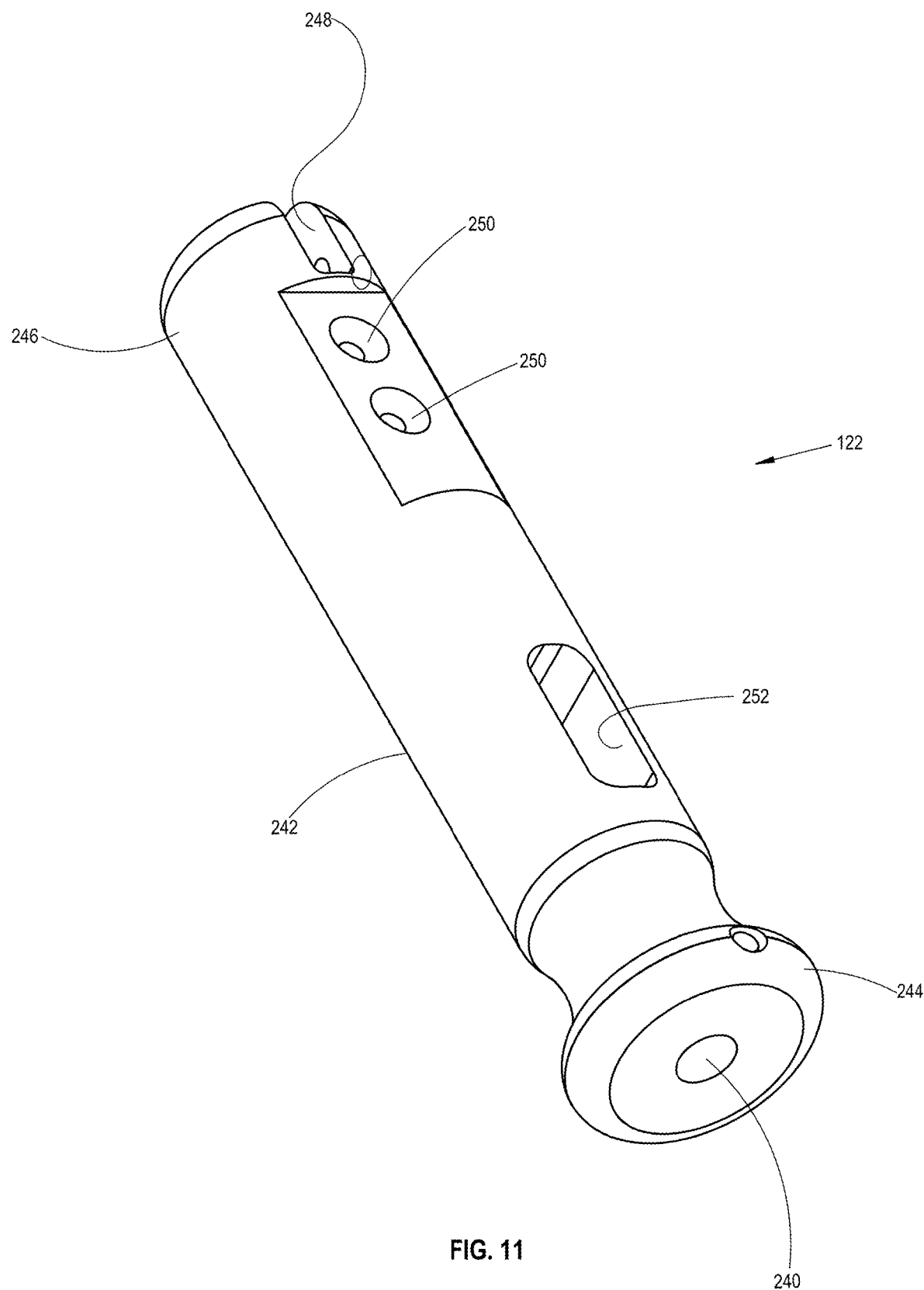
FIG. 11 is a simplified pictorial illustration of a cannula body, forming part of the cannula assembly of FIG. 3.

Reference is now made to FIG. 11, which is a simplified pictorial illustration of an exemplary embodiment of cannula body 122, that forms a part of the cannula assembly 120 e.g., the embodiment shown in FIG. 3.

Cannula body 122 is an integrally made hollow generally cylindrical longitudinal element, configured to be arranged along longitudinal axis 109. Cannula body 122 comprises a through bore 240 extending along longitudinal axis 109. The cannula body 122 further defines an outer gripping surface 242.

Cannula body 122 comprises a proximal end 244 and a distal end 246. As shown in FIG. 11 a recess 248 is formed at the distal end 246 of cannula body, the recess 248 configured for pivotal attachment of the cannula lever 124 thereto.

Generally two apertures 250 are disposed adjacent and slightly proximally to distal end 248 of cannula body. Apertures 250 are configured for fixed attachment of cannula lever biasing element 152 to cannula body 122.

A recess 252 is formed in a location between proximal end 244 and distal end 246 and extends transversely with respect to longitudinal axis 109. Recess 252 intersects with bore 240.

Figure 12:
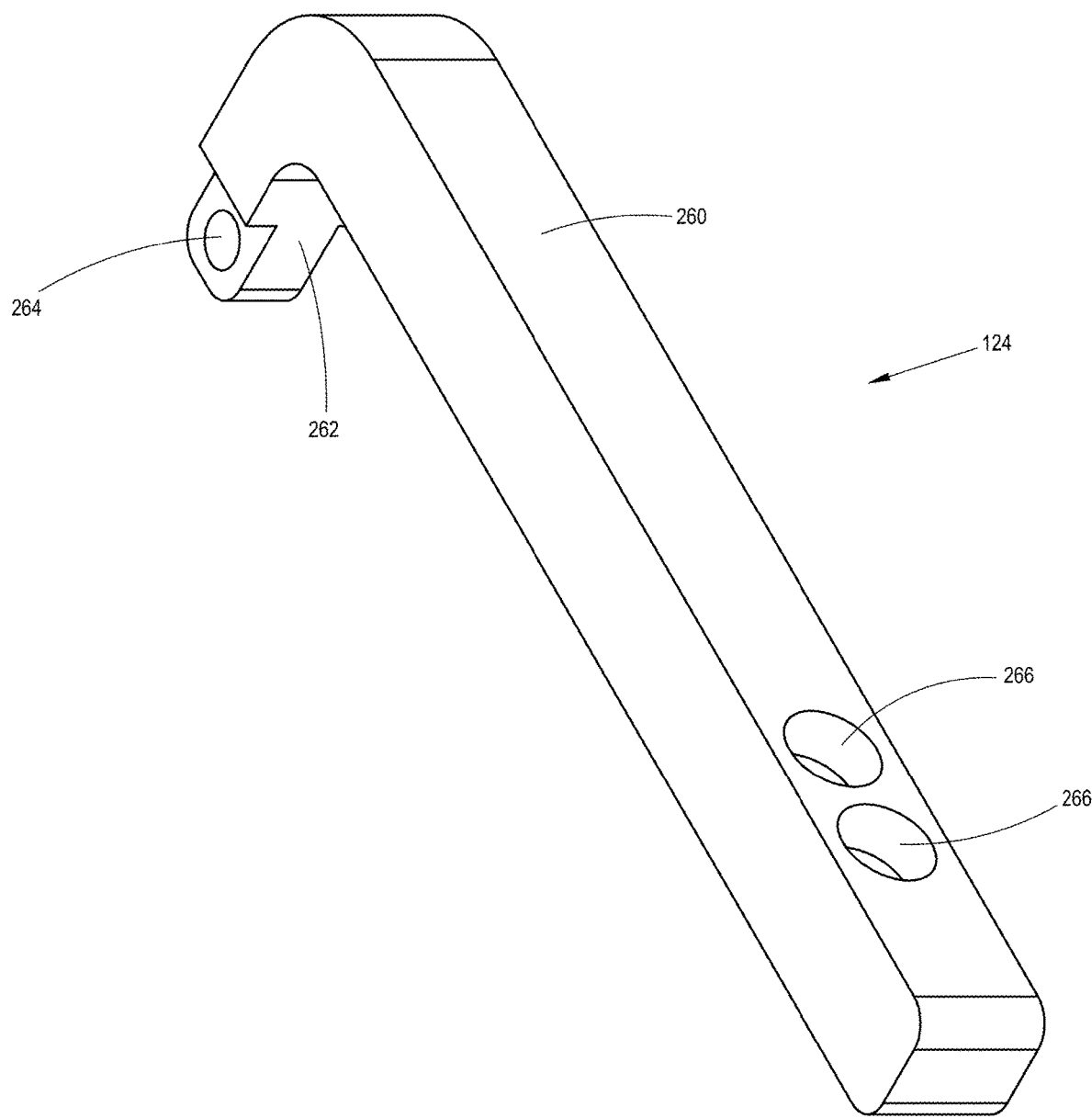
FIG. 12 is a simplified pictorial illustration of a cannula lever, forming part of the cannula assembly of FIG. 3.

Reference is now made to FIG. 12, which is a simplified pictorial illustration of an exemplary embodiment of cannula lever 124, that forms a part of the cannula assembly 120 e.g., as shown in FIG. 3.

It is seen in the embodiment shown in FIG. 12 that cannula lever 124 is an integrally formed element. In some embodiments, cannula lever 124 is generally L-shaped and comprises a longitudinal portion 260 and a connection portion 262. Connection portion 262 comprises a bore 264 for insertion of an axle therethrough to enable pivotable connection between cannula lever 124 and cannula body 122.

Longitudinal portion 260 comprises generally two apertures 266 formed therethrough for insertion of screws to enable fixed attachment of cannula break 150 to cannula lever 124.

Figure 13:
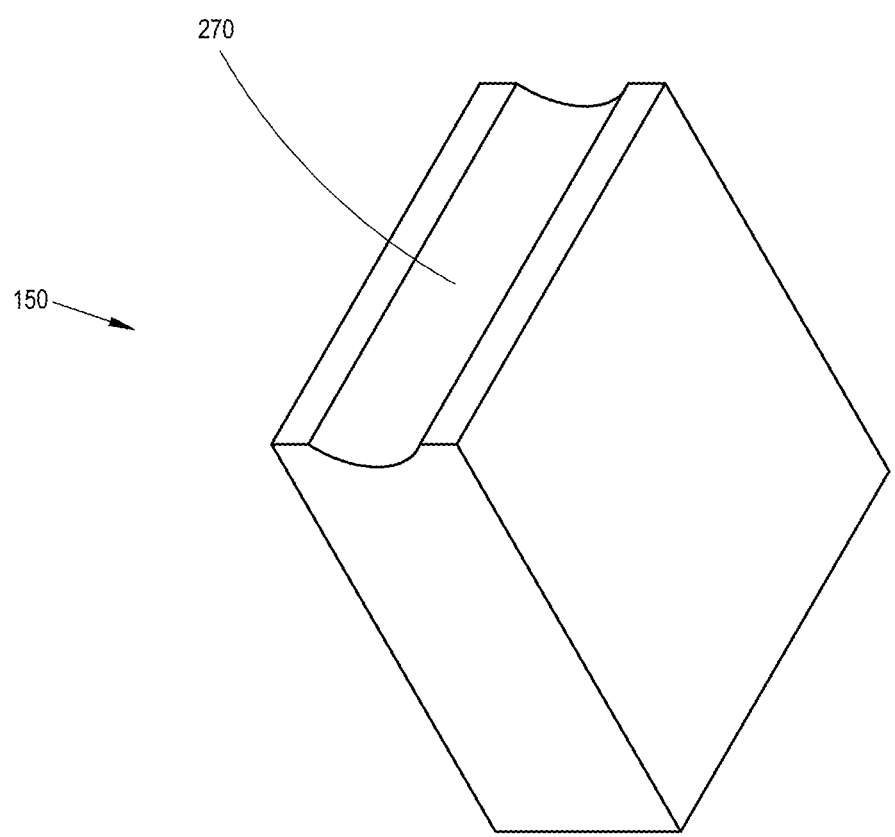
FIG. 13 is a simplified pictorial illustration of a cannula break, forming part of the cannula assembly of FIG. 3.

Reference is now made to FIG. 13, which is a simplified pictorial illustration of an exemplary embodiment of a cannula break 150, that forms a part of the cannula assembly 120 e.g., as shown in FIG. 3.

The cannula break 150 comprises two apertures 182 (FIG. 3) for insertion of screws thereto and attachment with cannula lever 124. The cannula break 150 comprises a longitudinally extending surface 270 for engagement with shaft element 130. In some embodiments, surface 270 is concave.

Figure 14:
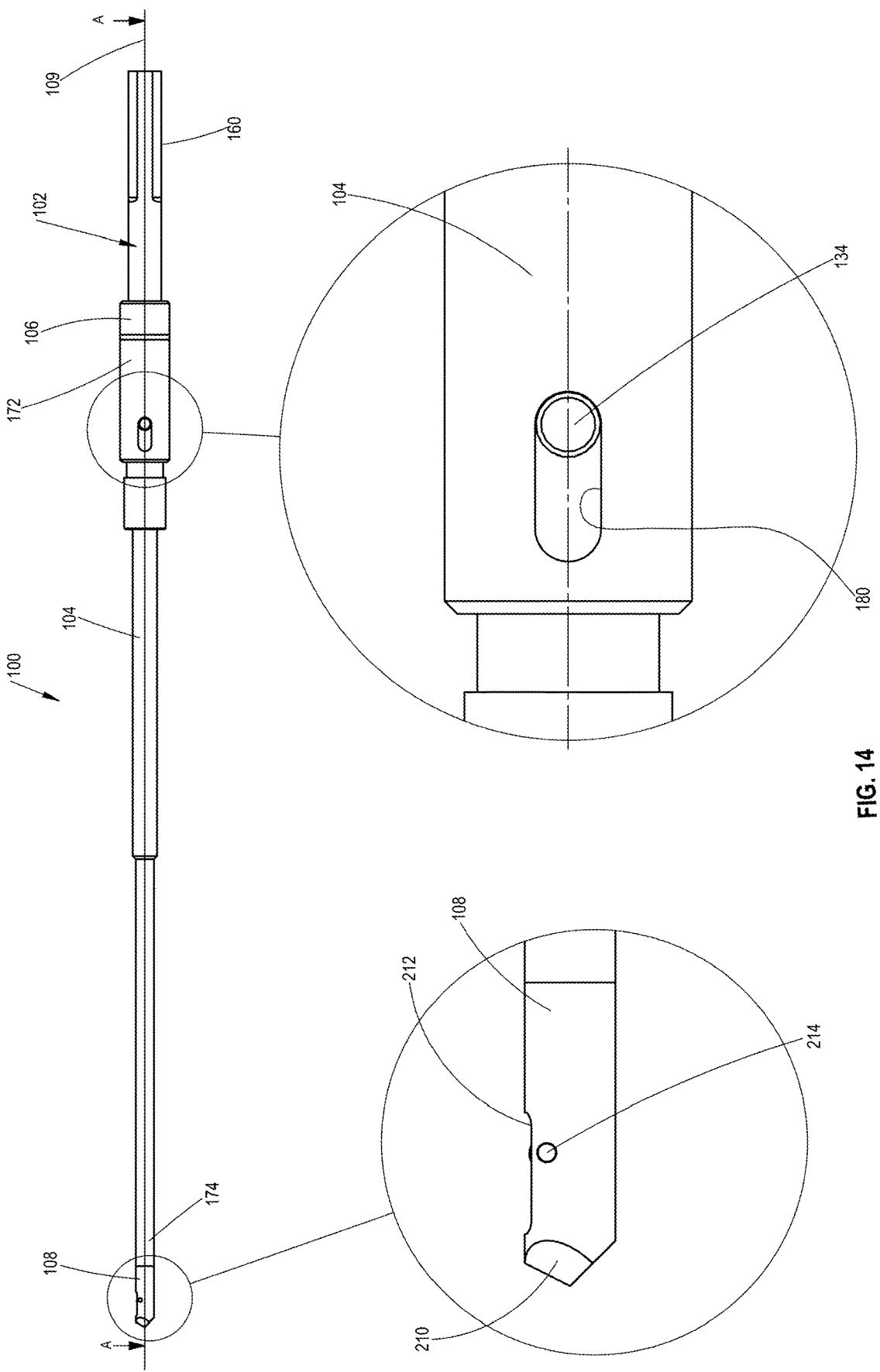
FIG. 14 is a simplified assembled plan view illustration of the bone material removal device of FIG. 2 shown in a closed operative orientation and enlargements thereof.
Figure 15:
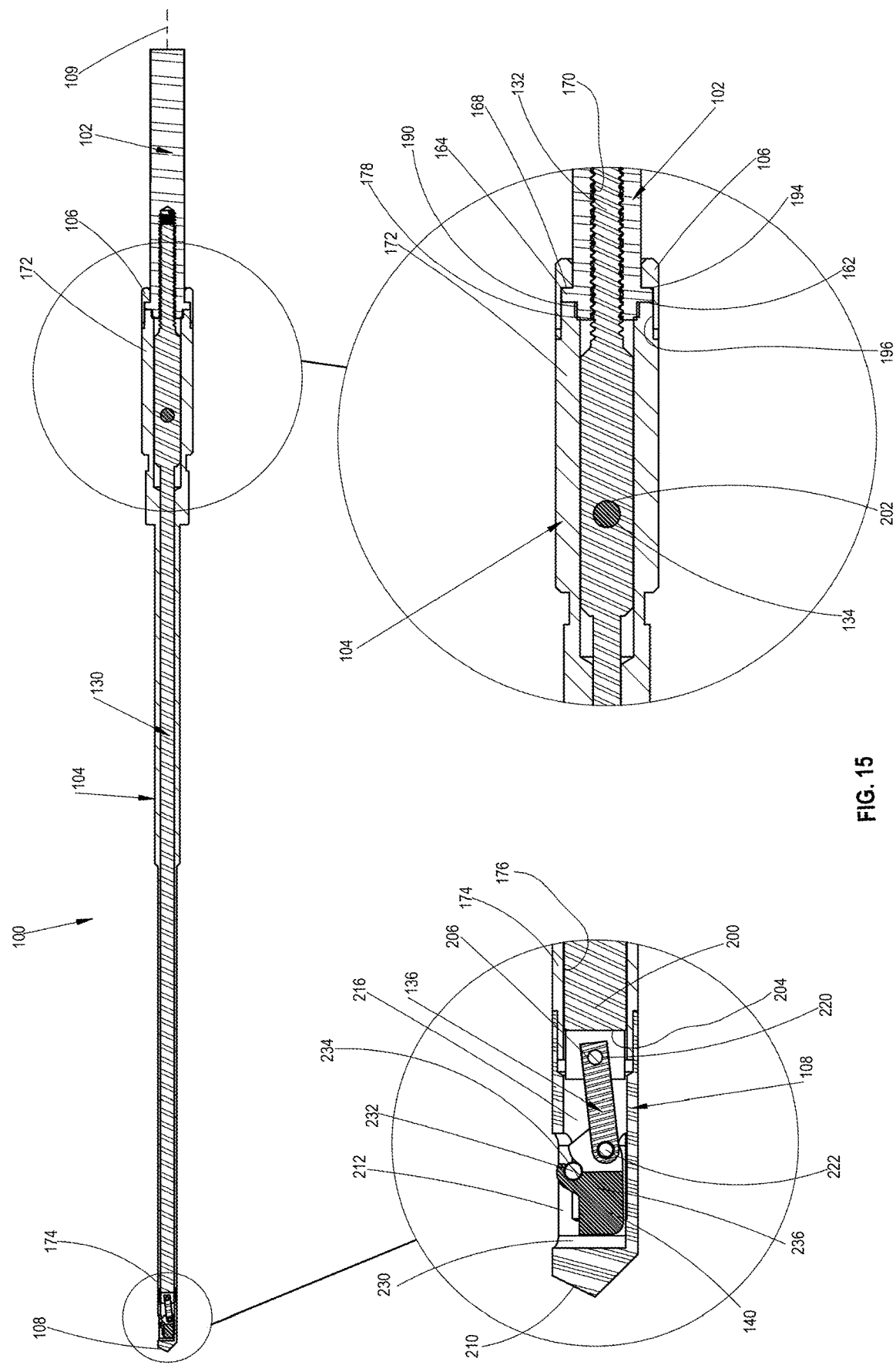
FIG. 15 is a simplified sectional view illustration of the bone material removal device of FIG. 14 shown in the closed operative orientation and enlargements thereof, section view being taken along lines A-A in FIG. 14.
Figure 16B:
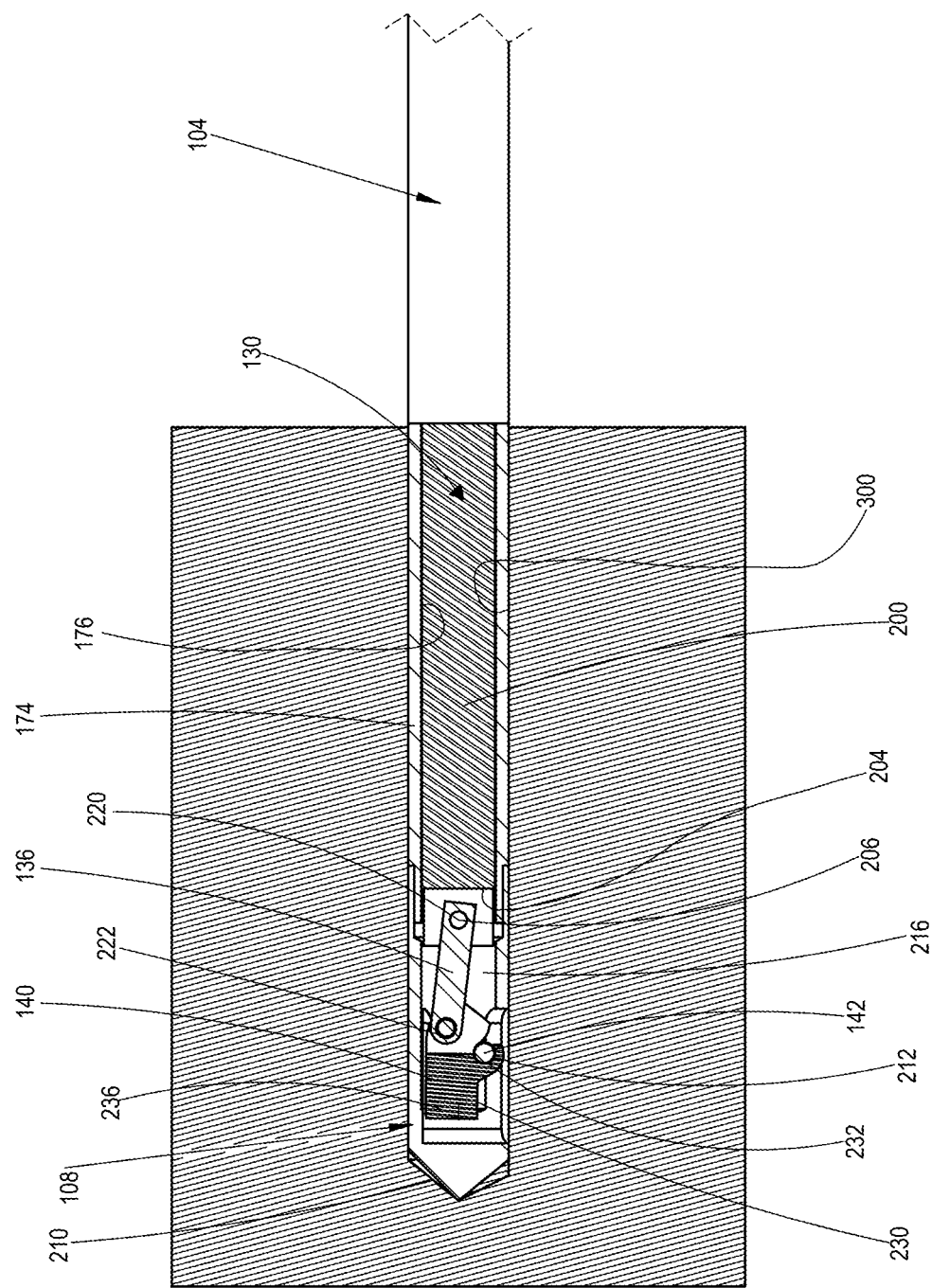

Reference is now made to FIG. 14, which is a simplified plan view illustration of an exemplary embodiment of the bone material removal device 100 (e.g., as shown in FIG. 2) shown in a closed operative orientation and enlargements thereof and to FIG. 15, which is a simplified sectional view illustration of the bone material removal device 100 embodiment depicted in FIG. 14 shown in a closed operative orientation and enlargements thereof, section view being taken along lines A-A in FIG. 14. Reference is additionally made to FIGS. 16A and 16B, which are simplified partial sectional view illustration of an exemplary embodiment of the bone material removal device 100 and the cannula assembly 120 (e.g., as depicted in FIG. 1) shown in a closed operative orientation partially inserted into a bone of a patient and an enlargement thereof.

As shown in the embodiment illustrated in FIGS. 14-16B bone material removal device 100 is positioned in a closed operative orientation, in which the cutting tooth 140 is closed, accommodated inside hollow 216 and does not protrude radially through guiding slot 212. In this closed orientation, a diameter of a bore formed in a bone while drilling is equal to the outer diameter of tip element 108.

As shown in FIG. 14 tubular element 104 is rotatably connected to rotating element 102 by means of sleeve element 106, such that a flange 164 of rotating element 102 lies sandwiched between and against distally facing shoulder 194 of sleeve 106 and proximal end of tubular element 104. The surface of bore 190 of sleeve element 106 abuts connecting portion 178 of tubular element 104 and allows rotation of tubular element 102.

It is a particular feature of some embodiments of the present invention that threaded portion 132 of shaft element 130 is threadably attached to an inner threading 170 of rotating element 102. The shaft element 130 is disposed at its proximal operative orientation in this closed position and is attached to the tubular element 104 by means of indicating pin 134.

It is a particular feature of some embodiments of the present invention that the indicating pin 134 is positioned at the forward end of guiding slot 180 of tubular element 104 when the bone material removal device is positioned at the closed operative orientation, since the indicating pin 134 is inserted into bore 202 of shaft element 130, which is disposed at the proximal operative orientation at this stage.

It is further particularly seen in FIGS. 15 and 16B that the shaft element 130 is pivotably connected to hinge element 136, which in turn is pivotably connected to cutting tooth 140.

It is a particular feature of some embodiments of the present invention that when the shaft element is positioned in its proximal operative orientation, the cutting tooth 140 is fully enclosed within the tubular element 104 hollow 216 and does not protrude through guiding slot 212.

It is particularly shown in FIGS. 16A and 16B that bone material removal device 100 is inserted into bore 240 of cannula body 122, which forms part of the cannula assembly 120. It is particularly seen in FIG. 16A that the cannula lever 124, which is pivotably connected to the cannula body 122, is not pressed at this operative orientation, thus cannula lever biasing element 152 is positioned at an unstressed orientation and the cannula break 150 is not in contact with the tubular element 104.

As illustrated in FIGS. 16A and 16B, an initial bore 300 of a first diameter is formed in the bone of the patient while drilling with the bone material removal device 100 positioned in its closed operative orientation. It is noted that this initial drilling is provided while the rotating element 102 is rotated in a first rotational direction, in this exemplary embodiment, in a clockwise direction.

While the rotating element 102 and the tubular element 104 rotate in a clockwise rotational direction, the sharp drilling tip 210 of tip 108 engages the bone of the patient and creates initial bore 300 therein.

Figure 17:
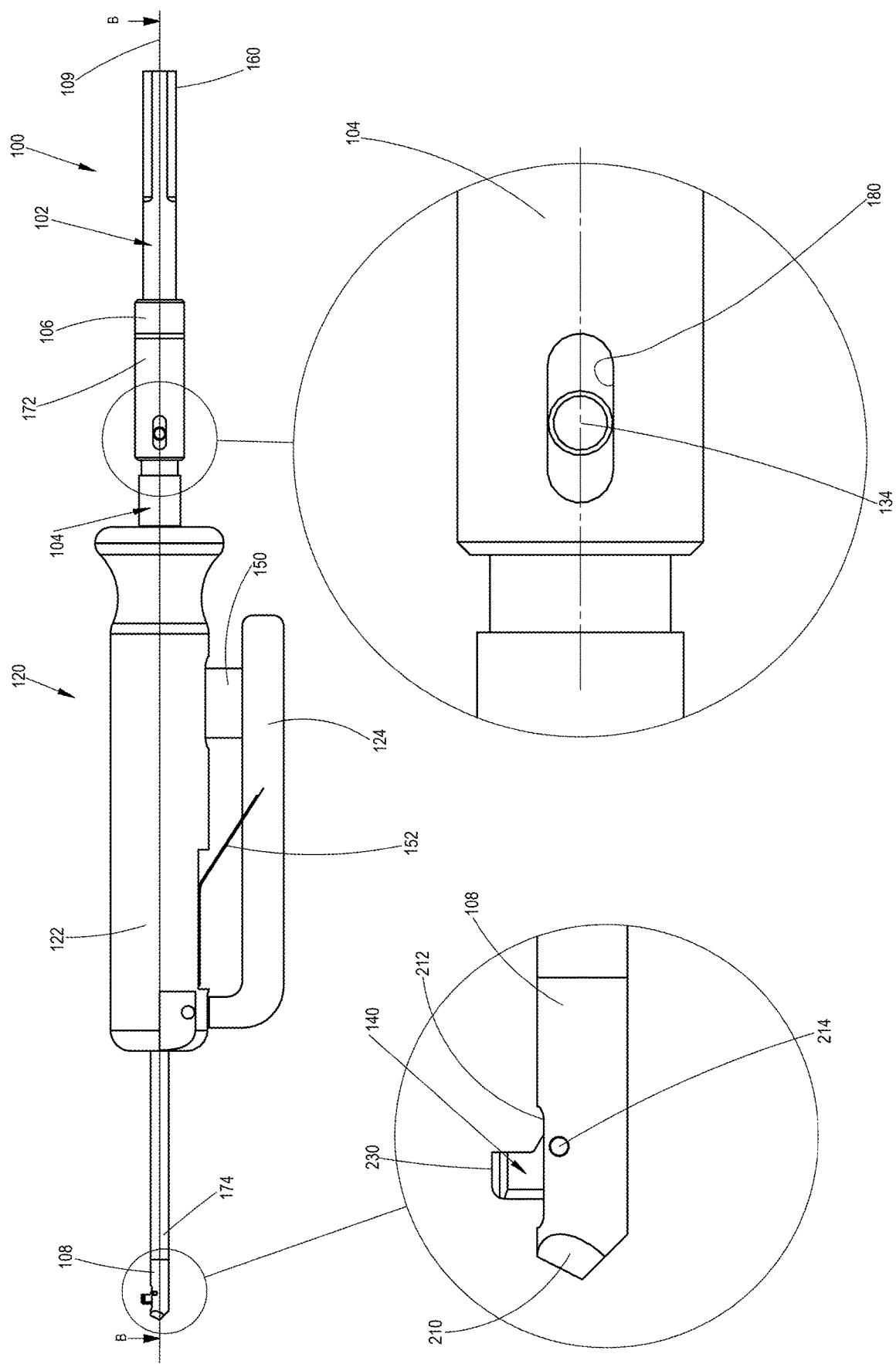
FIG. 17 is a simplified assembled plan view illustration of the bone material removal device of FIG. 2 shown in an open operative orientation and enlargements thereof.
Figure 18:
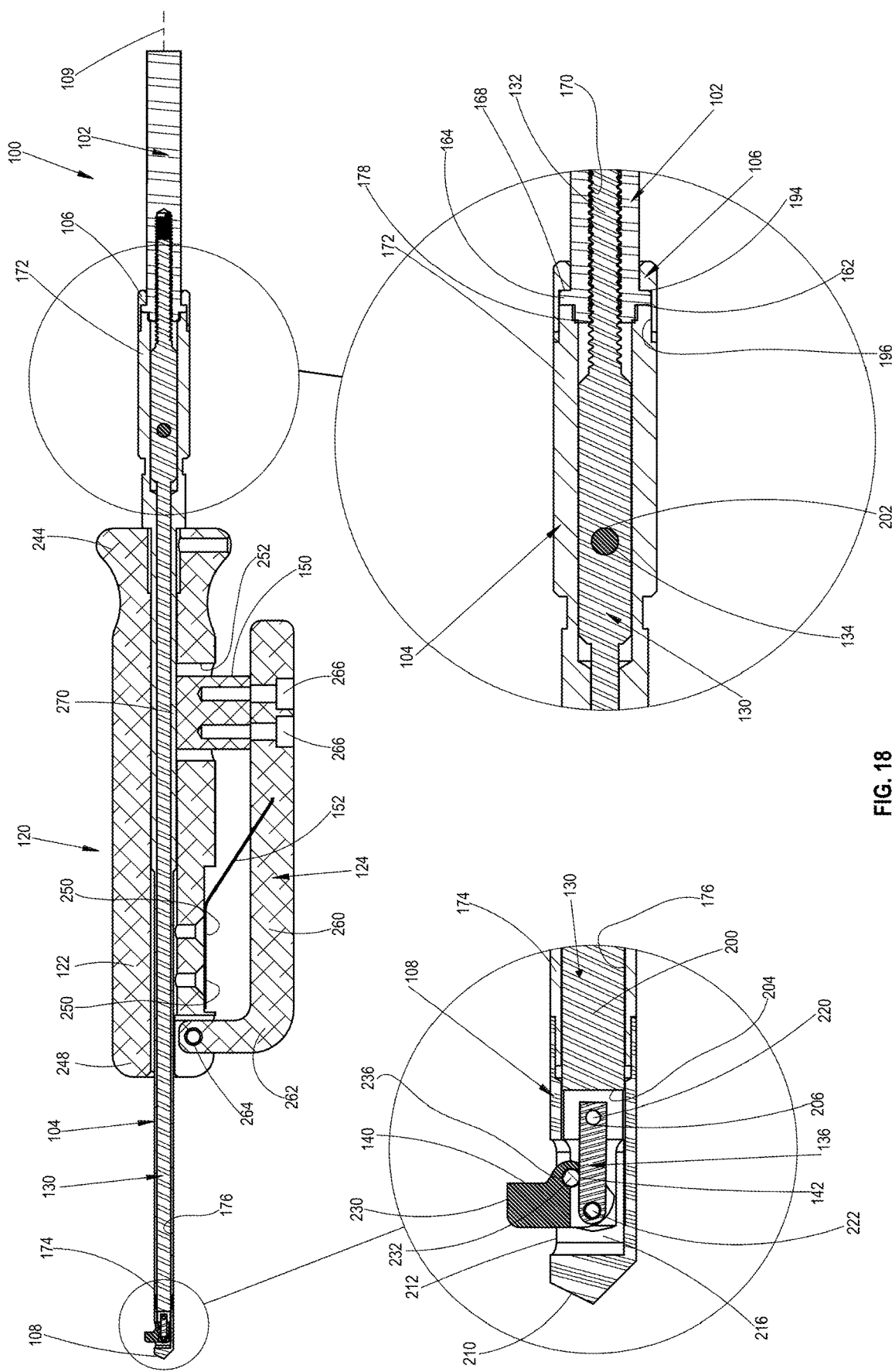
FIG. 18 is a simplified sectional view illustration of the bone material removal device of FIG. 17 shown in the open operative orientation and enlargements thereof, section view being taken along lines B-B in FIG. 17.
Figure 19A:
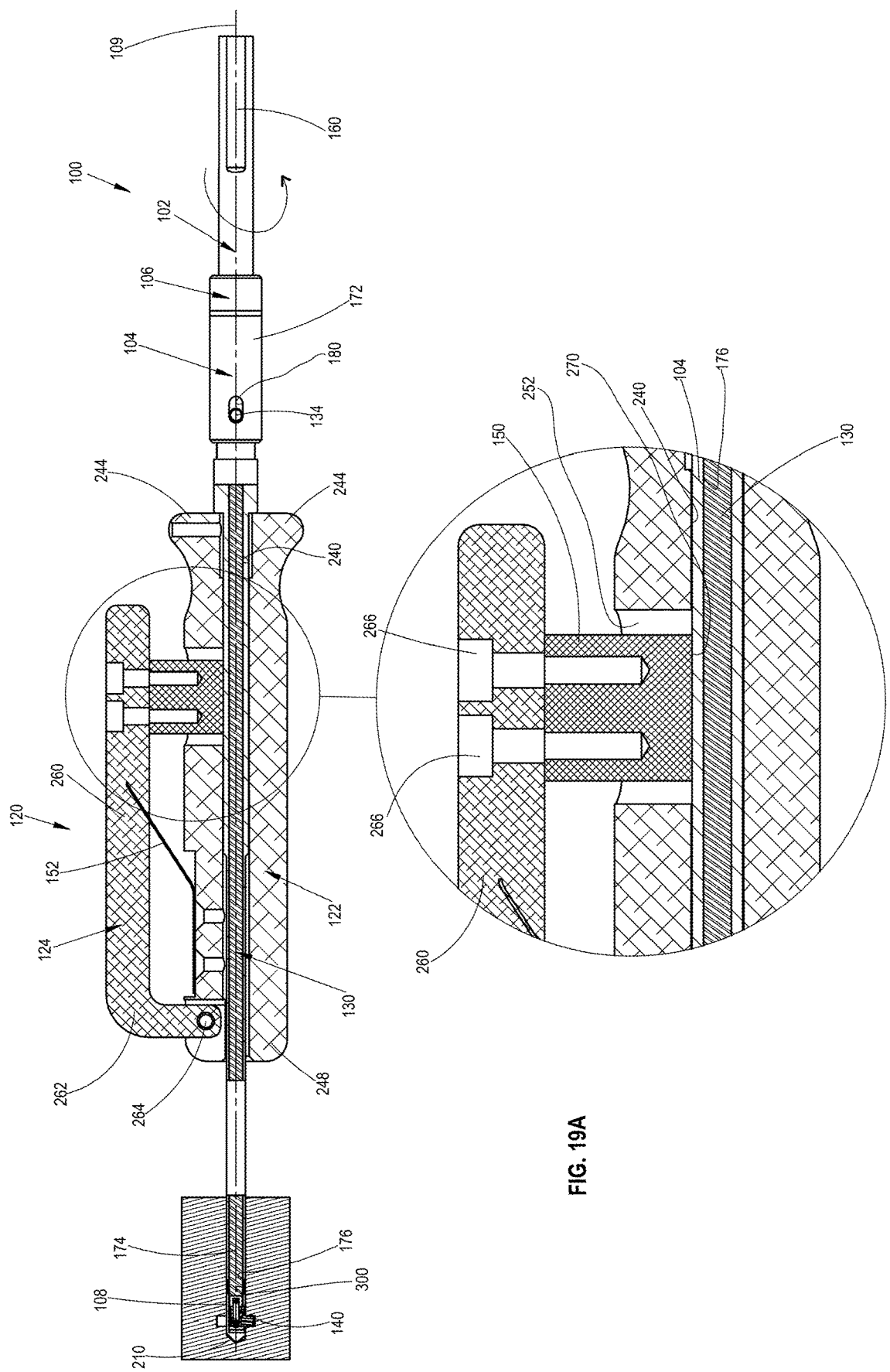
FIGS. 19A and 19B is a simplified partial sectional view illustration of the bone material removal device and the cannula assembly of FIG. 1 shown in the open operative orientation partially inserted into a bone of as patient and an enlargement thereof.
Figure 19B:
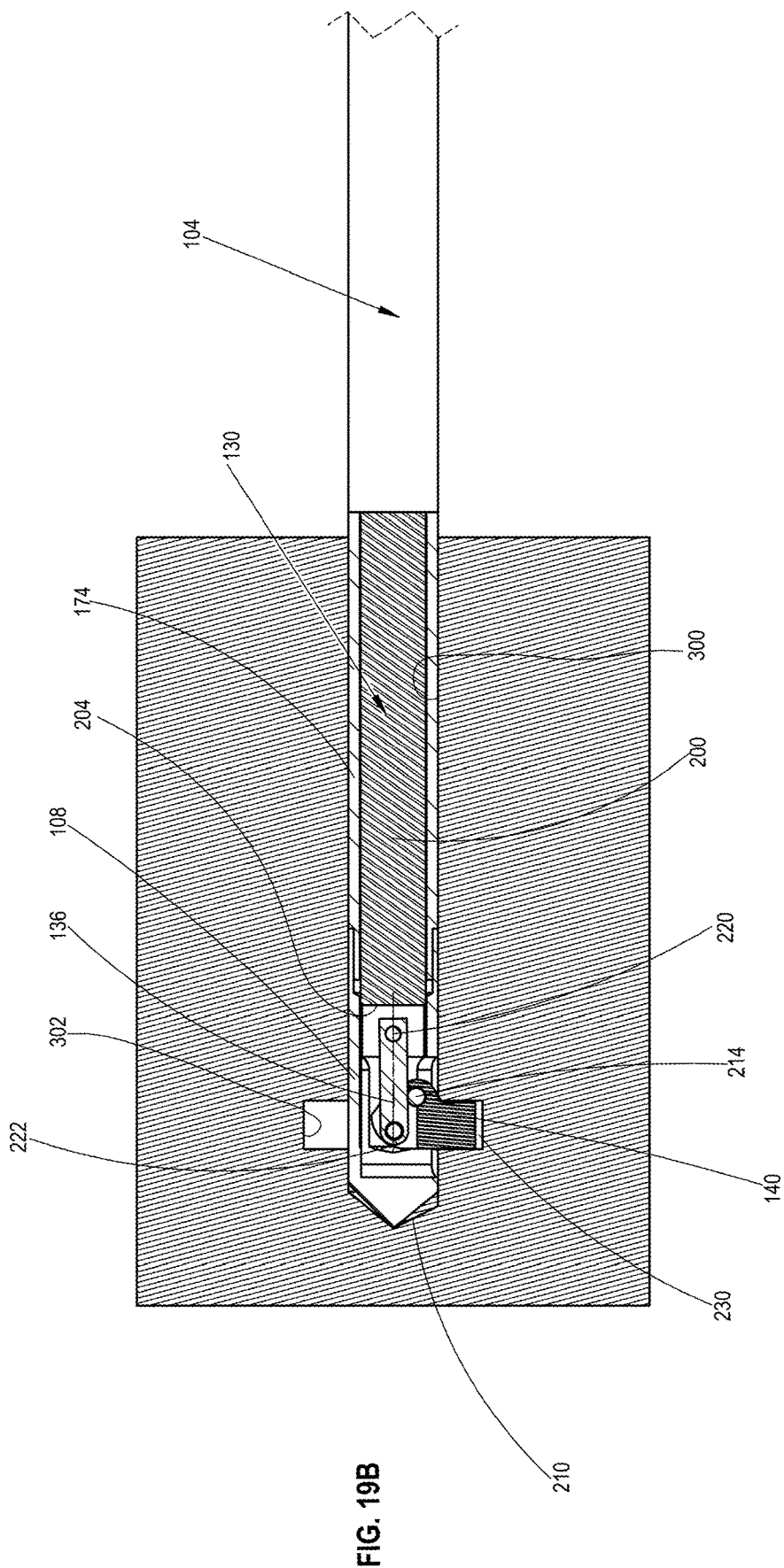

Reference is now made to FIG. 17, which is a simplified plan view illustration of an exemplary embodiment of the bone material removal device 100 e.g., as depicted in FIG. 2 shown in an open operative orientation and enlargements thereof and to FIG. 18, which is a simplified sectional view illustration of the embodiment of the bone material removal device 100 shown in FIG. 17 shown in the open operative orientation and enlargements thereof, section view being taken along lines B-B in FIG. 17. Reference is additionally made to FIGS. 19A and 19B, which is a simplified partial sectional view illustration of an exemplary embodiment of the bone material removal device 100 and the cannula assembly 120 e.g., as depicted in FIG. 1 shown in the open operative orientation partially inserted into a bone of as patient and an enlargement thereof and to FIG. 20, which is a simplified sectional enlargement illustration of the bone material removal device 100 of FIG. 1 shown during removal from the bone.

As shown in the embodiments depicted in FIGS. 17-20, the bone material removal device 100 is positioned in an open operative orientation, in which the cutting tooth 140 is open and protrudes through guiding slot 212, thus the diameter of the bore formed in the bone of the patient while drilling in the open operative orientation of the bone material removal device 100 is greater than the outer diameter of tip element 108.

It is a particular feature of some embodiments of the present invention that threaded portion 132 of shaft element 130 is threadably coupled to inner threading 170 of rotating element 102. The shaft element 130 is disposed at its distal operative orientation in this open position and is attached to the tubular element 104 by means of indicating pin 134. It is a particular feature of some embodiments of the present invention that the indicating pin 134 is positioned at the distal end of guiding slot 180 of tubular element 104 when the bone material removal device is positioned at the open operative orientation, since the indicating pin 134 is inserted into bore 202 of shaft element 130, which is disposed at the distal operative orientation at this stage.

It is further particularly shown that the shaft element 130 is pivotably connected to hinge element 136, which in turn is pivotably connected to cutting tooth 140.

In some embodiments, at least a portion of cutting tooth 140 is disposed in the path of, and interferes with, axial displacement of shaft element 130. Axial displacement of shaft element 130 distally urges hinge element 136 against tooth 140 axially. Pin 142 acts as a selective stopper, stopping tooth 140 from displacing axially but allowing movement in other directions, e.g., allowing cutting tooth 140 to rotate about pin 142 when urged axially distally and extend radially in respect to shaft 130. It is a particular feature of some embodiments of the present invention that when the shaft element is positioned in its distal operative orientation, the cutting tooth 140 is pivoted about axis 214 to extend radially outwardly, and preferably generally transversely to longitudinal axis 109 and to protrude through guiding slot 212 of tip element 108.

It is particularly seen in FIGS. 17-20 that bone material removal device 100 is inserted into bore 240 of cannula body 122, which forms part of the cannula assembly 120. It is particularly seen in FIGS. 18 and 19A that the cannula lever 124, which is pivotably connected to the cannula body 122, is pressed at this operative orientation, thus cannula lever biasing element 152 is positioned at a deflected stressed orientation and the cannula break 150 is engaged with the tubular element 104 to create friction force between the cannula lever 124 and the tubular element 104 in order to stop the rotational movement of the tubular element 104 to enable changing the drilling rotational direction.

It is seen in FIGS. 17-20 that an undercut bore 302 is formed over the initial bore 300, undercut bore 302 having a second diameter, which is greater than the first diameter while drilling with the bone material removal device 100 positioned in its open operative orientation. It is noted that this undercut bore drilling is provided while the rotating element 102 is rotated in a second rotational direction, in this exemplary embodiment, in a counter-clockwise direction.

It is a particular feature of some embodiments of the present invention that once the cannula lever 124 is pressed and the rotation of the tubular element 104 is momentarily stopped, the rotational direction of the drilling can be reversed, thus causing the threaded portion 132 of shaft element 130 to unthread i.e., unscrew (turn in a direction opposite to the initial direction of threading) from internal threading 170 of rotating element 102. Since indicating pin 134 attaches the shaft element 130 to the guiding slot 180 of the tubular element 104, rotation of the shaft element 130 is prevented and this unthreading causes axial displacement of the shaft element 130 in a distal direction. The extent of longitudinal displacement of the shaft element 130 depends on the length of guiding slot 180, thus during the axial displacement of shaft element 130 in a distal direction, the indicating pin 134 is displaced along the guiding slot 180 from its proximal end to its distal end.

It is a further particular feature of some embodiments of the present invention that axial longitudinal displacement of shaft element 130 distally urges the hinge element 136 to pivot about axis 220, thus urges pivoting of axis 222 of hinge element 136, which in turn urges pivoting of cutting tooth 140 about axis 221 of pin 142 and causes the cutting tooth 140 to pivot radially e.g., from its initial orientation and protrude through guiding slot 212 of tip element 108.

While the rotating element 102 and the tubular element 104 rotate in a counter-clockwise rotational direction, the cutting edge 230 of cutting tooth 140 engages the bone of the patient and creates undercut bore 302 therein. It is noted that the cannula lever 124 may be released once the drilling rotational direction is reversed and the bone material removal device 100 can be advanced and retracted in and out of the bone of the patient in order to create the desired length of undercut bore 302.

It is appreciated that in order to return to the closed operative orientation of the bone material removal device 100, cannula lever 124 has to be pressed to stop the rotation of drill element 130 and the drilling rotational directional has to be reversed in order to urge the shaft element 130 to be displaced axially in a proximal direction, thus axially pulling hinge element 136 which in turn axially pulls cutting tooth 140 bringing tooth 140 to pivot about pin 142 such that tooth 140 is fully drawn into hollow 216 and fully enclosed within tip element 108. At this stage, the bone material removal device can be removed from the bone of the patient and the resulted variable diameter bore, comprised of initial bore 300 and undercut bore 302, can be seen as illustrated in FIG. 20.

Reference is now made to FIG. 21, which is a simplified flow chart illustrating an example of the use of the bone material removal device 100 with the cannula assembly 120 shown in FIG. 1 and to FIG. 22, which is a simplified block diagram illustrating an example of the method of using the bone material removal device 100 and cannula assembly 120 of FIG. 1.

Figure 20:
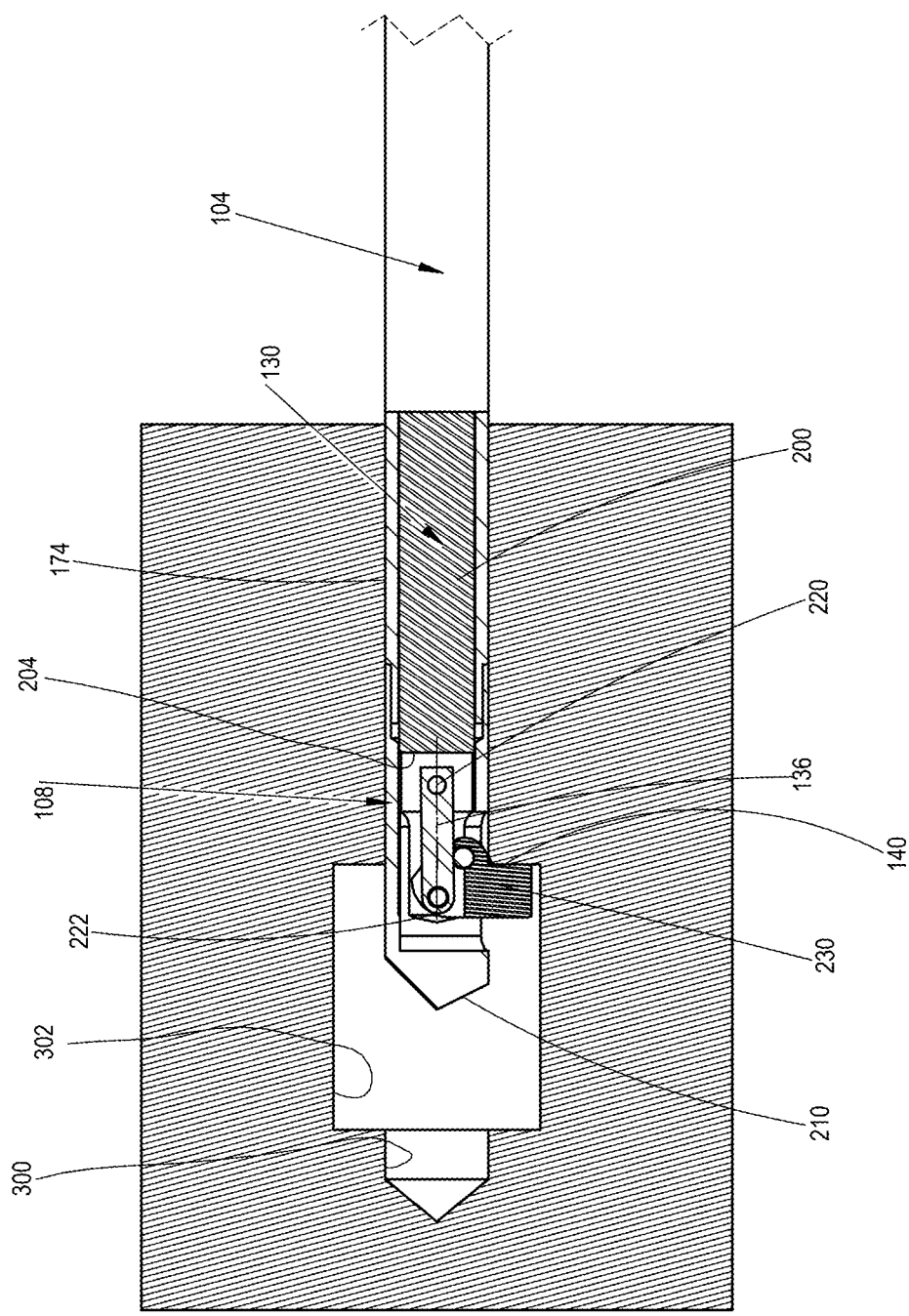
FIG. 20 is a simplified sectional enlargement illustration of the bone material removal device of FIG. 1 shown during removal from the bone of the patient.

The mechanism of the device and method of its operation as described in detail above is further illustrated particularly in FIGS. 20 and 21.

Reference is now made to FIGS. 23A-23C, which are three simplified plan view illustrations of a cutting tooth element, forming part of the bone material removal device 100 of FIG. 2, constructed and operative in accordance with some embodiments of the present invention.

In accordance with some embodiments of the present invention, an alternative and optional cutting tooth 440 is provided as part of the bone material removal device 100, instead of cutting tooth 140 as seen in FIG. 10.

In the exemplary embodiment shown in FIGS. 23A-23C, cutting tooth element 440 comprises an integrally made element having a central portion 442 having a sharp edge 444 formed thereon. Preferably, in some embodiments, one, two or more recesses 446 are formed within the central portion 442 for insertion of pins 448 therethrough to enable attachment of the cutting tooth 440 to tip element 108 while providing for axial displacement of the central portion 442 of the cutting tooth 440 along an axis 447 that is disposed transversely to longitudinal axis 109. In some embodiments, in operation, pins 448 act as selective stoppers, stopping tooth element 440 from displacing axially but allowing movement in other directions, e.g., allowing tooth element 440 to slide radially when urged axially distally and extend radially in respect to shaft 530. A leaf spring portion 450 is generally attached or integrally formed at the opposite proximal and distal sides of the central portion 442.

Figure 24:
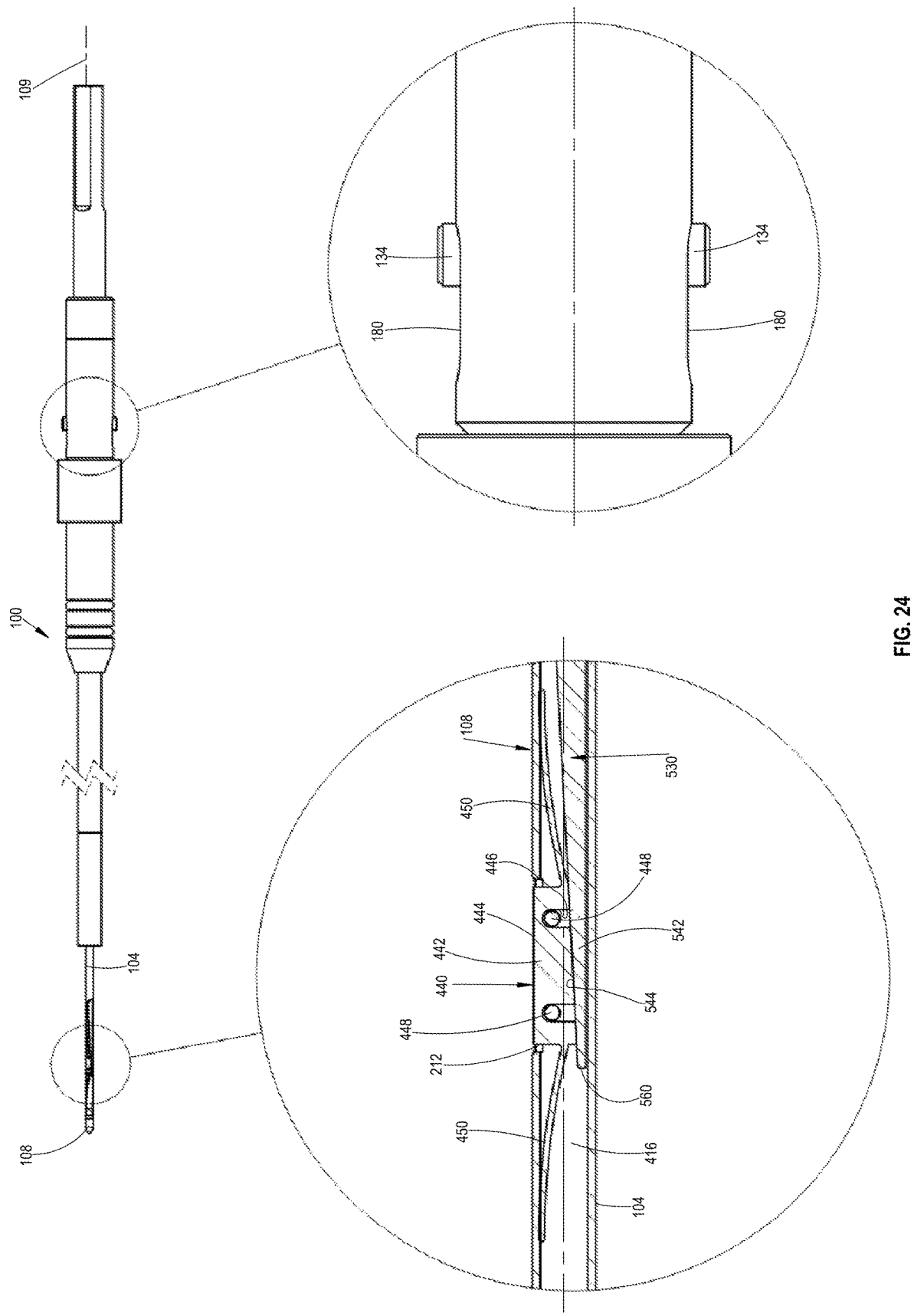
FIG. 24 is a simplified assembled plan view illustration of the bone material removal device of FIG. 2, constructed and operative in accordance with some embodiments of the present invention, shown in a closed operative orientation and a partial section view and an enlargement thereof.

Reference is now made to FIG. 24, which is a simplified assembled plan view illustration of the bone material removal device 100 of FIG. 2, constructed and operative in accordance with some embodiments of the present invention, shown in a closed operative orientation and a partial section view and an enlargement thereof.

As noted above, the longitudinal shaft 130 having a threaded portion 132 is configured to be partially inserted into the tubular element 104 and partially into rotating element 102, such that the threaded portion 132 of shaft 130 is engaged with the internal threading of the rotating element 102.

Figure 25:
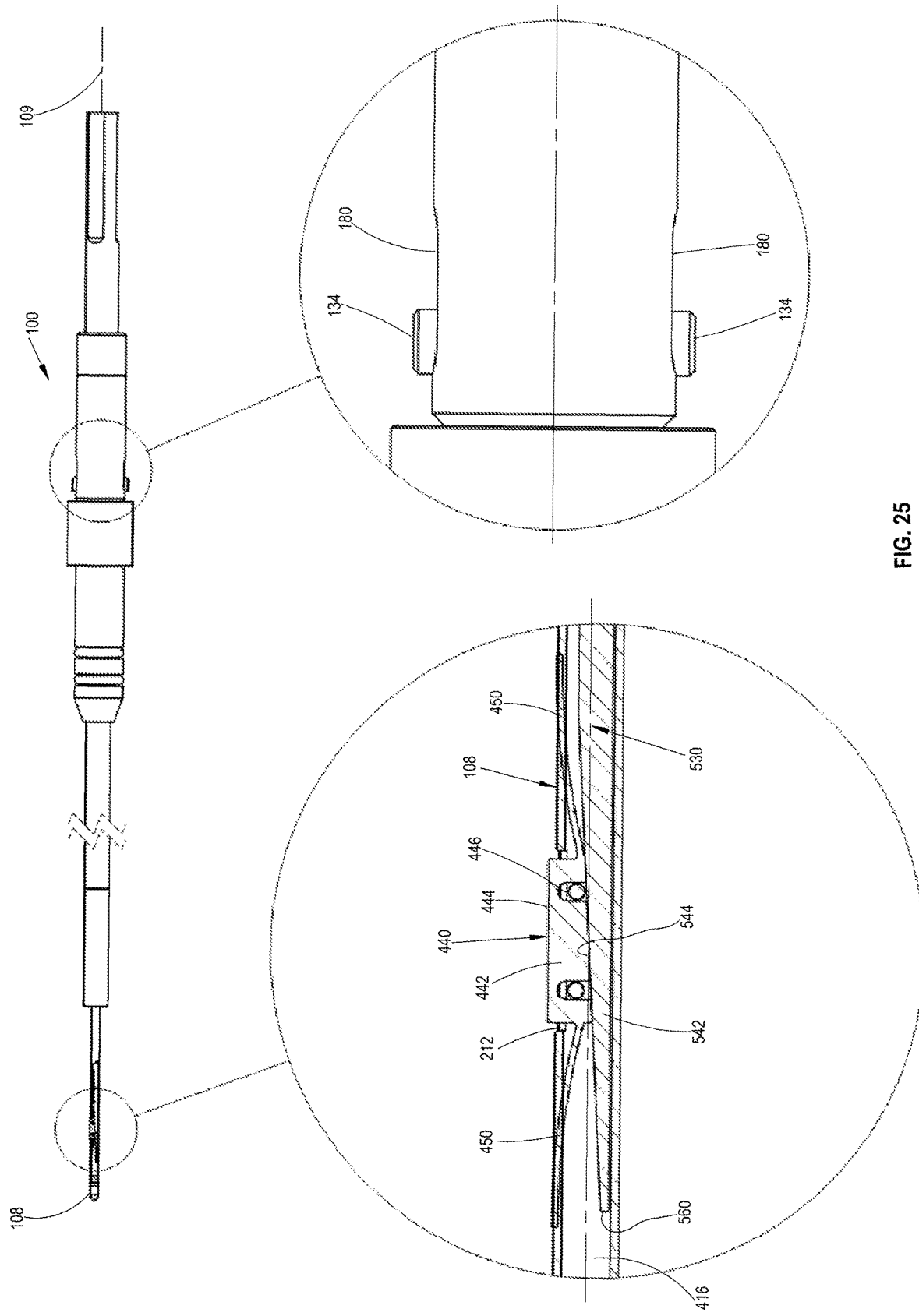
FIG. 25 is a simplified assembled plan view illustration of the bone material removal device of FIG. 2, constructed and operative in accordance with some embodiments of the present invention, shown in an open operative orientation and a partial section view and an enlargement thereof.

In the embodiments depicted in FIGS. 24 and 25 a shaft element 530 is provided as an optional alternative to shaft element 130. In some embodiments, shaft element 530 is preferably a longitudinal integrally made element having a proximal end with threaded portion 132 and a distal end 540 configured for partial insertion into the tip element 108. A through bore 202 extending transversely with respect to longitudinal axis 109 is located adjacent and slightly distally from threaded portion 132. Through bore 202 is configured for insertion of positioning pin 134 there through.

It is further seen in FIGS. 24 and 25 that the distal end 540 of shaft element 530 comprises a distally tapered portion 542 defining a tapered surface 544. The tapered surface 544 of shaft element 530 is configured for engagement with the central portion 442 of the cutting tooth 440.

In some embodiments, at least a portion of central portion 442 of the cutting tooth 440 is disposed in the path of, and interferes with, axial distal displacement of shaft element 530. Axial distal displacement of shaft element 530 brings distally tapered portion 542 to slide under central portion 442. Pins 448 act as a selective stoppers, stopping tooth element 440 from displacing axially but allowing displacement of central portion 442 in a radial direction and when urged distally axially by distally tapered portion 542 to extend radially in respect to shaft 530 as shown in FIG. 25.

It is further seen that the shaft 530 is configured to be connected to the tubular element 104 by an indicating pin 134, which is slidably disposed within guiding slot 180 of the tubular element 104.

Preferably and in some embodiments, a longitudinal guiding slot 212 formed on tip element 108 adjacent drilling edge 240. Guiding slot 212 extend along an axis, which is transversely disposed with respect to longitudinal axis 109. Guiding slot 212 is configured for partial insertion of cutting tooth 440 there through. It is appreciated that any number of guiding slots 212 can be formed in the tip element 108 for accommodating a number of cutting teeth 440.

It is seen in the embodiment depicted in FIG. 24 that the bone material removal device 100 is positioned in a closed operative orientation, in which the cutting tooth 440 is in a closed orientation, fully received by hollow 416 and does not protrude through guiding slot 212, thus the diameter of the bore formed in the bone of the patient while drilling in the closed operative orientation of the bone material removal device 100 is equal to the outer diameter of tip element 108.

It is further particularly seen in FIG. 24 that the shaft element 530 is slidably engaged with cutting tooth 440, such that the distally tapered surface 544 of the shaft element 530 engages the central portion 442 of the cutting tooth and the distal edge 560 of the shaft element 530 is generally aligned with or slightly distally extends with respect to the distal edge of the central portion 442 of the cutting tooth 440, this position is defined as the proximal operative orientation of the shaft element 530.

It is a particular feature of some embodiments of the present invention that when the shaft element 530 is positioned in its proximal operative orientation, the cutting tooth 440 is fully received by and enclosed within the tubular element 104 hollow 416 and does not protrude through guiding slot 212 due to the fact that the leaf springs 450 are positioned in their unstressed orientation, biasing the cutting tooth 440 to its closed position inside hollow 416, since there is no force exerted on the central portion 442 of the cutting tooth 440 at the proximal operative orientation of the shaft element 530.

FIG. 25 is a simplified assembled plan view illustration of the bone material removal device 100 of FIG. 2, constructed and operative in accordance with some embodiments of the present invention, shown in an open operative orientation and a partial section view and an enlargement thereof.

It is seen in FIG. 25 that the bone material removal device 100 is positioned in an open operative orientation, in which the cutting tooth 440 is open and protrudes through guiding slot 212, thus the diameter of the bore formed in the bone of the patient while drilling in the open operative orientation of the bone material removal device 100 is greater than the outer diameter of tip element 108.

It is a particular feature of some embodiments of the present invention that threaded portion 132 of shaft element 530 is threadably attached to inner threading 170 of rotating element 102. The shaft element 530 is disposed at its distal operative orientation in this open position and is attached to the tubular element 104 by means of indicating pin 134.

It is a particular feature of some embodiments of the present invention that the indicating pin 134 is positioned at the distal end of guiding slot 180 of tubular element 104 when the bone material removal device is positioned at the open operative orientation, since the indicating pin 134 is inserted into bore 202 of shaft element 530, which is disposed at the distal operative orientation at this stage.

It is further particularly seen in FIG. 25 that the shaft element 530 is slidably engaged with cutting tooth 440, such that the distally tapered surface 544 of the shaft element 530 engages the central portion 442 of the cutting tooth and the distal edge 560 of the shaft element 530 protrudes distally with respect to the distal edge of the central portion 442 of the cutting tooth 440, this position is defined as the distal operative orientation of the shaft element 530.

It is a particular feature of some embodiments of the present invention that when the shaft element 530 is positioned in its distal operative orientation, the cutting tooth 440 is forced radially outwardly through the guiding slot 212 of tip element 108 against the bias of leaf springs 450 that are now positioned in their stressed orientation. Force is exerted on the central portion 442 of the cutting tooth 440 at the distal operative orientation of the shaft element 530, since a wider portion of the shaft element 530 engages the central portion 442 of the cutting tooth and the leaf springs 450 are radially deflected outwardly in a stressed orientation, causing radial outward deflection of the central portion 442 of the cutting tooth 440, with the cutting edge 444 formed thereon. Once shaft element 530 is displaced proximally, radially deflected stressed leaf springs 450 tend to return to their resting unstressed state urging central portion 442 of the cutting tooth 440 radially inwardly into hollow 416 as shown in FIG. 24.

It is a particular feature of some embodiments of the present invention that when the shaft element 530 is positioned in its distal operative orientation, the cutting tooth 440 is axially displaced along an axis that extends transversely radially to longitudinal axis 109 to protrude through guiding slot 212 of tip element 108.

It is a further particular feature of some embodiments of the present invention that longitudinal displacement of shaft element 530 urges the movement of the central portion 442 of cutting tooth 440 from its initial orientation against leaf springs 450 and causes the cutting tooth 440 to protrude through guiding slot 212 of tip element 108.

It is appreciated that shaft element 530 and its engagement with other parts of the bone material removal device 100 is generally similar to shaft element 130 in all respects other than the features described in detail hereinabove.

Figure 26A:
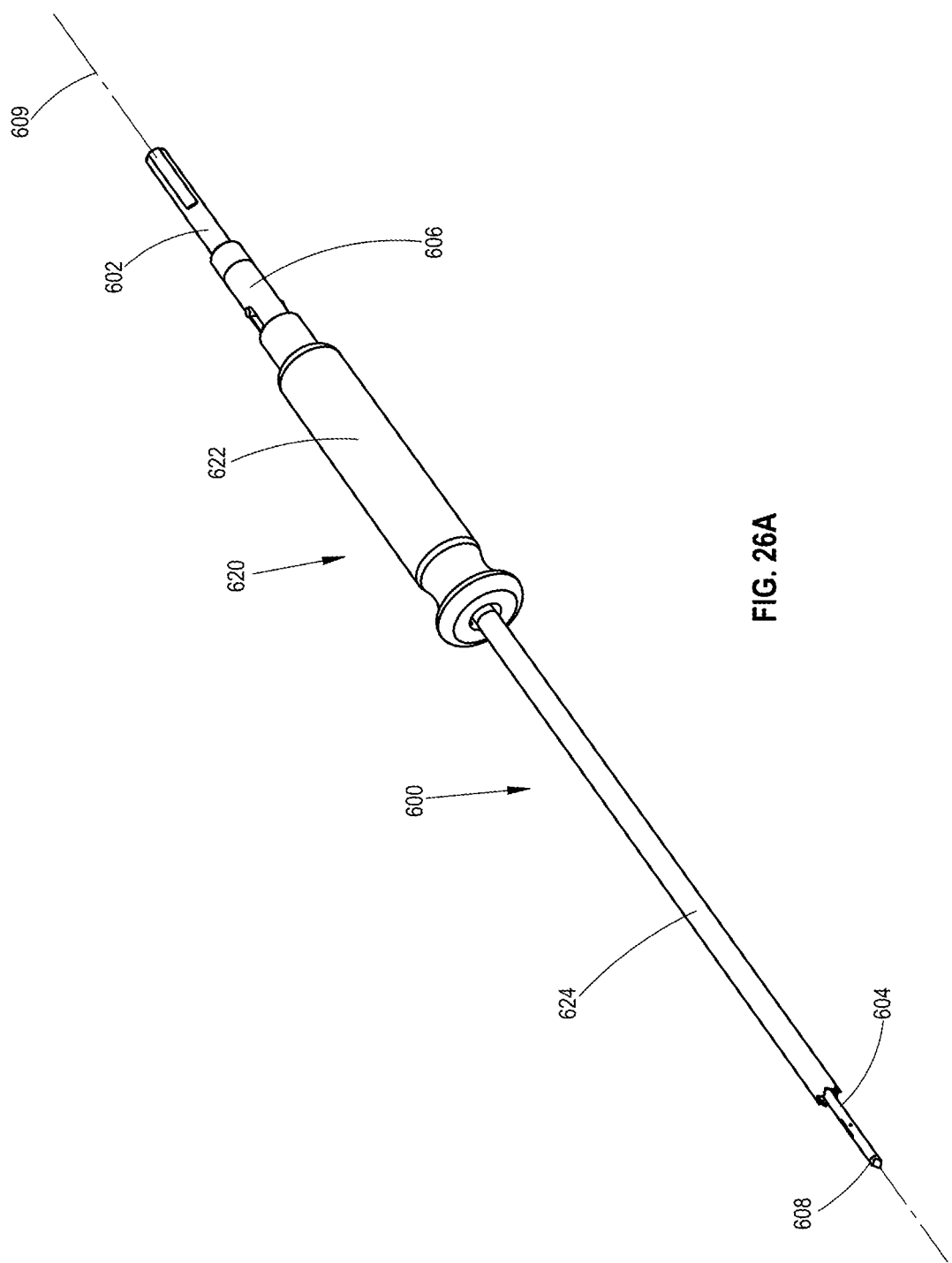
FIG. 26A is a simplified assembled view illustration of a bone material removal device and a cannula assembly, constructed and operative in accordance with still another embodiment of the present invention.

Reference is now made to FIG. 26A, which is a simplified assembled view illustration of an embodiment of a bone material removal device and a cannula assembly, constructed and operative in accordance with some embodiments of the present invention and to FIG. 26B, which is a simplified exploded view illustration of the bone material removal device of FIG. 26A.

It is seen in the embodiments shown in FIGS. 26A and 26B that a bone material removal device 600 includes a rotating element 602 configured to be rotatably attached to a tubular element 604 by a sleeve 606 and a cannula retaining element 607. A tip element 608 is attached or integrally made with the tubular element 604.

It is seen that rotating element 602, tubular element 604, sleeve 606, cannula retaining element 607 and tip element 608 are all arranged along a single mutual longitudinal axis 609.

It is additionally seen in FIG. 26B that a cannula assembly 620 is configured to be mounted over the tubular element 604 and arranged along longitudinal axis 609. Cannula assembly includes a cannula handle 622 and a cannula tube 624.

It is appreciated that the tubular element 604 is preferably made of a biocompatible material, e.g., metal.

It is additionally seen in FIG. 26B that a plurality of O-rings 625, or alternatively and optionally any other friction enhancing elements, are provided on cannula retaining element 607.

It is further seen in FIG. 26B that the rotating element 602 is configured to be rotatably attached to the sleeve element 606. Sleeve element 606 comprises a portion with an outer threading 626 which is configured to engage an inner threading of cannula retaining element 607. Cannula retaining element 607 in turn is configured to be fixedly connected to tubular element 604. The sleeve 606 enables free rotational movement of the rotating element 602 relative to the tubular element 604.

A longitudinal shaft 630 having a proximal portion 632 configured to be partially inserted into the tubular element 604 and partially into rotating element 602. It is further seen that the shaft 630 is configured to be connected to the sleeve 606 by an indicating pin 634.

It is seen in FIG. 26B that tip element 608 is either attached or integrally made with tubular element 604. A Cutting tooth 640 is configured to be attached to the distal end of the tubular element 604.

Figure 27:
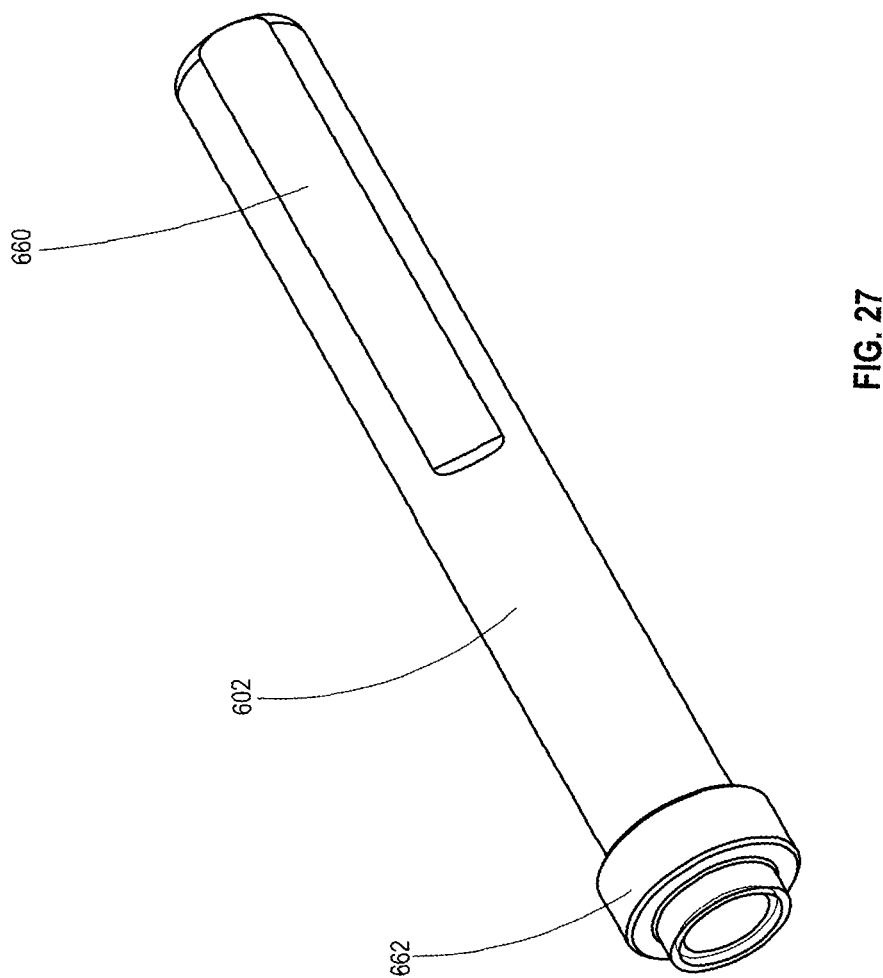
FIG. 27 is a simplified pictorial illustration of a rotating element, forming part of the bone material removal device of FIG. 26B.

Reference is now made to FIG. 27, which is a simplified pictorial illustration of rotating element 602, forming part of the bone material removal device 600 of FIG. 26B. Rotating element 602 is a generally longitudinal hollow cylindrical integrally made element having a proximal end 660 configured to be optionally inserted into a power tool (not shown) and a distal end 662 configured to be optionally inserted into the sleeve 606.

Figure 28:
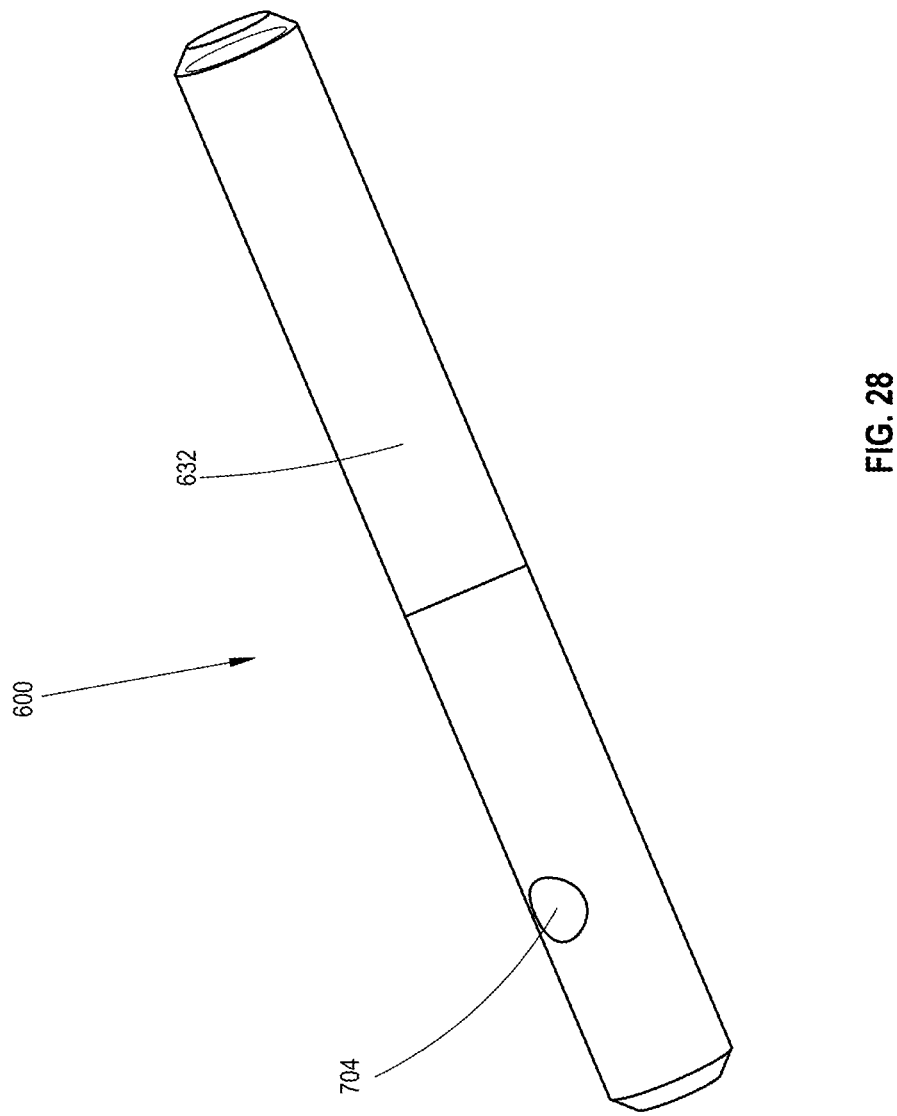
FIGS. 28 and 29 are pictorial illustrations of a shaft element, forming part of the bone material removal device of FIG. 26B.
Figure 29:
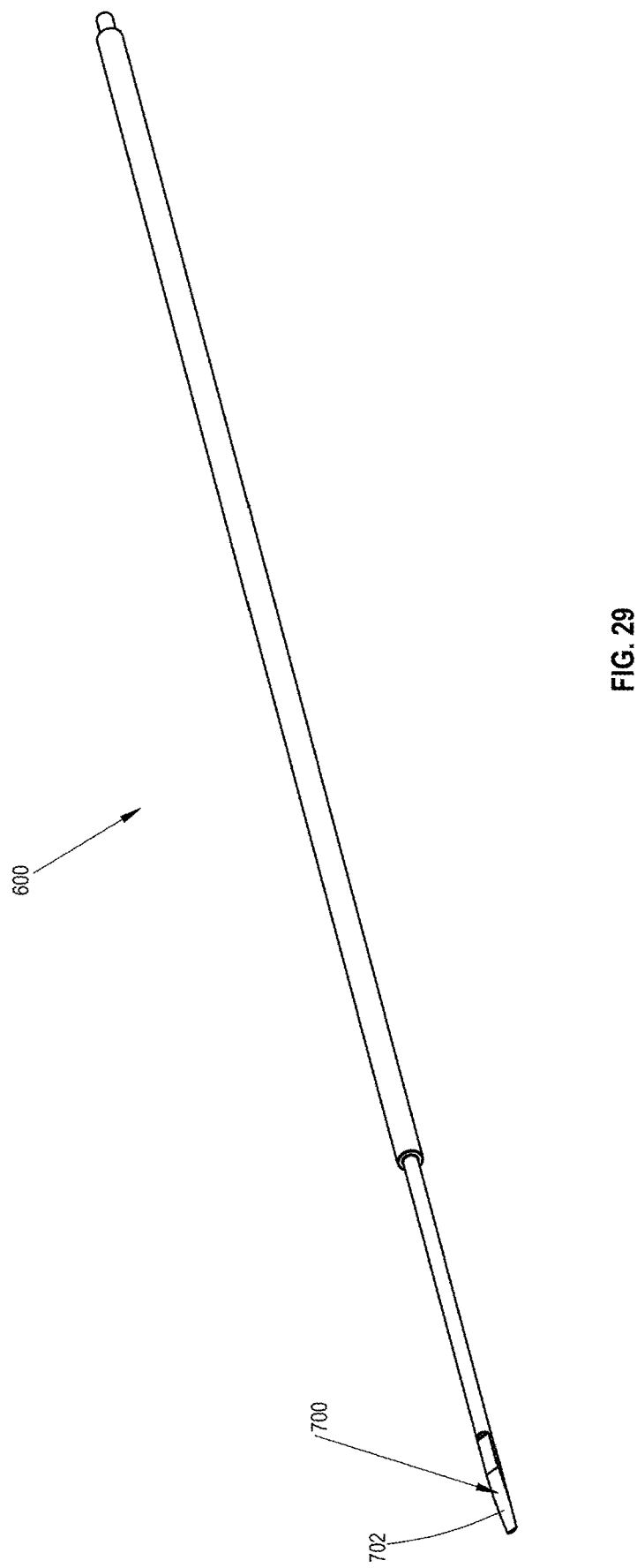

Reference is now made to FIGS. 28 and 29, which are pictorial illustrations of two parts of shaft element 630, forming part of the bone material removal device 600 of FIG. 26B.

It is seen in FIGS. 28 and 29, which together form the shaft element 630 that it is preferably longitudinal integrally made element having proximal portion 632 and a distal end 700 for insertion into the tubular element 604. The distal end 700 of shaft element 600 comprises a distally extending tapered surface 702. A through bore 704 extending transversely with respect to longitudinal axis 609 is located adjacent and slightly distally from the proximal end of proximal portion 632. Through bore 704 is configured for insertion of positioning pin 634 there through.

Figure 30:
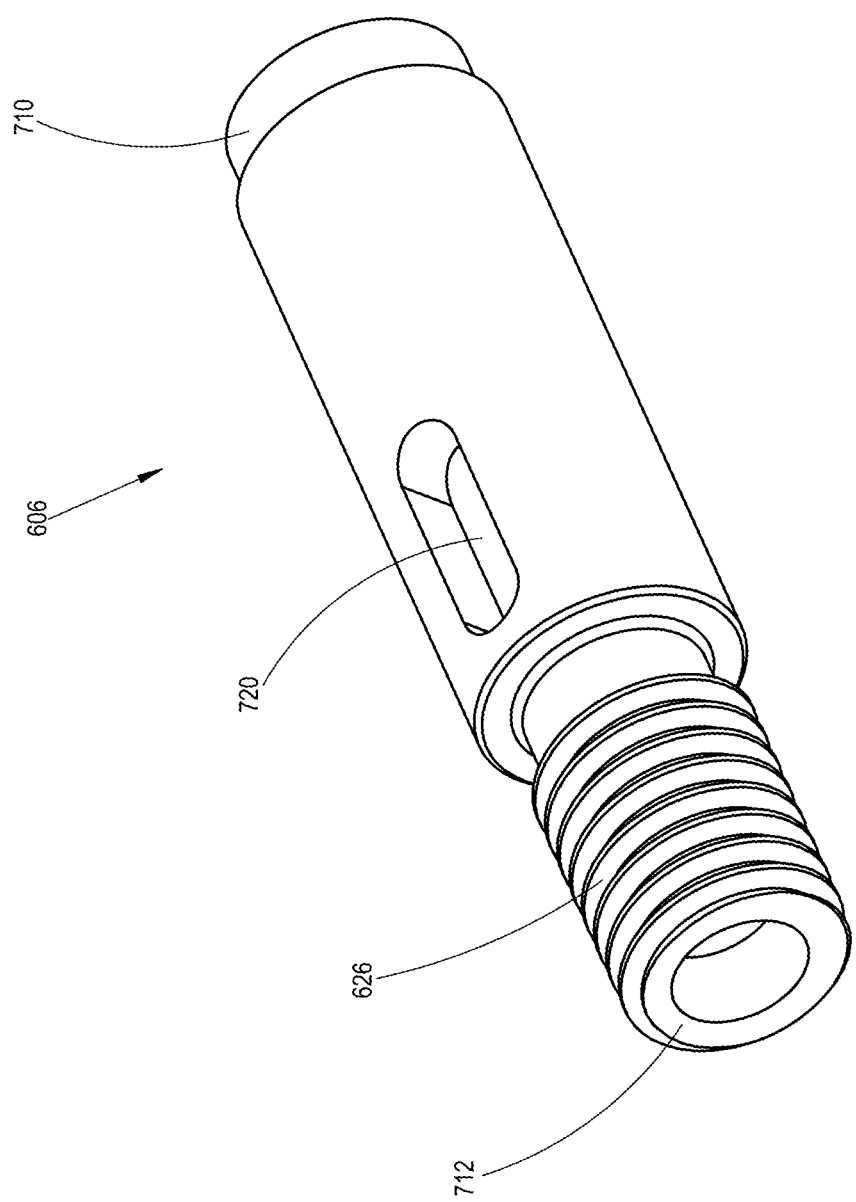
FIG. 30 is a simplified pictorial illustration of a sleeve element, forming part of the bone material removal device of FIG. 26B.

Reference is now made to FIG. 30, which is a simplified pictorial illustration of sleeve 606, forming part of the bone material removal device of FIG. 26B.

It is appreciated that sleeve 606 forms the distal portion of tubular element 604. Sleeve 606 comprises a generally longitudinal hollow cylindrical integrally made element having a proximal end 710 configured to be attached to rotating element 602 and a distal end 712 configured to be attached to cannula retaining element 607.

It is further seen in FIG. 30 that preferably two longitudinal guiding slots 720 are formed on sleeve 606. Guiding slots 720 extend along an axis, which is transversely disposed with respect to longitudinal axis 609 and are preferably aligned with each other.

Figure 31:
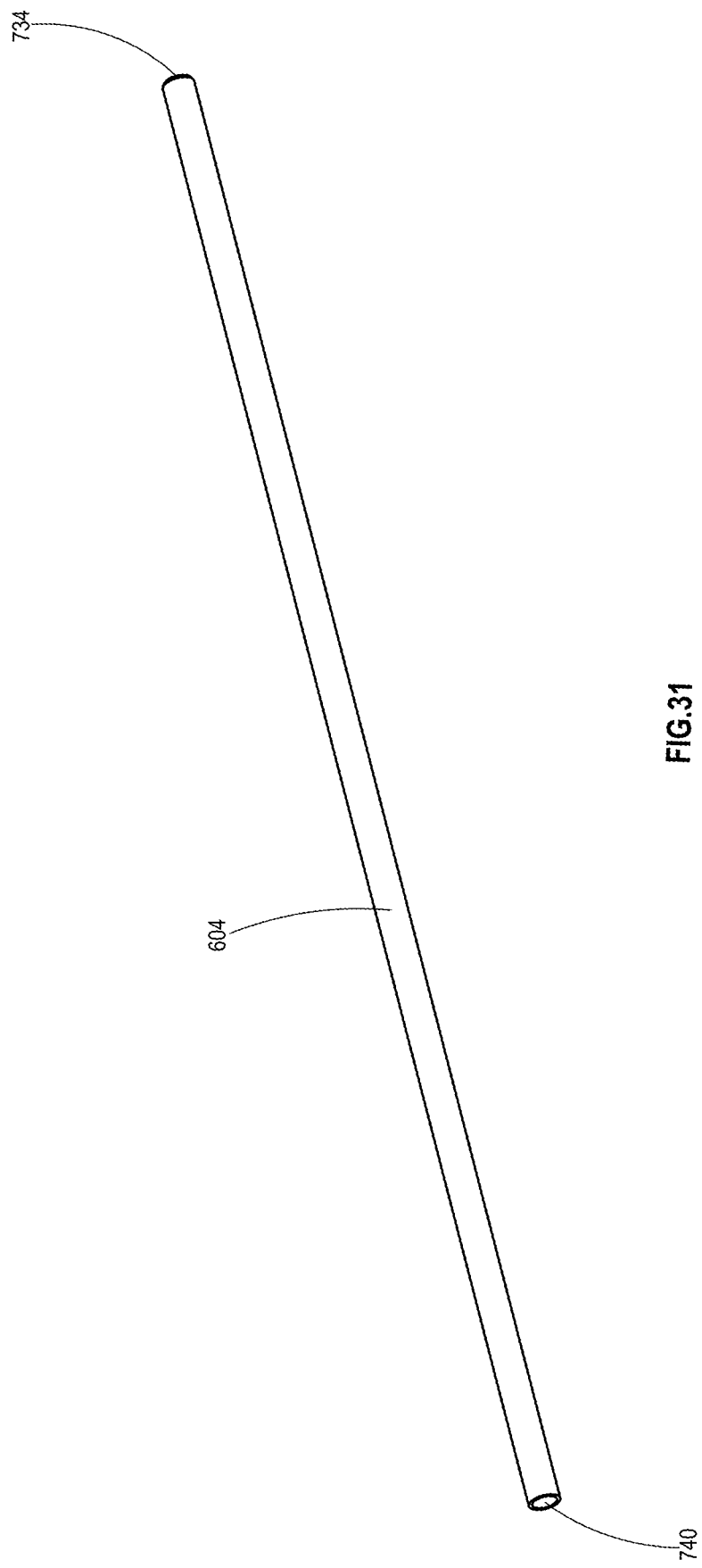
FIG. 31 is a simplified pictorial illustration of a proximal portion of a tubular element, forming part of the bone material removal device of FIG. 26B.
Figure 32:
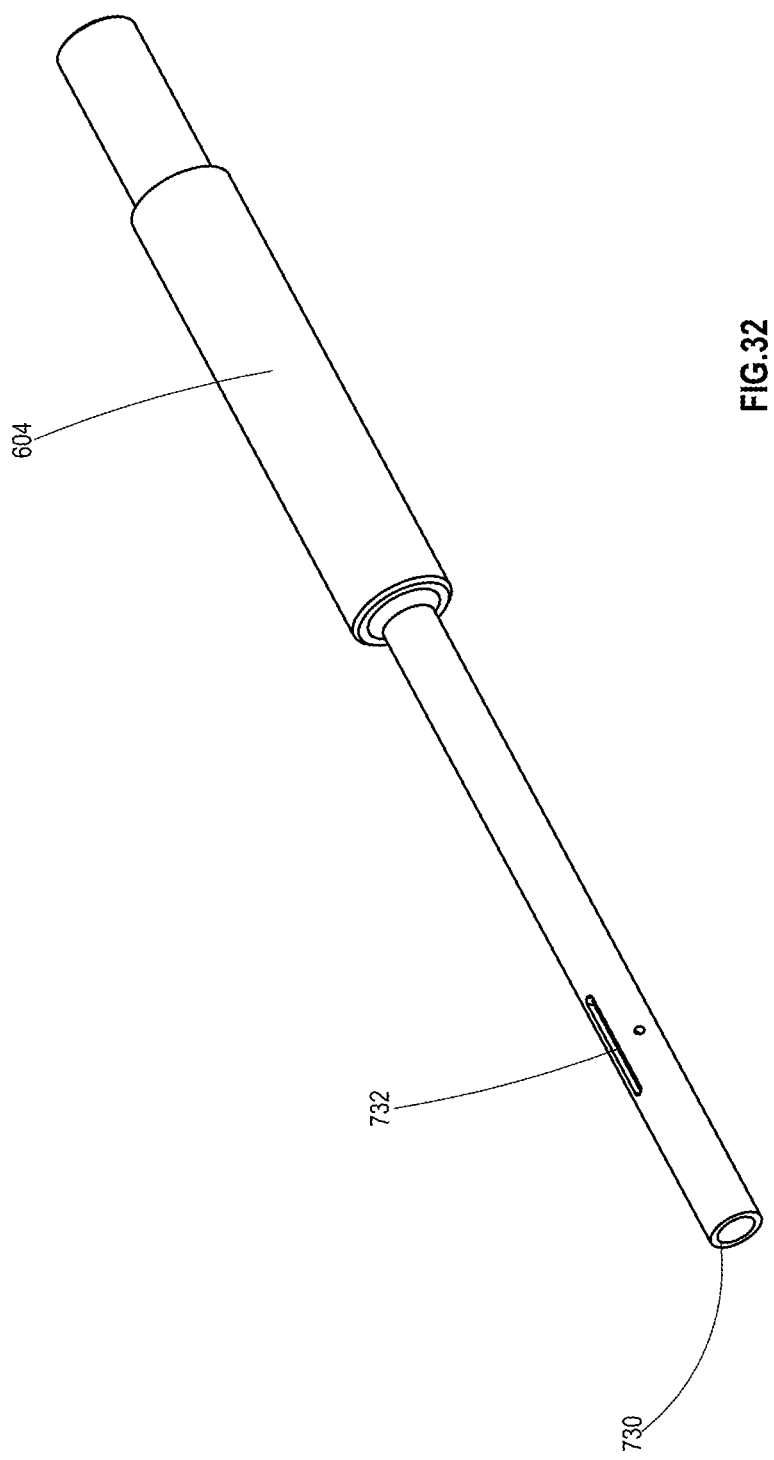
FIG. 32 is a pictorial illustration of a distal portion of the tubular element, forming part of the bone material removal device of FIG. 26B.

Reference is now made to FIG. 31, which is a simplified pictorial illustration of a proximal portion of a tubular element 604, forms part of the bone material removal device 600 of FIG. 26B and to FIG. 32, which is a pictorial illustration of a distal portion of the tubular element 604, forming part of the bone material removal device 600 of FIG. 26B.

It is appreciated that the distal and the proximal portions of the tubular element 604 can be either attached to each other or integrally made with each other.

The distal portion of the tubular element 604 comprises a distal end 730, which is configured to be connected to the tip element 608. In some embodiments, tubular element 604 comprises an opening 732 adjacent the distal end 730 for receiving the cutting tooth 640 therein and allow the cutting tooth 640 to protrude through the opening 732 when the cutting tooth 640 is situated in an open operative orientation.

The proximal portion of the tubular element 604 comprises a proximal end 734 that is configured to be attached to cannula retaining element 607.

Tubular element 604 comprises a bore 740 throughout at least a portion of its length, which is configured to receive and enclose shaft element 630.

Figure 33:
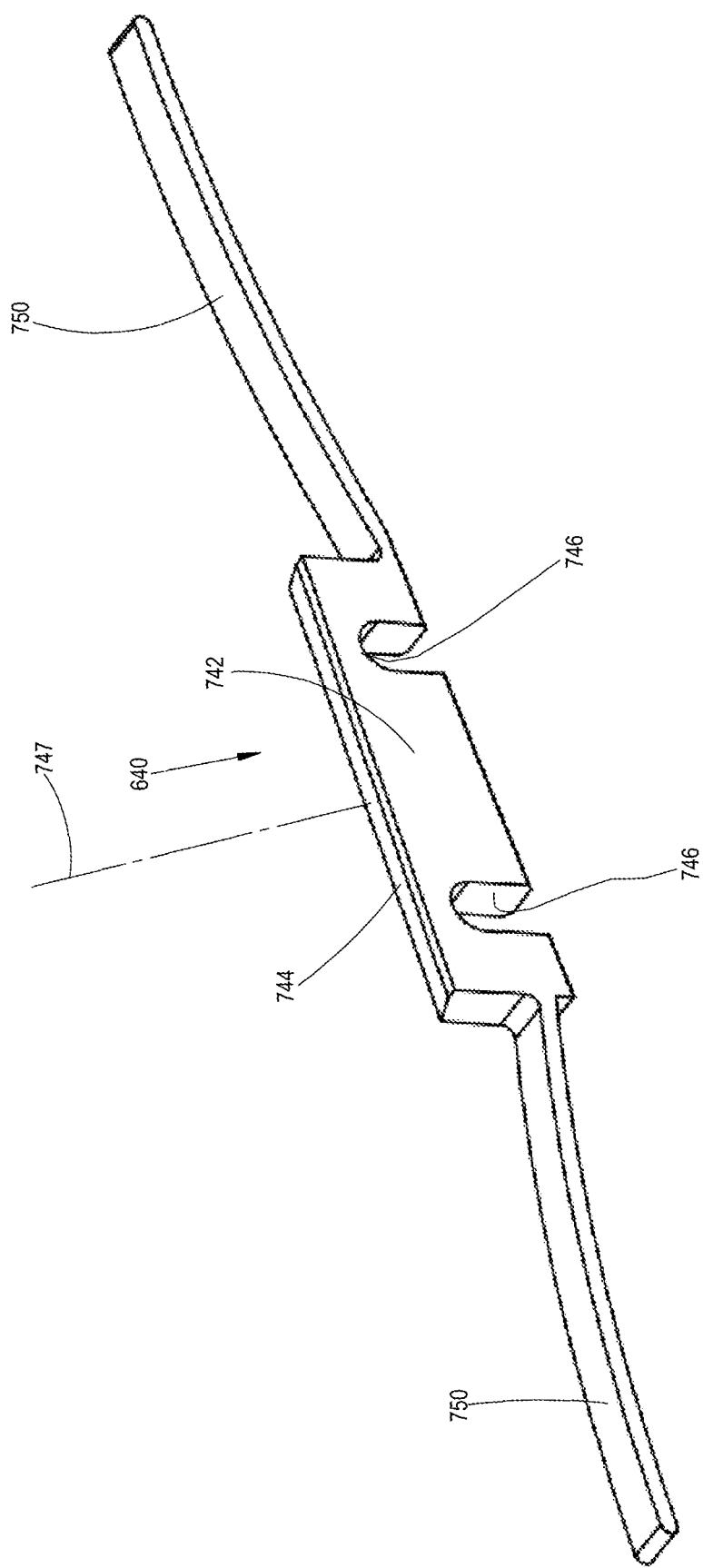
FIG. 33 is a simplified pictorial illustration of a cutting tooth element, forming part of the bone material removal device of FIG. 26B.

Reference is now made to FIG. 33, which is a simplified pictorial illustration of cutting tooth 640, forms part of the bone material removal device 600 of FIG. 26B.

Cutting tooth 640 comprises an integrally made element having a central portion 742 having a sharp edge 744 formed thereon. Preferably one, two or more recesses 746 are formed within the central portion 742 for insertion of pins 448 therethrough to enable attachment of the cutting tooth 740 to tubular element 604 while providing for axial displacement of the central portion 742 of the cutting tooth 640 along an axis 747 that is disposed transversely to longitudinal axis 609. In some embodiments, in operation, pins 448 act as selective stoppers, stopping cutting tooth 640 from displacing axially but allowing movement in other directions, e.g., allowing tooth element 440 to slide radially when urged axially distally and extend radially in respect to longitudinal axis 609. A leaf spring portion 750 is generally attached or integrally formed at the opposite distal and proximal sides of the central portion 742.

Figure 34:
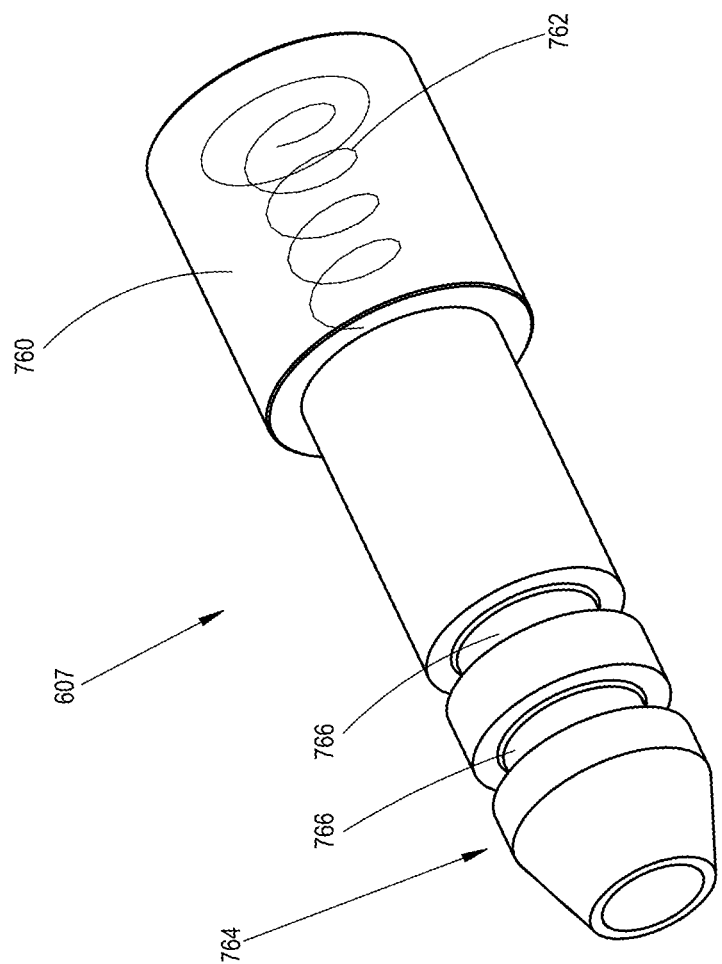
FIG. 34 is a pictorial illustration of a cannula retaining element, forming part of the bone material removal device of FIG. 26B.

Reference is now made to FIG. 34, which is a pictorial illustration of cannula retaining element 607, forms part of the bone material removal device 600 of FIG. 26B.

Cannula retaining element 607 is preferably and in some embodiments an integrally made generally elongate cylindrical element having a proximal portion 760 having a threaded inner portion 762 which is configured to engage an outer threaded portion of sleeve 606. The cannula retaining element 607 also comprises a distal portion 764. Typically and in some embodiments one, two or more circumferential grooves 766 are located adjacent the distal portion 764 for positioning of O-rings 625 therein.

Figure 35:
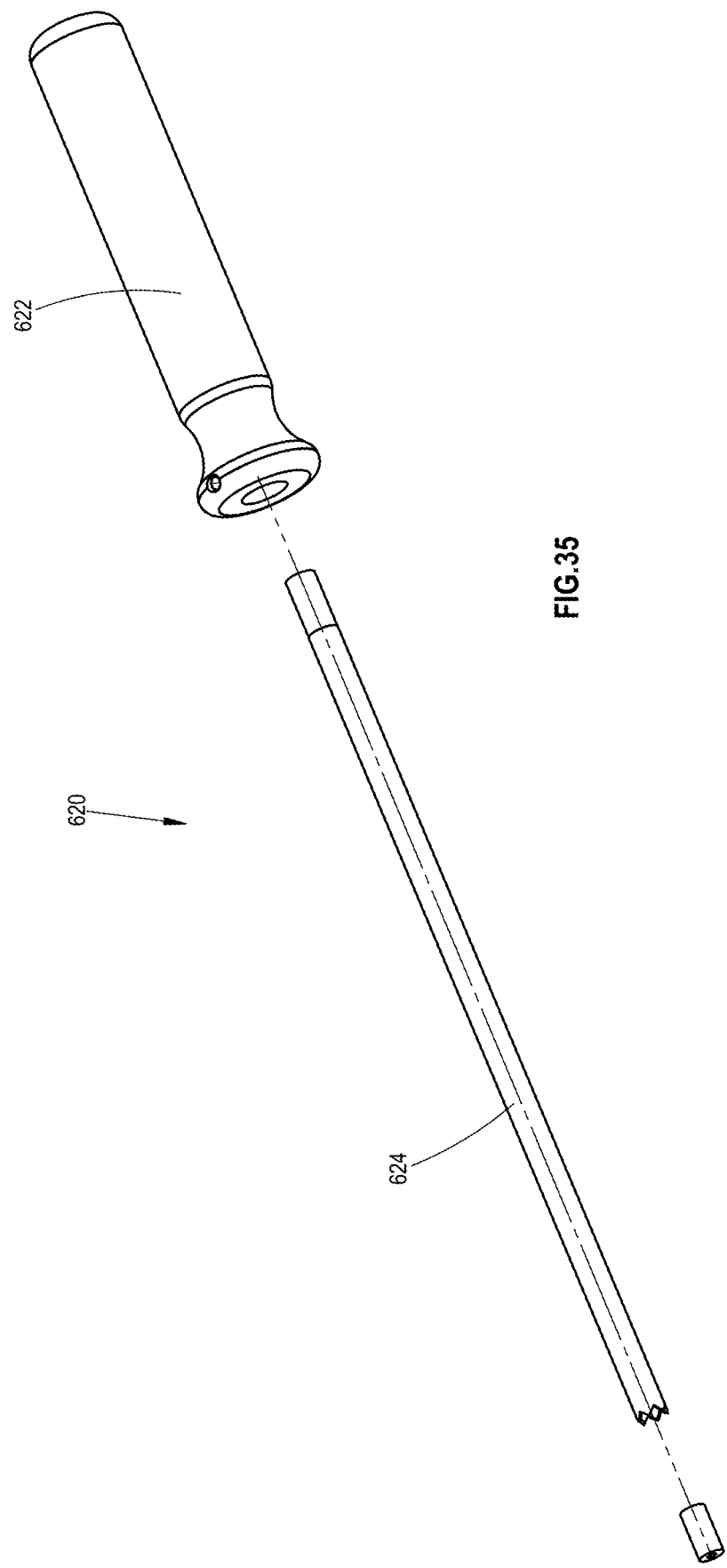
FIG. 35 is a simplified exploded view illustration of the cannula assembly, constructed and operative in accordance with some embodiments of the present invention.

Reference is now made to FIG. 35, which is a simplified exploded view illustration of the cannula assembly 620, constructed and operative in accordance with some embodiments of the present invention.

It is seen in FIG. 35 that the cannula assembly 620 includes a handle 622 and a hollow cannula 624, which is configured to be connected to the handle 622 and mounted over the bone material removal device 600 and arranged along longitudinal axis 609.

Figure 36:
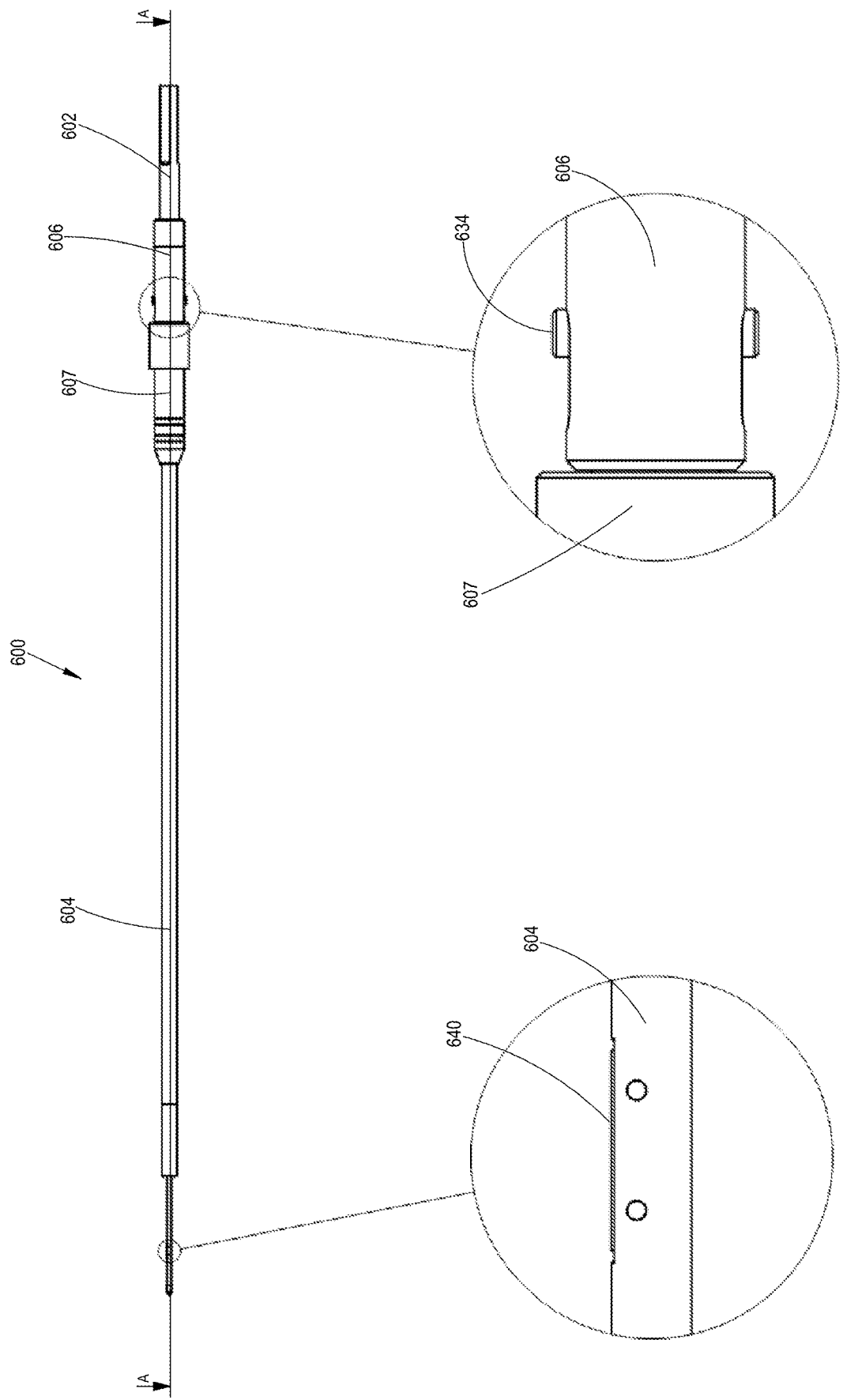
FIG. 36 is a simplified assembled plan view illustration of the bone material removal device of FIG. 26B shown in a closed operative orientation and enlargements thereof.
Figure 37:
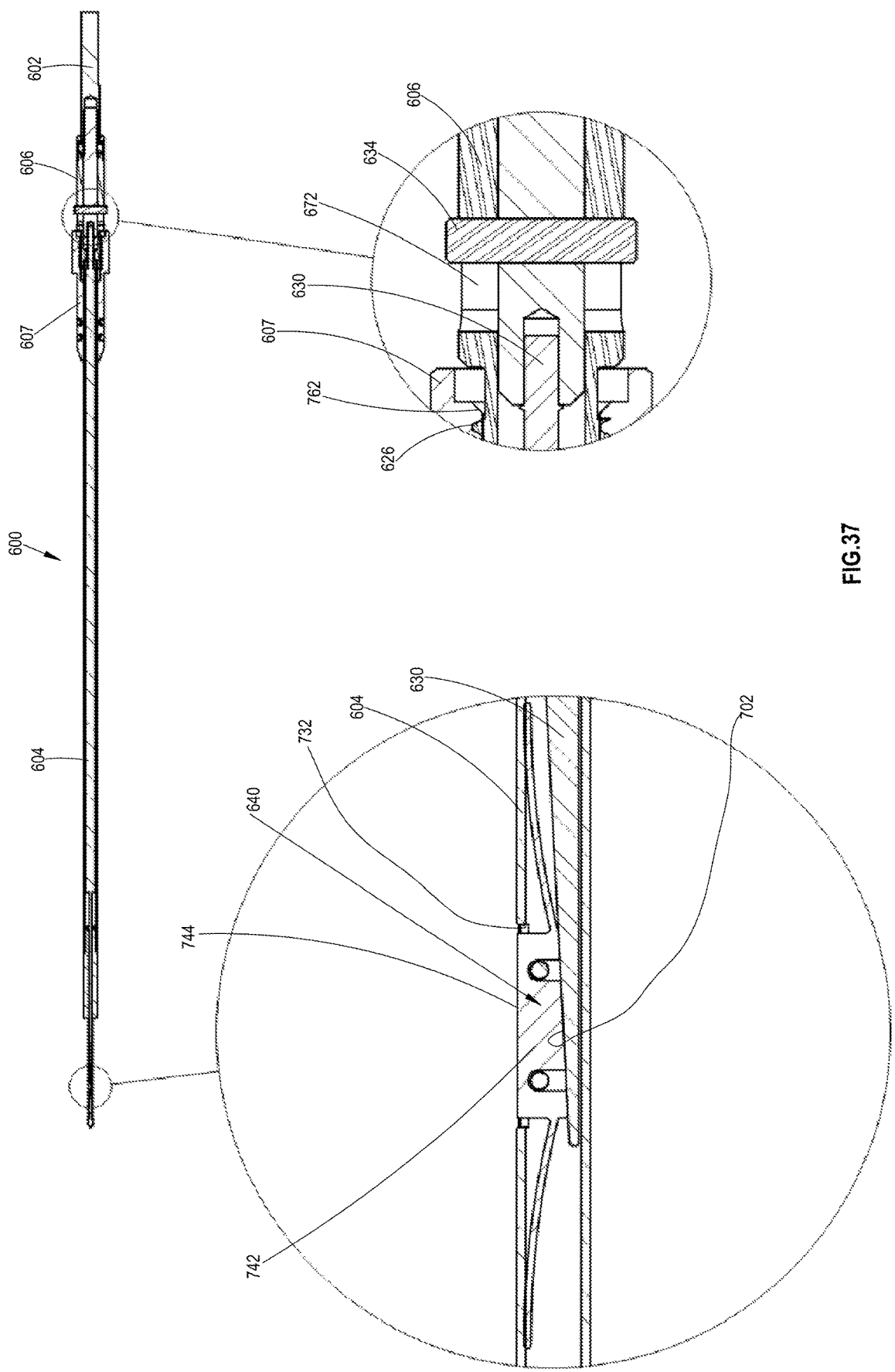
FIG. 37 is a simplified sectional view illustration of the bone material removal device of FIG. 36 shown in the closed operative orientation and enlargements thereof, section view being taken along lines A-A in FIG. 36.

Reference is now made to FIG. 36, which is a simplified assembled plan view illustration of an exemplary embodiment of the bone material removal device 600 of FIG. 26B shown in a closed operative orientation and enlargements thereof and to FIG. 37, which is a simplified sectional view illustration of the bone material removal device 600 of FIG. 36 shown in the closed operative orientation and enlargements thereof, section view being taken along lines A-A in FIG. 36.

Figure 40A:
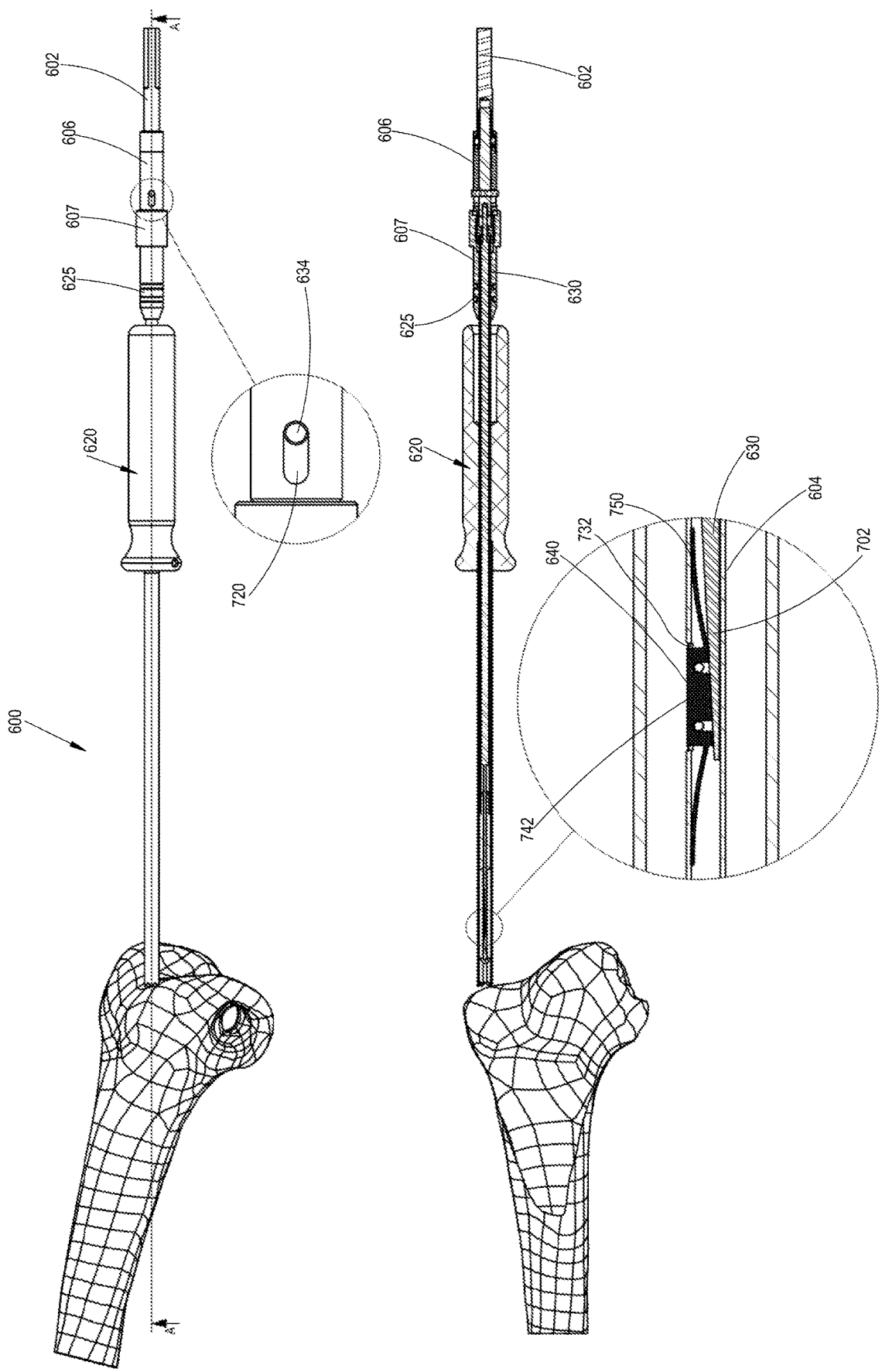
FIGS. 40A and 40B are simplified sectional illustrations of the bone material removal device and the cannula assembly of FIG. 26A shown in the closed operative orientation partially inserted into a bone of a patient and an enlargement thereof.
Figure 40B:
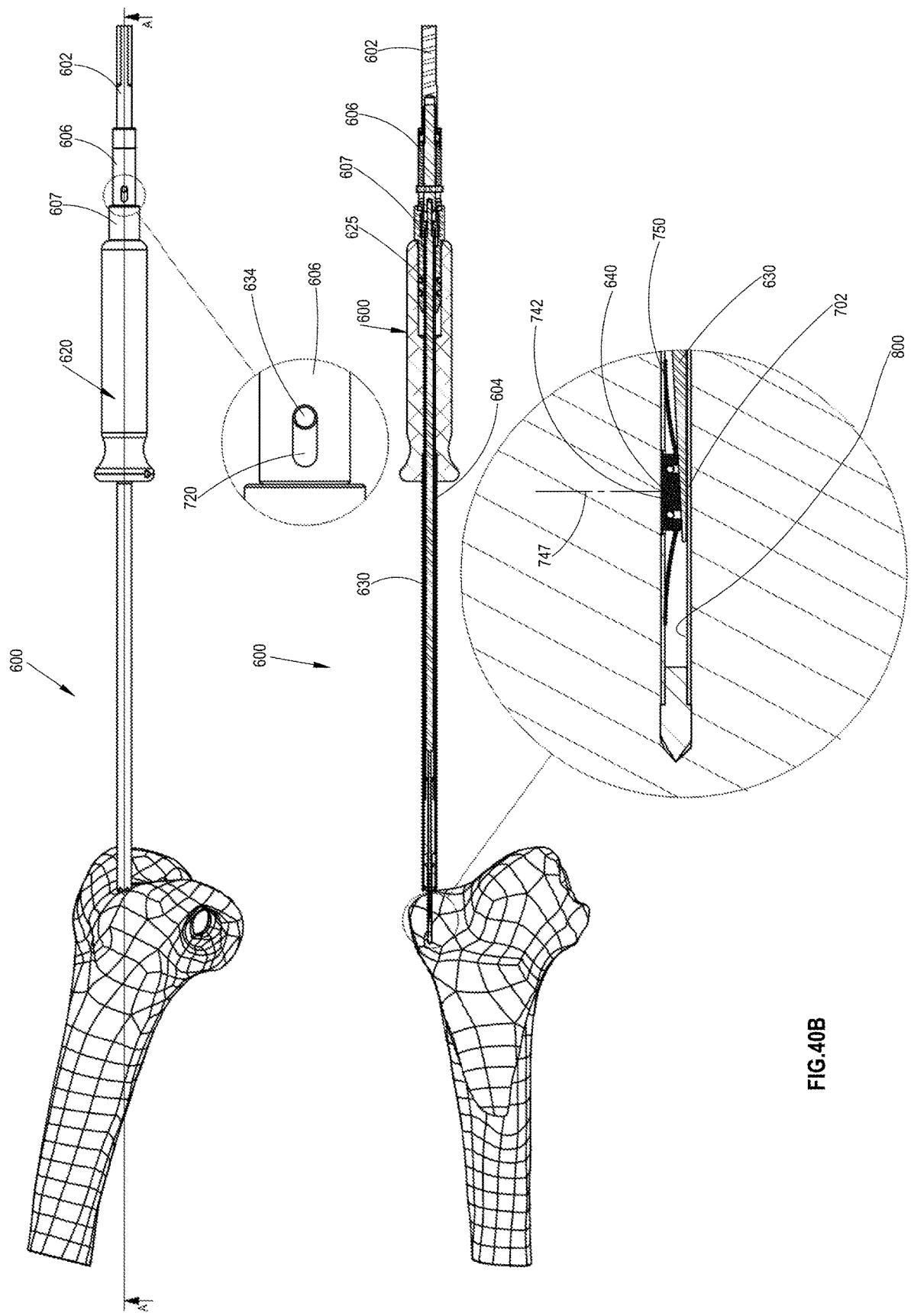

Reference is additionally made to FIGS. 40A and 40B, which are simplified sectional illustrations of an exemplary embodiment of the bone material removal device 600 and the cannula assembly 620 of FIG. 26A shown in the closed operative orientation partially inserted into a bone of a patient and an enlargement thereof.

It is seen in FIGS. 36 and 37 and in FIGS. 40A and 40B that the bone material removal device 600 is positioned in a closed operative orientation, in which the cutting tooth 640 is closed and received inside hollow 416, and does not protrude through opening 732, thus the diameter of the bore formed in the bone of the patient while drilling in the closed operative orientation of the bone material removal device 600 is equal to the outer diameter of the distal portion of tubular element 604 shown in FIG. 32.

It is seen that tubular element 604 is rotatably connected to rotating element 602 by means of sleeve 606.
It is a particular feature of some embodiments of the present invention that threaded portion 626 of sleeve 606 is interthreaded with inner threading 762 of cannula retaining element 607. The shaft element 630 is disposed at its proximal operative orientation in this closed position and is attached to the tubular element 604 by means of indicating pin 634.

It is a particular feature of some embodiments of the present invention that the indicating pin 634 is positioned at the proximal end of guiding slot 720 of sleeve 606 when the bone material removal device is positioned at the closed operative orientation, since the indicating pin 634 is inserted into bore 704 of shaft element 630, which is disposed at the proximal operative orientation at this stage.

It is further particularly seen in FIGS. 37, 40A and 40B that the proximally tapered surface 702 of shaft element 630 engages the central portion 742 of cutting tooth 640 but does not urge it to be radially displaced, thus the cutting tooth 640 remains closed in this operative orientation inside hollow 416.

It is a particular feature of some embodiments of the present invention that when the shaft element is positioned in its proximal operative orientation, the cutting tooth 640 is fully enclosed within the tubular element 604 hollow 416 and does not protrude through opening 732.

It is particularly seen in the embodiments shown in FIGS. 40A and 40B that bone material removal device 600 is inserted into the bore of cannula assembly 620. It is appreciated that the cannula assembly is positioned at its distal position in respect to tubular element 604, thus the cannula handle does not engage the cannula retaining element 607 and the tubular element 604 freely rotates with respect to cannula assembly 620 to drill or ream a bore in a bone.

It is seen in FIG. 40B that an initial bore 800 of a first diameter is formed in the bone of the patient while drilling with the bone material removal device 600 positioned in its closed operative orientation. It is noted that this initial drilling is provided while the rotating element 602 is rotated in a first rotational direction, in this exemplary embodiment, in a clockwise direction.

While the rotating element 602 and the tubular element 604 are rotating in a clockwise rotational direction, the sharp drilling tip of tip 608 engages the bone of the patient and creates initial bore 800 therein.

It is appreciated that any number of openings 732 can be formed in tubular element 604 for accommodating one or more cutting teeth 640.

It is appreciated that the shaft element 630 is slidably engaged with cutting tooth 640, such that the distally tapered surface 702 of the shaft element 630 engages the central portion 742 of the cutting tooth and the distal edge of the shaft element 630 is generally aligned with or slightly distally extends with respect to the distal edge of the central portion 642 of the cutting tooth 640, this position is defined as the proximal operative orientation of the shaft element 630.

It is a particular feature of some embodiments of the present invention that when the shaft element 630 is positioned in its proximal operative orientation, the cutting tooth 640 is fully enclosed within the tubular element 604 hollow 416 and does not protrude through opening 732 due to the fact that the leaf springs 750 are positioned in their unstressed orientation, biasing the cutting tooth 640 into its closed position, since there is no force exerted on the central portion 742 of the cutting tooth 640 at the proximal operative orientation of the shaft element 630.

Figure 38:
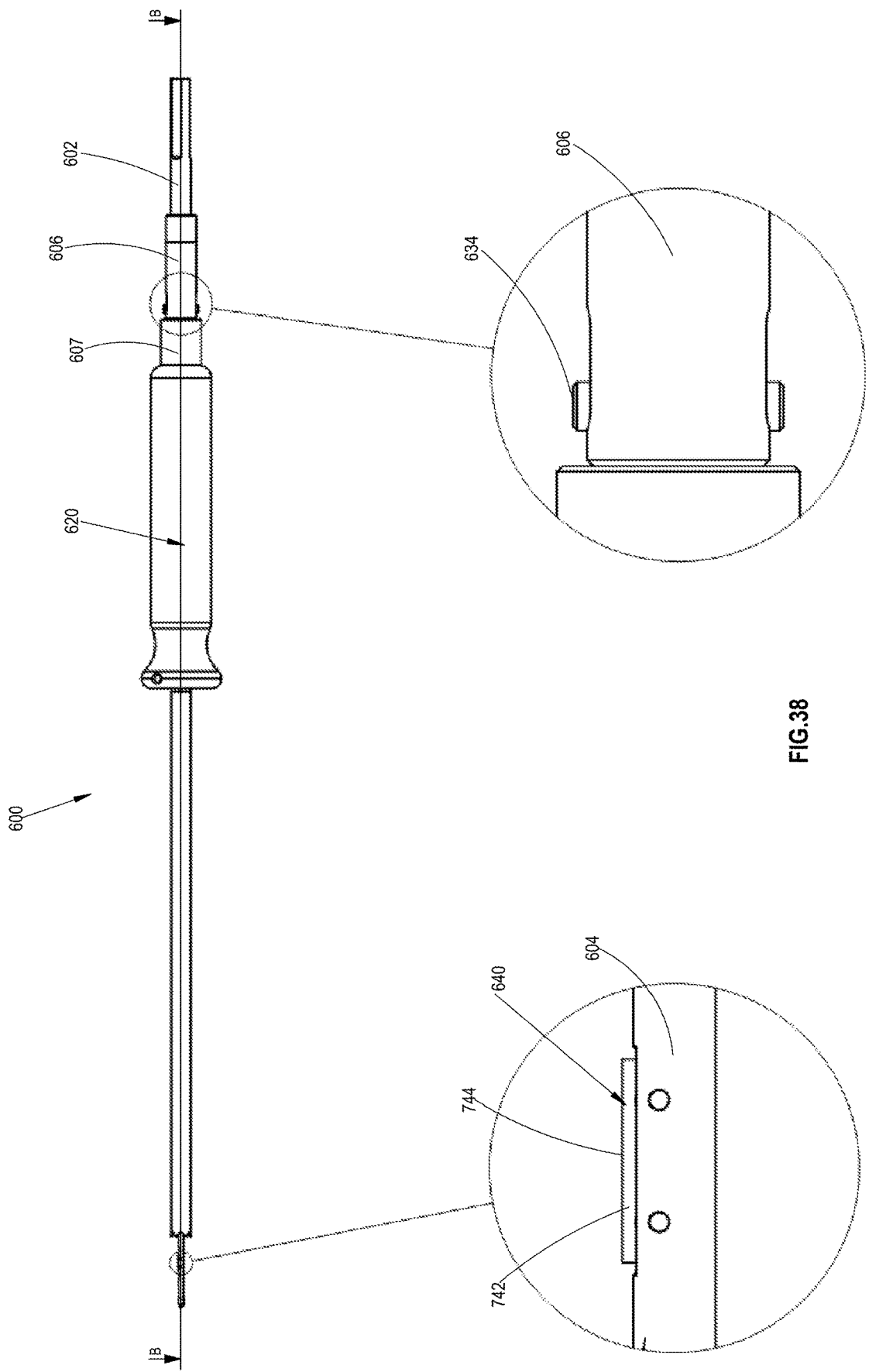
FIG. 38 is a simplified assembled plan view illustration of the bone material removal device of FIG. 26B shown in an open operative orientation and enlargements thereof.
Figure 39:
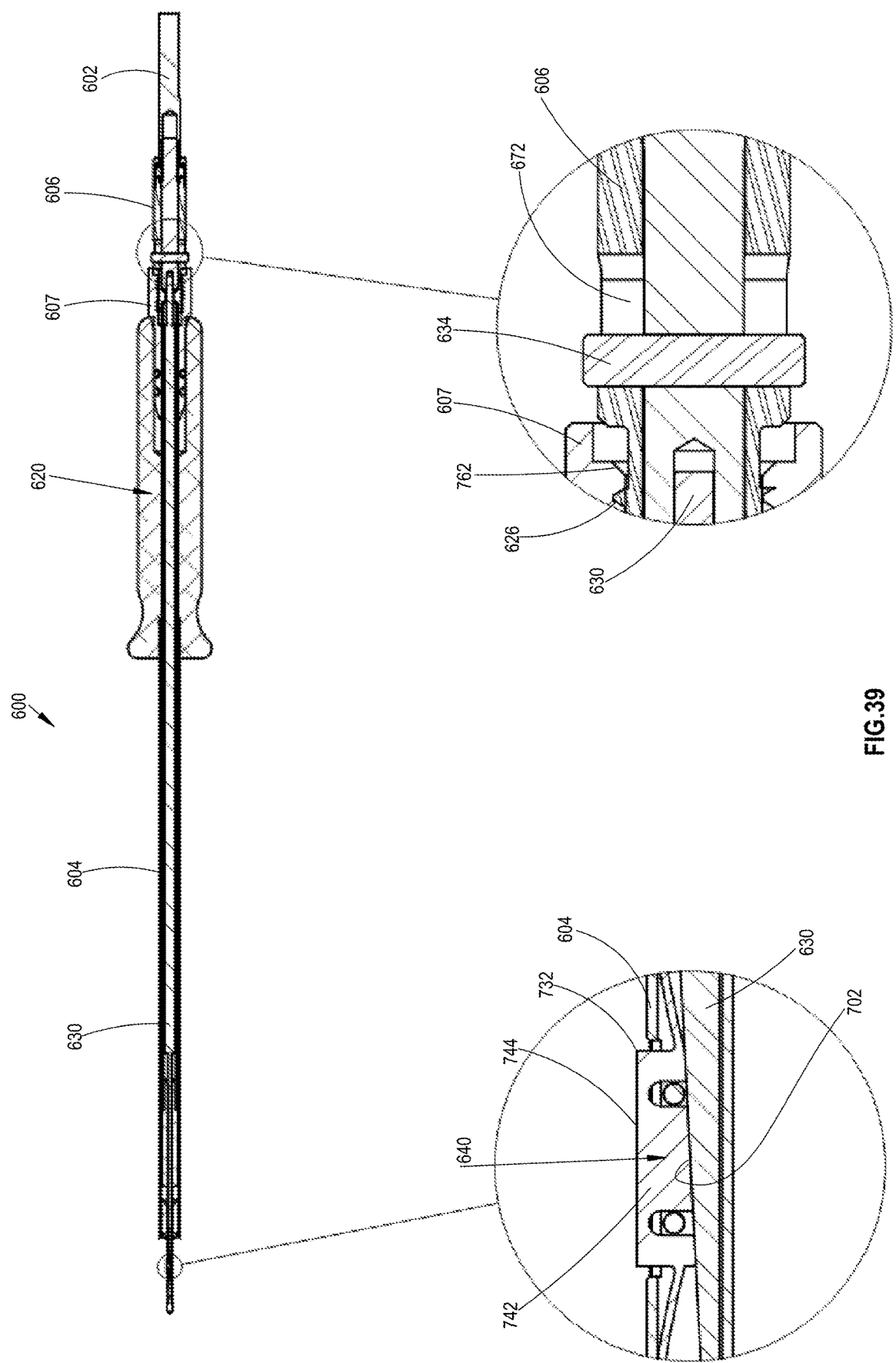
FIG. 39 is a simplified sectional view illustration of the bone material removal device of FIG. 38 shown in the open operative orientation and enlargements thereof, section view being taken along lines B-B in FIG. 38.
Figure 41:
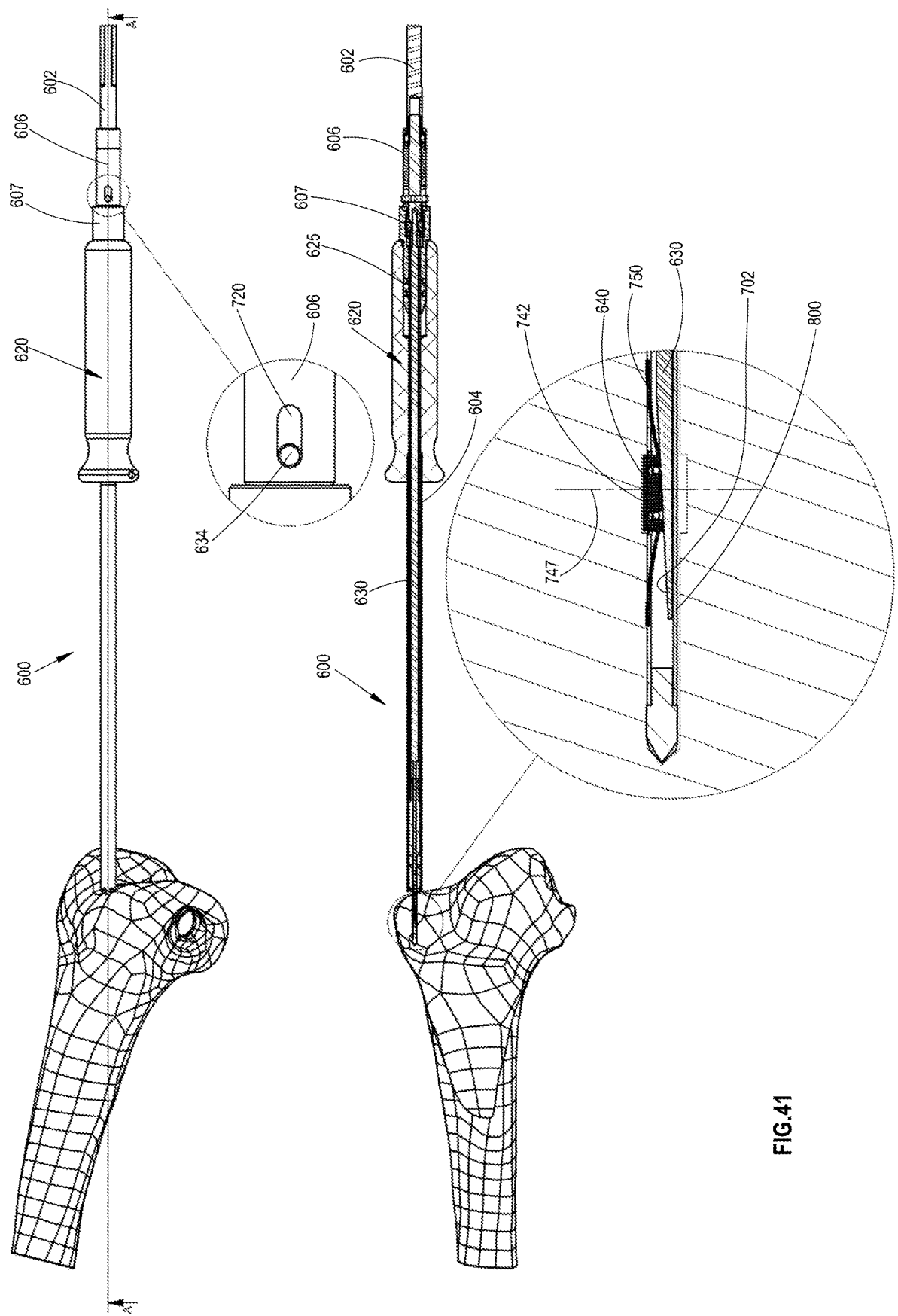
FIG. 41 is a simplified sectional view illustration of the bone material removal device of FIG. 26A shown in an open operative orientation and enlargements thereof.
Figure 42:
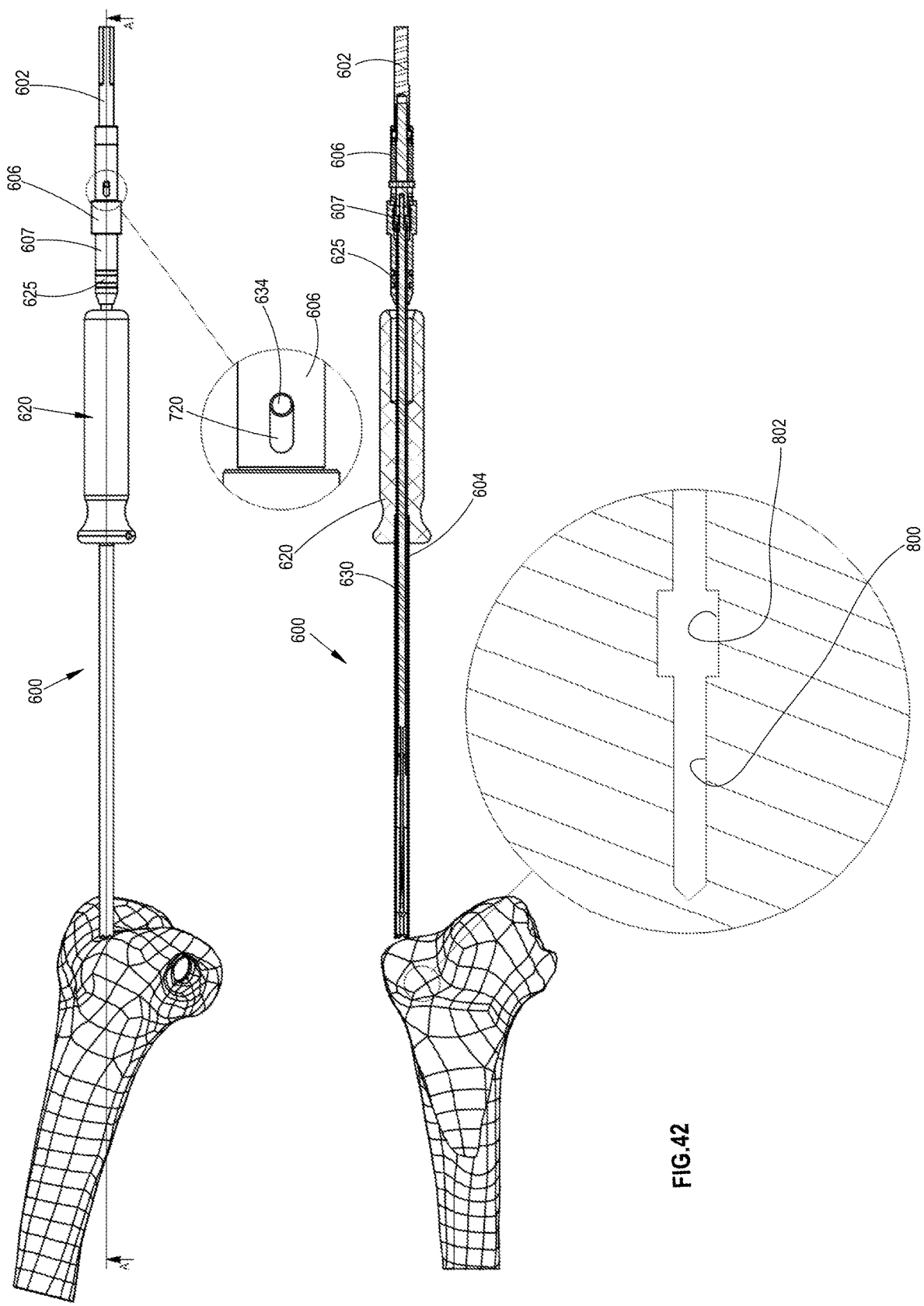
FIG. 42 is a simplified sectional view illustration of the bone material removal device of FIG. 26A shown during removal from the bone of the patient.

Reference is now made to FIG. 38, which is a simplified assembled plan view illustration of an exemplary embodiment of the bone material removal device 600 of FIG. 26B shown in an open operative orientation and enlargements thereof and to FIG. 39, which is a simplified sectional view illustration of the bone material removal device 600 of FIG. 38 shown in the open operative orientation and enlargements thereof, section view being taken along lines B-B in FIG. 38. Reference is now made to FIG. 41, which is a simplified sectional view illustration of an exemplary embodiment of the bone material removal device 600 of FIG. 26A shown in an open operative orientation and enlargements thereof. Reference is further made to FIG. 42, which is a simplified sectional view illustration of an exemplary embodiment of the bone material removal device 600 of FIG. 26A shown during removal from the bone of the patient.

It is seen in FIGS. 38, 39 and 41 that the bone material removal device 600 is positioned in an open operative orientation, in which the cutting tooth 640 is open, extends radially and protrudes through opening 732, thus the diameter of the bore formed in the bone of the patient while drilling in the open operative orientation of the bone material removal device 600 is greater than the outer diameter of tubular element 604.

It is a particular feature of some embodiments of the present invention that threaded portion 626 of sleeve 606 is interthreaded with threading 762 along a portion of an inner wall of cannula retaining element 607. The shaft element 630 is disposed at its distal operative orientation in this open position and is attached to the tubular element 604 by means of indicating pin 634.

It is a particular feature of some embodiments of the present invention that the indicating pin 634 is positioned at the distal end of guiding slot 720 of tubular element 604 when the bone material removal device is positioned at the open operative orientation, since the indicating pin 634 is inserted into bore 704 of shaft element 630, which is disposed at the distal operative orientation at this stage.

It is further particularly seen in FIGS. 37, 40A and 40B that the proximally tapered surface 702 of shaft element 630 engages the central portion 742 of cutting tooth 640 and urges it to be axially displaced, thus the cutting tooth 640 moves to its open operative orientation.

It is a particular feature of some embodiments of the present invention that when the shaft element 630 is positioned in its distal operative orientation, the cutting tooth 640 protrudes from tubular element 604 through opening 732.

It is particularly seen in FIG. 41 that bone material removal device 600 is inserted into the bore of cannula assembly 620. It is appreciated that the cannula assembly is positioned at its proximal position, thus the cannula handle engages the cannula retaining element 607 and friction force is created between the tubular element 604 and the cannula assembly 620 in order to stop the rotational movement of the tubular element 104 to enable changing the drilling rotational direction. Frictional force is created by engagement of cannula assembly 620 with O-rings 625 that are located on the cannula retaining element 607.

It is particularly seen in FIG. 41 that bone material removal device 600 is inserted into the bore of cannula assembly. It is seen in FIG. 41 that an undercut bore 802 is formed over the initial bore 800, undercut bore 802 having a second diameter, which is greater than the first diameter while drilling with the bone material removal device 600 positioned in its open operative orientation in which central portion 742 extends radially beyond opening 732. It is noted that this undercut bore drilling is provided while the rotating element 602 is rotated in a second rotational direction, in this exemplary embodiment, in a counter-clockwise direction.

It is a particular feature of some embodiments of the present invention that once the cannula assembly is located at its proximal position, the rotation of the tubular element 604 is momentarily stopped, the rotational direction of the drilling can be reversed, thus causing the threaded portion 626 of shaft element 630 to unthread from internal threading 762 of cannula retaining element 607. Since indicating pin 634 attaches the shaft element 630 to the guiding slot 720 of the sleeve 606, rotation of the shaft element 630 is prevented and this unthreading causes axial displacement of the shaft element 630 in a distal direction. The extent of longitudinal displacement of the shaft element 630 depends on the length of guiding slot 720, thus during the axial displacement of shaft element 630 in a distal direction in respect to cannula retaining element 607, the indicating pin 634 is displaced along the guiding slot 720 from its proximal end to its distal end.

It is a further particular feature of some embodiments of the present invention that longitudinal displacement of shaft element 630 urges the cutting tooth 640 to be displaced radially along axis 747 and protrude through opening 732 of tubular element 604.

In some embodiments, while the rotating element 602 and the tubular element 604 are rotating in a counter-clockwise rotational direction, the cutting edge 744 of cutting tooth 740 engages the bone of the patient and creates undercut bore 802 therein. It is noted that the drilling rotational direction can be reversed at any time by displacing the cannula assembly 620 to its proximal position and the bone material removal device 600 can be advanced and retracted to and from the bone of the patient in order to create the desired length of undercut bore 802.

It is appreciated that in some embodiments, in order to return to the closed operative orientation of the bone material removal device 600, cannula assembly has to be displaced proximally to engage the cannula retaining element 607 so that the drilling rotational directional is reversed in order to urge the shaft element 630 to be displaced axially to the proximal position, thus releasing the cutting tooth 640 to be biased to the closed position. At this stage, the bone material removal device 600 can be removed from the bone of the patient and the resulted variable diameter bore, comprised of initial bore 800 and undercut bore 802, can be seen as illustrated in FIG. 42.

It is further particularly seen in FIG. 41 that the shaft element 630 is slidably engaged with cutting tooth 640, such that the distally tapered surface 702 of the shaft element 630 engages the central portion 742 of the cutting tooth and the distal edge of the shaft element 630 protrudes distally with respect to the distal edge of the central portion 742 of the cutting tooth 640, this position is defined as the distal operative orientation of the shaft element 630.

It is a particular feature of some embodiments of the present invention that when the shaft element 630 is positioned in its distal operative orientation, the cutting tooth 640 is forced radially outwardly through and beyond the opening 732 of tubular element 604 against bias the leaf springs 750 now positioned in their stressed orientation. Cutting tooth 640 is forced radially outwardly into its open position, extending radially through and beyond opening 732, since there is force exerted on the central portion 742 of the cutting tooth 640 at the distal operative orientation of the shaft element 630, resulting from the geometry of a wider portion of the shaft element 630 that engages the central portion 742 of the cutting tooth. the leaf springs 750 are radially deflected outwardly, thus causing radial outward deflection of the central portion 742 of the cutting tooth 640, with the cutting edge 744 formed thereon.

It is a particular feature of some embodiments of the present invention that when the shaft element 630 is positioned in its distal operative orientation, the cutting tooth 640 is axially displaced along an axis 747 that extends radially transversely to longitudinal axis 609 to protrude through opening 732 of tubular element 604.

It is noted that the bone material removal device 100 according to some embodiments of the present invention can be useful in various surgical procedures, such as for example, insertion of an anchor, administration of a drug, insertion of a graft and insertion of an implant in AVN treatment procedures.

Figure 43:
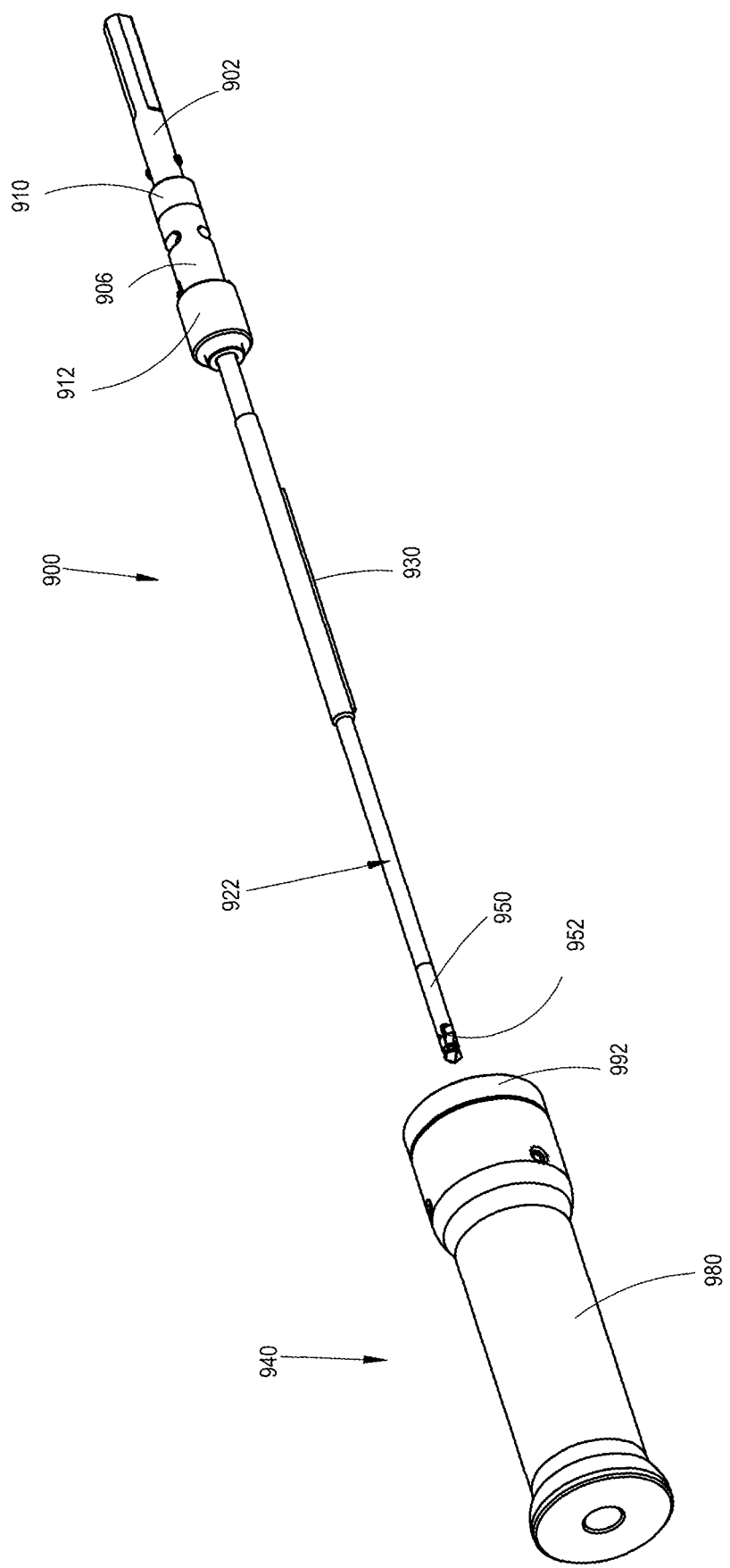
FIG. 43 is a simplified exploded view illustration of a bone material removal device and a cannula assembly, constructed and operative in accordance with still another embodiment of the present invention.
Figure 44:
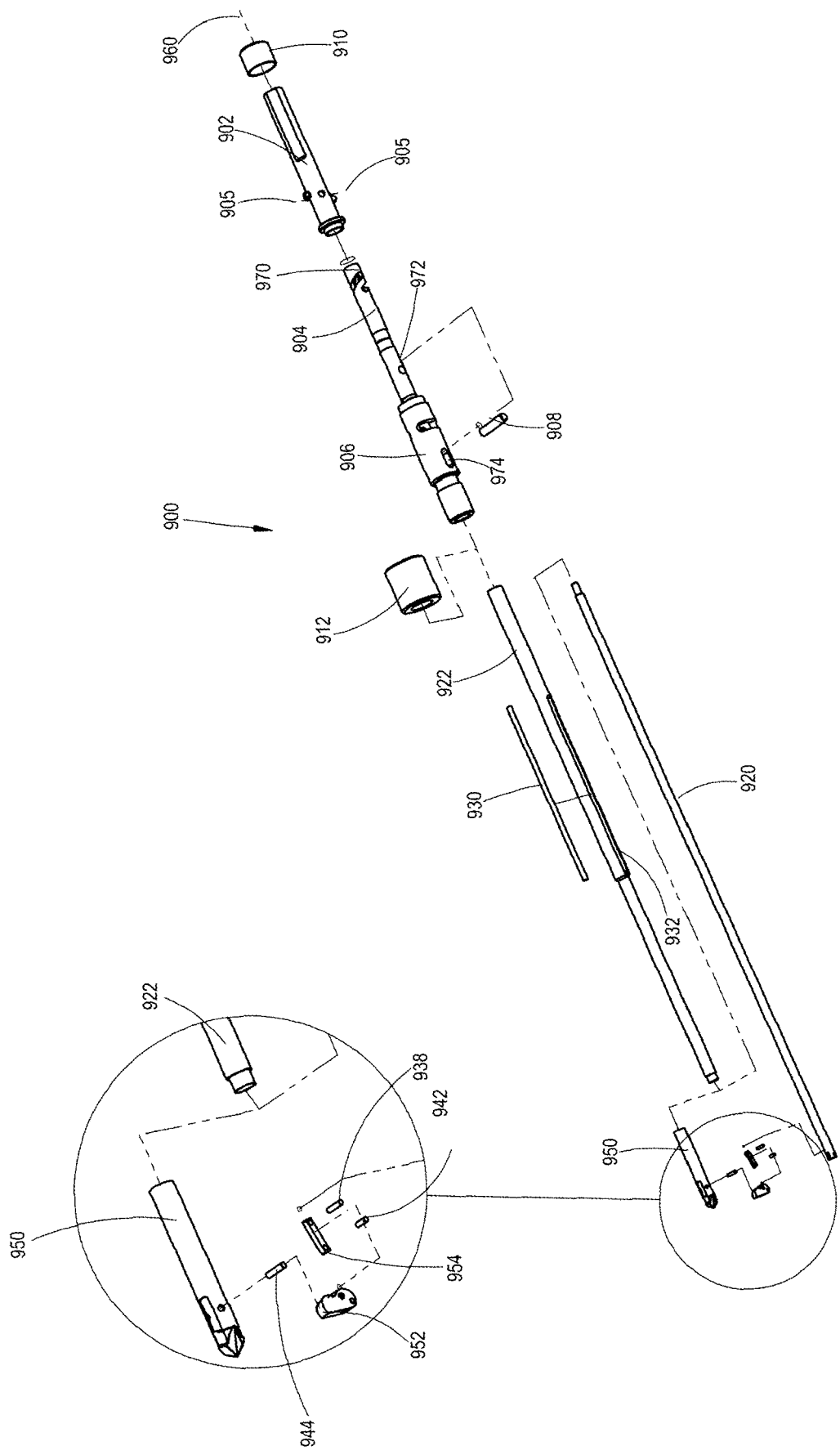
FIG. 44 is a simplified exploded view illustration of the bone material removal device of FIG. 43, constructed and operative in accordance with some embodiments of the present invention.

Reference is now made to FIG. 43, which is a simplified exploded view illustration of a bone material removal device and a cannula assembly, constructed and operative in accordance with some embodiments of the present invention. Reference is additionally made to FIG. 44, which is a simplified exploded view illustration of the bone material removal device of FIG. 43, constructed and operative in accordance with some embodiments of the present invention.

It is seen in FIGS. 43 and 44 that a bone material removal device 900 includes a rotating element 902 configured to be rotatably attached to a guiding element 904 by means of pins 905. Guiding element 904 is in turn slidably attached to a body crank element 906 by means of guiding pin 908 and bearing crank 910.

It is seen that a stopper 912 is arranged to be mounted onto body crank element 906 for limiting axial displacement of guiding pin 908.

It is further seen in FIGS. 43 and 44 that a shaft element 920 is fixedly attached to guiding element 904 and a tubular element 922 is fixedly attached to body crank element 906 and surrounds shaft element 920. It is noted that a tennon 930 is configured to be insertable into a groove 932 formed in the tubular element 922 for cooperation with a cannula assembly 940.

A tip element 950 is attached or integrally made with the tubular element 922. A tooth 952 is arranged to be connected to the shaft element 920 by means of a hinge 954 and pivotably connected to the tip element 950. It is seen in the embodiment in FIG. 44 that hinge element 954 is configured to be rotatably attached at a first end by a pin 938 to an end of the shaft element 920 and at a second end to a cutting tooth 952 via pin 942. The cutting tooth 952 is configured to be rotatably attached to a tip element 950 via a pin 944.

It is seen that rotating element 902, guiding element 904, body crank element 906, bearing crank 910, stopper 912, shaft element 920, tubular element 922 and tip element 950 are all arranged along a single mutual longitudinal axis 960.

It is seen in the embodiment shown in FIG. 43 that cannula assembly 940 is configured to be mounted over the tubular element 922 and arranged along longitudinal axis 960.

It is appreciated that the tubular element 922 is preferably made of a biocompatible material, e.g. metal.

It is further seen in FIGS. 43 and 44 an is described in greater detail elsewhere herein, that the guiding element 904 includes typically at least one helical path 970 cut through a wall of guiding element 904 that typically slidingly receives at least one pin 905 coupled to rotating element 902 and at least one aperture 972 accommodating a guiding pin 908. It is a particular feature of some embodiments of the present invention that rotational displacement of pins 905 along and within helical path 970 of guiding element 904 is converted into axial linear displacement of guiding element 904 bringing about axial linear displacement of guiding pin 908 within a slot 974 formed in body crank element 906. axial linear displacement of guiding element 904 urges shaft element 920 to axial displace along longitudinal axis 960. This longitudinal displacement of shaft element 920, urges pivoting of hinge 954, and thereby causes pivoting of tooth 952 relative to tip element 950.

Figure 45:
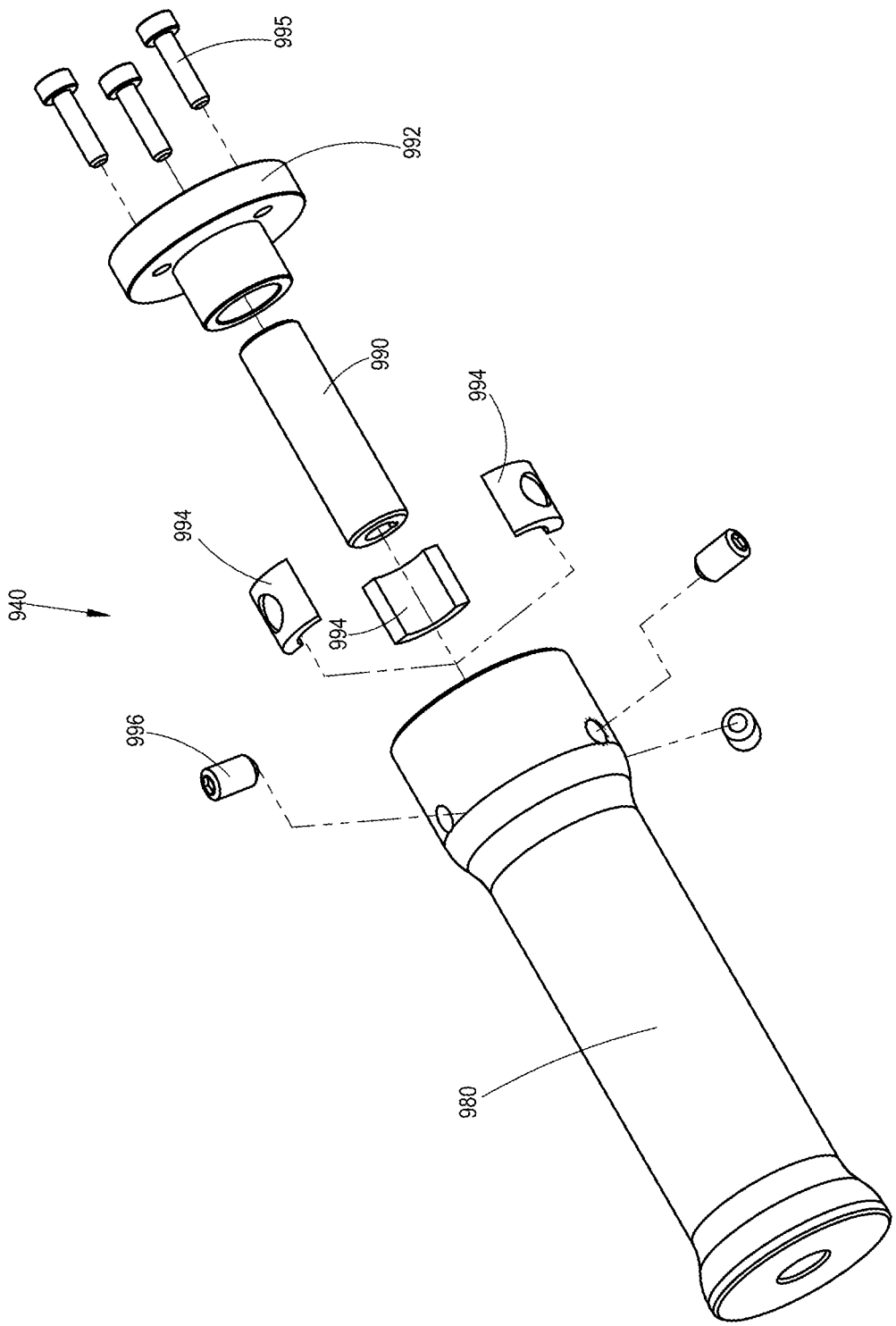
FIG. 45 is a simplified exploded view illustration of the cannula assembly of FIG. 43, constructed and operative in accordance with some embodiments of the present invention.

Reference is now made to FIG. 45, which is a simplified exploded view illustration of an exemplary embodiment of the cannula assembly 940 of FIG. 43, constructed and operative in accordance with some embodiments of the present invention.

It is seen in FIG. 45 that the cannula assembly 940 includes hollow cannula body 980 and a cannula inner sleeve 990, which is configured to be mounted over the bone material removal device 900 and arranged along longitudinal axis 960. Cannula assembly 940 further includes a cannula cover 992, which is con figured to be fixedly attached to the cannula body 980 and a plurality of cannula breaks 994, which engage the cannula inner sleeve 990.

The cannula cover 992 is configured to be fixedly attached to cannula body 980 by means of fixating pins 995. The cannula breaks 994 are fixedly mounted between cannula body 980 and cannula inner sleeve 990 by means of fixating pins 996.

Figure 46:
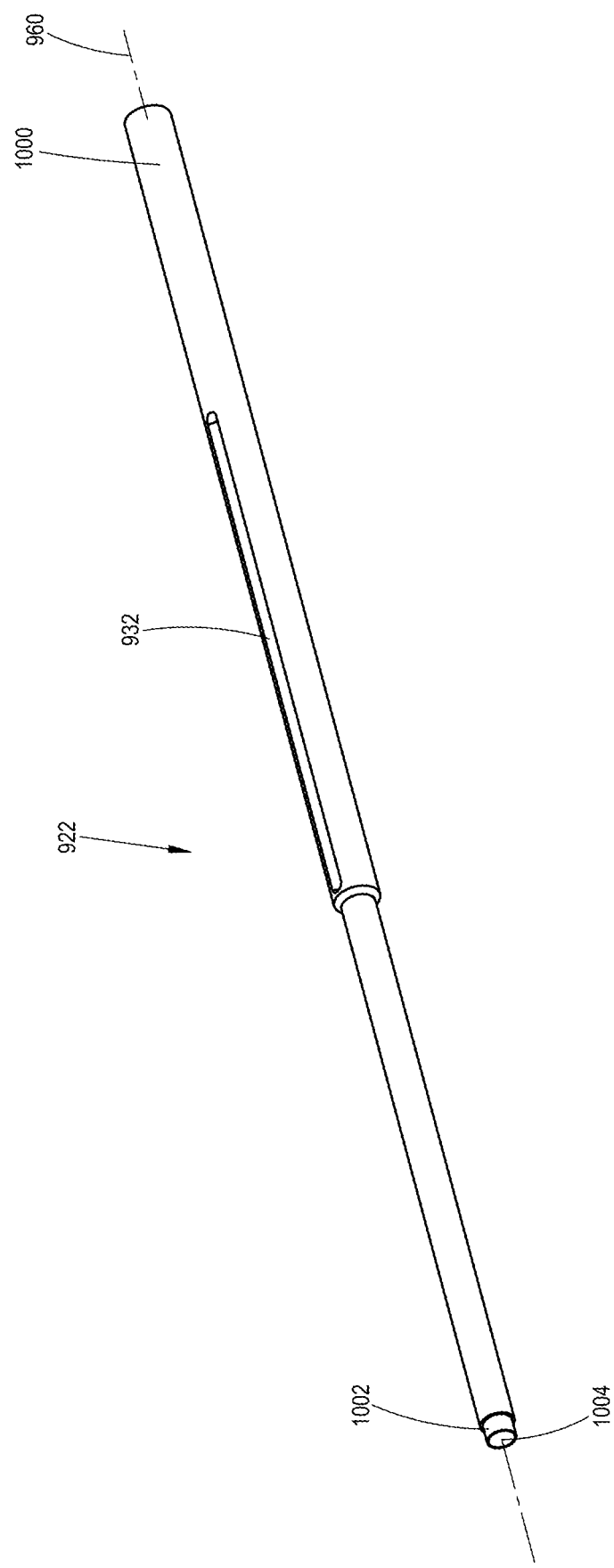
FIG. 46 is a simplified pictorial illustration of a tubular element, forming part of the bone material removal device of FIG. 44.

Reference is now made to FIG. 46, which is a simplified pictorial illustration of a tubular element 922, forms part of the bone material removal device 900 of FIG. 44.

Tubular element 922 is a generally longitudinal hollow cylindrical integrally made element having a proximal end 1000 configured to be attached to body crank element 906 and a distal end 1002 configured to be attached to tip element 950 or integrally made therewith. Tubular element 922 comprises a bore 1004 that extends throughout tubular element 922, which is configured to receive and enclose shaft element 920.

It is further seen in FIG. 46 that groove 932 is formed on tubular element 922 and is configured to receive tennon 930 thereinto.

Figure 47:
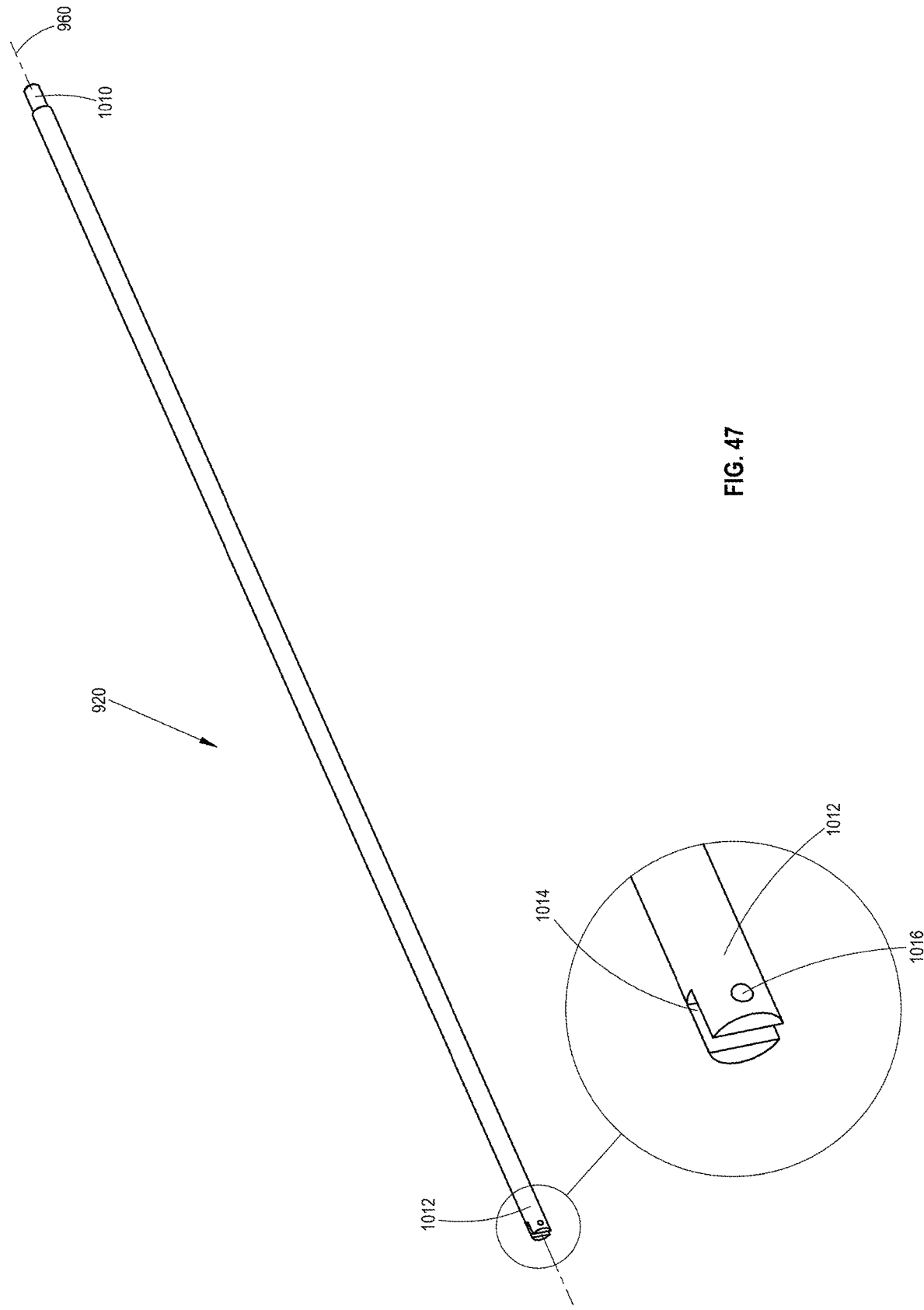
FIG. 47 is a simplified pictorial illustration of a shaft element, forming part of the bone material removal device of FIG. 44.

Reference is now made to FIG. 47, which is a simplified pictorial illustration of an exemplary embodiment of the shaft element 920, forming part of the bone material removal device 900 of FIG. 44.

It is seen in FIG. 47 that shaft element 920 is preferably longitudinal integrally made element having a proximal end 1010, configured to be attached to guiding element 904 and a distal end 1012 for partial insertion into the tip element 950.

It is further seen in FIG. 47 that a recess 1014 is formed at the distal end 1012 of shaft element 920 and extends slightly longitudinally therefrom. A bore 1016 is formed at the distal end 1012 of shaft element 920 and extends transversely with respect to recess 1014. The recess 1014 and bore 1016 are configured for attachment of the hinge 954 to shaft element 920.

Figure 48:
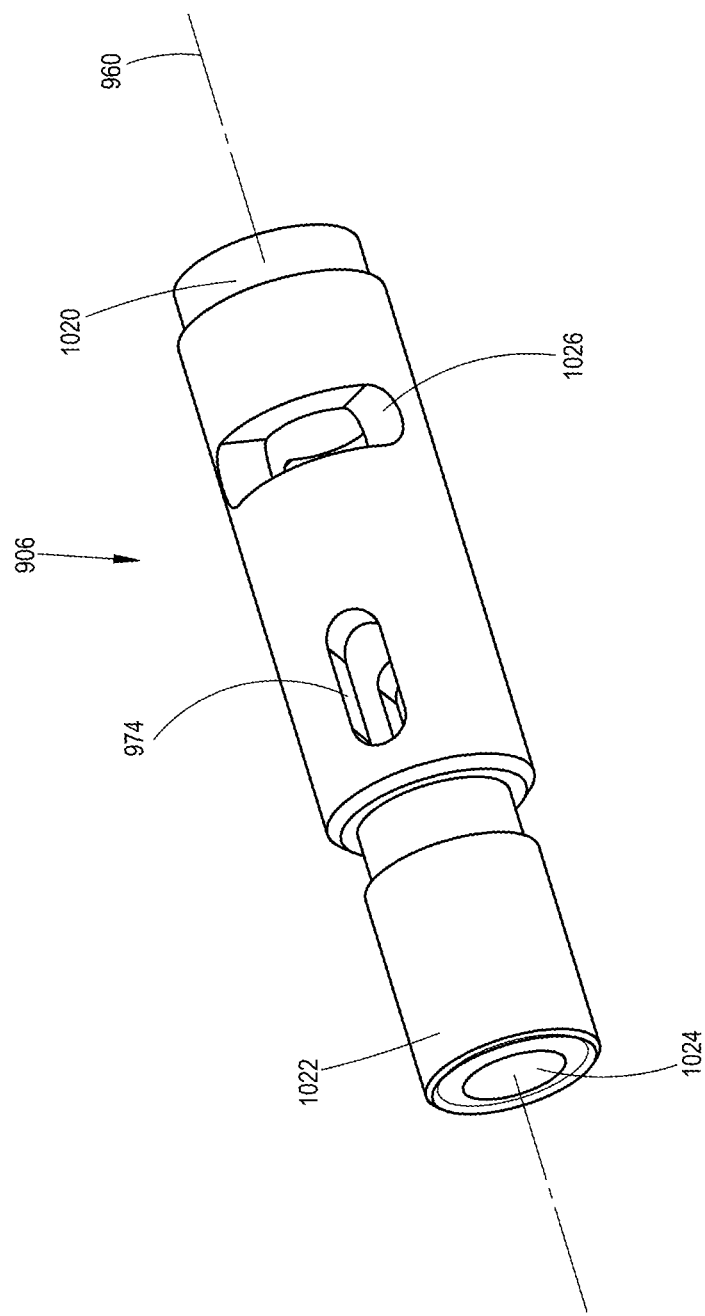
FIG. 48 is a simplified pictorial illustration of a body crank element, forming part of the bone material removal device of FIG. 44.

Reference is now made to FIG. 48, which is a simplified pictorial illustration of the body crank element 906, forms part of the bone material removal device 900 of FIG. 44.

It is seen in the embodiment shown in FIG. 48 that body crank element 906 is preferably longitudinal integrally made element having a proximal end 1020, configured to be attached to bearing crank 910 and a distal end 1022 configured to be attached to the tubular element 922.

The body crank element 906 defines a hollow bore 1024 therewithin for partial insertion of guiding element 904 thereinto. As mentioned above, slot 974 is formed in the body crank element 906 for guiding of guiding pin 908 therealong and an indication window 1026 is formed through body crank element 906 and is spaced proximally from slot 974.

Figure 49:
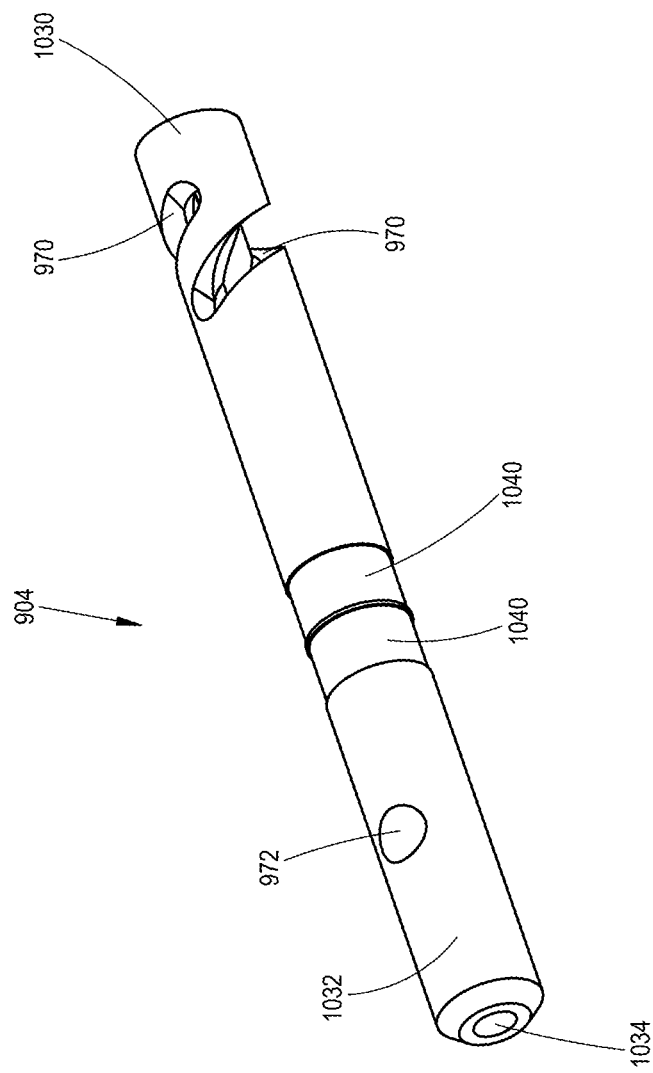
FIG. 49 is a simplified pictorial illustration of a guiding element, forming part of the bone material removal device of FIG. 44.

Reference is now made to FIG. 49, which is a simplified pictorial illustration of the guiding element 904, forms part of the bone material removal device 900 of FIG. 44.

It is seen in FIG. 49 that guiding element 904 is preferably longitudinal integrally made element having a proximal end 1030, configured to be attached to the rotating element 902 and a distal end 1032 configured to be attached to the shaft element 920.

A recess 1034 is formed at the distal end 1032 of guiding element 904. Typically, one, two or more indication elements 1040 are formed in a generally intermediate location of guiding element 904, which may be coated with different colors, in order to indicate whether the cutting tooth 952 is disposed in its closed or open operative orientation, using the longitudinal displacement of the guiding element 904 as indication of the operative orientation of tooth 952.

Figure 50:
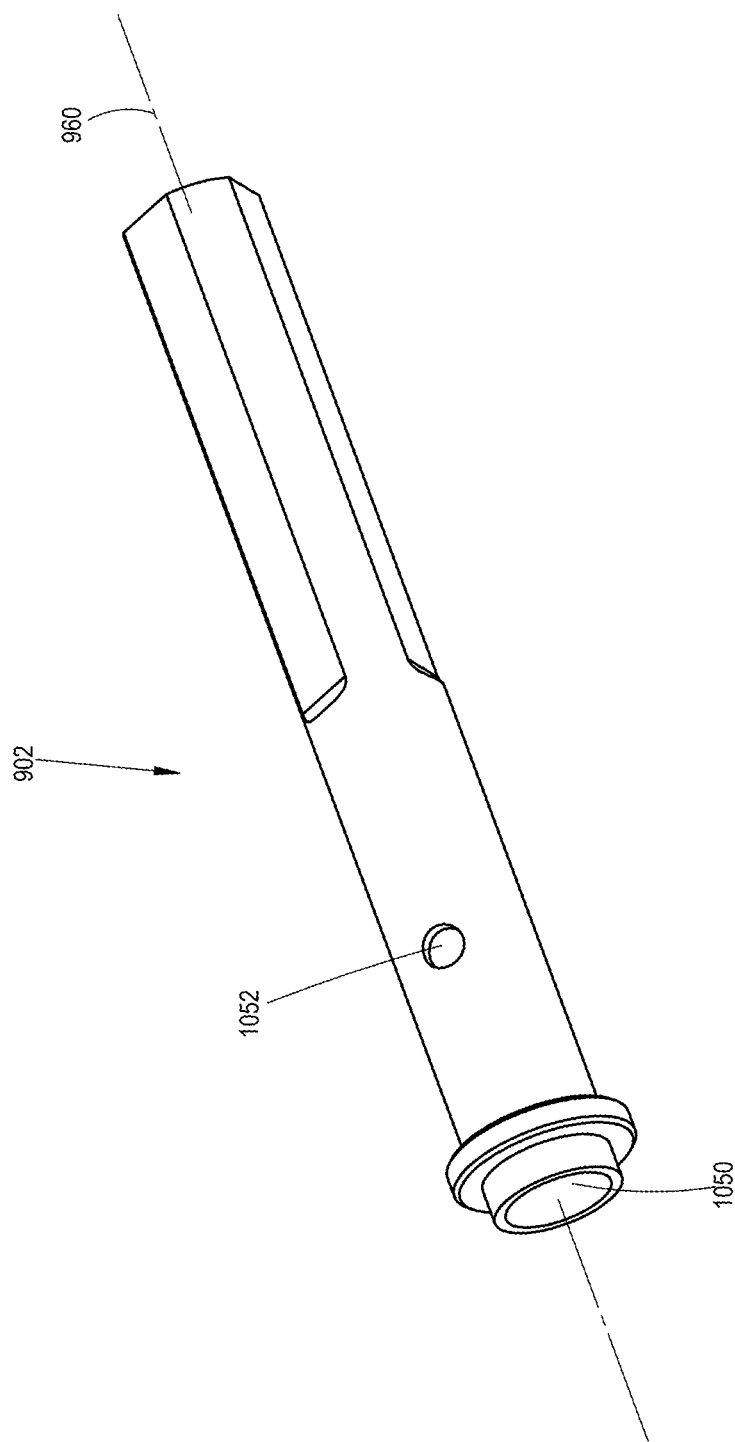
FIG. 50 is a simplified pictorial illustration of a rotating element, forming part of the bone material removal device of FIG. 44.

Reference is now made to FIG. 50, which is a simplified pictorial illustration of an exemplary embodiment of the rotating element 902, forms part of the bone material removal device 900 of FIG. 44.

A recess 1050 is formed in the distal end of rotating element 902 for insertion of the proximal end 1010 of shaft element 920 thereinto.

A bore 1052 is formed proximally of distal end of the rotating element 902 for insertion of pins 905 therethrough.

Figure 51:
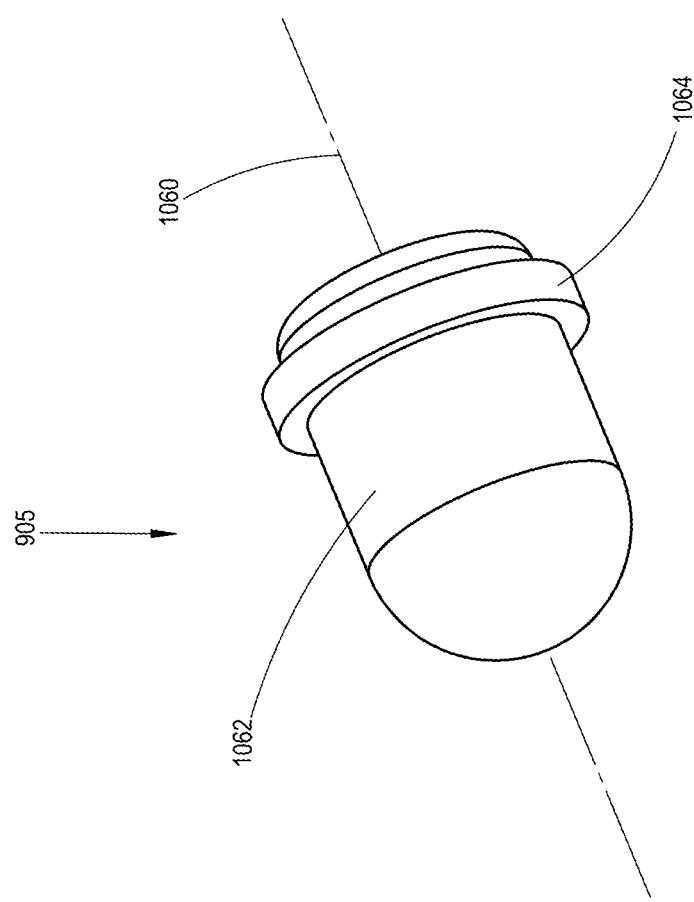
FIG. 51 is a simplified pictorial illustration of a pin element, forming part of the bone material removal device of FIG. 44.

Reference is now made to FIG. 51, which is a simplified pictorial illustration of pin element 905, forming part of the bone material removal device 900 of FIG. 44.

Pin element 905 is an integrally formed element arranged along an axis 1060, which is generally perpendicular to longitudinal axis 960.

It is noted that pin element 905 includes a longitudinal portion 1062 for engagement with helical paths 970 in guiding element 904 and an outwardly extending circumferential flange 1064 for attaching the pin elements 905 to rotating element 902.

It is noted that the tip element 950, tooth 952 and hinge 954 in accordance to this embodiment of the present invention are substantially similar to the tip element, tooth and hinge element described and shown in FIGS. 8-10 of the present application.

Figure 52:
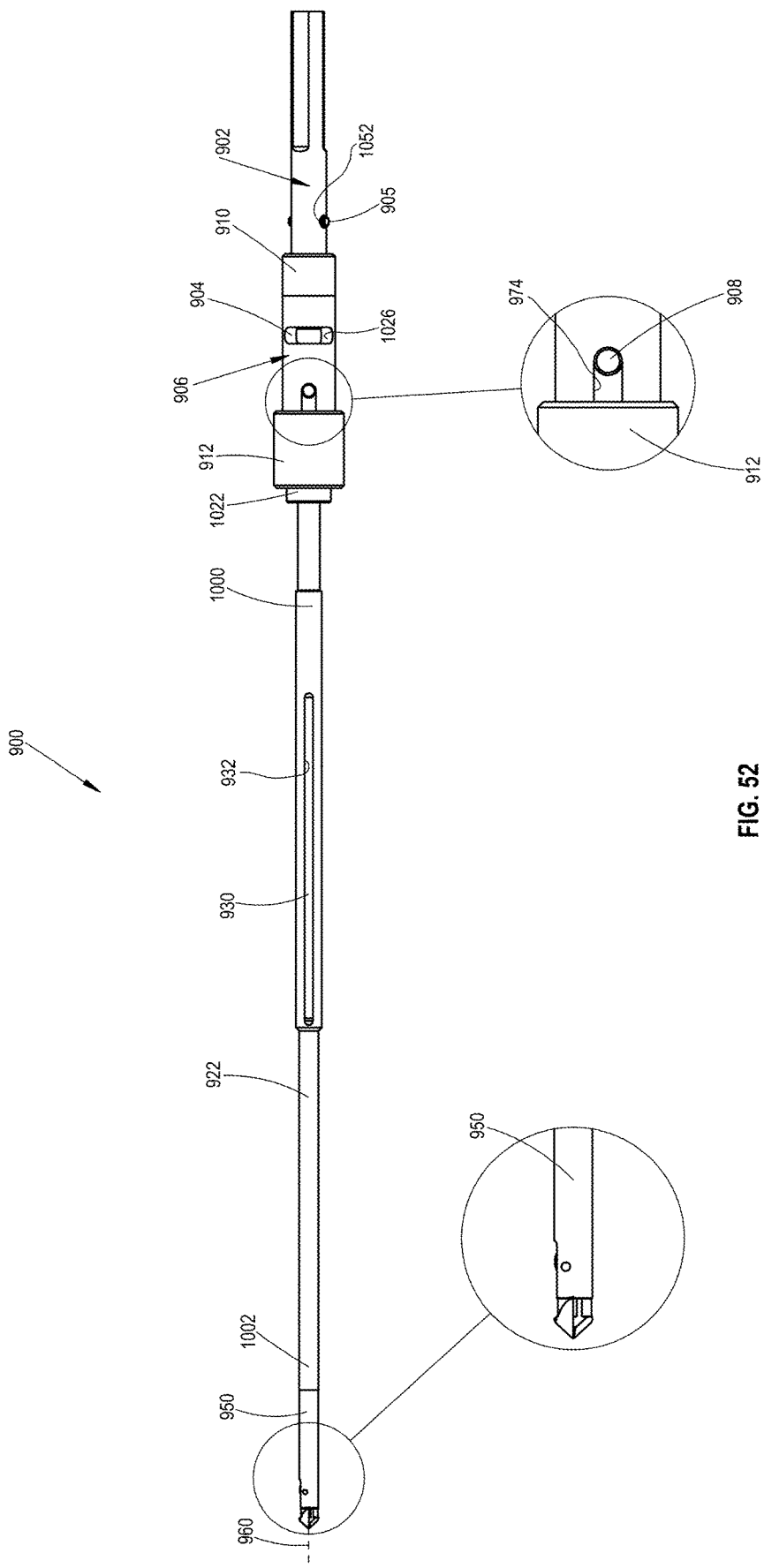
FIG. 52 is a simplified assembled plan view illustration of the bone material removal device of FIG. 44 shown in a closed operative orientation and enlargements thereof.

Reference is now made to FIG. 52, which is a simplified assembled plan view illustration of an exemplary embodiment of the bone material removal device 900 of FIG. 44 shown in a closed operative orientation and enlargements thereof. Reference is additionally made to FIGS. 53A and 53B, which are respective plan view and section view illustration of an exemplary embodiment of the bone material removal device 900 of FIG. 44 shown in the closed operative orientation.

It is seen in FIGS. 52, 53A and 53B where an exemplary embodiment of the bone material removal device 900 is shown in an assembled and closed operative orientation that guiding element 904 is received into recess 1050 of rotating element 902, such that pins 905 are received within helical paths 970 of guiding element 904 and provide for longitudinal displacement of the guiding element 904 relative to the rotating element 902 along longitudinal axis 960. As shown in FIG. 53B, a shaft displacement actuator comprises a first portion mainly guide element 904 that is rigidly coupled to shaft element 920 and a second portion mainly rotating element 902, rotatingly coupled to guide element 904.

Guiding element 904 is inserted into bore 1024 of body crank element 906 through the proximal end thereof, and guiding pin 908 connects the guiding element 904 and body crank element 906, such that guiding pin 908 is slidably moveable along slot 974 of body crank element 906. It is also seen that the proximal end 1010 of shaft element 920 is fixed within recess 1034 of guiding element 904.

Stopper 912 is mounted onto and partially encircles body crank element 906, such as to limit the slidable longitudinal displacement of pin 908 along slot 974 of body crank element 906. Proximal end 1000 of tubular element 922 is fixed within the bore 1024 of body crank element 906.

It is further seen particularly in FIG. 53B that hinge element 954 is hingedly attached by a pin within recess 1014 of shaft element 920, and the hinge element 954 is additionally hingedly attached to the cutting tooth 952, which is in this closed operative orientation of the bone material removal device 900 is fully enclosed within tip element 950, since the shaft element 920 is positioned in its proximal position.

It is seen in FIGS. 52-53B that the bone material removal device 900 is positioned in the closed operative orientation, in which the cutting tooth 952 is closed, thus the diameter of the bore formed in the bone of the patient while drilling in the closed operative orientation of the bone material removal device 900 is equal to the outer diameter of tip element 950.

It is a particular feature of some embodiments of the present invention that pins 905 are engaged with helical paths 970 of guiding element 904 and the guiding element 904 is disposed in its proximal position, in which the cutting tooth 952 is closed.

It is a further particular feature of some embodiments of the present invention that a first indication element 1040 formed on guiding element 904 is seen through indication window 1026 formed in body crank element 906, thus indicating to the user that the cutting tooth 952 is disposed in its closed operative orientation.

It is a particular feature of some embodiments of the present invention that the guiding pin 908 is positioned in the proximal end of slot 974 of body crank element 906 when the bone material removal device 900 is positioned at the closed operative orientation, since the guiding pin 908 is inserted into bore 972 of guiding element 904, which is disposed at the proximal operative orientation at this stage.

Figure 54:
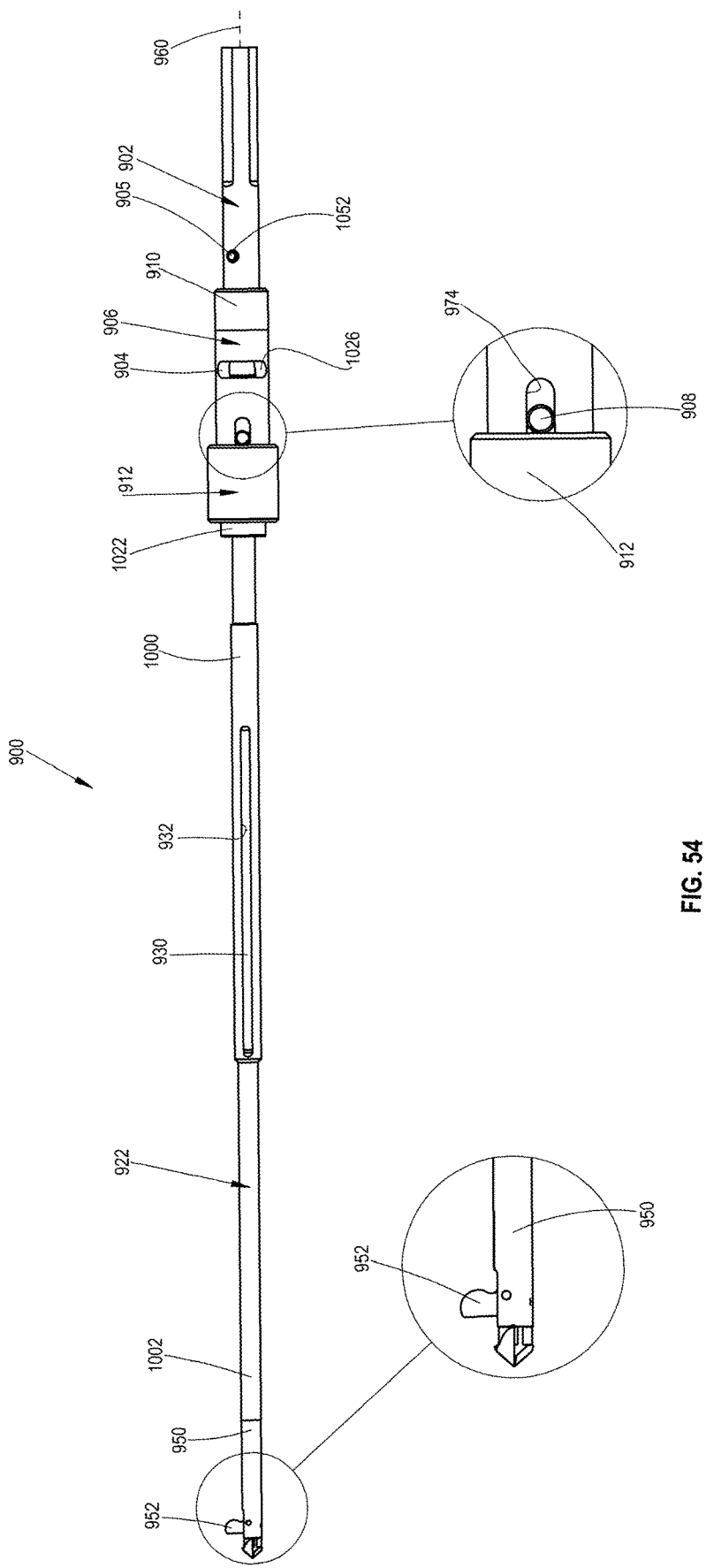
FIG. 54 is a simplified assembled plan view illustration of the bone material removal device of FIG. 44 shown in an open operative orientation and enlargements thereof.

Reference is now made to FIG. 54, which is a simplified assembled plan view illustration of an exemplary embodiment of the bone material removal device 900 of FIG. 44 shown in an open operative orientation and enlargements thereof. Reference is additionally made to FIGS. 55A and 55B, which are respective plan view and section view illustration of an exemplary embodiment of the bone material removal device 900 of FIG. 44 shown in the open operative orientation.

It is seen in FIGS. 54-55B that the bone material removal device 900 is shown in an assembled and open operative orientation. It is seen particularly in FIG. 55B that hinge element 954 is hingedly attached by a pin within recess 1014 of shaft element 920, and the hinge element 954 is additionally hingedly attached to the cutting tooth 952, which is in this open operative orientation of the bone material removal device 900 extends radially outwardly from tip element 950, since the shaft element 920 is positioned in its distal position in this open operative orientation.

It is seen in FIGS. 54-55B that the bone material removal device 900 is positioned in the open operative orientation, in which the cutting tooth 952 is open, thus the diameter of the bore formed in the bone of the patient while drilling in the open operative orientation of the bone material removal device 900 is larger than the outer diameter of tip element 950.

It is a particular feature of some embodiments of the present invention that pins 905 are displaced along helical paths 970 of guiding element 904, thus positioning the guiding element 904 in its distal position, the displacement of the guiding element 904 urges distal longitudinal displacement of shaft element 920, thus providing for pivoting of the hinge element 954 and in turn pivoting of tooth 952 and positioning thereof in the open operative orientation.

It is a further particular feature of some embodiments of the present invention that a second indication element 1040 formed on guiding element 904 is seen through indication window 1026 formed in body crank element 906, thus indicating to the user that the cutting tooth 952 is disposed in its open operative orientation.

It is a particular feature of some embodiments of the present invention that the guiding pin 908 is positioned in the distal end of slot 974 of body crank element 906 when the bone material removal device 900 is positioned at the open operative orientation, since the guiding pin 908 is inserted into bore 972 of guiding element 904, which is disposed at the distal operative orientation at this stage.

Reference is now made to FIGS. 56A and 56B, which are respective simplified pictorial and sectional illustrations of an exemplary embodiment of the cannula body 980, forms part of the cannula assembly 940 of FIG. 45.

It is seen in FIGS. 56A and 56B that the cannula body 980 is an elongate integrally formed element, that is arranged along longitudinal axis 960. The cannula body 980 comprises a proximal end 1100, a distal end 1102 and abore 1104.

In some embodiments the bore 1104 extends throughout the full length cannula body 980 and comprises a distal generally cylindrical portion 1106 having a first diameter, an intermediate cylindrical portion 1108 having a second diameter, which is greater than the first diameter and a proximal cylindrical portion 1110 having a third diameter, generally greater than the second diameter.

It is further seen that a plurality of bores 1112 are formed in the proximal cylindrical portion 1110 for insertion of fixation pins therethrough. Bores 1112 extend along axes that are generally perpendicular to longitudinal axis 960. Additional bores 1114 are formed in proximal cylindrical portion 1110 and extend along axes parallel to longitudinal axis 960 for insertion of different fixation pins therethrough.

Reference is now made to FIGS. 57A and 57B, which are respective simplified pictorial and sectional illustrations of the cannula inner sleeve 990, forming part of the cannula assembly 940 of FIG. 45.

It is seen in FIGS. 57A and 57B that the cannula inner sleeve 990 is an elongate integrally formed element, that is arranged along longitudinal axis 960.

The cannula inner sleeve 990 defines an outer cylindrical surface 1120 and a bore 1122, which extends throughout the full length of cannula sleeve 990 and defines an inner cylindrical surface 1124. A longitudinal groove 1126 is formed on the inner cylindrical surface 1124.

Figure 58:
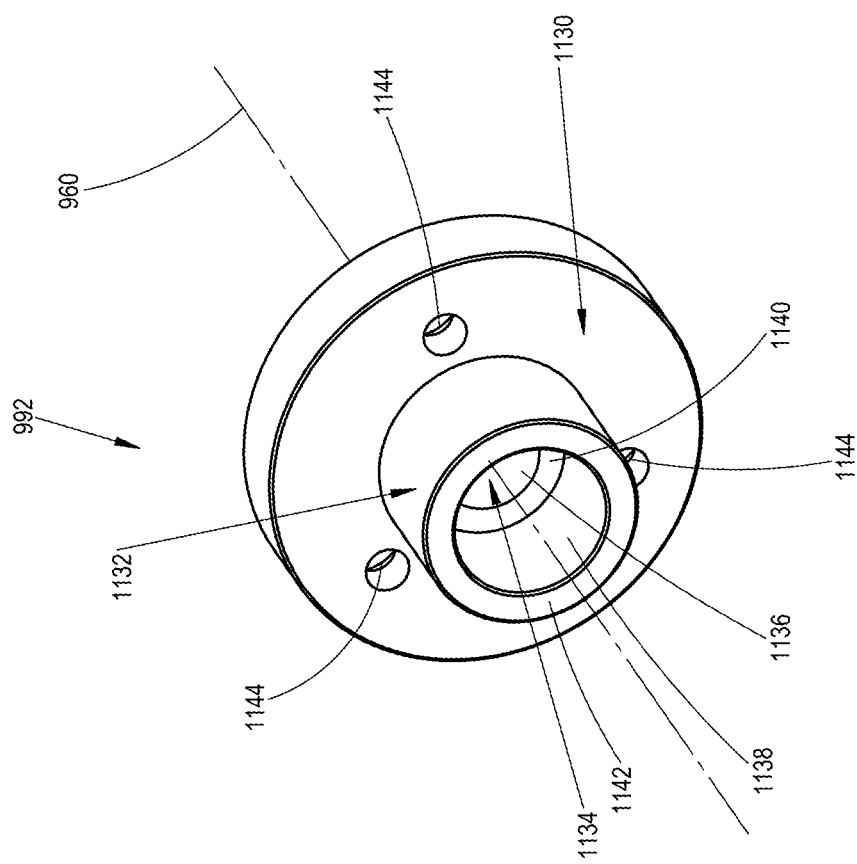
FIG. 58 is a simplified pictorial illustration of a cannula cover, forming part of the cannula assembly of FIG. 45.

Reference is now made to FIG. 58, which is a simplified pictorial illustration of the cannula cover 992, forms part of the cannula assembly 940 of FIG. 45.

It is seen in FIG. 58 that cannula cover 992 is an integrally formed element, that is arranged along longitudinal axis 960. Cannula cover 992 comprises a generally annular portion 1130 and a generally cylindrical portion 1132 extending distally therefrom. A bore 1134 extends throughout the full length of cannula cover 992 and along both the annular portion 1130 and through cylindrical portion 1132.

Bore 1134 comprises a proximal portion 1136 having a first diameter and extending along annular portion 1130 and a distal portion 1138 having a second diameter, generally greater than the first diameter and extending along the cylindrical portion 1132.

A distally facing shoulder 1140 is formed between proximal portion 1136 and distal portion 1138. The cylindrical portion 1132 defines a distally facing edge surface 1142.

It is also seen that a plurality of bores 1144 are formed through the annular portion 1130 of cannula cover 992, which extend along axes that are parallel to longitudinal axis 960.

Figure 59B:
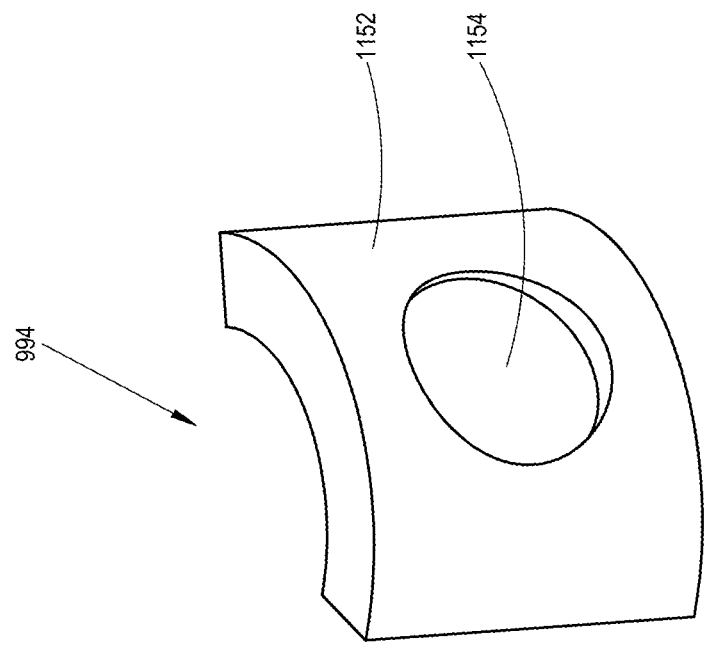
FIGS. 59A and 59B are a simplified pictorial illustration of a cannula break, forming part of the cannula assembly of FIG. 45.
Figure 59A:
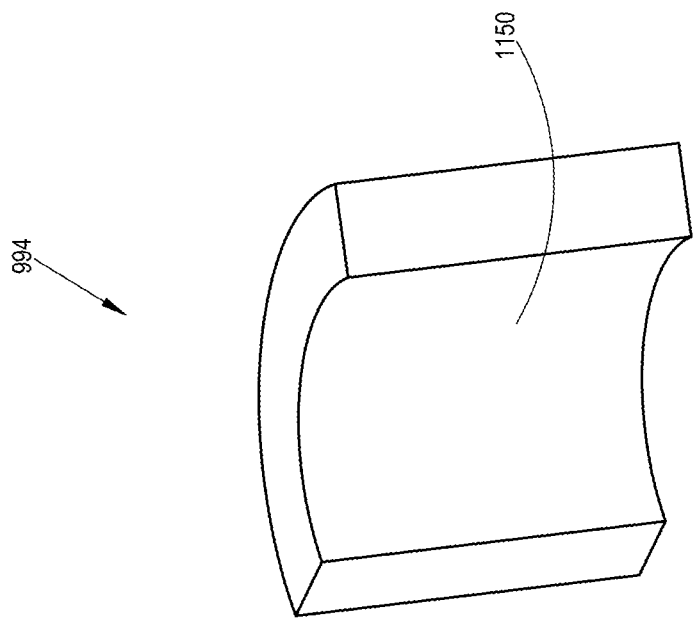

Reference is now made to FIGS. 59A and 59B, which are simplified pictorial illustrations of an exemplary embodiment of the cannula break 994, forming part of the cannula assembly 940 of FIG. 45.

In some embodiments, cannula break 994 is generally an arc-shaped element defining an inner surface 1150 and an outer surface 1152. A recess 1154 is formed on the outer surface 1152.

Reference is now made to FIGS. 60A and 60B, which are simplified planar and sectional view illustrations of the cannula assembly 940 of FIG. 45.

It is seen in FIGS. 60A and 60B that the cannula cover 992 is fixedly attached to cannula body 980 by pins 995, which are inserted into bores 1144 of the cannula cover 992 and bores 1114 of the cannula body 980. The cylindrical portion 1132 of the cannula cover 992 lies within proximal portion 1110 of the cannula body 980.

It is further seen particularly in FIG. 60B that cannula inner sleeve 990 is mounted partially within cannula body 980 and partially within cannula cover 992, such that outer surface 1120 of cannula inner sleeve 990 lies partially against intermediate portion 1108 of cannula body 980 and partially against distal portion 1138 of cannula cover 992.

It is additionally seen that a plurality of cannula breaks 994 tighten the inner sleeve 990 within the cannula body 980, in order to momentarily stop rotation of inner sleeve 990 and thereby reverse the direction of rotation. The cannula breaks 994 are tightened by pins 996, which are inserted into recesses 1154 formed in cannula breaks 994. The inner surfaces 1150 of the breaks 994 lie against outer surface 1120 of inner sleeve 990. The breaks 994 are disposed in the proximal portion 1110 of the cannula body 980.

Figure 61A:
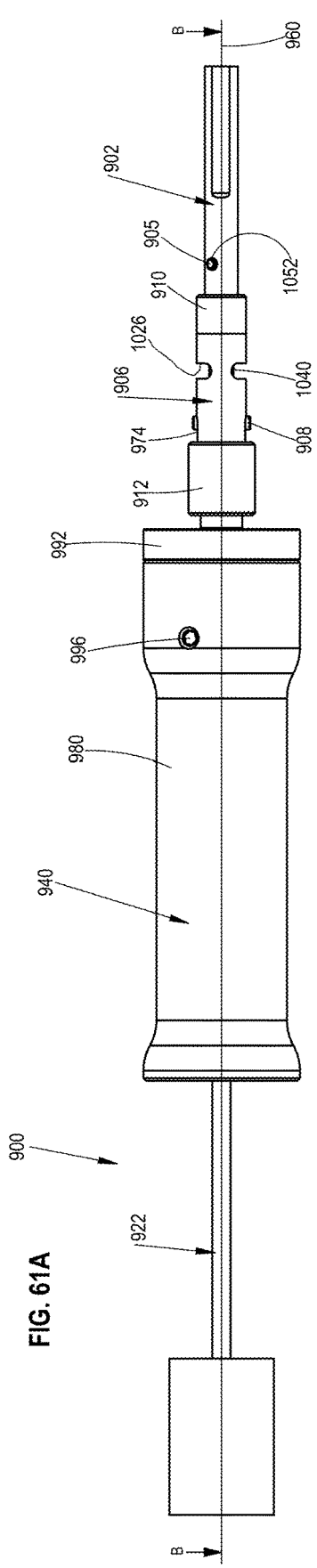
FIGS. 61A and 61B are simplified planar and sectional view illustrations of the bone material removal device and the cannula assembly of FIGS. 44 and 45 shown in the closed operative orientation partially inserted into a bone of a patient.
Figure 61B:
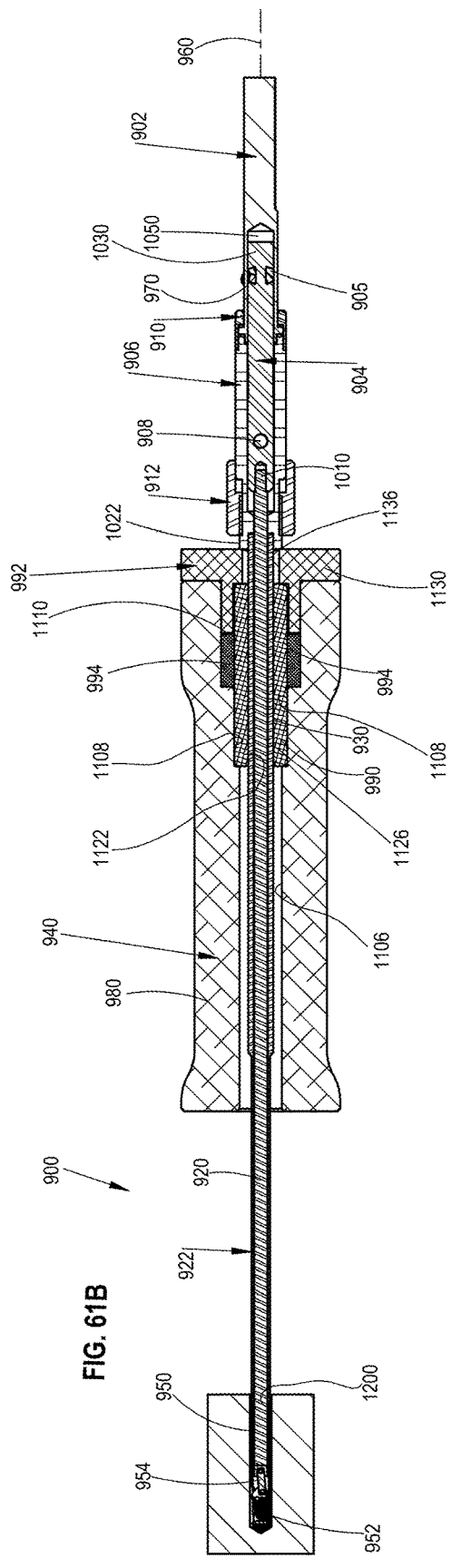

Reference is now made to FIGS. 61A and 61B, which are simplified planar and sectional view illustrations of an exemplary embodiment of the bone material removal device 900 and the cannula assembly 940 of FIGS. 44 and 45 shown in the closed operative orientation partially inserted into a bone of a patient.

It is seen in FIGS. 61A and 61B that cannula assembly 940 is mounted over bone material removal device 900, such that groove 1126 of inner sleeve 990 engages tennon 930 that is mounted in tubular element 922. Tubular element 922 of bone material removal device 900 is partially inserted through cylindrical portion 1106 of cannula body 980, bore 1122 of inner sleeve 990 and proximal portion 1136 of cannula cover 992 of the cannula assembly 940.

It is further seen in FIGS. 61A and 61B that an initial bore 1200 of a first diameter is formed in the bone of the patient while drilling with the bone material removal device 900 positioned in its closed operative orientation. It is noted that this initial drilling is provided while the rotating element 902 is rotated in a first rotational direction, in this exemplary embodiment, in a clockwise direction.

While the rotating element 902 rotates in a clockwise rotational direction, the pins 905 are prevented from being displaced along helical paths 970, thus preventing displacement of the guiding element 904 distally, thereby the cutting tooth 952 remains closed and initial bore 1200 of a first diameter is created in the bone of a patient.

Reference is now made to FIGS. 62A and 62B, which are simplified planar and sectional view illustrations of an exemplary embodiment of the bone material removal device 900 and the cannula assembly 940 of FIGS. 44 and 45 shown in an open operative orientation partially inserted into a bone of the patient. Reference is additionally made to FIGS. 63A and 63B, which are simplified planar and sectional view illustrations of the bone material removal device 900 and the cannula assembly 940 of FIGS. 44 and 45 shown in the open operative orientation while an undercut is created within the bone of the patient.

It is particularly seen in FIGS. 62A and 62B that the direction of rotation of the rotational element 902 is reversed and the bone material removal device 900 is now positioned in its open operative orientation, configured to create an undercut bore 1202 of a second diameter, which is generally greater than the first diameter of initial bore 1200. It is noted that once the direction of rotation of the rotating element 902 is reversed, the tennon 930 that is mounted into tubular element 922 is seated within groove 1126 of inner sleeve 990 of cannula assembly 940 and due to press-fit engagement of cannula breaks 994 with inner sleeve 990, friction force is created between the tubular element 922 and the inner sleeve 990, thus permitting stopping the rotational movement of the tubular element 922 momentarily in order to enable changing the drilling rotational direction.

It is seen in FIGS. 62A-63B that the undercut bore 1202 is formed over the initial bore 1200, undercut bore 1202 having a second diameter, which is greater than the first diameter while drilling with the bone material removal device 900 positioned in its open operative orientation. It is noted that this undercut bore drilling is provided while the rotating element 902 is rotated in a second rotational direction, in this exemplary embodiment, in a counter-clockwise direction.

It is a particular feature of some embodiments of the present invention that once tennon 930 that is mounted into tubular element 922 is seated within groove 1126 of inner sleeve 990 of cannula assembly 940, the rotation of the tubular element 922 is momentarily stopped, the rotational direction of the drilling can be reversed, thus causing the pins 905 to be displaced along helical path 970 formed in guiding element 904, thus providing for distal longitudinal displacement of guiding element 904, thereby pushing the shaft element 920 distally, which in turn causes pivoting of hinge element 954 and pivoting of tooth 952 to assume its open operative orientation. The cutting tooth 952 can pivot up to 90 degrees from its initial orientation and protrude through tip element 950.

The extent of longitudinal displacement of the shaft element 920 depends on the length of guiding slot 974 or the location of the stopper 912 in this particular embodiment of the present invention, thus during the axial displacement of shaft element 920 in a distal direction, the guiding pin 908 is displaced along the guiding slot 974 from its proximal end to its distal end.

While the rotating element 902 and the tubular element 922 are rotating in a counter-clockwise rotational direction, the cutting tooth 952 engages the bone of the patient and creates undercut bore 1202 therein. It is noted that the cutting tooth 952 can be closed once the direction of rotation is reversed and the bone material removal device 900 can be advanced and retracted to and from the bone of the patient in order to create the desired length of undercut bore 1202.

Reference is now made to FIGS. 64A and 64B, which are perspective simplified planar and sectional view illustrations of an exemplary embodiment of the bone material removal device 900 and the cannula assembly 940 of FIGS. 44 and 45 shown in the closed operative orientation following removal from the bone of the patient.

It is appreciated that in order to return to the closed operative orientation of the bone material removal device 900, direction of drilling rotation has to be changed using the friction created between the tubular element 922 and the inner sleeve 990 due to brakes 994. This drilling direction urges the pins 905 to be displaced in the opposite direction along helical paths 970 of guiding element 904, thus urging the shaft element 920 to be displaced axially in a proximal direction, thus urging pivoting of the hinge element 954 and in turn pivoting of the cutting tooth 952 such that it is fully enclosed within tip element 950. At this stage, the bone material removal device 900 can be removed from the bone of the patient and the resulting variable diameter bore, comprised of initial bore 1200 and undercut bore 1202, can be seen as illustrated in FIG. 64B.

Figure 65:
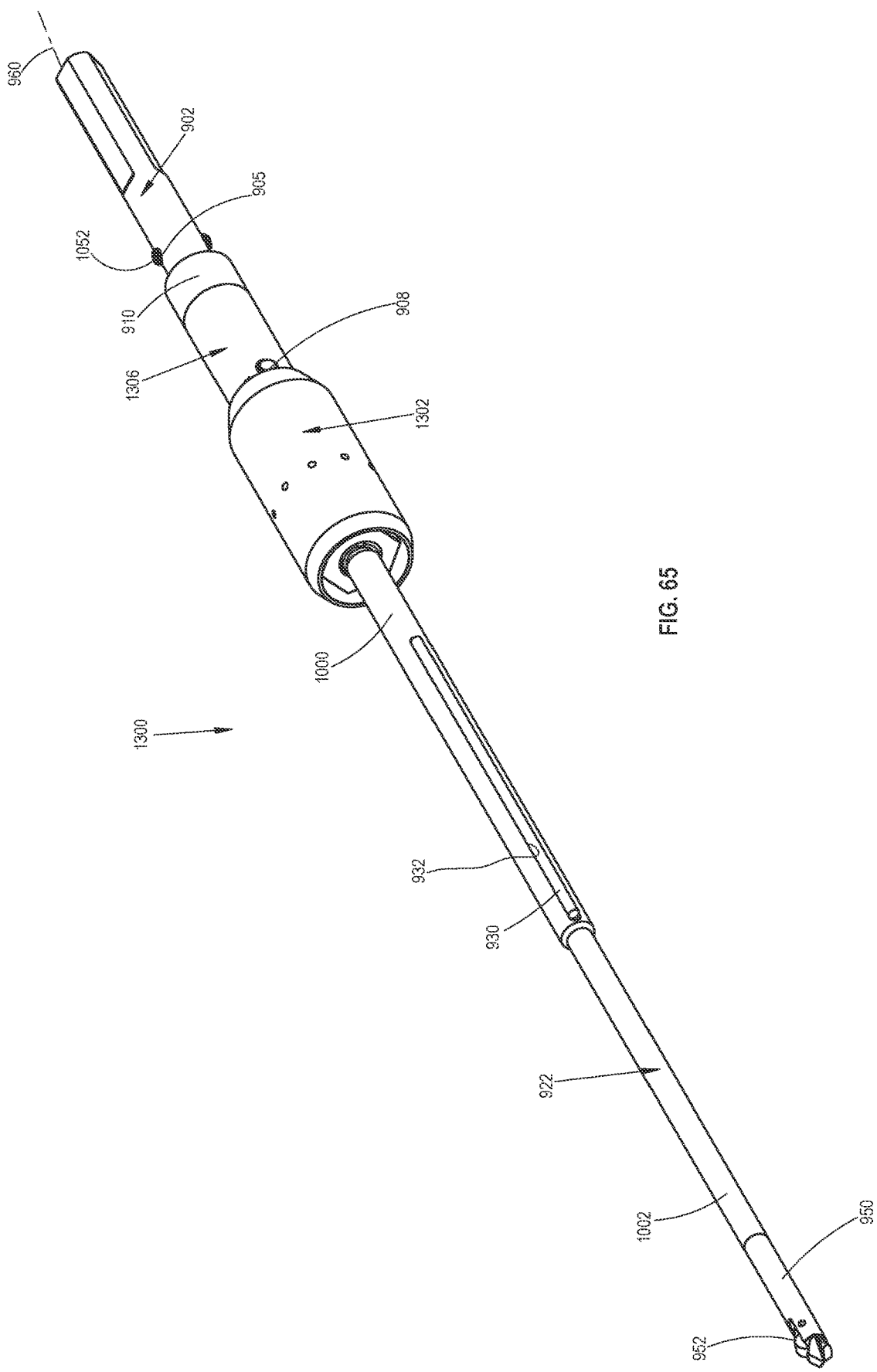
FIG. 65 is a simplified pictorial illustration of a bone material removal device, constructed and operative in accordance with some embodiments of the present invention.

Reference is now made to FIG. 65, which is a simplified pictorial illustration of a bone material removal device 1300, constructed and operative in accordance with some embodiments of the present invention.

It is noted that bone material removal device 1300 is substantially similar to bone material removal device 900 shown in FIG. 44 in all respects other than the features that are described in detail hereinbelow. Similar elements are indicated by the same reference numerals that are used for bone material removal device 900.

It is a particular feature of some embodiments of the present invention that bone material removal device 1300 provides for creating undercut bores of various diameters, by opening the cutting tooth to a different radial extent as is described in detail hereinbelow.

It is noted that the following relations between the different components of the exemplary bone material removal device 1300 of FIG. 65 are at least in part similar to the relations between the different components of the exemplary bone material removal device 900 of FIG. 44.

In some embodiments, the bone material removal device 1300 comprises a rotating element 902 configured to be rotatably attached to a guiding element 904 by means of pins 905. Guiding element 904 is in turn slidably attached to an adjustable body crank element 1306 by means of guiding pin 908 and bearing crank 910.

It is noted that in some embodiments, an adjustable element 1302 is arranged to be mounted onto adjustable body crank element 1306 for selectably limiting axial displacement of guiding pin 908.

It is further noted that in some embodiments, a shaft element 920 is fixedly attached to guiding element 904 and a tubular element 922 is fixedly attached to adjustable body crank element 906 and surrounds shaft element 920. It is noted that a tennon 930 is configured to be insertable into a groove 932 formed in the tubular element 922 for cooperation with a cannula assembly 940.

In some embodiments, a tip element 950 is attached or integrally made with the tubular element 922. A tooth 952 is arranged to be connected to the shaft element 920 by means of a hinge 954 and pivotably connected to the tip element 950.

It is seen that in some embodiments, rotating element 902, guiding element 904, adjustable body crank element 1306, bearing crank 910, adjustable element 1302, shaft element 920, tubular element 922 and tip element 950 are all arranged along a single mutual longitudinal axis 960.

It is additionally noted that cannula assembly 940 is configured to be mounted over the tubular element 922 and arranged along longitudinal axis 960.

It is appreciated that the tubular element 922 is preferably made of a biocompatible material, e.g., titanium.

It is further noted, as described in detail hereinabove that the guiding element 904 includes typically two helical paths 970 cooperating with typically two pins 905 and an aperture 972 cooperating with guiding pin 908. It is a particular feature of some embodiments of the present invention that the rotational displacement of pins 905 within helical path 970 of guiding element 940 is converted to a linear displacement of guiding pin 908 within a slot formed in adjustable body crank element 1306, thereby urging axial displacement of shaft element 920 along longitudinal axis 960. This longitudinal displacement of shaft element 920, urges pivoting of hinge 954, and thereby causes pivoting of tooth 952 relative to tip element 950.

The bone material removal device 1300 is shown in an assembled and open operative orientation. Hinge 954 is hingedly attached by a pin within recess 1014 of shaft element 920, and the hinge 954 is additionally hingedly attached to the cutting tooth 952, which is in this open operative orientation of the bone material removal device 1300 fully extends radially outwardly from tip element 950, since the shaft element 920 is positioned in its distal position in this open operative orientation. In this open operative orientation of bone material removal device 1300, the diameter of the bore formed in the bone of the patient is larger than the outer diameter of tip element 950.

It is a particular feature of some embodiments of the present invention that pins 905 are displaced along helical paths 970 of guiding element 904, thus positioning the guiding element 904 in its distal position, the displacement of the guiding element 904 urges distal longitudinal displacement of shaft element 920, thus providing for pivoting of the hinge 954 and in turn pivoting of tooth 952 and positioning thereof in the open operative orientation.

It is a further particular feature of some embodiments of the present invention that bone material removal device 1300 includes an adjuster element 1302, which is configured to cooperate with an adjustable body crank element 1306, this cooperation enables opening the cutting tooth 952 to various radial extends and thus forms various diameters of undercut bores in the bone of the patient.

Figure 66:
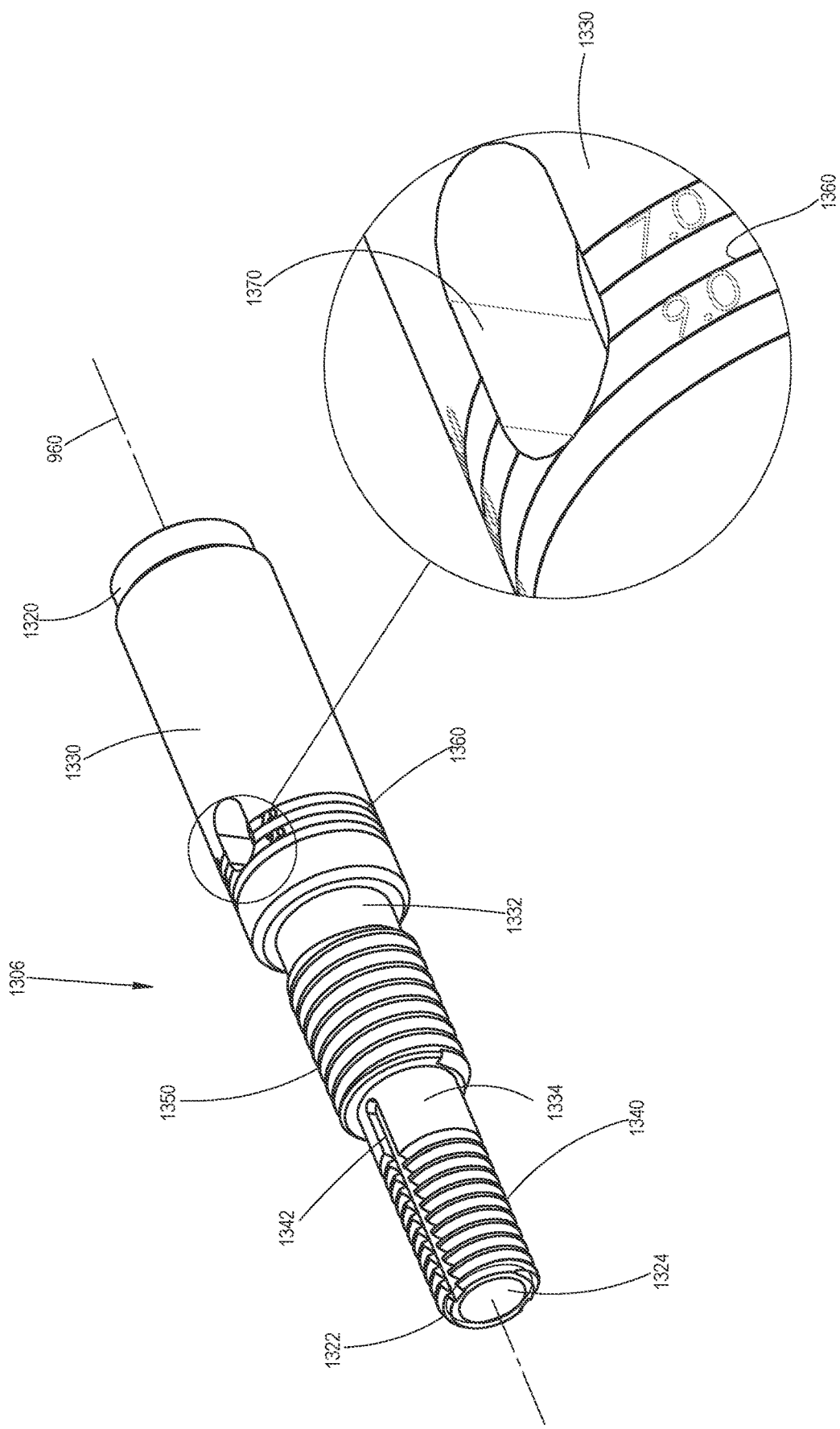
FIG. 66 is a simplified pictorial illustration of a body crank element, forming part of the bone material removal device of FIG. 65.

Reference is now made to FIG. 66, which is a simplified pictorial illustration of an exemplary embodiment of the body crank element 1306, forming part of the bone material removal device 1300 of FIG. 65.

It is seen in FIG. 66 that adjustable body crank element 1306 is preferably longitudinal integrally made element having a proximal end 1320, configured to be attached to bearing crank 910 and a distal end 1322 configured to be attached to the tubular element 922.

The adjustable body crank element 1306 defines a hollow bore 1324 therewithin for partial insertion of guiding element 904 at its proximal end and partial insertion of shaft element 920 at its distal end.

Adjustable body crank element 1306 preferably includes a proximal generally cylindrical portion 1330, an intermediate generally cylindrical portion 1332 and a distal generally cylindrical portion 1334. The outer diameter of the distal portion 1334 is preferably smaller than the outer diameter of the intermediate portion 1332, the diameter of which in turn is smaller than the outer diameter of the proximal portion 1330.

It is a particular feature of some embodiments of the present invention that a first outer threading 1340 is formed on the outer surface of the distal portion 1334. Typically, two longitudinal grooves 1342 extend in parallel to longitudinal axis 960 along the distal portion 1334.

It is a further particular feature of some embodiments of the present invention that a second outer threading 1350 is formed on the outer surface of the intermediate portion 1332.

It is a yet further particular feature of some embodiments of the present invention that a marking scale 1360 is provided on the proximal portion 1330 of the adjustable body crank element 1306 for indication the undercut bore diameter formed in the bone of the patient, which is substantially equal to the radial extent of cutting tooth 952 opening.

It is also seen that a longitudinal slot 1370 is formed in the adjustable body crank element 1306, at the proximal portion 1330 for guiding of guiding pin 908 therealong. The longitudinal slot 1370 preferably extends through the marking scale 1360 in order to provide visual indication for the user of the bore diameter that is set up.

Reference is now made to FIGS. 67A, 67B and 67C, which are simplified pictorial illustration, end plan view and a section view of adjusting element 1302, forming part of an exemplary embodiment of the bone material removal device 1300 of FIG. 65, section being taken along lines C-C in FIG. 67A.

Adjusting element 1302 is an integrally made generally cylindrical hollow element having a proximal end 1380 and a distal end 1382.

It is seen in FIGS. 67A-67C that longitudinal bore 1390 is formed through adjusting element 1302. The bore 1390 preferably includes a proximal portion 1392, an intermediate portion 1394 and a distal portion 1396.

It is a particular feature of some embodiments of the present invention that an inner thread 1400 is formed on the intermediate portion 1394 of the bore 1390.

It is noted that in some embodiments, the diameter of the distal portion 1396 is greater than the diameter of the intermediate portion 1394, such that a distally facing annular shoulder surface 1402 is formed between the intermediate portion 1394 and distal portion 1396.

As particularly seen in FIG. 67B, a plurality of mutually radially spaced grooves 1410 are formed on annular shoulder surface 1402.

Figure 68:
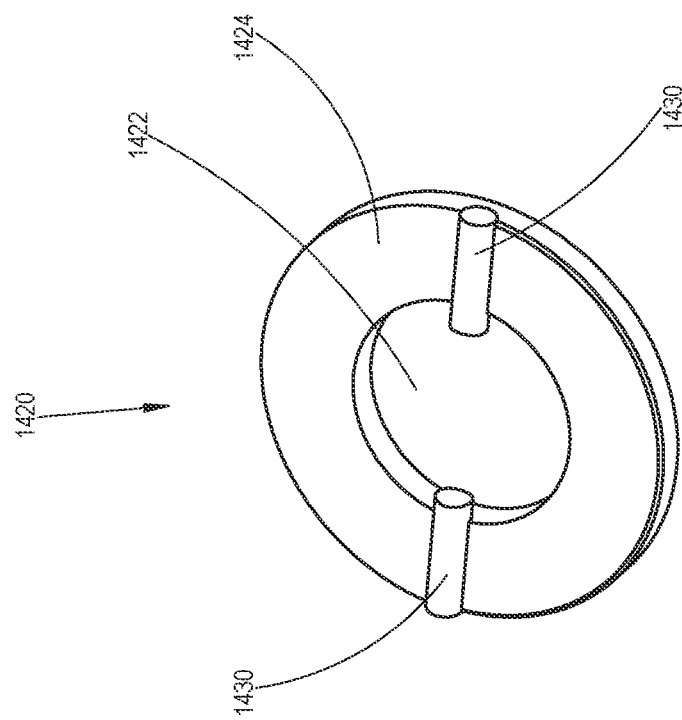
FIG. 68 is a simplified pictorial illustration of a disc element, forming part of the bone material removal device of FIG. 65.

Reference is now made to FIG. 68, which is a simplified pictorial illustration of an embodiment of a disc element 1420, forming part of an exemplary embodiment of the bone material removal device 1300 of FIG. 65.

Disc element 1420 is configured to cooperate with adjusting element 1302. Disc element 1420 comprises a bore 1422 extending longitudinally and at the center thereof and it defines a proximally facing annular surface 1424. Typically, one, two or more mutually radially opposed protrusions 1430 are formed on the proximally facing annular surface 1424 and are configured to cooperate with groves 1410 formed on adjusting element 1302.

Figure 69:
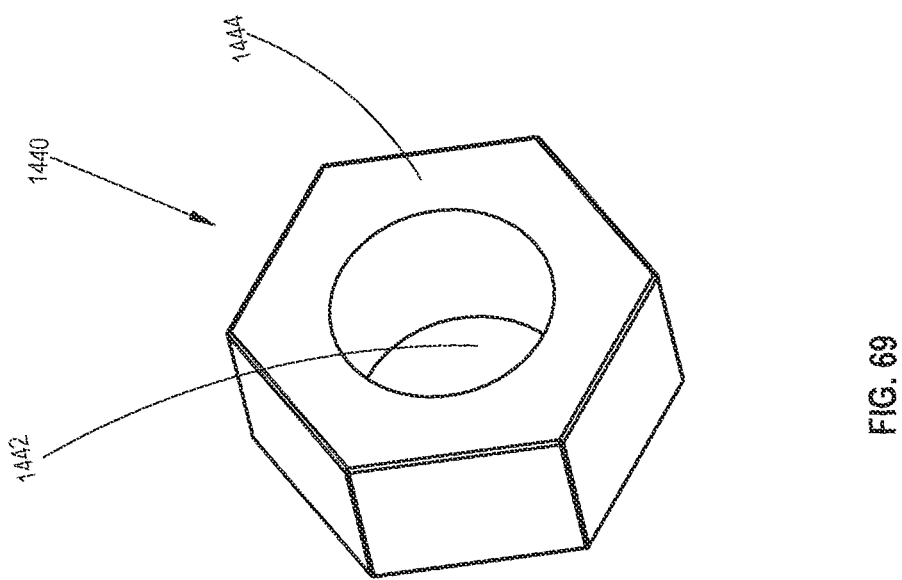
FIG. 69 is a simplified pictorial illustration of a nut element, forming part of the bone material removal device of FIG. 65.

Reference is now made to FIG. 69, which is a simplified pictorial illustration of a nut element 1440, forms part of an exemplary embodiment of the bone material removal device 1300 of FIG. 65.

It is seen in FIG. 69 that the nut element 1440 is integrally formed and comprises a longitudinal bore 1442 extending at the center thereof. The nut element 1440 defines a proximally facing surface 1444.

Figure 70:
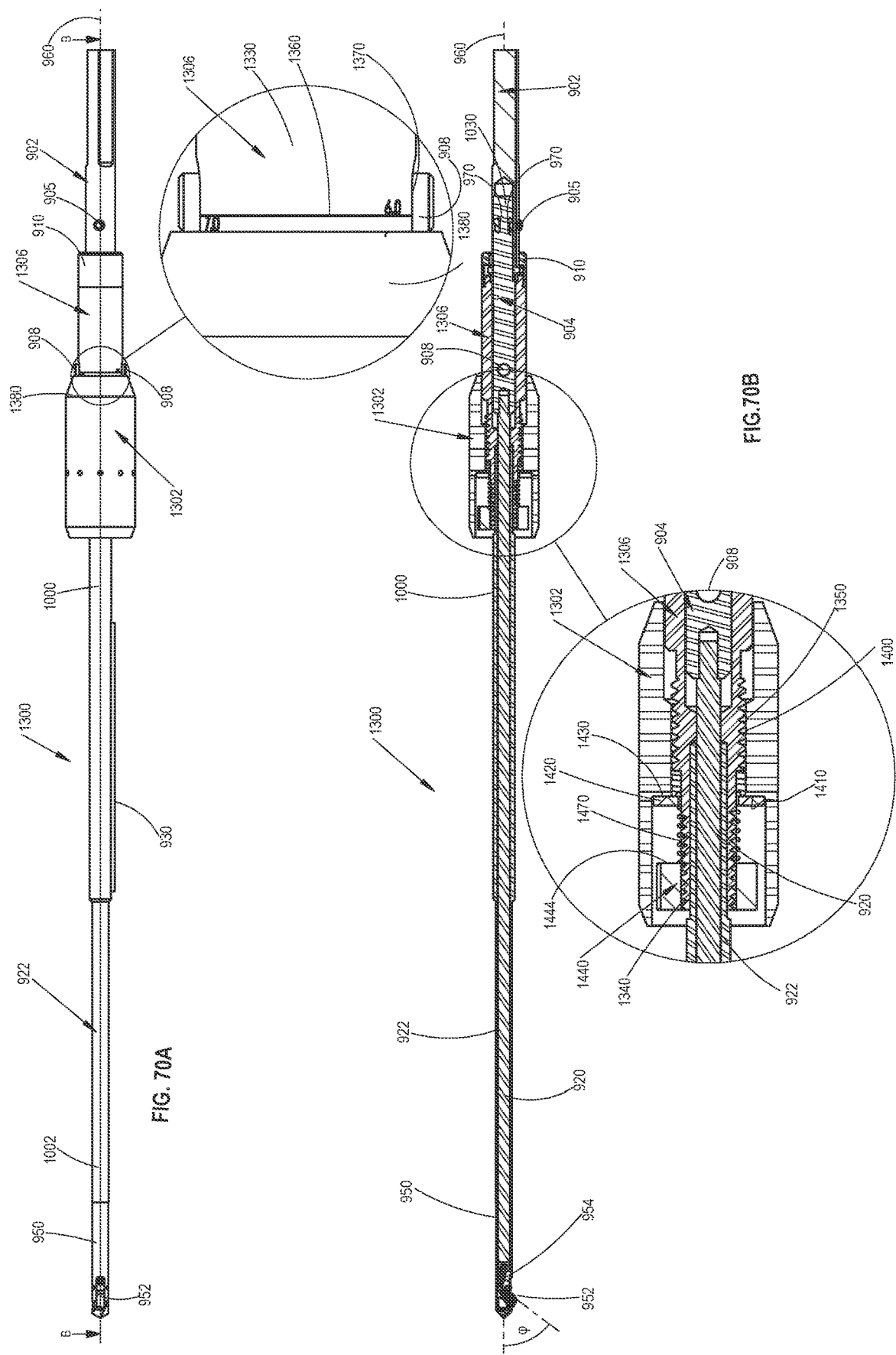
FIGS. 70A and 70B are respective plan view and section view illustrations of the bone material removal device of FIG. 65 shown in a partially open operative orientation.

Reference is now made to FIGS. 70A and 70B, which are plan view and section view illustrations of an exemplary embodiment of the bone material removal device 1300 of FIG. 65 shown in a partially open operative orientation.

It is appreciated that most of the relations between the different components of bone material removal device 1300 is similar in the embodiments shown in FIGS. 70A and 70B and the embodiments shown in FIGS. 53A and 53B for example. The relations that are different from these shown in FIGS. 53A and 53B are described in detail hereinbelow.

The adjusting element 1302 is threadably mounted onto adjustable body crank element 1306 of bone material removal device 1300, by means of engagement of inner threading 1400 of adjusting element 1302 with outer threading 1350 of adjustable body crank element 1306.

It is seen in FIG. 70A that guiding pin 908 engages the proximal end 1380 of adjusting element 1302 and additionally the guiding pin 908 is inserted through longitudinal slot 1370 of adjustable body crank element 1306. The position of the guiding pin 908 along slot 1370 and relative to the proximal end 1380 of adjusting element 1302 indicates the radial extent of the opening of cutting tooth 952, by means of marking scale 1360, which is provided on adjustable body crank element 1306.

It is seen particularly in the embodiment shown in FIG. 70B that disc element 1420 is mounted on distal portion 1334 of adjustable body crank element 1306, such that the radially inwardly facing ends of protrusions 1430 of disc element 1420 are guided within grooves 1342 of adjustable body crank element 1306.

It is a particular feature of some embodiments of the present invention that the plurality of protrusions 1430 of disc element 1420 are registered with the plurality of grooves 1410 formed on adjusting element 1302.

A nut element 1410 is threadably mounted onto outer threading 1340 of adjustable body crank element 1306.

It is further seen in FIG. 70B that a compression spring 1470 is supported between the distally facing surface of disc element 1420 and proximally facing surface 1444 of the nut element 1410.

It is a particular feature of some embodiments of the present invention that upon rotation of the adjusting element 1302 relative to adjustable body crank element 1306, and due to the threadable engagement therebetween, the displacement of the guiding pin 908 within longitudinal slot 1370 of the adjustable body crank element 1306 is controlled, since the guiding pin 908 is supported on the proximal end 1380 of adjusting element 1302. Upon rotation of the adjusting element 1302, the adjusting element is translated axially along longitudinal axis 960 due to its threadable engagement with the adjustable body crank element 1306. The further the adjusting element 1302 is translated distally, the further the guide pin 908 can be translated within the longitudinal slot 1370 towards the distal end of slot 1370. The guide pin 908 is rigidly coupled to the guiding element 904, which is in turn connected to shaft element 920, which is hingedly connected to the cutting tooth 952, thus the extent of radial pivoting of the cutting tooth 952 depends on the axial position of the guiding pin 908 within slot 1370 of the adjustable body crank element 1306. It is thus particularly appreciated that rotation of adjusting element 1302 controls the extent of radial pivoting of the cutting tooth 952.

It is a further particular feature of some embodiments of the present invention that a particular increment of rotation of the adjusting element 1302 is defined by registration of the protrusions 1430 of disc element 1420 with grooves 1410 of the adjusting element 1302, whereas the disc element 1420 is biased to engage the distally facing surface 1402 of adjusting element 1302 by the force of spring 1470. Upon rotation of the adjusting element 1302, the disc element 1420 is displaced axially distally against the force of spring 1470, while guided by grooves 1342 of the adjustable body crank element 1306. The threading of the adjusting element 1302 relative to the adjustable body crank element 1306 is divided into a plurality of increments, each increment is completed once protrusion 1430 of disc element 1420 is seated within the successive groove 1410 of adjusting element 1302. This division to increments enables accurate determination of the diameter of undercut bore created in the bone of the patient, while the user can see this determined diameter using the marking scale 1360 provided on the adjustable body crank element 1306. When the desired bore diameter is determined by rotation of the adjusting element 1302 relative the adjustable body crank element 1306, the displacement of the guiding pin 908 within slot 1370 is limited and thus the distal displacement of shaft element 920 is limited, thereby pivoting the cutting tooth 952 using the hinge element 954 only to a certain extent, rather than fully opening the cutting tooth 952.

It is a further particular feature of some embodiments of the present invention that spring 1470 is operative to bias the disc element 1420 proximally, towards grooves 1410 of adjustable element 1302, thereby the protrusions 1430 are firmly seated in one of a plurality of grooves 1410 while providing tactile indication of this insertion to the user and thereby avoiding inadvertent change of drilling diameter.

It is seen in this particular example shown in FIGS. 70A and 70B that the adjusting element [1320]1302 is slightly rotated with respect to adjustable body crank element 1306, such that the inner threading 1400 of adjusting element 1302 is disposed slightly distally to the proximal end of the outer threading 1350 of the adjustable body crank element 1306, thus the guiding pin 908 is slightly displaced distally along slot 1370 and the marking scale 1360 indicates diameter of 7 mm in this particular example. It is seen that in this operative orientation, the cutting tooth 952 is only partially open, it is pivoted such that the cutting tooth 952 extends radially at an acute angle with respect to longitudinal axis 960.

Figure 71:
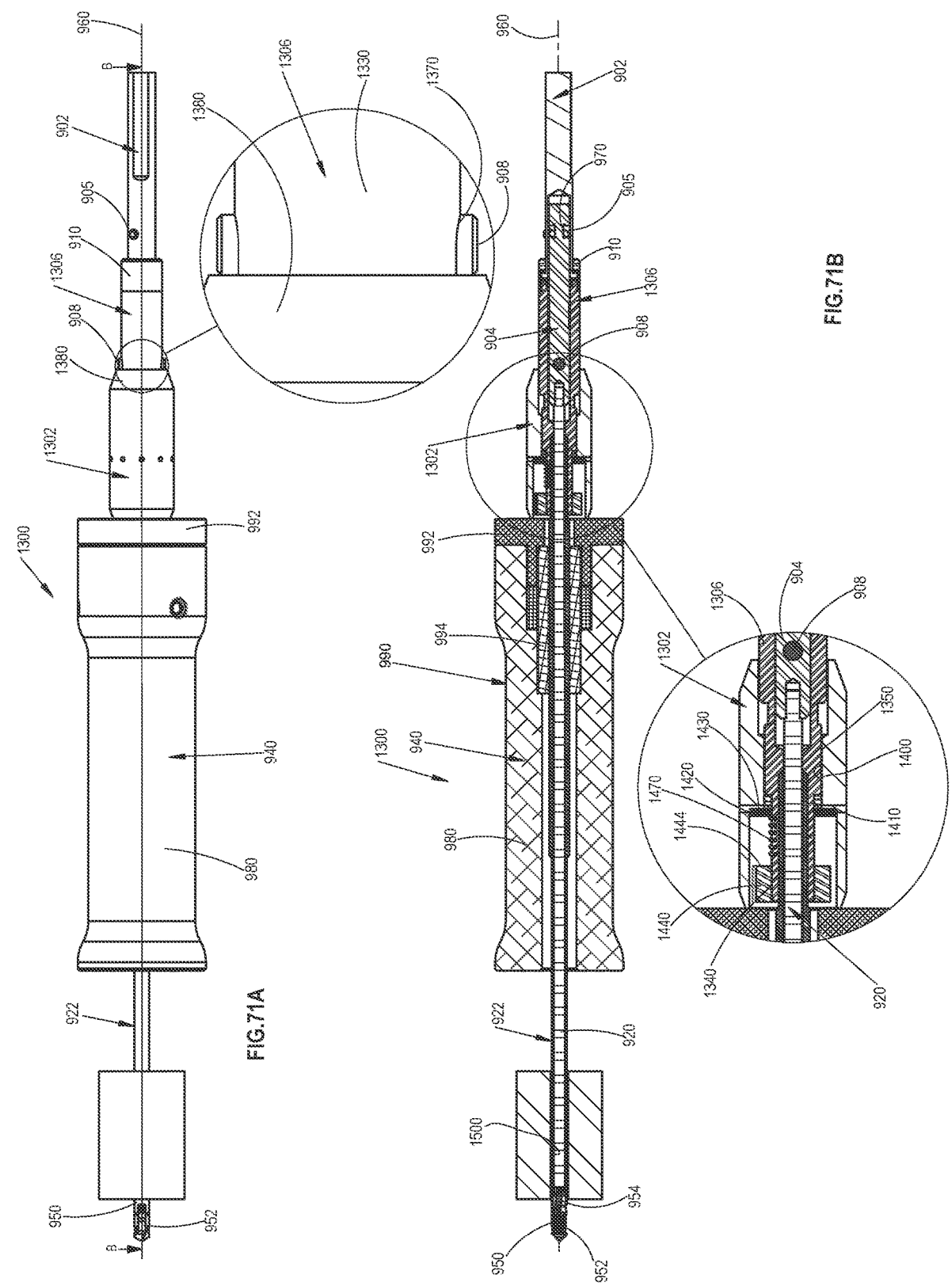
FIGS. 71A and 71B are simplified planar and sectional view illustrations of the bone material removal device and the cannula assembly of FIGS. 65 and 45 shown in the closed operative orientation inserted into a bone of a patient.

Reference is now made to FIGS. 71A and 71B, which are simplified planar and sectional view illustrations of an exemplary embodiment of the bone material removal device 1300 and the cannula assembly 940 of FIGS. 65 and 45 shown in the closed operative orientation inserted into a bone of a patient.

It is seen in this particular example shown in FIGS. 71A and 71B that the adjusting element 1302 is not rotated with respect to adjustable body crank element 1306, thus the guiding pin 908 is disposed at the proximal end of slot 1370 and the marking scale 1360 is not seen in this operative orientation. It is seen that in this operative orientation, the cutting tooth 952 is fully closed.

It is seen in FIGS. 71A and 71B that cannula assembly 940 is mounted over bone material removal device 1300, such that groove 1126 of inner sleeve 990 engages tennon 930 that is mounted in tubular element 922. Tubular element 922 of bone material removal device 900 is partially inserted through cylindrical portion 1106 of cannula body 980, bore 1122 of inner sleeve 990 that extends throughout the cannula body 980 and proximal portion 1136 of cannula cover 992 of the cannula assembly 940.

It is further seen in FIGS. 71A and 71B that an initial bore 1500 of a first diameter is formed in the bone of the patient while drilling with the bone material removal device 1300 positioned in its closed operative orientation. It is noted that this initial drilling is provided while the rotating element 902 is rotated in a first rotational direction, in this exemplary embodiment, in a clockwise direction.

While the rotating element 902 rotates in a clockwise rotational direction, the pins 905 are prevented from being displaced along helical paths 970, thus preventing displacement of the guiding element 904 distally, thereby the cutting tooth 952 remains closed and initial bore 1500 of a first diameter is created in the bone of a patient.

Figure 72:
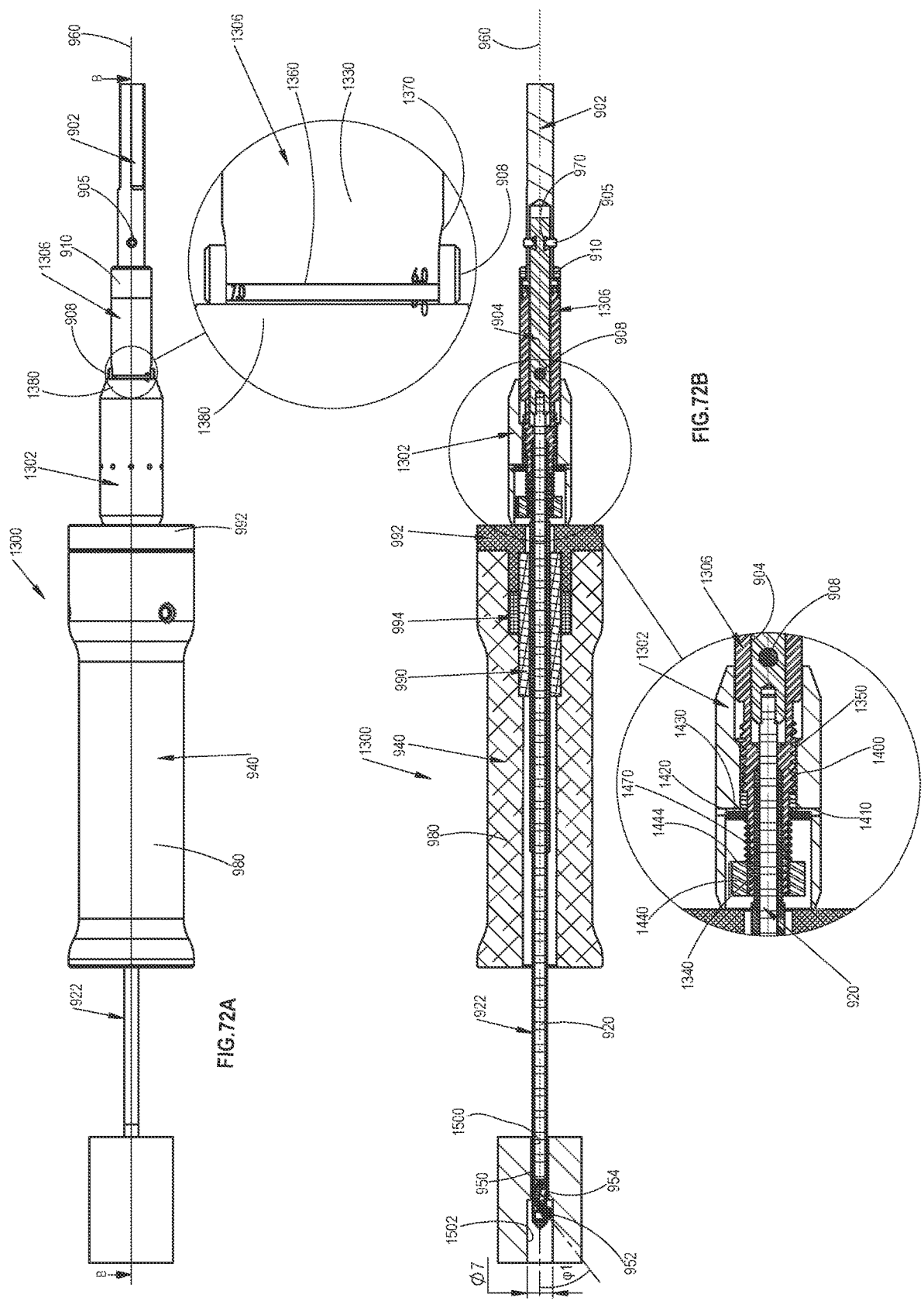
FIGS. 72A and 72B are simplified planar and sectional view illustrations of the bone material removal device and the cannula assembly of FIGS. 65 and 45 shown in a first partially open operative orientation inserted into a bone of the patient.

Reference is now made to FIGS. 72A and 72B, which are simplified planar and sectional view illustrations of an exemplary embodiment of the bone material removal device 1300 and the cannula assembly 940 of FIGS. 65 and 45 shown in a first partially open operative orientation inserted into a bone of the patient.

It is seen in this particular example shown in FIGS. 72A and 72B that the adjusting element 1302 is slightly rotated with respect to adjustable body crank element 1306, such that the inner threading 1400 of adjusting element 1302 is disposed slightly distally to the proximal end of the outer threading 1350 of the adjustable body crank element 1306, thus the guiding pin 908 is slightly displaced distally along slot 1370 and the marking scale 1360 indicates diameter of 7 mm in this particular example. It is seen that in this operative orientation, the cutting tooth 952 is only partially open, it is pivoted such that the cutting tooth 952 extends radially at an acute angle with respect to longitudinal axis 960.

It is particularly seen in FIGS. 72A and 72B that the direction of rotation of the rotational element 902 is reversed and the bone material removal device 1300 is now positioned in its partially open operative orientation, configured to create an undercut bore 1502 of a second diameter, which is generally greater than the first diameter of initial bore 1500.

It is noted that once the direction of rotation of the rotating element 902 is reversed, the tennon 930 that is mounted into tubular element 922 is seated within groove 1126 of inner sleeve 990 of cannula assembly 940 and due to press-fit engagement of cannula breaks 994 with inner sleeve 990, friction force is created between the tubular element 922 and the inner sleeve 990, thus permitting stopping the rotational movement of the tubular element 922 momentarily in order to enable changing the drilling rotational direction.

It is seen in FIGS. 72A and 72B that the undercut bore 1502 is formed over the initial bore 1500, undercut bore 1502 having a second diameter, which is greater than the first diameter while drilling with the bone material removal device 1300 positioned in its partially open operative orientation. It is noted that this undercut bore drilling is provided while the rotating element 902 is rotated in a second rotational direction, in this exemplary embodiment, in a counter-clockwise direction.

It is a particular feature of some embodiments of the present invention that once tennon 930 that is mounted into tubular element 922 is seated within groove 1126 of inner sleeve 990 of cannula assembly 940, the rotation of the tubular element 922 is momentarily stopped, the rotational direction of the drilling can be reversed, thus causing the pins 905 to be displaced along helical path 970 formed in guiding element 904, thus providing for distal longitudinal displacement of guiding element 904, thereby pushing the shaft element 920 distally, which in turn causes pivoting of hinge element 954 and pivoting of tooth 952 to assume its partially open operative orientation. It is a particular feature of some embodiments of the present invention that the guiding element 904 is distally advanced only up to the point where the guiding pin 908 is limited by the adjusting element 1302, thus the cutting tooth 952 in this operative orientation pivots up to an acute angle phi1 and protrudes through tip element 950, such as to form an undercut bore 1502 of 7 mm in this particular example.

The extent of longitudinal displacement of the shaft element 920 depends on the position of guiding pin 908 along slot 1370 of adjustable body crank element 1306, which is limited by engagement with adjusting element 1302. During the axial displacement of shaft element 920 in a distal direction, the guiding pin 908 is displaced along slot 1370 from its proximal end up to the point where the pin 908 engages the proximal end 1380 of adjusting element 1302.

While the rotating element 902 and the tubular element 922 are rotating in a counter-clockwise rotational direction, the cutting tooth 952 engages the bone of the patient and creates undercut bore 1502 therein. It is noted that the cutting tooth 952 can be closed once the direction of rotation is reversed and the bone material removal device 1300 can be advanced and retracted to and from the bone of the patient in order to create the desired length of undercut bore 1502.

Figure 73:
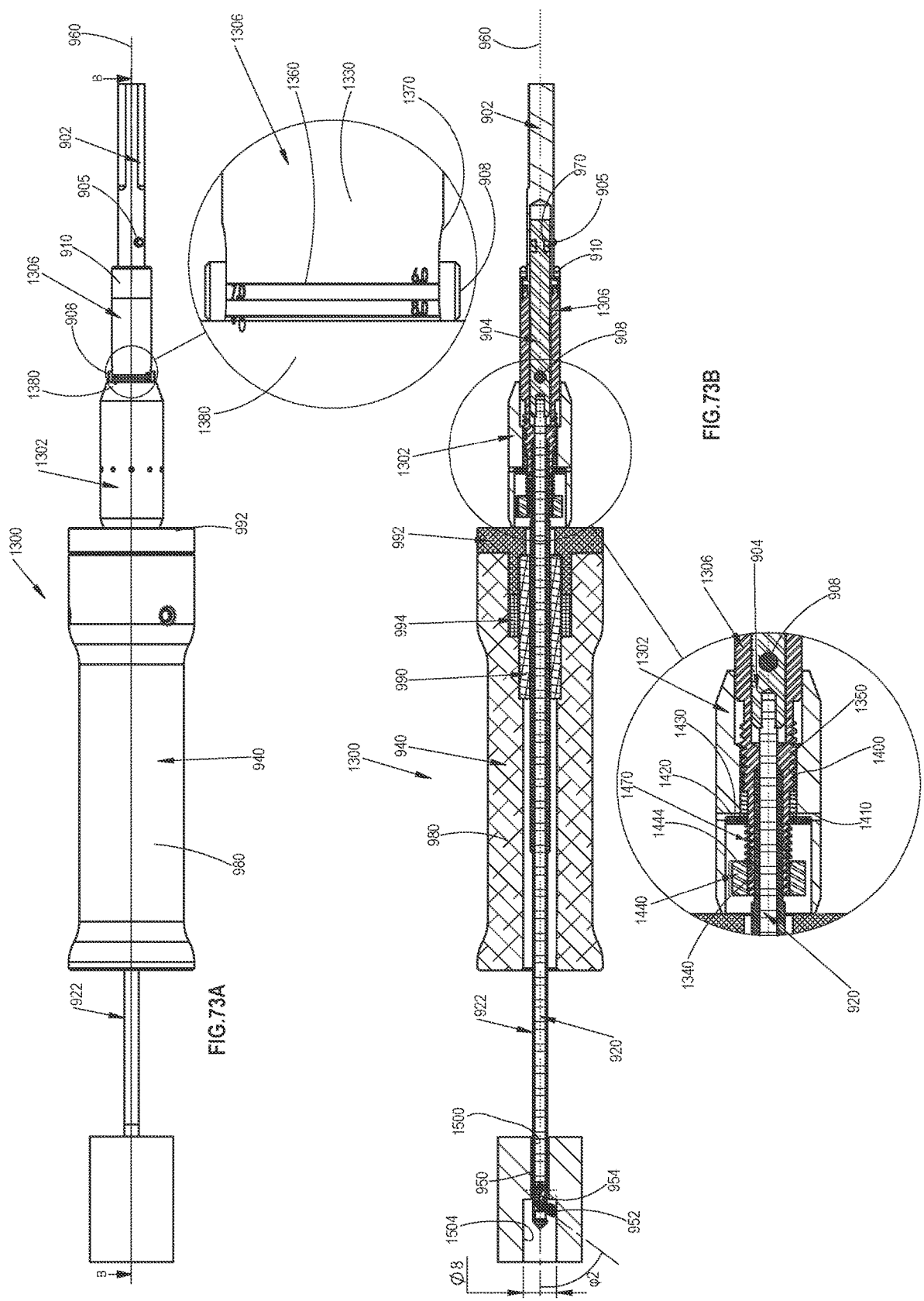
FIGS. 73A and 73B are simplified planar and sectional view illustrations of the bone material removal device and the cannula assembly of FIGS. 65 and 45 shown in a second partially open operative orientation inserted into a bone of the patient.

Reference is now made to FIGS. 73A and 73B, which are simplified planar and sectional view illustrations of an exemplary embodiment of the bone material removal device 1300 and the cannula assembly 940 of FIGS. 65 and 45 shown in a second partially open operative orientation inserted into a bone of the patient.

It is seen in this particular example shown in FIGS. 73A and 73B that the adjusting element 1302 is slightly more rotated with respect to adjustable body crank element 1306 than in FIGS. 72A and 72B, such that the inner threading 1400 of adjusting element 1302 is disposed slightly distally in comparison to its position as shown in FIGS. 72A and 72B, thus the guiding pin 908 is slightly displaced distally along slot 1370 and the marking scale 1360 indicates diameter of 8 mm in this particular example. It is seen that in this operative orientation, the cutting tooth 952 is only partially open, but more so than in FIGS. 72A and 72B, it is pivoted such that the cutting tooth 952 extends radially at an acute angle with respect to longitudinal axis 960.

It is particularly seen in the embodiment shown in FIGS. 73A and 73B that the cutting tooth 952 is configured to create an undercut bore 1504 of a third diameter, which is generally greater than the first and the second diameter.

It is seen in the embodiment shown in FIGS. 73A and 73B that the undercut bore 1504 is formed over the initial bore 1500, undercut bore 1504 having a third diameter, which is greater than the first diameter and the second diameter while drilling with the bone material removal device 1300 positioned in its partially open operative orientation. It is noted that this undercut bore drilling is provided while the rotating element 902 is rotated in a second rotational direction, in this exemplary embodiment, in a counter-clockwise direction.

It is a particular feature of some embodiments of the present invention that once tennon 930 that is mounted into tubular element 922 is seated within groove 1126 of inner sleeve 990 of cannula assembly 940, the rotation of the tubular element 922 is momentarily stopped, the rotational direction of the drilling can be reversed, thus causing the pins 905 to be displaced along helical path 970 formed in guiding element 904, thus providing for distal longitudinal displacement of guiding element 904, thereby pushing the shaft element 920 distally, which in turn causes pivoting of hinge element 954 and pivoting of tooth 952 to assume its partially open operative orientation. It is a particular feature of some embodiments of the present invention that the guiding element 904 is distally advanced only up to the point where the guiding pin 908 is limited by the adjusting element 1302, thus the cutting tooth 952 in this operative orientation pivots up to an acute angle phi2 and protrudes through tip element 950, such as to form an undercut bore 1504 of 8 mm in this particular example.

The extent of longitudinal displacement of the shaft element 920 depends on the position of guiding pin 908 along slot 1370 of adjustable body crank element 1306, which is limited by engagement with adjusting element 1302. During the axial displacement of shaft element 920 in a distal direction, the guiding pin 908 is displaced along slot 1370 from its proximal end up to the point where the pin 908 engages the proximal end 1380 of adjusting element 1302.

While the rotating element 902 and the tubular element 922 are rotating in a counter-clockwise rotational direction, the cutting tooth 952 engages the bone of the patient and creates undercut bore 1504 therein. It is noted that the cutting tooth 952 can be closed once the direction of rotation is reversed and the bone material removal device 1300 can be advanced and retracted to and from the bone of the patient in order to create the desired length of undercut bore 1504.

Figure 74:
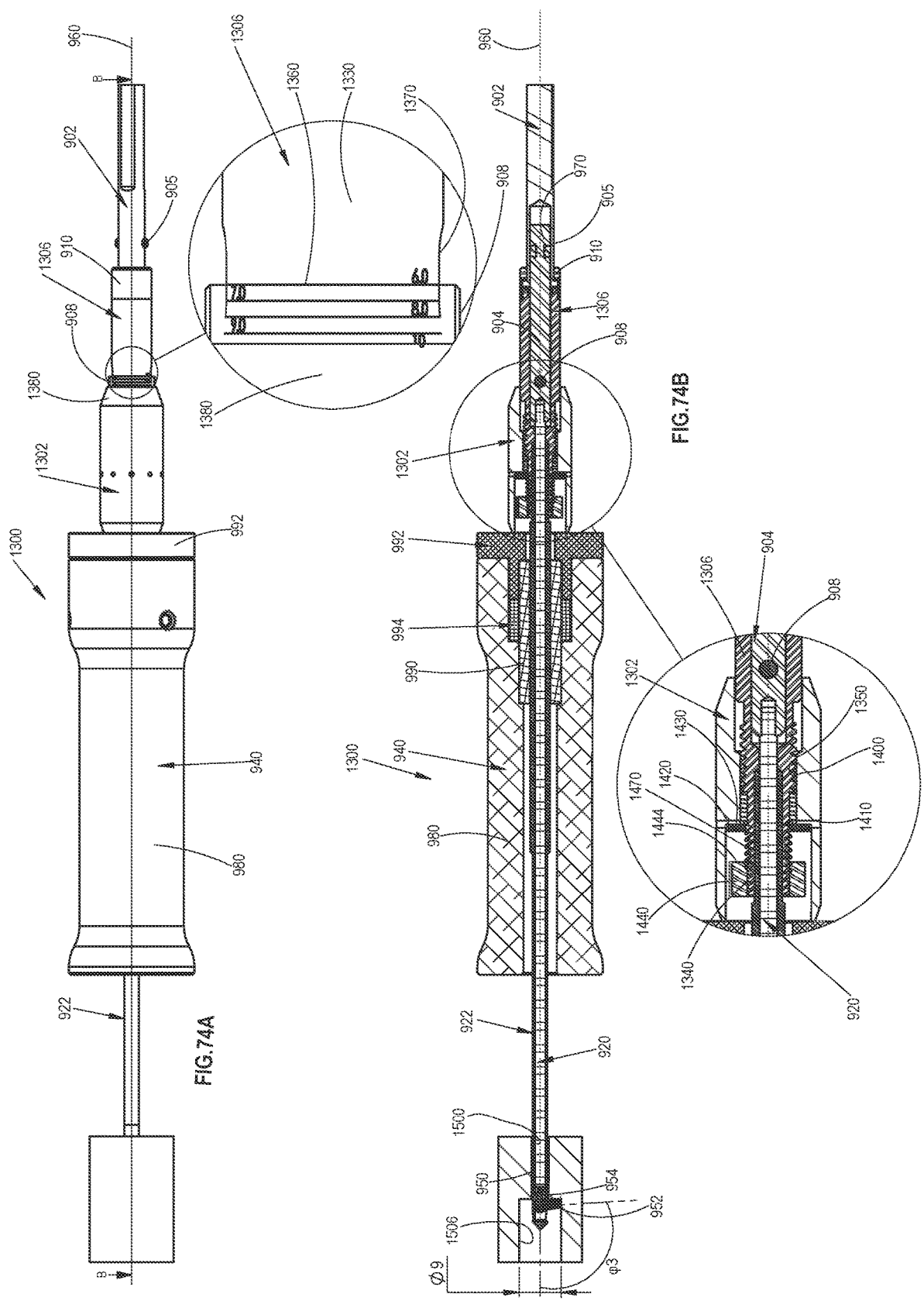
FIGS. 74A and 74B are simplified planar and sectional view illustrations of the bone material removal device and the cannula assembly of FIGS. 65 and 45 shown in a fully open operative orientation inserted into a bone of the patient.

Reference is now made to FIGS. 74A and 74B, which are simplified planar and sectional view illustrations of an exemplary embodiment of the bone material removal device 1300 and the cannula assembly 940 of FIGS. 65 and 45 shown in a fully open operative orientation inserted into a bone of the patient.

It is seen in this particular example shown in FIGS. 74A and 74B that the adjusting element 1302 is slightly more rotated with respect to adjustable body crank element 1306 than in FIGS. 73A and 73B, such that the inner threading 1400 of adjusting element 1302 is disposed slightly distally in comparison to its position as shown in FIGS. 73A and 73B, thus the guiding pin 908 is slightly displaced distally along slot 1370 and the marking scale 1360 indicates diameter of 9 mm in this particular example. It is seen that in this operative orientation, the cutting tooth 952 is now fully open, it is pivoted such that the cutting tooth 952 extends transversely with respect to longitudinal axis 960.

It is particularly seen in FIGS. 74A and 74B that the cutting tooth 952 is configured to create an undercut bore 1506 of a fourth diameter, which is generally greater than the first, the second and the third diameter.

It is seen in FIGS. 74A and 74B that the undercut bore 1506 is formed over the initial bore 1500, undercut bore 1506 having a fourth diameter, which is greater than the first, the second and the third diameter while drilling with the bone material removal device 1300 positioned in its fully open operative orientation. It is noted that this undercut bore drilling is provided while the rotating element 902 is rotated in a second rotational direction, in this exemplary embodiment, in a counter-clockwise direction.

It is a particular feature of some embodiments of the present invention that once tennon 930 that is mounted into tubular element 922 is seated within groove 1126 of inner sleeve 990 of cannula assembly 940, the rotation of the tubular element 922 is momentarily stopped, the rotational direction of the drilling can be reversed, thus causing the pins 905 to be displaced along helical path 970 formed in guiding element 904, thus providing for distal longitudinal displacement of guiding element 904, thereby pushing the shaft element 920 distally, which in turn causes pivoting of hinge element 954 and pivoting of tooth 952 to assume its fully open operative orientation. It is a particular feature of some embodiments of the present invention that the guiding element 904 is distally advanced only up to the point where the guiding pin 908 is limited by the adjusting element 1302, thus the cutting tooth 952 in this operative orientation pivots up to a straight angle phi3 and protrudes through tip element 950, such as to form an undercut bore 1506 of 9 mm in this particular example, which is the maximal diameter that can be formed using the particular cutting tooth 952 of this particular example. It is appreciated that any tooth configuration can be used which provides for any other range of diameters. It is also noted that the particular range of diameters exemplified in FIGS. 72A-74B is not limiting the scope of the present invention, any range of diameters can be formed using bone material removal device 1300.

The extent of longitudinal displacement of the shaft element 920 depends on the position of guiding pin 908 along slot 1370 of adjustable body crank element 1306, which is limited by engagement with adjusting element 1302. During the axial displacement of shaft element 920 in a distal direction, the guiding pin 908 is displaced along slot 1370 from its proximal end up to the point where the pin 908 engages the proximal end 1380 of adjusting element 1302.

While the rotating element 902 and the tubular element 922 are rotating in a counter-clockwise rotational direction, the cutting tooth 952 engages the bone of the patient and creates undercut bore 1504 therein. It is noted that the cutting tooth 952 can be closed once the direction of rotation is reversed and the bone material removal device 1300 can be advanced and retracted to and from the bone of the patient in order to create the desired length of undercut bore 1506.

A bone material removal device is disclosed herein, which is particularly useful for drilling a small diameter bore with varying diameters.

Figure 75:
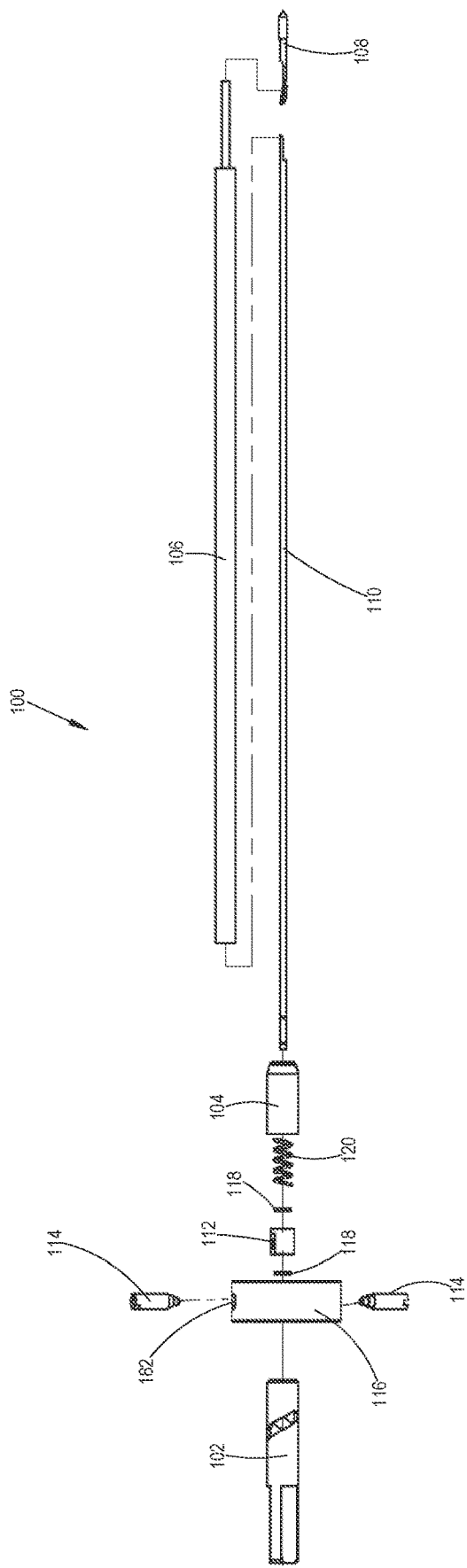
FIG. 75 is a simplified exploded view illustration of a bone material removal device constructed and operative in accordance with some embodiments of the present invention.

Reference is now made to FIG. 75, which is a simplified exploded view illustration of a bone material removal device constructed and operative in accordance with an embodiment of the present invention.

It is seen in FIG. 75 that a bone material removal device 10000 includes a rotating element 10200 at its proximal end, a connecting tube 10400 adapted to be distally attached thereto or integrally made therewith and a drill tube 10600 adapted to be distally attached to connecting tube 10400 or integrally made therewith.

A drilling tip 10800 is adapted to be connected or integrally formed with drill tube 10600. An activating rod 11000 is adapted to be coaxially arranged within the rotating element 10200, connecting tube 10400 and drill tube 10600.

As shown in FIG. 75, the bone material removal device 10000 comprises a shaft displacement actuator comprising a rotating element 10200 coupled to an eccentric rotatable mass, e.g., a flywheel, rotatingly and slidingly coupled to bushing 11200 and limiting screws 11400. The activating rod 11000 is adapted to be inserted into the rotating element 10200 and slidably attached to rotating element 10200 by means of a bushing 11200 and limiting screws 11400. The limiting screws 11400 extend generally radially with respect to activating rod 11000 and protrude through an eccentric rotatable mass 11600, which is mounted onto the rotating element 10200. In some embodiments, the rotatable eccentric mass comprises a flywheel. It is additionally seen that generally two locking rings 11800 are disposed at each side of bushing 11200 and a resilient element, such as a coil spring 12000 is generally adapted to be disposed partially within the rotating element 10200 and partially within connecting tube 10400. Reference numerals in FIGS. 75-86 can be interpreted to refer to corresponding reference numerals in the specification, with a trailing '00' added. For example, in FIG. 75, reference numeral 100 can be interpreted to refer to reference numeral 10000 in the specification.

It is additionally seen that generally two locking rings 11800 are disposed at each side of bushing 11200 and a resilient element, such as a coil spring 12000 is generally adapted to be disposed partially within the rotating element 10200 and partially within connecting tube 10400.

Figure 76:
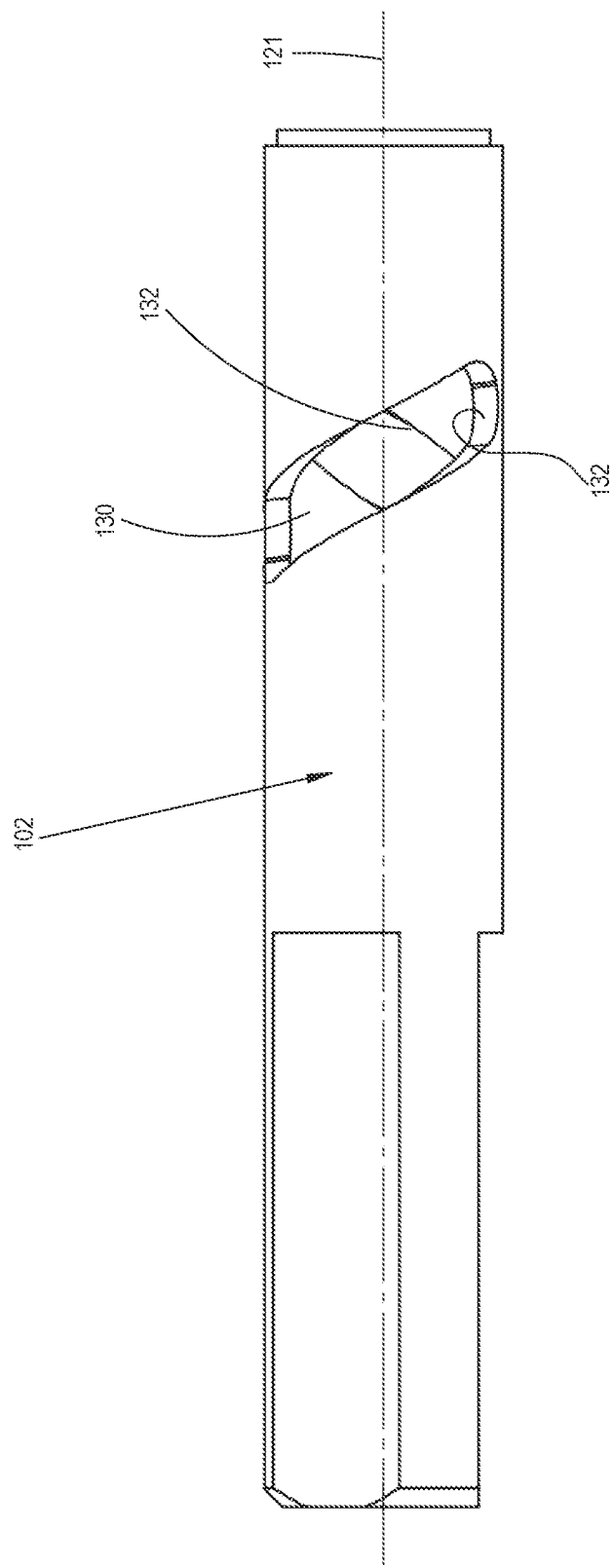
FIG. 76 is a simplified pictorial side view illustration of a rotating element of the bone material removal device of FIG. 75.

Reference is now made to FIG. 76, which is a simplified pictorial side view illustration of the rotating element 10200 of the bone material removal device 10000 of FIG. 75.

Figure 82A:
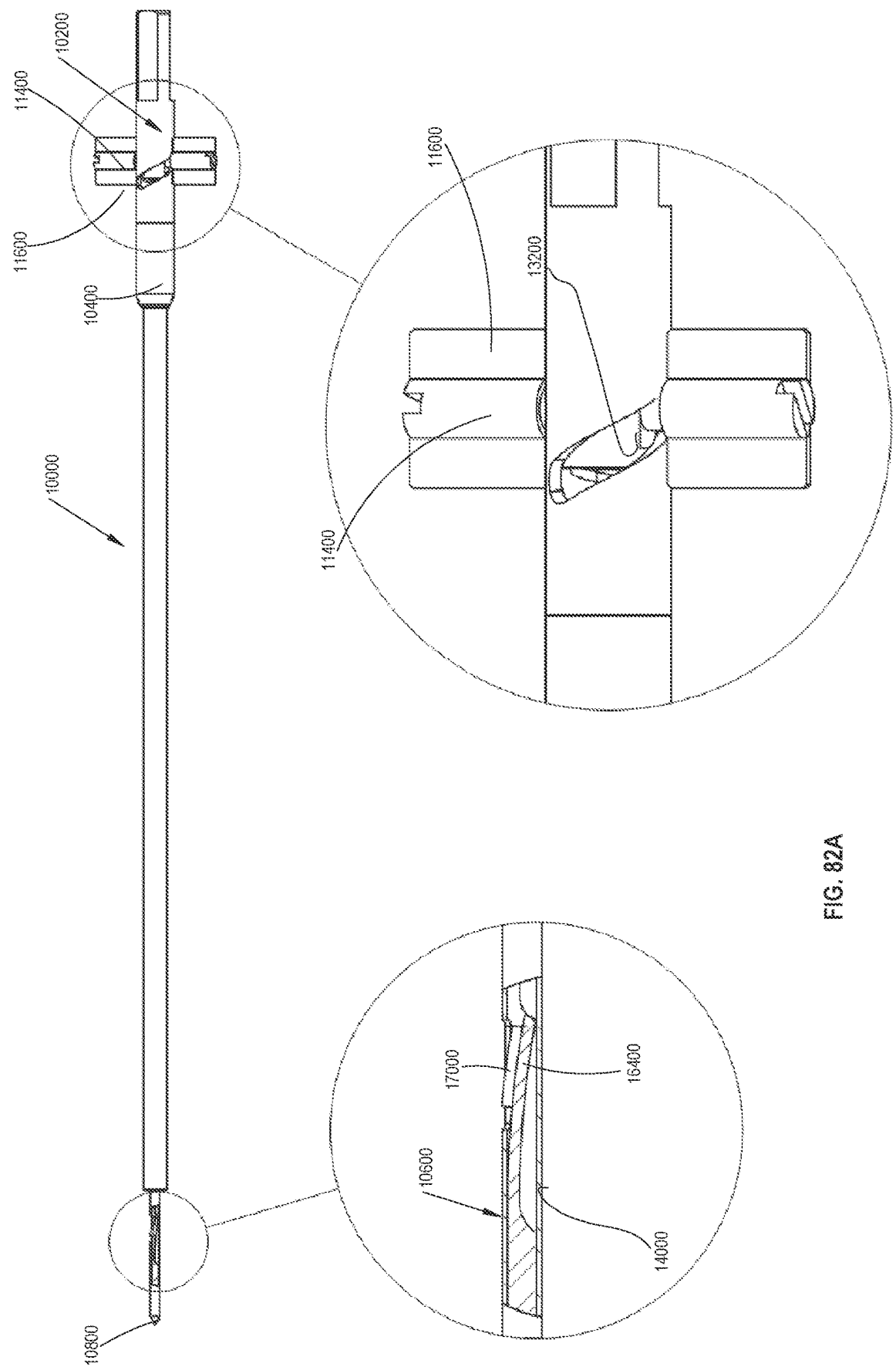
FIGS. 82A and 82B are simplified respective pictorial and sectional view illustrations of an embodiment of the bone material removal device of FIG. 75 shown in a first closed operative drilling orientation.
Figure 83A:
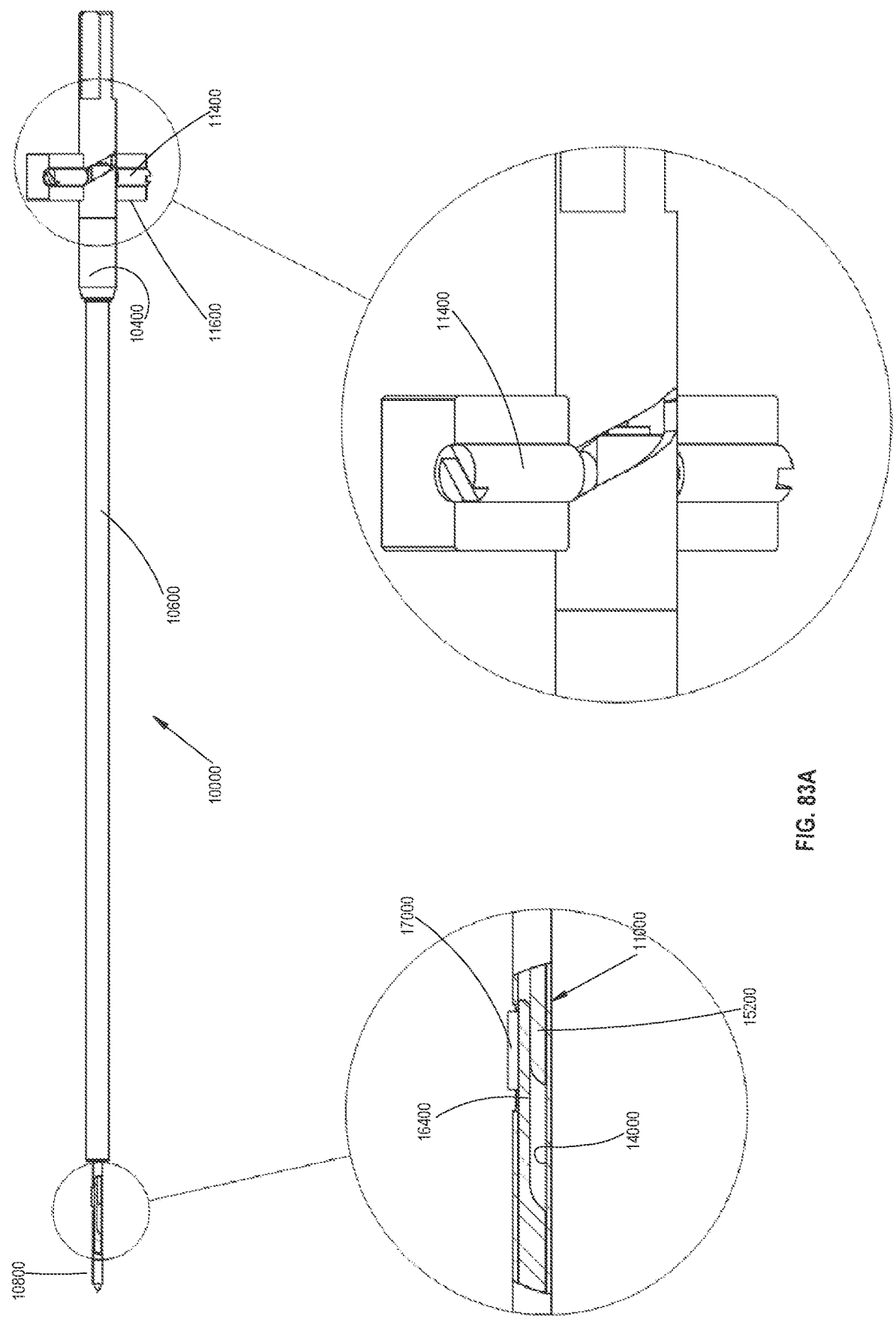
FIGS. 83A and 83B are simplified pictorial and sectional view illustrations of an embodiment of the bone material removal device of FIG. 75 shown in a second open operative drilling orientation.

It is seen in FIG. 76 and additionally seen in FIGS. 82A and 83A that the rotating element 10200 is a generally cylindrical element arranged along a longitudinal axis 12100. Rotating element 10200 has a distal end, which is adapted to be connected to a power tool and a proximal end, which is adapted to be attached to connecting tube 10400.

Rotating element 10200 has an internal socket 13000 extending distally from its proximal end.

It is additionally seen in FIG. 76 that typically two circumferential guiding slots 13200 are arranged on the rotating element 10200 adjacent the proximal end thereof. The guiding slots 13200 are generally oriented in opposite directions.

Figure 77:
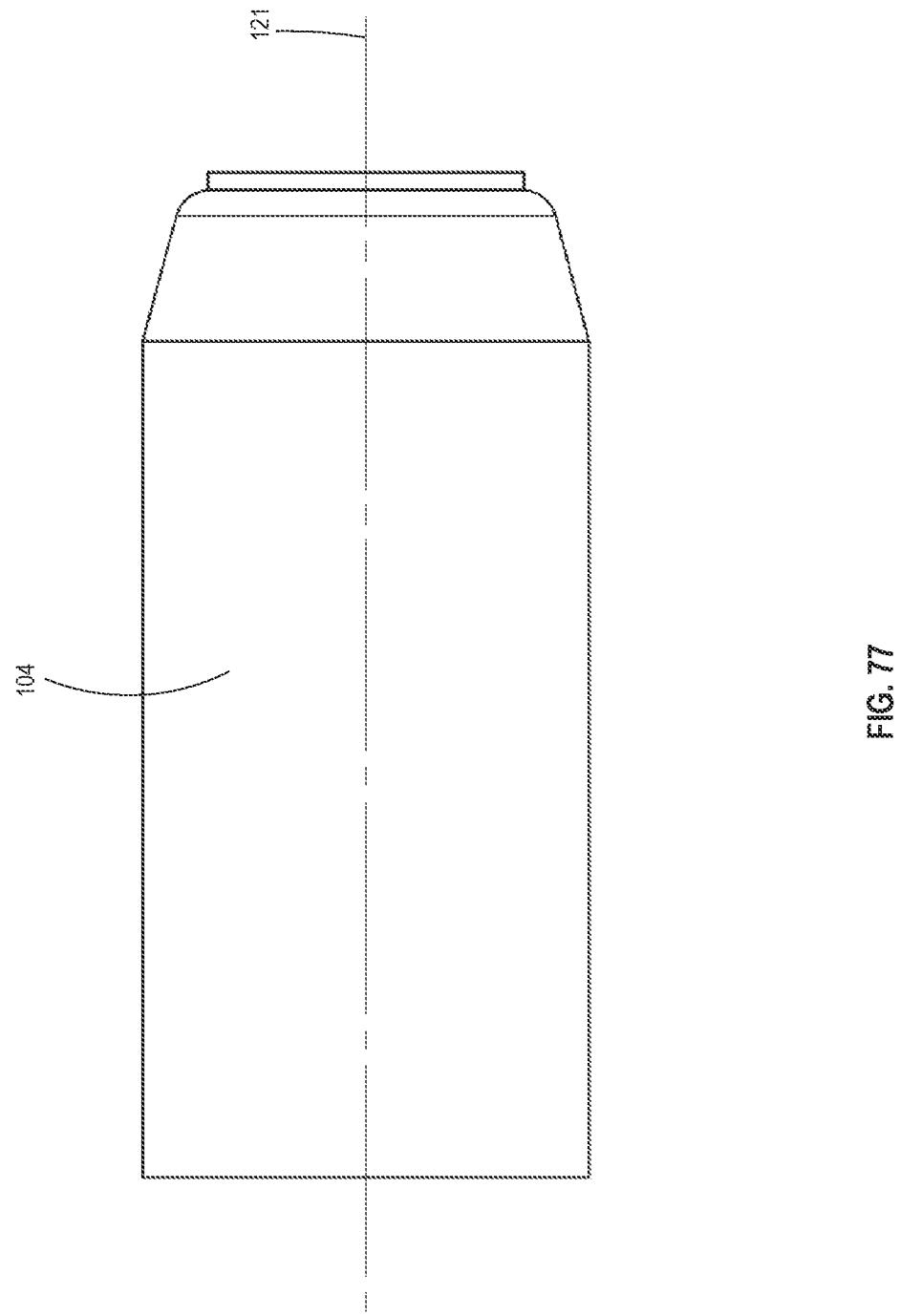
FIG. 77 is a simplified pictorial side view illustration of an embodiment of a connecting tube of the bone material removal device of FIG. 75.

Reference is now made to FIG. 77, which is a simplified pictorial side view illustration of the connecting tube 10400 of the bone material removal device 10000 of FIG. 75.

It is seen in FIG. 77 and additionally seen in FIGS. 82A and 83A that the connecting tube 10400 is a generally cylindrical element arranged along longitudinal axis 12100. Connecting tube 10400 has a distal end, which is adapted to be connected to the rotating element 10200 and a proximal end, which is adapted to be attached to drill tube 10600. Connecting tube 10400 has an internal socket 13600 extending distally from its proximal end for attachment of the drill tube 10600. Connecting tube 10400 additionally has an internal socket 13800 extending proximally from its distal end for supporting one end of spring 12000.

Figure 78:
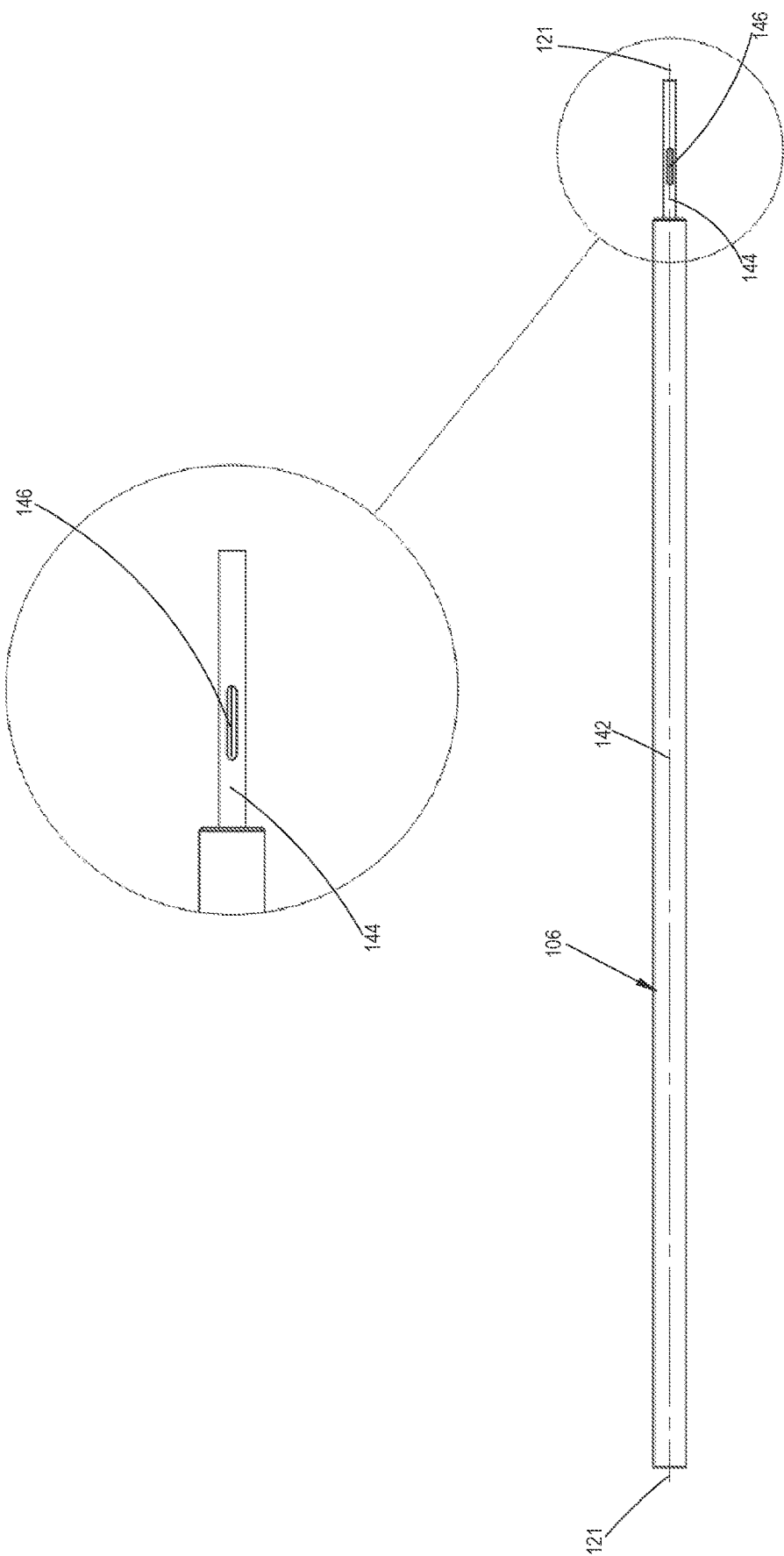
FIG. 78 is a simplified pictorial side view illustration of an embodiment of a drill tube of the bone material removal device of FIG. 75.

Reference is now made to FIG. 78, which is a simplified pictorial side view illustration of the drill tube 10600 of the bone material removal device 10000 of FIG. 75.

It is seen in FIG. 78 and additionally seen in FIGS. 82A and 83A that the drill tube 10600 is a generally cylindrical element arranged along longitudinal axis 12100. Drill tube 10600 has a distal end, which is adapted to be connected to the rotating element 10200 and a proximal end, which is adapted to be attached to connecting tube 10400. The drilling tube has a longitudinal bore 14000 extending therethrough.

It is additionally seen that the drill tube 10600 has a main portion 14200 having a first outer diameter and a proximal portion 14400 having a second diameter, generally smaller than the first diameter.

It is seen that a slot 14600 is generally formed in proximal portion 14400.

Reference is now made to FIG. 79, which is a simplified pictorial side view illustration of the activating rod 11000 of the bone material removal device 10000 of FIG. 75.

It is seen in FIG. 79 and additionally seen in FIGS. 82A and 83A that the activating rod 11000 is a generally cylindrical element arranged along longitudinal axis 12100. Activating rod 11000 has a distal end having typically two circumferential recesses 15000 formed thereon and spaced one from each other. The recesses 15000 are adapted for mounting of locking rings 11800 therewithin in order to lock the bushing 11200 to the activating rod 11000.

It is additionally seen in FIG. 78 that an activating tip 15200 protrudes proximally from the proximal end of the activating rod 11000. The activating tip 15200 defines a proximally facing shoulder 15400 therebetween and between the distal end of the activating rod 11000. The activating tip 15200 has a generally rounded distal tip 15600 and a generally flat surface 15800 between the rounded activating tip 15200 and shoulder 15400.

Figure 80A:
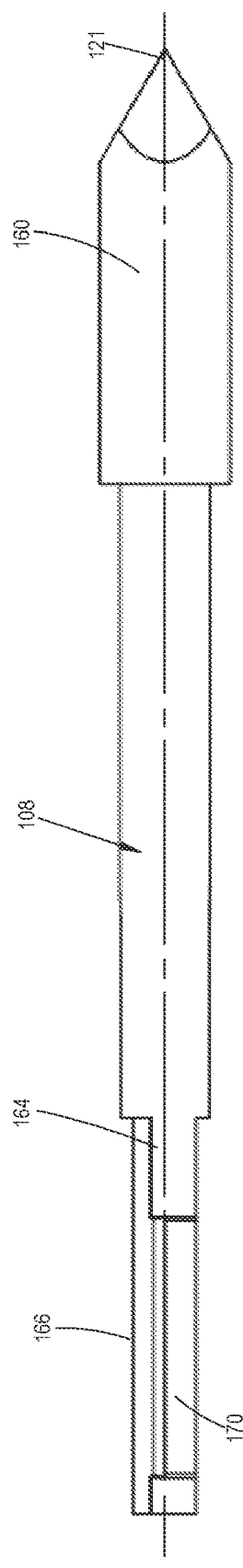
FIGS. 80A and 80B are simplified two different side view illustrations of an embodiment of a drilling tip of the bone material removal device of FIG. 75.
Figure 80B:
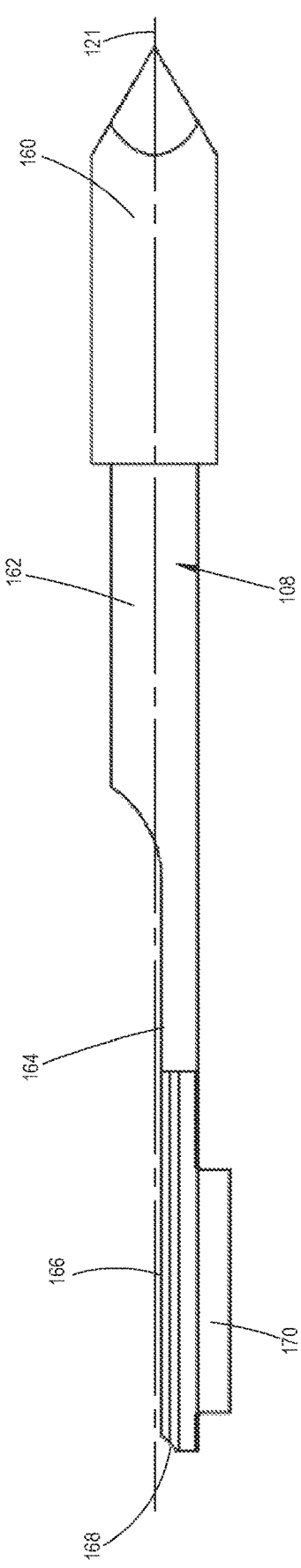

Reference is now made to FIGS. 80A and 80B, which are simplified two different side view illustrations of the drilling tip 10800 of the bone material removal device 10000 of FIG. 75.

It is seen in FIGS. 80A and 80B and additionally seen in FIGS. 82A and 83A that the drilling tip 10800 is a generally cylindrical element arranged along longitudinal axis 12100. Drilling tip 10800 has a sharp proximal end 16000 and a main portion 16200 adapted to be inserted into and attached to the drill tube 10600. A distal portion 16400 of the drilling tip 10800 defines a generally flat surface 16600 and a slightly rounded distal end 16800.

It is particularly seen that a cutting tooth 17000 is disposed on a surface located opposite to surface 16600 and protrudes radially outwardly therefrom. It is appreciated that alternatively a plurality of cutting teeth 17000 may be disposed on the drilling tip 10800.

It is appreciated that in an un-stressed position the distal portion 16400 of the drilling tip 10800 is deflected, as particularly shown in FIG. 82A.

Figure 81:
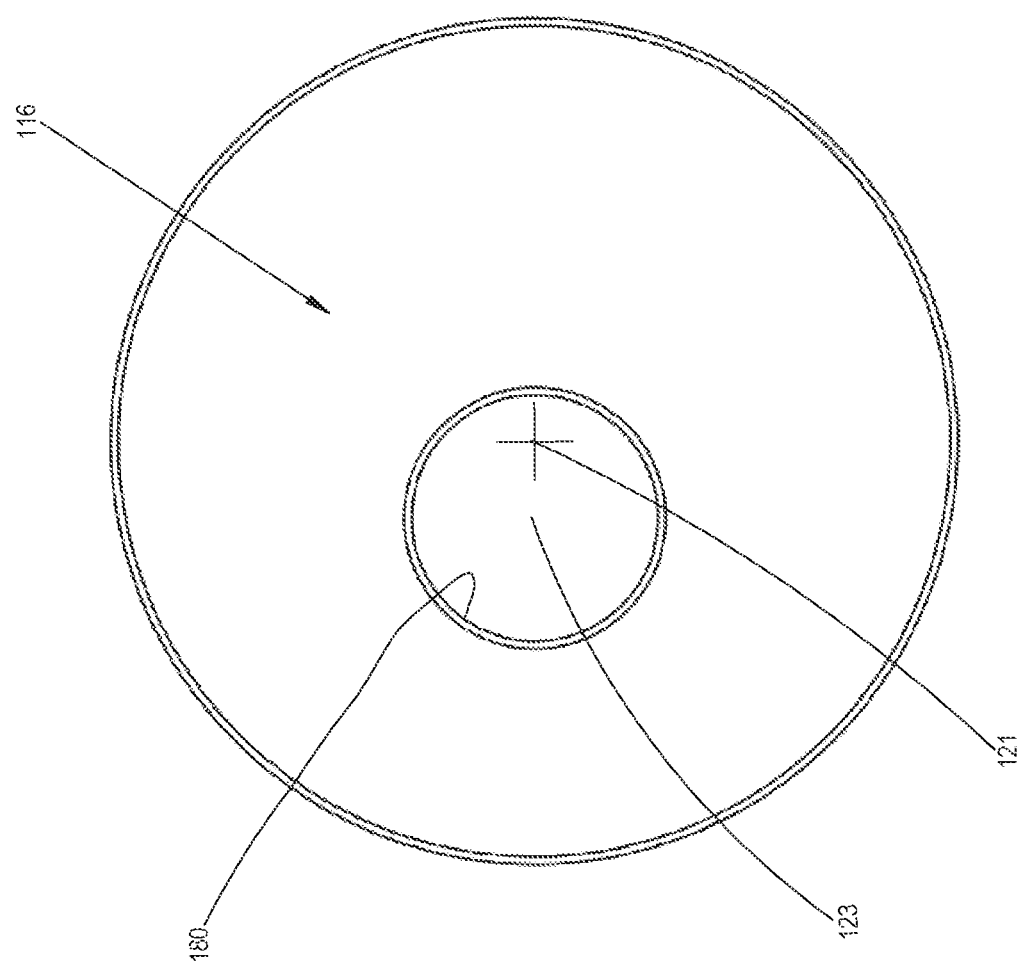
FIG. 81 is a simplified side view illustration of an embodiment of an eccentric mass portion of a shaft displacement actuator of the bone material removal device of FIG. 75.

Reference is now made to FIG. 81, which is a simplified side view illustration of the eccentric mass, (e.g., flywheel) 11600 of the bone material removal device 10000 of FIG. 75.

It is seen in FIGS. 75, 81, 82A-B and 83A-B that eccentric mass 11600 is a ring-shaped element having a longitudinally extending bore 18000 extending therethrough for mounting the eccentric mass 11600 onto rotating element 10200. It is seen particularly in FIG. 81 that bore 18000 is arranged along a longitudinal axis 12300, which is offset from longitudinal axis 12100.

Figure 82B:
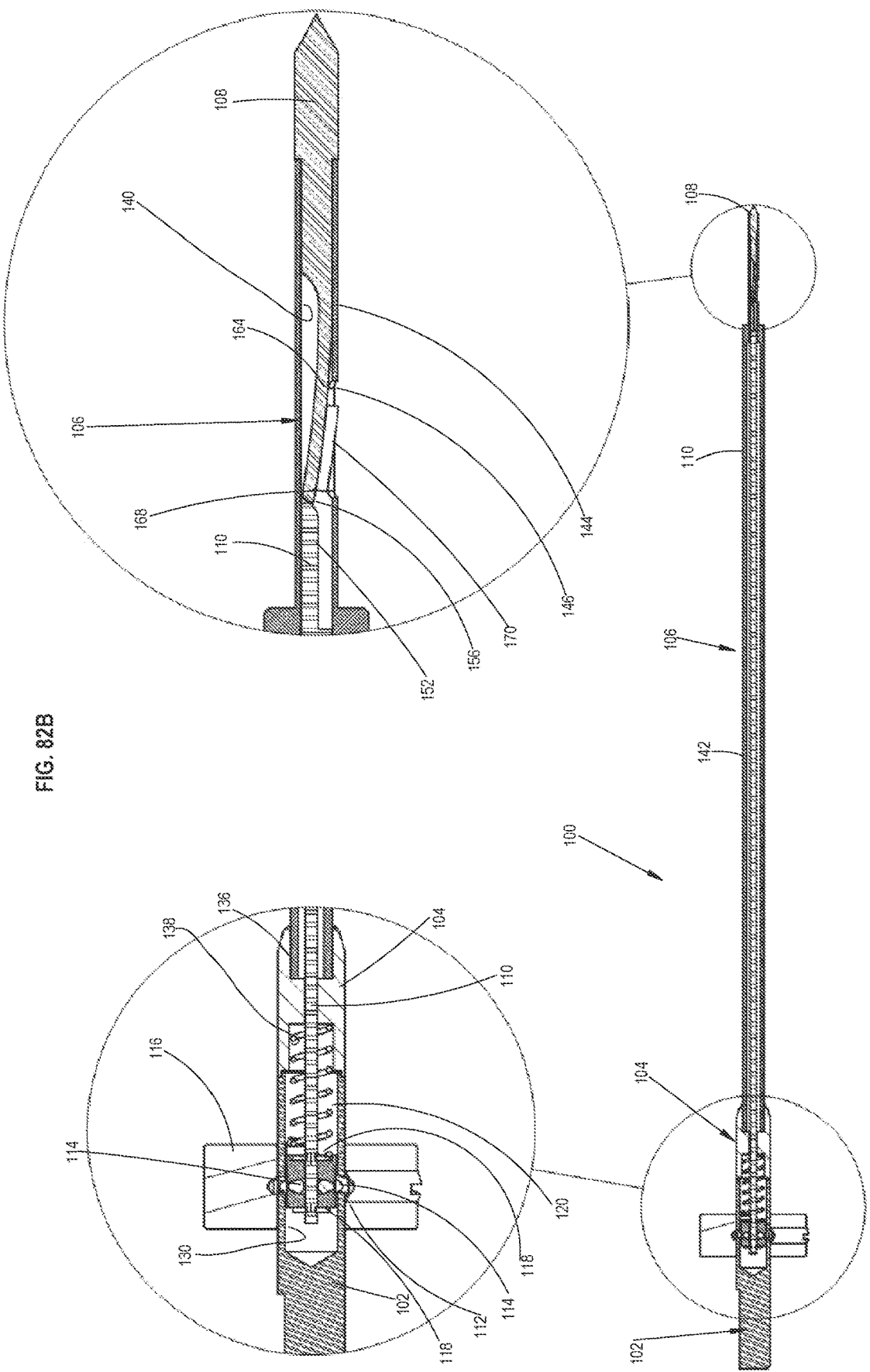

It is noted that typically two radially extending bores 18200 (seen in FIG. 75) extend through eccentric mass 11600 for insertion of limiting screws 11400 therethrough. Reference is now made to FIGS. 82A and 82B, which are simplified respective pictorial and sectional view illustrations of the bone material removal device 10000 of FIG. 75 shown in a first closed operative drilling orientation.

The bone material removal device 10000 is shown in a closed operative drilling orientation in FIGS. 82A-B.

It is seen that connecting tube 10400 is attached to rotating element 10200 and drill tube 10600 is attached to connecting tube 10400, such that the distal end of drill tube 10600 is inserted into socket 13600 of connecting tube 10400.

Drilling tip 10800 is attached to the proximal end of the drill tube 10600. Activating rod 11000 is inserted into the drill tube 10600 and drilling tip 10800 is attached to the drill tube 10600, such that distal portion 16400 of drilling tip 10800 is in the non-stressed position and the cutting tooth 17000 is contained within the diameter of the proximal portion 14400 of drill tube 10600. In this orientation, the cutting tooth 17000 is located adjacent slot 14600 but does not protrude therethrough.

The proximal end 15200 of the activating rod 11000 is positioned adjacent the distal portion 16400 of drilling tip 10800, such that round tip 15600 of activating rod 11000 abuts rounded tip 16800 of drilling tip 10800.

It is additionally seen in FIG. 82B that bushing 11200 is retained on activating rod 11000 by locking rings 11800 positioned within recesses 15000. Limiting screws 11400 protrude from the bushing 11200 through guiding slots 13200 in the rotating element 10200 and through bores 18200 in the eccentric mass 11600.

Spring 12000 is disposed between the proximal locking ring 11800 and the distally facing surface of socket 13800 of the connecting tube 10400. The spring 12000 is positioned in a normally un-stressed operative orientation in this closed operative orientation of the bone material removal device 10000. The bushing 11200 is slightly proximally spaced from the proximally facing surface of socket 13000 of the rotating element 10200.

It is a particular feature of an embodiment of the present invention that the distal portion 16400 of the drilling tip 10800 is positioned in a normally radially inwardly deflected orientation, such that the cutting tooth 170 is contained within the inner volume of the drill tube 10600.

It is a particular feature of an embodiment of the present invention that once the bone material removal device 10000 is rotated in a first rotational direction, limiting screws 11400 are positioned at one end of the circumferential slots 13200 and prevented from further radial movement, thus the activating rod 11000 is positioned in a retracted position, in which the spring 12000 is released and the flat surface 15800 of activating rod 11000 does not engage flat surface 16600 of the drilling tip 10800, thus the cutting tooth 17000 remains contained within the inner volume of drill tube 10600 and the bone material removal device 10000 is positioned in a closed operative orientation.

Figure 83B:
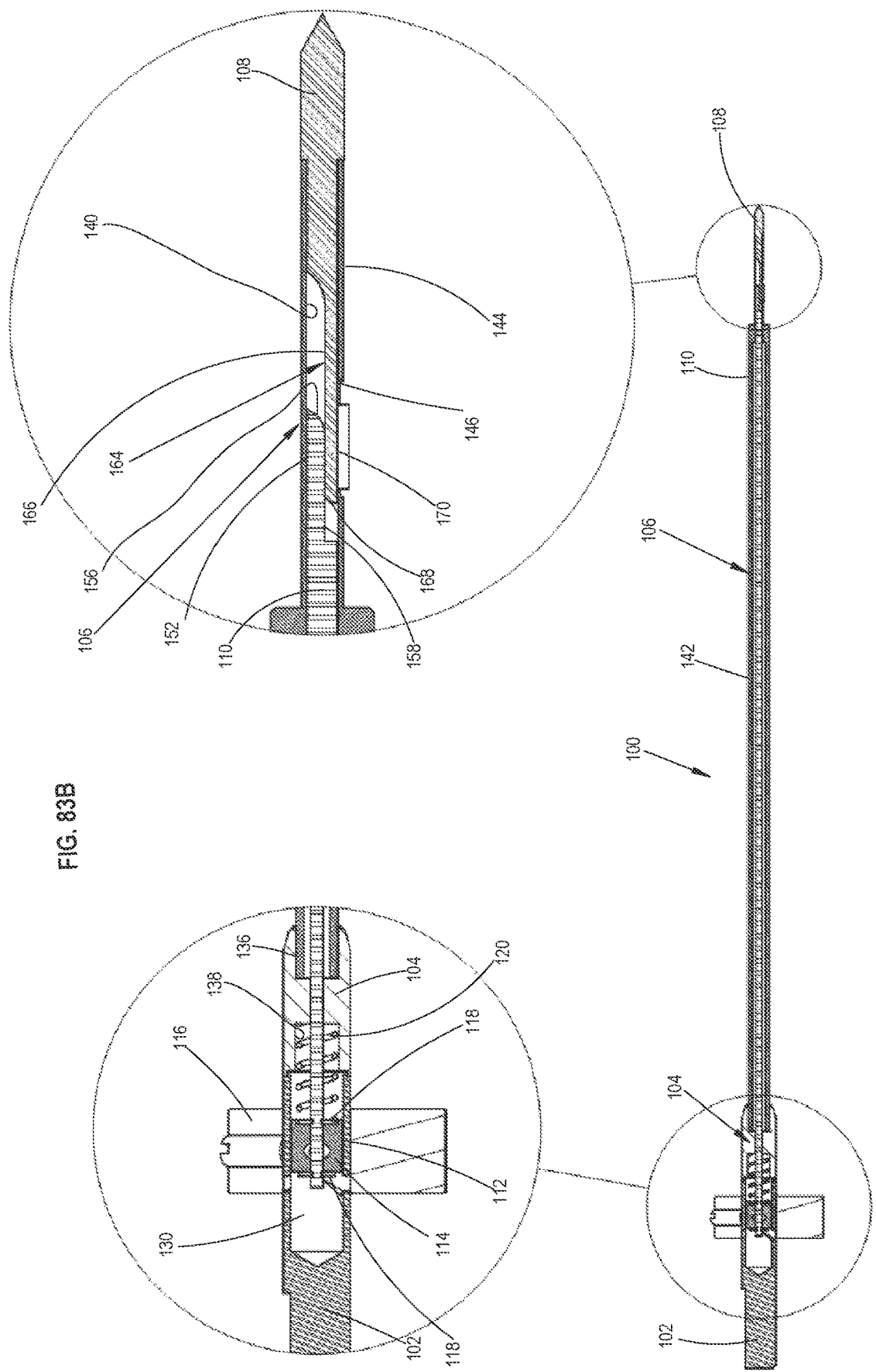

Reference is now made to FIGS. 83A and 83B, which are simplified respective pictorial and sectional view illustrations of the bone material removal device 10000 of FIG. 75 shown in a second open operative drilling orientation.

The bone material removal device 10000 is shown in an open operative drilling orientation in FIGS. 83A-B.

It is seen that connecting tube 10400 is attached to rotating element 10200 and drill tube 10600 is attached to connecting tube 10400, such that the distal end of drill tube 10600 is inserted into socket 13600 of connecting tube 10400.

Drilling tip 10800 is attached to the proximal end of the drill tube 10600. Activating rod 11000 is inserted into the drill tube 10600 and drilling tip 10800 is attached to the drill tube 10600, such that distal portion 16400 of drilling tip 10800 is positioned in a stressed position in this open orientation, such that the cutting tooth 170 protrudes through slot 14600 formed in proximal portion 14400 of drill tube 10600. The cutting tooth 17000 protrudes through slot 14600 due to the fact that the activating rod 11000 is displaced proximally, the spring 12000 is compressed and the proximal portion 15200 of the activating rod 11000 slides under the distal portion 16400 of the drilling tip 10800, by means of engagement of rounded tip 16800 of the drilling tip 10800 and rounded tip 15600 of actuating rod 11000. Once flat surface 15800 of activating rod 11000 abuts flat surface 16600 of drilling tip 10800, the distal portion 16400 is deflected radially outwardly and the cutting tooth 17000 protrudes through slot 14600 of drill tube 10600.

It is a particular feature of an embodiment of the present invention that once the bone material removal device 10000 is rotated in a second rotational direction, which is opposite to the first rotational direction, the eccentric mass 11600 is rotated and due to centrifugal force exertion, limiting screws 11400 are positioned at an opposite end of the circumferential slots 13200 and prevented from further radial movement, thus the activating rod 11000 is displaced to an advanced position, in which the spring 12000 is compressed and the flat surface 15800 of activating rod 11000 engages flat surface 16600 of the drilling tip 10800, thus the cutting tooth 17000 is radially outwardly deflected to protrude from the inner volume of drill tube 10600 and the bone material removal device 10000 is positioned in an open operative orientation.

In an alternative embodiment, the activating rod 11000 may be displaced proximally manually in order to outwardly deflect the cutting tooth 17000, such that it protrudes from the inner volume of drill tube 10600 and the bone material removal device 10000 is positioned in an open operative orientation.

It is additionally seen in FIG. 83B that bushing 11200 is retained on activating rod 11000 by locking rings 11800 positioned within recesses 15000. Limiting screws 11400 protrude from the bushing 11200 through guiding slots 13200 in the rotating element 10200 and through bores 182 in the eccentric mass 11600.

Spring 12000 is disposed between the proximal locking ring 11800 and the distally facing surface of socket 13800 of the connecting tube 10400. The spring 12000 is positioned in a compressed operative orientation in this open operative orientation of the bone material removal device 10000. The bushing 11200 is slightly more proximally spaced from the proximally facing surface of socket 130 of the rotating element 10200 as compared to the bushing position in FIG. 82B.

Figure 84:
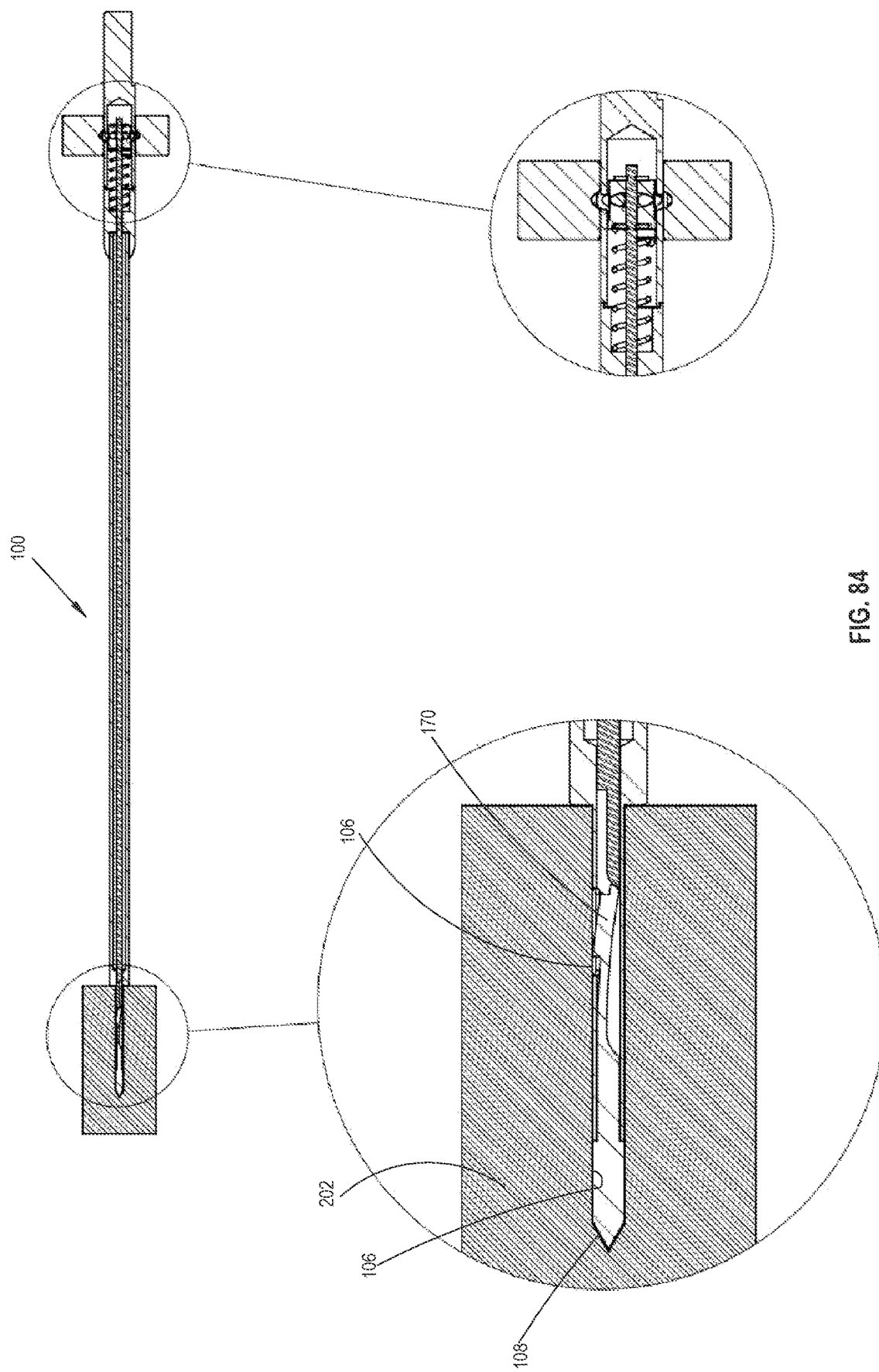
FIG. 84 is a simplified partial sectional view illustration of an embodiment of the bone material removal device of FIG. 75 shown in the first closed operative drilling orientation within the bone of a patient.
Figure 85:
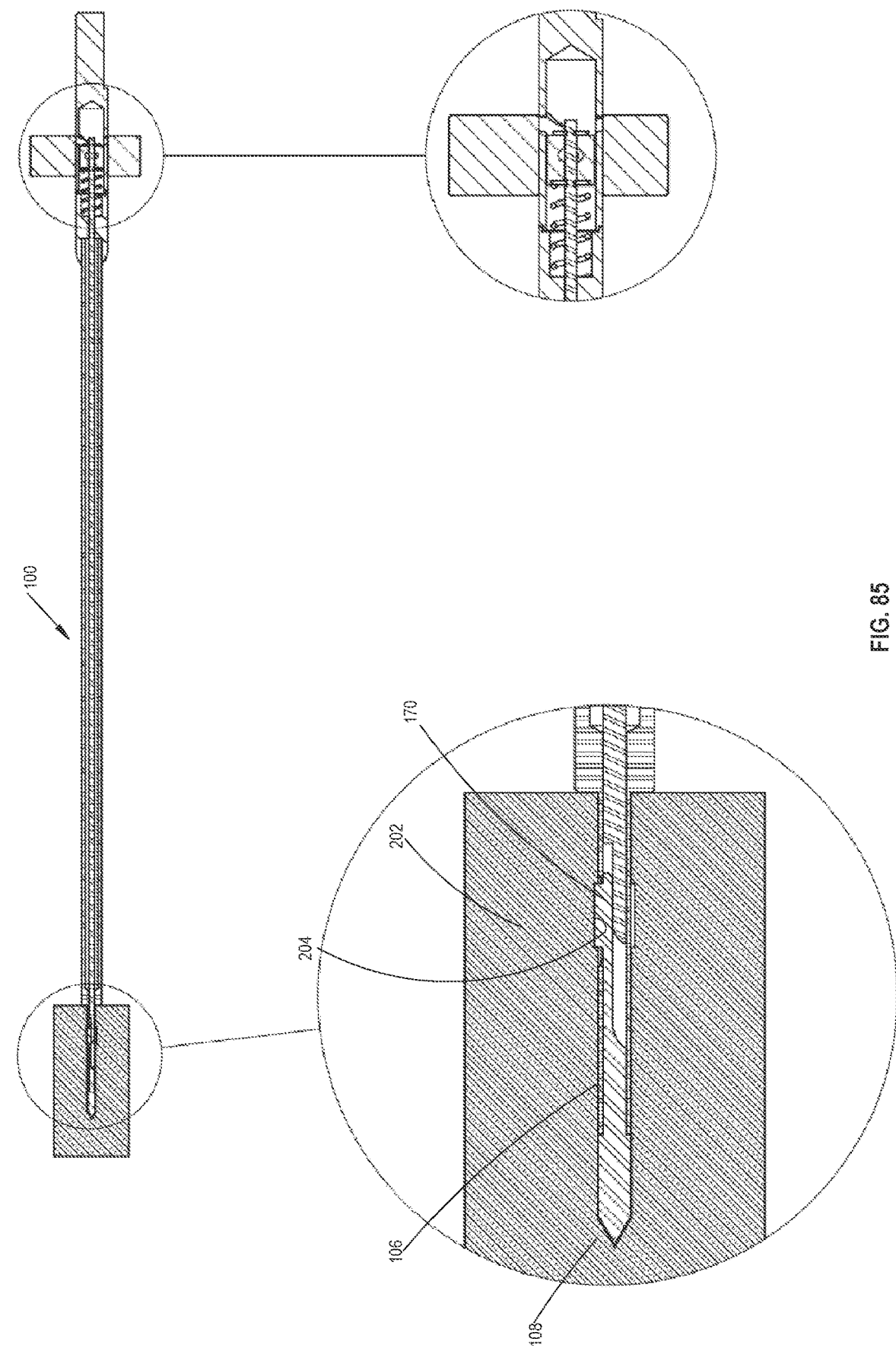
FIG. 85 is a simplified partial sectional view illustration of an embodiment of the bone material removal device of FIG. 75 shown in the second open operative drilling orientation within the bone of a patient.

Reference is now made to FIG. 84, which is a simplified partial sectional view illustration of the bone material removal device 10000 of FIG. 75 shown in the first closed operative drilling orientation within the bone of a patient and to FIG. 85, which is a simplified partial sectional view illustration of the bone material removal device 10000 of FIG. 75 shown in the second open operative drilling orientation within the bone of a patient. Reference is additionally made to FIG. 86, which is a simplified partial sectional view illustration of the patient bone following removal of the bone material removal device.

It is a particular feature of an embodiment of the present invention that the cutting tooth 17000 is at least partially contained within the inner volume of the drill tube 10600 and is selectively positioned in a closed position enabling drilling a bore of a first diameter within the bone of a patient and in an open position enabling drilling a bore of a second diameter within the bone of a patient, whereas the first diameter is preferably equal to the outer diameter of the drill tube 10600 and second diameter is preferably greater than the first diameter, thus an undercut is formed within the bone of a patient.

It is appreciated that biological material, such as a medicament may be retained within this cavity.

It is seen particularly in FIG. 84 that an initial bore 20000 of a first diameter is formed within the bone 20200 of a patient.

The radius of the initially drilled bore can be for example in the range of 0.5 mm-1 mm or any other radius, preferably equal to the outer diameter of drill tube 10600.

It is a particular feature of an embodiment of the present invention that in the open operative orientation of the bone material removal device 10000, the cutting tooth 17000 extends radially outwardly from the outer diameter of the drill tube 10600. Thus, the drilling radius formed by the cutting tooth 17000 is substantially greater than the drilling radius initially formed by the outer diameter of the drill tube 10600.

It is seen particularly in FIG. 85 that an undercut 20400 having a second diameter is formed over the initial bore 20000 of a first diameter in the bone 20200 of a patient, whereas the second diameter is substantially greater than the first diameter.

The radius of the undercut can be for example in the range of 0.75 mm-1.25 mm.

It is a further particular feature of an embodiment of the present invention that the length of the undercut 20400 formed in the bone 20200 of a patient is a function of the length of the cutting tooth 17000 of the drilling tip 10800.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of drilling a varying diameter bore, comprising:
    rotating a second actuator portion of an actuator of a bone material removal device in a first rotational drilling direction while pushing a drilling tip of the bone material removal device in a distal direction into a bone of a patient to form an initial bore in the bone of the patient;
    wherein said rotating the second actuator portion in the first rotational drilling direction maintains a selectably openable cutting tooth in a closed position; and
    reversing the drilling rotational direction by rotating the second actuator portion in a second rotational drilling direction, said second actuator portion rotatably coupled to a first actuator portion, and wherein said rotating of the second actuator portion in the second drilling direction causes the first actuator portion to be displaced distally relative to the second actuator portion, the distal displacement of the first actuator portion distally causing the cutting tooth to extend to an open position.

2. A method according to claim 1, said method further including, before said reversing, stopping said rotating of the bone material removal device in the first direction.

3. A method according to claim 1, wherein said actuator includes a first adjustment portion and a second adjustment portion, whereby said first adjustment portion is rotatable in increments relative to said second adjustment portion to thereby to incrementally bring said cutting tooth from said closed position to said open position, each said increment of said rotation of said first adjustment portion relative to said second adjustment portion in said first rotational drilling direction urges said cutting tooth further towards said open position.

4. A method according to claim 3, wherein said second adjustment portion includes a marking scale, wherein at least one of a degree of opening of said cutting tooth between said closed and open positions and a diameter of an undercut bore in the bone is shown in said marking scale.

5. A method according to claim 1, wherein said rotatable coupling includes at least one slot in a wall of the first actuator portion, said slot having a longitudinal axis; and
    wherein the bone material removal device includes a shaft having a longitudinal axis, said slot longitudinal axis being at an angle relative to said shaft longitudinal axis, and wherein said angle determines a ratio of axial displacement of said shaft in respect to amount of rotation of said second actuator portion.

6. A method according to claim 1, wherein said rotating said second actuator portion includes rotating a portion of said second actuator portion at least partially in a spiral path about said bone material removal device.

7. A method according to claim 6, wherein said rotatable coupling includes at least one slot in a wall of the first actuator portion, and wherein said spiral path is along said at least one slot.

8. A method according to claim 1, wherein the bone material removal device includes a shaft, and wherein said rotatable coupling comprises a threaded portion at a proximal end of said shaft interthreaded with a threaded portion of said first actuator portion, whereby said rotating said second actuator portion causes rotation of said threaded shaft.

9. A method according to claim 1, wherein said actuator comprises at least one eccentric rotatable mass.

10. A method of claim 9, wherein said rotatable coupling includes at least one slot in a wall of the first actuator portion, and wherein said actuator includes pins configured to travel along said slot;
    wherein said rotating said second actuator portion includes causing said pins to travel along said slot; and
    wherein at least partial rotation of said second actuator portion in the second rotational drilling direction includes moving said pins within said slot from a first slot position to a second slot position and bringing said cutting tooth to travel from the closed position to the open position.

11. A method according to claim 1, wherein the bone material removal device includes a tubular element having a distal end, wherein said cutting tooth comprises at least one resilient portion, and wherein at least a portion of said cutting tooth engages said tubular element distal end via said resilient portion when said cutting tooth is in a closed position, wherein said resilient portion exerts a constant bias in a radially inward direction that resists outward radial extension of the cutting tooth, when said cutting tooth is in said closed position.

12. A method according to claim 1, wherein the bone material removal device includes a tubular element having a proximal end rigidly coupled to the first actuator portion and a shaft disposed within said tubular element, and wherein at least partial rotation of said second actuator portion displaces said shaft axially;
    wherein said cutting tooth is positioned in said tubular element distal end to interfere with a path of axial displacement of said shaft; and
    wherein at least partial rotation of said second actuator portion in the second rotational drilling direction displaces said shaft axially distally relative to said tubular element, said axially displaced shaft, being engaged with at least a portion of said cutting tooth, brings said tooth to travel from said closed position to said open position in which at least a portion of said cutting tooth extends in a radial direction beyond an outside surface of said tubular element.

13. A method according to claim 1, further including, after said reversing, forming an undercut bore in the bone by the cutting tooth in the open position, while pulling the bone material removal device in a proximal direction and continuing rotating the bone material removal device in said second rotational drilling direction.

14. A device for drilling a varying diameter bore, comprising:
a bone material removal device having a drilling tip and a selectably openable cutting tooth at a first end of said bone material removal device;
an actuator comprising a first actuator portion and a second actuator portion rotatably coupled to said first actuator portion;
wherein said second actuator portion is at least partially rotatable in a first rotational drilling direction, wherein rotation of said second actuator portion in the first rotational drilling direction is associated with a corresponding maintaining of a selectably openable cutting tooth in a closed position;
wherein said second actuator portion is at least partially rotatable in a second rotational drilling direction, wherein rotation of said second actuator portion in the second rotational drilling direction is associated with a corresponding extending of said cutting tooth to travel from the closed position to an open position.

15. A device according to claim 14, wherein said actuator includes a first adjustment portion and a second adjustment portion, whereby said first adjustment portion is rotatable in increments relative to said second adjustment portion, said incremental rotation of said first adjustment portion relative to said second adjustment portion associated with a corresponding bring of said cutting tooth from said closed position to said open position, each said increment of said rotation of said first adjustment portion relative to said second adjustment portion in said first rotational actuating direction configured to urge said cutting tooth further towards said open position.

16. A device according to claim 14, wherein said rotatable coupling includes at least one slot in a wall of the first actuator portion, said slot having a longitudinal axis; and
wherein said bone material removal device includes a shaft, said slot longitudinal axis being at an angle relative to said shaft, and wherein said angle determines a ratio of axial displacement of said shaft in respect to amount of rotation of said second actuator portion.

17. A device according to claim 14, wherein a portion of said second actuator portion is configured to rotate at least partially in a spiral path about said bone material removal device.

18. A device according to claim 14, wherein said rotatable coupling includes at least one slot in a wall of the first actuator portion, and wherein said bone material removal device includes a shaft wherein said spiral path is along said at least one slot.

19. A device according to claim 14, wherein said bone material removal device includes a shaft, and wherein said rotatable coupling comprises a threaded portion at a proximal end of said shaft interthreaded with a threaded portion of said first actuator portion, whereby said rotation of said second actuator portion is associated with a corresponding rotation of said threaded shaft.

20. A device according to claim 14, wherein said actuator comprises at least one eccentric rotatable mass.

21. A device of claim 20, wherein said rotatable coupling includes at least one slot in a wall of the first actuator portion, and wherein said actuator includes pins configured to travel along said slot;
wherein said pins are configured to travel along said slot when said second actuator portion is rotated; and
wherein said at least partial rotation of said second actuator portion in the second rotational drilling direction is associated with a corresponding movement of said pins within said slot from a first slot position to a second slot position and a bringing of said cutting tooth to travel from the closed position to the open position.

22. A device according to claim 14, wherein said bone material removal device includes a tubular element having a proximal end rigidly coupled to said first actuator portion and a shaft disposed inside said tubular element, and wherein said at least partial rotation of said second actuator portion is associated with a corresponding displacement of said shaft axially;
wherein said cutting tooth is positioned in said tubular element distal end to interfere with a path of axial displacement of said shaft; and
wherein said at least partial rotation of said second actuator portion in the second rotational drilling direction is associated with a corresponding displacement of said shaft axially distally relative to said tubular element wherein said axially displaced shaft, being engaged with at least a portion of said cutting tooth, is configured to bring said tooth to travel from said closed position to said open position in which at least a portion of said cutting tooth extends in a radial direction beyond an outside surface of said tubular element.

* * * * *